US011027043B1

(12) United States Patent
Stockman et al.

(10) Patent No.: US 11,027,043 B1
(45) Date of Patent: Jun. 8, 2021

(54) CROSSLINKED GELS COMPRISING POLYALKYLENEIMINES, AND THEIR USES AS MEDICAL DEVICES

(71) Applicant: HyperBranch Medical Technology, Inc., Durham, NC (US)

(72) Inventors: Kenneth E. Stockman, Raleigh, NC (US); Michael A. Carnahan, Durham, NC (US); Keith R. D'Alessio, Carey, NC (US); Mark W. Grinstaff, Brookline, MA (US)

(73) Assignee: HyperBranch Medical Technology, Inc., Durham, NC (US)

( * ) Notice: Subject to any disclaimer, the term of this patent is extended or adjusted under 35 U.S.C. 154(b) by 0 days.

(21) Appl. No.: 16/894,107

(22) Filed: Jun. 5, 2020

Related U.S. Application Data

(63) Continuation of application No. 15/882,244, filed on Jan. 29, 2018, now Pat. No. 10,688,216, which is a
(Continued)

(51) Int. Cl.
| *A61K 31/74* | (2006.01) |
| *A61L 26/00* | (2006.01) |
| *A61K 31/787* | (2006.01) |
| *A61L 27/18* | (2006.01) |
| *A61L 24/04* | (2006.01) |
| *A61L 24/00* | (2006.01) |
| *A61L 27/26* | (2006.01) |

(Continued)

(52) U.S. Cl.
CPC ........ *A61L 26/0019* (2013.01); *A61K 31/785* (2013.01); *A61K 31/787* (2013.01); *A61L 24/0031* (2013.01); *A61L 24/0036* (2013.01); *A61L 24/043* (2013.01); *A61L 24/046* (2013.01); *A61L 26/008* (2013.01); *A61L 26/0052* (2013.01); *A61L 26/0085* (2013.01); *A61L 27/18* (2013.01); *A61L 27/26* (2013.01); *A61L 27/52* (2013.01); *A61L 27/56* (2013.01); *A61B 2017/0065* (2013.01); *A61B 2017/00951* (2013.01); *A61K 51/1279* (2013.01); *A61L 24/00* (2013.01)

(58) Field of Classification Search
CPC .. A61B 2017/0065; A61B 2017/00951; A61K 51/1279; A61L 24/00; A61L 24/04
See application file for complete search history.

(56) References Cited

U.S. PATENT DOCUMENTS

| 2,254,008 A | 8/1941 | French |
| 4,254,008 A | 3/1981 | Krsek |

(Continued)

FOREIGN PATENT DOCUMENTS

| EP | 1120428 A2 | 8/2001 |
| WO | 2006031358 A2 | 3/2006 |

(Continued)

OTHER PUBLICATIONS

Australian Search Report for AU Application No. 2007204872, dated Mar. 15, 2012.
Cosgrove et al., "Safety and efficacy of a novel polyethylene glycol hydrogel sealant for watertight dural repair", J. Neurosurg, vol. 106, pp. 52-58, Jan. 2007.

(Continued)

*Primary Examiner* — James W Rogers
(74) *Attorney, Agent, or Firm* — Lerner, David, Littenberg, Krumholz & Mentlik, LLP

(57) ABSTRACT

One aspect of the present invention generally relates to methods of sealing a wound or tissue plane or filling a void splace. In a preferred embodiment, the wound is an ophthalmic, pleural or dural wound. In certain instances, the compositions used to seal the wound or tissue plane comprises a polyalkyleneimine. In a preferred embodiment, the polyalkyleneimine is polyethyleneimine. Treatment of the polyethyleneimine with a cross-linking reagent causes the polyethyleneimine polymers to polymerize forming a seal. In certain instances, the cross-linking reagent is a polyethylene glycol having reactive terminal groups. In certain instances, the reactive terminal groups are activated esters, such as N-hydroxy succinimide ester. In certain instances, the reactive terminal groups are isocyanates. In certain instances, the polyethyleneimine has a lysine, cysteine, isocysteine or other nucleophilic group attached to the periphery of the polymer. In certain instances, the polyethyleneimine is mixed with a second polymer, such as a polyethylene glycol containing nucleophilic groups. In certain instances, the compositions used to seal the wound or tissue plane are formed by reacting a polyalkyleneimine bearing electrophilic groups with a cross-linking reagent containing nucleophilic groups. In certain instances, the electrophilic groups on the polyalkyleneimine are activated esters, such as N-hydroxy succinimide ester. In certain instances, the compositions used to seal the wound or tissue plane are formed by reacting a polyalkyleneimine bearing photopolymerizable groups with ultraviolet or visibile light. Compositions used to seal the wound which contain PEI or a derivative of PEI are found to adhere tightly to the tissue. Other aspects of the present invention relate to methods of filling a void of a patient or adhering tissue. In certain instances, the methods use a polyalkyleneimine. In a preferred embodiment, the polyalkyleneimine is polyethyleneimine. Another aspect of the present invention relates to a polymeric composition formed by exposing a polyalkyleneimine to an activated polyalkylene glycol. In certain instances, the composition is attached to mammalian tissue.

1 Claim, 39 Drawing Sheets

Related U.S. Application Data continuation of application No. 15/213,147, filed on Jul. 18, 2016, now Pat. No. 9,878,066, which is a continuation of application No. 11/653,433, filed on Jan. 11, 2007, now Pat. No. 9,393,344.

(60) Provisional application No. 60/837,199, filed on Aug. 11, 2006, provisional application No. 60/758,105, filed on Jan. 11, 2006.

(51) Int. Cl.
*A61L 27/52* (2006.01)
*A61L 27/56* (2006.01)
*A61K 31/785* (2006.01)
*A61K 51/12* (2006.01)
*A61B 17/00* (2006.01)

(56) References Cited

U.S. PATENT DOCUMENTS

| | | | |
|---|---|---|---|
| 4,477,604 A | 10/1984 | Oechsle, III | |
| 4,940,737 A | 7/1990 | Braatz et al. | |
| 4,988,358 A | 1/1991 | Eppley et al. | |
| 5,162,430 A | 11/1992 | Rhee et al. | |
| 5,306,504 A | 4/1994 | Lorenz | |
| 5,318,780 A | 6/1994 | Viegas et al. | |
| 5,328,955 A | 7/1994 | Rhee et al. | |
| 5,514,379 A | 5/1996 | Weissleder et al. | |
| 5,527,856 A | 6/1996 | Rhee et al. | |
| 5,583,114 A | 12/1996 | Barrows et al. | |
| 5,587,175 A | 12/1996 | Viegas et al. | |
| 5,614,587 A | 3/1997 | Rhee et al. | |
| 5,645,855 A | 7/1997 | Lorenz | |
| 5,744,545 A | 4/1998 | Rhee et al. | |
| 5,752,974 A | 5/1998 | Rhee et al. | |
| 5,874,500 A | 2/1999 | Rhee et al. | |
| 5,936,035 A | 8/1999 | Rhee et al. | |
| 5,958,443 A | 9/1999 | Viegas et al. | |
| 6,051,248 A | 4/2000 | Sawhney et al. | |
| 6,051,648 A | 4/2000 | Rhee et al. | |
| 6,060,534 A | 5/2000 | Ronan et al. | |
| 6,136,334 A | 10/2000 | Viegas et al. | |
| 6,149,931 A | 11/2000 | Schwartz et al. | |
| 6,165,489 A | 12/2000 | Berg et al. | |
| 6,166,130 A | 12/2000 | Rhee et al. | |
| 6,179,862 B1 | 1/2001 | Sawhney | |
| 6,214,966 B1 | 4/2001 | Harris | |
| 6,217,894 B1 | 4/2001 | Sawhney et al. | |
| 6,248,800 B1 | 6/2001 | Greff et al. | |
| 6,312,725 B1 | 11/2001 | Wallace et al. | |
| 6,323,278 B2 | 11/2001 | Rhee et al. | |
| 6,352,710 B2 | 3/2002 | Sawhney et al. | |
| 6,458,889 B1 | 10/2002 | Trollsas et al. | |
| 6,495,127 B1 | 12/2002 | Wallace et al. | |
| 6,514,534 B1 | 2/2003 | Sawhney | |
| 6,534,591 B2 | 3/2003 | Rhee et al. | |
| 6,566,406 B1 | 5/2003 | Pathak et al. | |
| 6,579,916 B1 | 6/2003 | Askill et al. | |
| 6,652,886 B2 | 11/2003 | Ahn et al. | |
| 6,673,093 B1 | 1/2004 | Sawhney | |
| 6,703,047 B2 | 3/2004 | Sawhney et al. | |
| 6,743,521 B2 | 6/2004 | Hubbell et al. | |
| 6,818,018 B1 | 11/2004 | Sawhney | |
| 6,833,408 B2 | 12/2004 | Sehl et al. | |
| 7,009,034 B2 | 3/2006 | Pathak et al. | |
| 7,025,990 B2 | 4/2006 | Sawhney | |
| 7,176,256 B2 | 2/2007 | Rhee et al. | |
| 7,332,566 B2 | 2/2008 | Pathak et al. | |
| 7,592,418 B2 | 9/2009 | Pathak et al. | |
| 2002/0141965 A1 | 10/2002 | Ahn et al. | |
| 2003/0035786 A1 | 2/2003 | Hendriks et al. | |
| 2003/0223957 A1 | 12/2003 | Schwartz et al. | |
| 2004/0023842 A1 | 2/2004 | Pathak et al. | |
| 2004/0086479 A1 | 5/2004 | Grinstaff et al. | |
| 2004/0131582 A1 | 7/2004 | Grinstaff et al. | |
| 2004/0235708 A1 | 11/2004 | Rhee et al. | |
| 2005/0027069 A1 | 2/2005 | Rhee et al. | |
| 2005/0266086 A1 | 12/2005 | Sawhney | |
| 2008/0195040 A1 | 8/2008 | Clark et al. | |
| 2009/0215923 A1 | 8/2009 | Carnahan et al. | |
| 2010/0010473 A1 | 1/2010 | D'Alessio et al. | |
| 2010/0069927 A1 | 3/2010 | Clark et al. | |
| 2010/0280312 A1 | 11/2010 | D'Alessio et al. | |
| 2010/0280547 A1 | 11/2010 | D'Alessio et al. | |
| 2011/0044932 A1 | 2/2011 | Carnahan et al. | |

FOREIGN PATENT DOCUMENTS

| | | |
|---|---|---|
| WO | 2006031388 A2 | 3/2006 |
| WO | 2007001926 A2 | 1/2007 |
| WO | 2007005249 A2 | 1/2007 |

OTHER PUBLICATIONS

Gayet, J.-C. et al., "High water content BSA-PEG hydrogel for controlled release device: Evaluation of the drug release properties", Journal of Controlled Release, 38:177-184 (Elsevier Science B.V., Montreal, Canada), Feb. 1996.

International Search Report for Application No. PCT/US2007/000819 dated Jul. 24, 2008.

Mohamed, S. et al., "Physical Properties of Polyethyleneimine-Alginate Gels", Biotechnology Letters, 4(9):611-614 (Kew, Surrey, GB, Jan. 1, 1982).

Pathak, C. P. et al., "Rapid Photopolymerization of Immunoprotective Gels in Contact with Cells and Tissue," J. Am. Chem. Soc., 114:8311-8312, Oct. 1992.

Pouyani, T. et al., "Novel Hydrogels of Hyaluronic Acid: Synthesis, Surface Morphology, and Solid-State NMR," J. Am. Chem. Soc., 116:7515-7522, Aug. 1994.

Preul, et al., "Toward Optimal Tissue Sealants for Neurosurgery: Use of a Novel Hydrogel Sealant in a Canine Durotomy Repair Model", Neurosurgery vol. 53, No. 5, Nov. 2003, pp. 1189-1199.

Vinogradov, S. V. et al., "Self-Assembly of Polyamine-Poly(ethylene glycol) Copolymers with Phosphorothioate Oligonucleotides", Bioconjugate Chem., 9:805-812, Oct. 1998.

Figure 1a
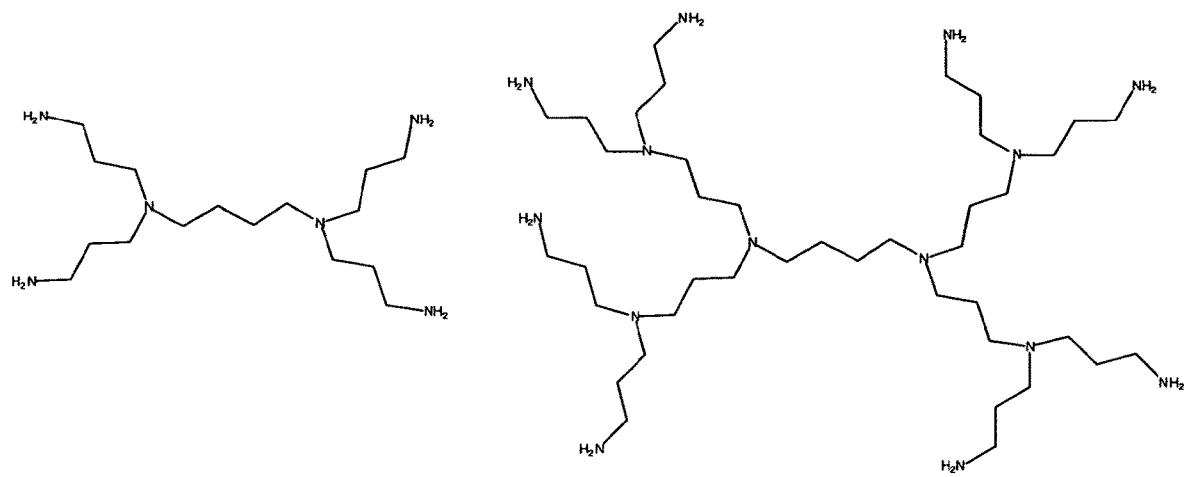
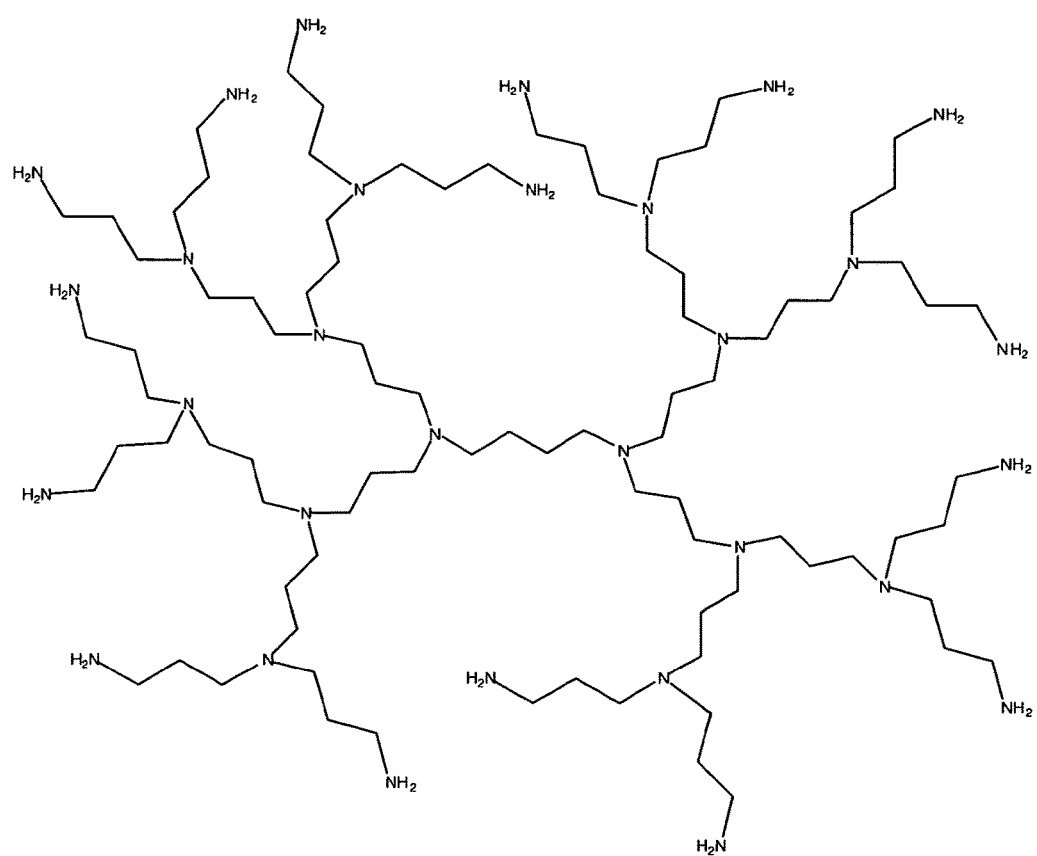

Figure 4
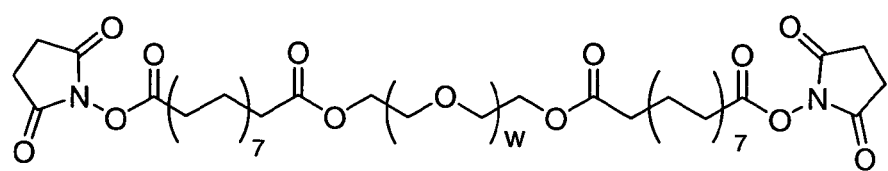
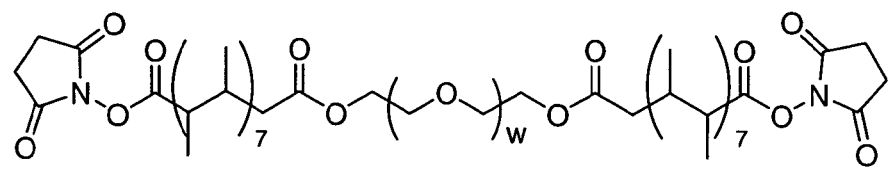
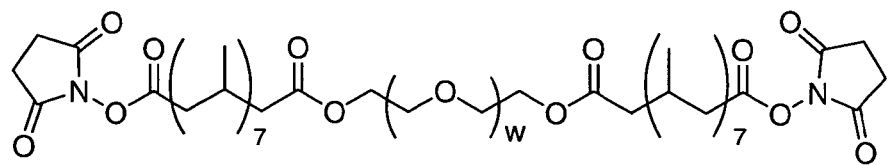
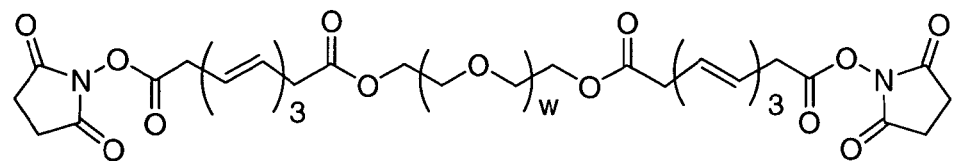

Figure 5
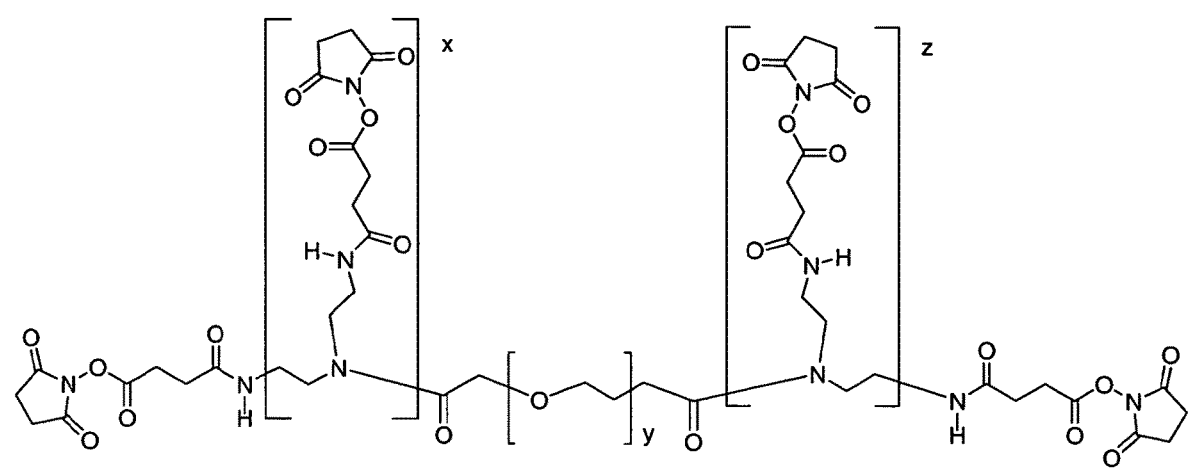
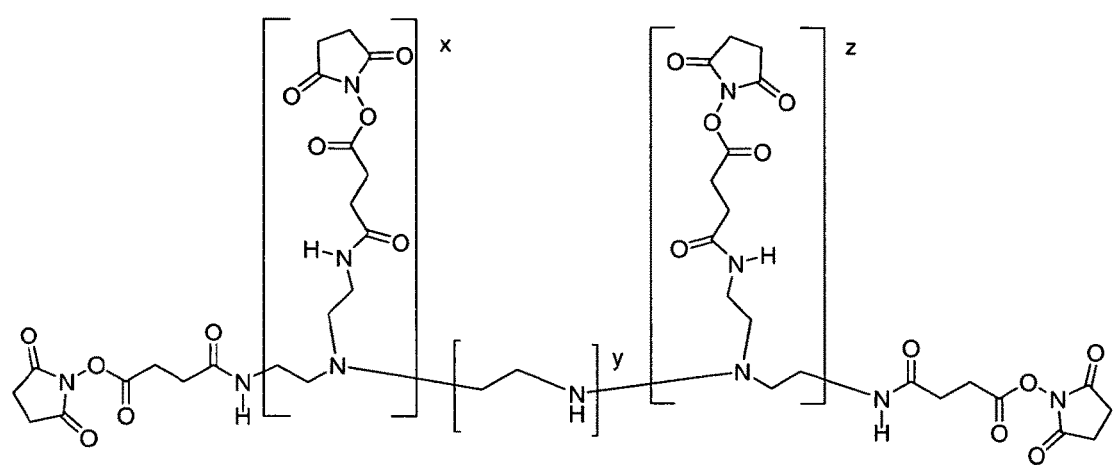

Figure 7
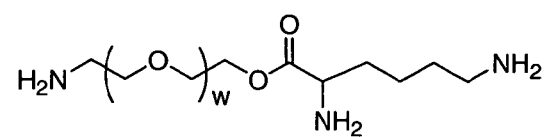
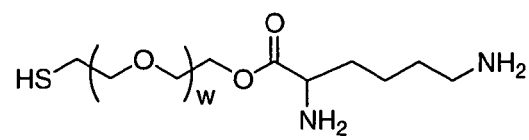
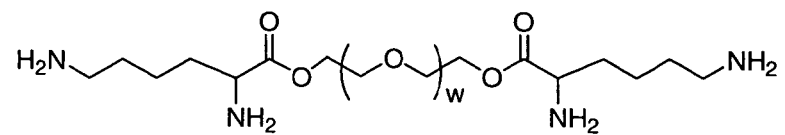
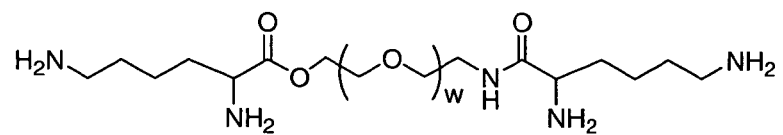
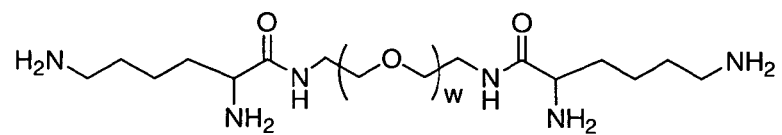

Figure 8
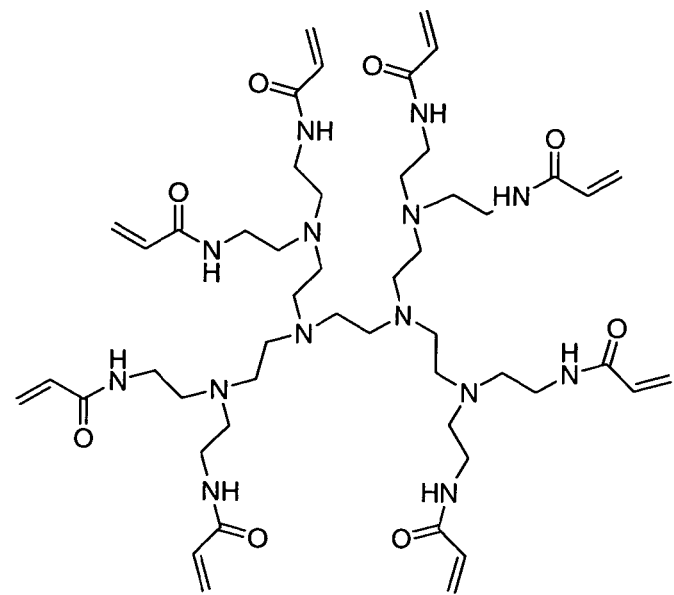
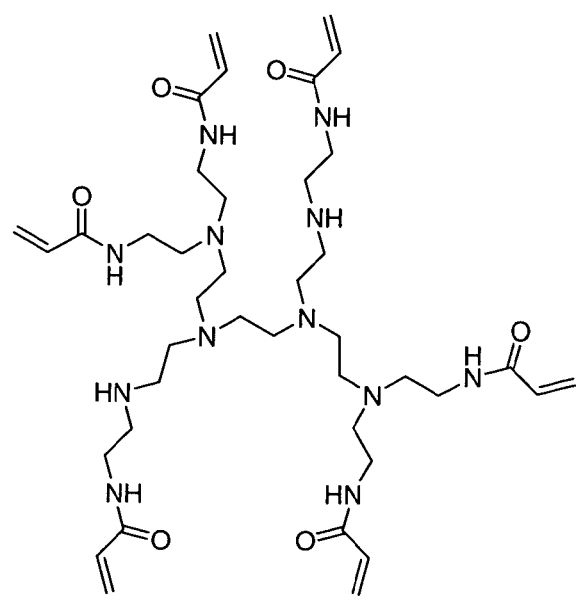

Figure 9
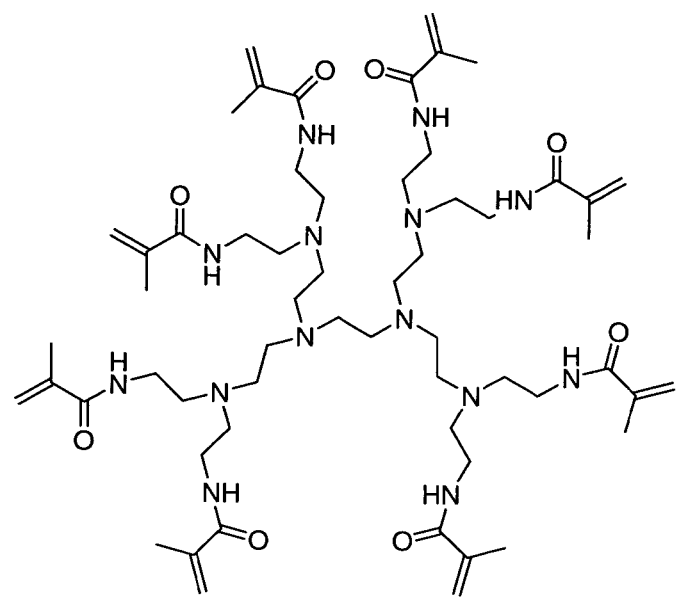
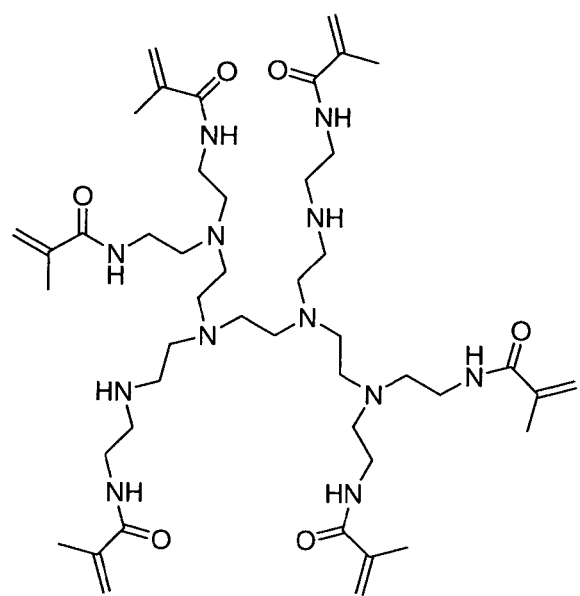

Figure 12

| Formulation | Last Off Time (hours) | Swelling @ 48 hours | Crosslinker | Crosslinker code | Polymer | Polymer Code |
|---|---|---|---|---|---|---|
| A4-2000 | 55.08 | 210 | PEI-2000 | 3 | TMXDI-1000 | 2 |
| PEI 1300/PEG-15% 10:1 PEG:PEI | 161.25 | 228.8 | PEI-1300 | 2 | PEG | 1 |
| PEI 1300/PEG-15% 10:1 (contaminated with other hydrogel) | 97.25 | 228.8 | PEI-1300 | 2 | PEG | 1 |
| 54:1 TMXDI 1000 PrePoly:dendron | 54.5 | 127 | Dendron | 1 | TMXDI-1000 | 2 |
| 36:1 TMXDI 1000 PrePoly:dendron | 8.25 | 153 | Dendron | 1 | TMXDI-1000 | 2 |
| PEG-SPA 3400 dendron 15% | 16.5 | 195.7 | Dendron | 1 | PEG | 1 |
| PEI 2000-7.5% PEI-10:1 PEG:PEI (10-7B) | 163 | 142.2 | PEI-2000 | 3 | PEG | 1 |
| PEI 2000-7.5% PEI-10:1 PEG:PEI (10-7B) | 163 | 133.2 | PEI-2000 | 3 | PEG | 1 |
| PEI 2000-7.5% PEI-20:1 PEG:PEI (10-7C) | 168.75 | 46 | PEI-2000 | 3 | PEG | 1 |
| PEI 1300-7.5% PEI-20:1 PEG:PEI (10-7D) | 162.5 | 146.1 | PEI-1300 | 2 | PEG | 1 |
| B3-2000 | 22.75 | 270 | PEI-2000 | 3 | TMXDI-1500 | 3 |
| B4-2000 | 22.75 | 275 | PEI-2000 | 3 | TMXDI-1500 | 3 |
| A1-1300 | 75.75 | 230 | PEI-1300 | 2 | TMXDI-1000 | 2 |
| A2-1300 | 28.25 | 150 | PEI-1300 | 2 | TMXDI-1000 | 2 |
| A3-2000 | 28 | 110 | PEI-2000 | 3 | TMXDI-1000 | 2 |
| A5-2000 | 13.5 | 210 | PEI-2000 | 3 | TMXDI-1000 | 2 |

Figure 15
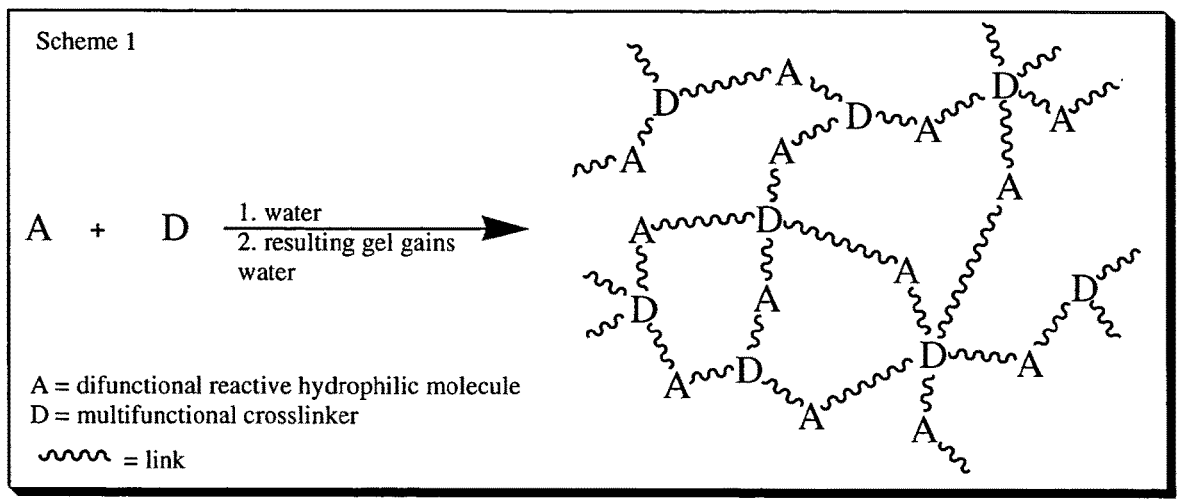
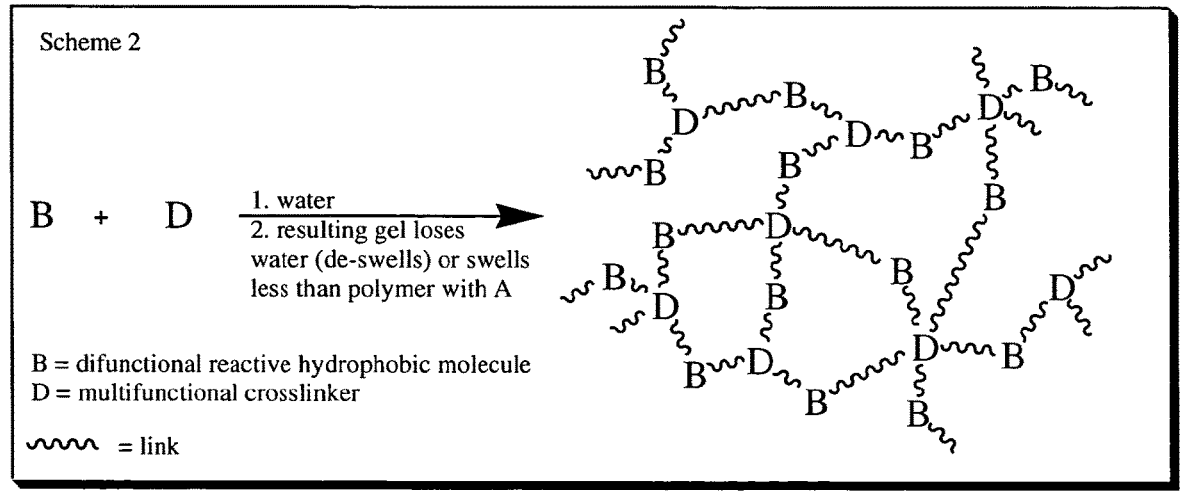

A = difunctional reactive hydrophillic molecule with a pendent acid group, such as TMXDI prepolymers
D = multifunctional crosslinker, such as PEI or dendron
T = aziridine trifunctional cross linker, which will react with the pendent acid but not with water A = difunctional reactive hydrophillic molecule with a pendent acid group, such as TMXDI prepolymers
B = Difunctional linker molecule-no other reactive groups
D = multifunctional crosslinker, such as PEI or dendron
T = aziridine trifunctional cross linker, which will react with the pendent acid but not with water

Figure 32
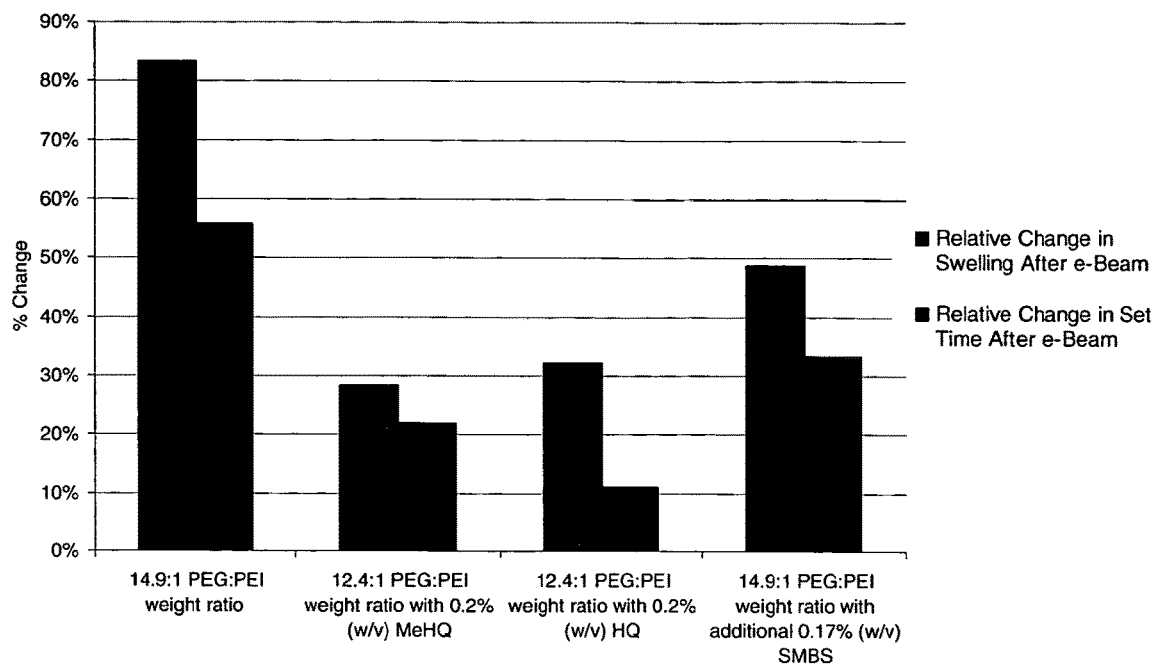
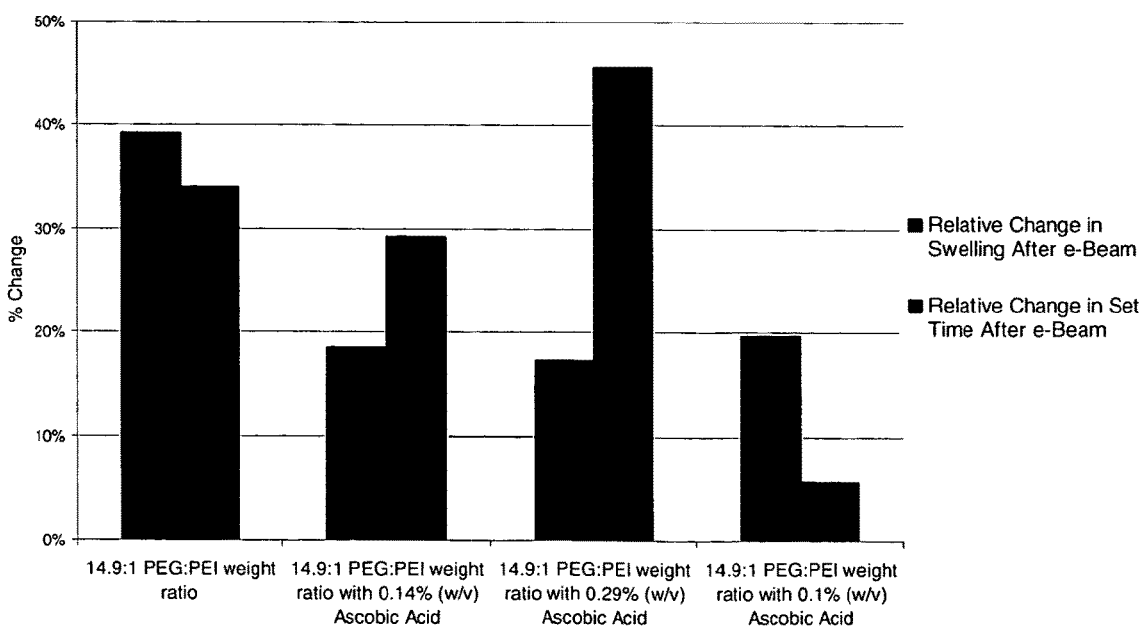

Figure 37
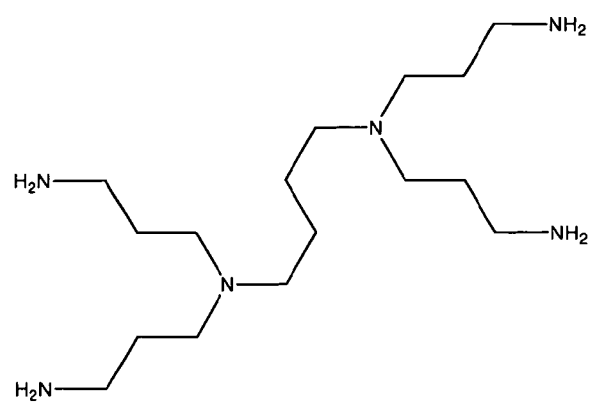
[A]
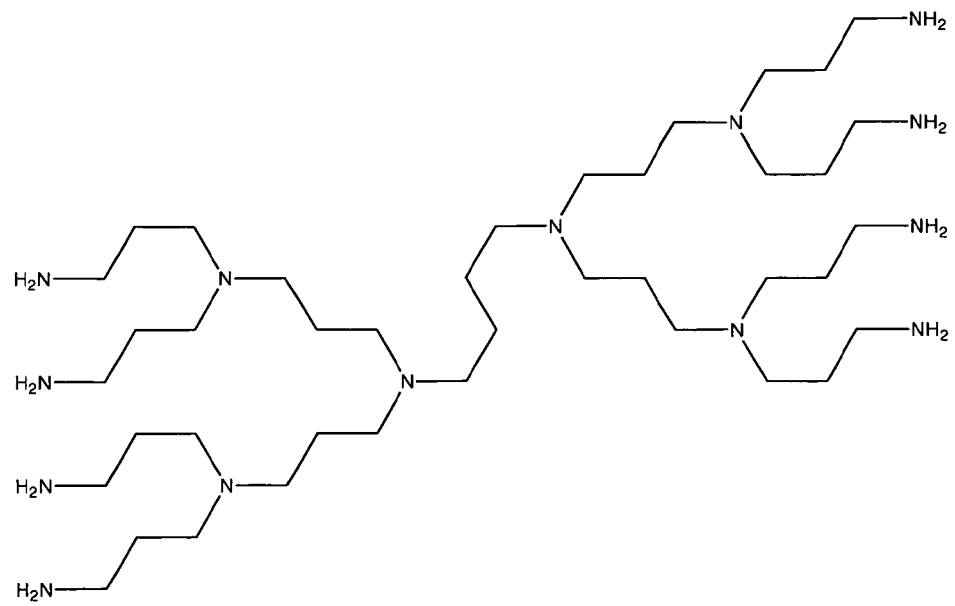
[B]

Figure 38

| PAG-NHS | PAI or Trilysine | Weight % crosslinking components | Ratio PEG:PAI (w/w) | Swelling @ 24 hr 37 °C (%) | Set Time (Sec) | Phosphate Conc. (mM) | Borate Conc. (mM) | Carbonate Conc. (mM) |
|---|---|---|---|---|---|---|---|---|
| PPG-PEG-PPG $_{2000}$-(ASG)$_2$ | PEI$_{2000}$ | 10 | 9:1 | 8 | 30 | 130.2 | 24.3 | 24.3 |
| PPG-PEG-PPG $_{2000}$-(ASG)$_2$ | PEI$_{2000}$ | 30 | 8.1:1 | 144 | 35 | 398.5* | 35 | 0 |
| PPG-PEG-PPG $_{2000}$-(ASG)$_2$ | G1-PPI(DAB) | 30 | 18.4:1 | 242 | 66 | 160.2* | 25 | 0 |
| Pluronic F-127-(SG)$_2$ | PEI$_{2000}$ | 15 | 58:1 | - | 9 | 63 | 35 | 25 |
| PEG$_{3400}$-(SMB)$_2$ | PEI$_{2000}$ | 15 | 15:1 | - | 33 | 53 | - | 25 |
| PEG$_{3400}$-(SPA)$_2$ | PEI$_{25000}$ | 15 | 14.5:1 | - | 23 | H$_3$PO$_4$ added until solution pH 8.6 | | |
| PEG$_{3400}$-(SPA)$_2$ | PEI$_{2000}$ | 30 | 15:1 | - | 25 | 451 | 25 | 25 |
| PEG$_{3400}$-(SPA)$_2$ | PEI$_{2000}$ | 15 | 15:1 | 60 | 20 | 141 | 25 | 25 |
| PEG$_{3400}$-(SPA)$_2$ | PEI$_{2000}$ | 10 | 16.4:1 | 45 | 35 | 75 | 25 | 25 |
| PEG$_{3400}$-(SPA)$_2$ | PEI$_{2000}$ | 9 | 16.4:1 | 39 | 33 | 85 | 25 | 25 |
| PEG$_{3400}$-(SPA)$_2$ | PEI$_{2000}$ | 8 | 16.4:1 | 30 | 28 | 70 | 25 | 25 |
| PEG$_{3400}$-(SPA)$_2$ | PEI$_{2000}$ | 7.5 | 16.4:1 | 39 | 29 | 60 | 25 | 25 |
| PEG$_{3400}$-(SPA)$_2$ | PEI$_{2000}$ | 7 | 16.4:1 | 27 | 30 | 50 | 25 | 25 |
| PEG$_{3400}$-(SPA)$_2$ | PEI$_{2000}$ | 6 | 16.4:1 | 20 | 34 | 50 | 25 | 25 |
| PEG$_{3400}$-(SPA)$_2$ | PEI$_{1300}$ | 15 | 17.2:1 | NR | 29 | 142.8 | 25 | 25 |
| PEG$_{3400}$-(SPA)$_2$ | G1-PPI(DAB) | 15 | 29:1 | 52 | 27 | 51 | 28 | - |
| PEG$_{3400}$-(SPA)$_2$ | Trilysine | 15 | 14.7:1 | 109 | 22 | - | 66 | - |
| PEG$_{10000}$-(SPA)$_2$ | PEI$_{2000}$ | 7.5 | 46.1:1 | 100 | 27 | 23 | 25 | 25 |
| PEG$_{10000}$-(SPA)$_2$ | PEI$_{2000}$ | 15 | 46.1:1 | 208 | 29 | 75 | 35 | 25 |
| PEG$_{3400}$-(SG)$_2$ | PEI$_{2000}$ | 15 | 16.6:1 | 92 | 27 | 158 | 25 | 25 |
| PEG$_{3400}$-(SG)$_2$ | PEI$_{2000}$ | 9 | 16.4:1 | 66 | 31 | 85 | 25 | 25 |
| PEG$_{3400}$-(SG)$_2$ | PEI$_{2000}$ | 8 | 16.4:1 | 70 | 27 | 70 | 25 | 25 |
| PEG$_{3400}$-(SG)$_2$ | PEI$_{2000}$ | 7.5 | 12.6:1 | 96 | 40 | 97.5 | 25 | - |
| PEG$_{3400}$-(SG)$_2$ | PEI$_{2000}$ | 7 | 16.4:1 | 65 | 29 | 60 | 25 | 25 |
| PEG$_{3400}$-(SG)$_2$ | PEI$_{2000}$ | 6 | 16.4:1 | 67 | 32 | 50 | 25 | 25 |
| PEG$_{3400}$-(SG)$_2$ | PEI$_{1300}$ | 15 | 17.2:1 | 98 | 29 | 142 | 25 | 25 |
| PEG$_{3400}$-(SG)$_2$ | G1-PPI(DAB) | 15 | 29:1 | 52 | 27 | 51 | 28 | - |
| PEG$_{3400}$-(SG)$_2$ | Trilysine | 15 | 14.7:1 | 109 | 22 | - | 66 | - |
| PEG$_{3400}$-(S3MG)$_2$ | PEI$_{2000}$ | 15 | 15:1 | - | 19 | 143 | 25 | 25 |
| PEG$_{3400}$-(S3,3DMG)$_2$ | PEI$_{2000}$ | 15 | 15:1 | 191 | 21 | 0 | 25 | 25 |
| PEG$_{3400}$-(S3,3DMG)$_2$ | G1-PPI(DAB) | 15 | 15:1 | - | 141 | 51 | 28 | 0 |
| PEG$_{4600}$-(SG)$_2$ | PEI$_{2000}$ | 15 | 18.5:1 | 143 | 16 | 130.4 | 35 | 0 |
| PEG$_{4600}$-(SG)$_2$ | PEI$_{1300}$ | 15 | 22.9:1 | - | 35 | 144 | 25 | 25 |
| PEG$_{6000}$-(SG)$_2$ | PEI$_{2000}$ | 15 | 23.6:1 | 99 | 18 | 123.7 | 35 | 0 |
| PEG$_{8000}$-(SG)$_2$ | PEI$_{2000}$ | 15 | 30.8:1 | 190 | 33 | 116.6 | 35 | 0 |
| PEG$_{10000}$-(SG)$_2$ | PEI$_{25000}$ | 15 | 41:1 | - | 30 | H$_3$PO$_4$ added until solution pH 8.32 | | |
| PEG$_{10000}$-(SG)$_2$ | PEI$_{2000}$ | 7.5 | 45:1 | 113 | 30 | 75 | 25 | 25 |
| PEG$_{10000}$-(SG)$_2$ | PEI$_{2000}$ | 10 | 45:1 | 153 | 36 | 83 | 25 | 25 |
| PEG$_{10000}$-(SG)$_2$ | PEI$_{2000}$ | 15 | 40.4:1 | 222 | 26 | 130 | 25 | 25 |
| PEG$_{10000}$-(SG)$_2$ | PEI$_{1300}$ | 15 | 47.5:1 | - | 25 | 94 | 25 | 25 |
| PEG$_{10000}$-(SG)$_2$ | PEI$_{800}$ | 15 | 51:1 | - | 57 | 92.4 | 25 | 25 |
| PEG$_{10000}$-(SG)$_4$ | PEI$_{2000}$ | 15 | 22.5:1 | 163 | 25 | 53 | 0 | 5 |
| PEG$_{20000}$-(SG)$_4$ | PEI$_{2000}$ | 15 | 51:1 | 130 | 9 | 101 | 35 | 25 |
| PEG$_{20000}$-(ASG)$_4$ | PEI$_{2000}$ | 10 | 46.6:1 | 45 | 15 | 50 | 25 | 25 |
| PEG$_{20000}$-(ASG)$_4$ | PEI$_{2000}$ | 15 | 39.6:1 | 76 | 17 | 90 | 25 | 25 |
| PEG$_{20000}$-(ASG)$_4$ | PEI$_{2000}$ | 25 | 46.6:1 | - | 29 | 144.8 | 25 | 25 |
| Ethox CO-200-(SG)$_3$ | PEI$_{2000}$ | 15 | 30.5 | 51 | 32 | 138.2 | 25 | 25 |
| TMXDI(1000) | PEI$_{2000}$ | 15 | 100:1 | 95 | 30 | H$_3$PO$_4$ added until solution pH 9.0 | | |
| TMXDI(1000) | PEI$_{1300}$ | 15 | 100:1 | 125 | 30 | H$_3$PO$_4$ added until solution pH 8.8 | | |

\* denotes phosphoric acid

CROSSLINKED GELS COMPRISING POLYALKYLENEIMINES, AND THEIR USES AS MEDICAL DEVICES

RELATED APPLICATIONS

This application claims the benefit of priority to U.S. Provisional Patent Application Ser. No. 60/758,105, filed Jan. 11, 2006; and U.S. Provisional Patent Application Ser. No. 60/837,199, filed Aug. 11, 2006.

BACKGROUND OF THE INVENTION

Sealants and adhesives play an important role in helping patients recover from surgery or trauma. Sealants and adhesives are useful in treating patients suffering from a variety of in vivo (e.g., internal) or topical conditions, including lacerations, tears, wounds, ulcers, astamoses, and surgical procedures. Sealants or adhesives can generally be used in any indication or application for which a suture or staple is presently used, and the sealant or adhesive often provides a better outcome than a suture or staple. Sealants or adhesives can also be applied more quickly to the injury site and often provide a better seal over the wound and healing. Various medicinal applications for sealants and adhesives are described below.

Skin Lacerations

Skin lacerations are tears in the skin produced by accidents, trauma, or as a result of a surgical procedure. Lacerations often require treatment in order to close the hole in the skin, stop bleeding, and prevent infection. Minor lacerations in the skin may be treated using an adhesive tissue to cover the wound. However, larger laceractions often require sutures or a glue to help seal the wound. For example, it is generally recommended that sutures or a glue be used to treat lacerations deeper than 0.25 inches having a jagged edge or loose flap of tissue. The location of the laceration may also affect the form of treatment. For example, it is advantageous to treat a skin laceration on a joint using a glue because adhesive tissue tends to limit mobility of the joint. The use of sutures or glues to treat skin lacerations can also reduce the chance of scar formation.

Liver Lacerations

Lacerations of the liver can occur from trauma or as a result of a surgical procedure. The liver is a highly vascularized organ and bleeds profusely when lacerated or traumatized. Liver lacerations are difficult to repair owing to the nature of liver tissue. Liver tissue has very weak cohesive strength, and, consequently, sutures and staples are not satisfactory because they may pull through the liver tissue. The lack of satisfactory wound treatment methods for liver lacerations combined with the fact that it is difficult to reach the veins that feed the liver renders liver lacerations particularly serious. In fact, severe lacerations of the liver often result in the patient's death due to bleeding. Thus, new materials to treat liver lacerations are needed.

Lung Surgery

The sealants and methods of the present invention are useful in lung surgery. Types of lung surgery include lobectomy, lung biopsy, lung-tissue removal, pneumonectomy, thoracoscopy, and thoracotomy. Risks associated with lung surgery include wound infection; post-surgical internal bleeding; air leaks through the lung wall; pain or numbness at the incision site; and inflammation of the lungs (pneumonia). Further, air leakage is frequently observed after thoracic procedures, such as pulmonary resection and decortication. It is important to create an air-tight seal so as to prevent or reduce severe complications, such as bronchopleural fistulas and infection resulting from extended chest tube drainage, extended recovery time, and postoperative morbidity related to pulmonary surgery. The sealants and methods of the invention should decrease or eliminate some of the problematic aspects of lung surgery, such as treatment of pneumothorax and pulmonary leaks.

Cornea—Corneal Lacerations/Perforations

Corneal perforations are produced by a variety of medical conditions (e.g., infection, inflammation, xerosis, neurotrophication, and degeneration) and traumas (chemical, thermal, surgical, and penetrating). Unfortunately, corneal perforations often lead to loss of vision and a decrease in an individual's quality of life. Depending on the type and the origin of the perforation, different treatments may be effective, ranging from suturing the wound to a cornea graft. However, the surgical procedures are difficult given the delicate composition of the cornea and the severity of the wound which increase the likelihood for leakage and severe astigmatism after surgery. In certain cases, for example, perforations that cannot be treated by standard suture procedures, tissue adhesives (glues) are used to repair the wound. This type of treatment is very attractive because the method is simple, quick and safe, and corresponds to the requirement of a quick restoration of the integrity of the globe, avoiding further complications. Besides an easy and fast application on the wound, the characteristics of an adhesive include: 1) bind to the tissue (necrosed or not, very often wet) with an adequate adhesion force; 2) be non-toxic; 3) be biodegradable or resorbable; 4) be sterilizable; and 5) not interfere with the healing process.

Various alkyl-cyanoacrylates are available for the repair of small perforations. However, these "super glues" present major inconveniences. Their monomers, in particular those with short alkyl chains, can be toxic, in part due to their ability to produce formaldehyde in situ. They also polymerize too quickly leading to applications that might be difficult and, once polymerized, the surface of the glue is rough and hard which leads to patient discomfort and a need to wear contact lens. Even though cyanoacrylate is tolerated as a corneal sealant, a number of complications have been reported including cataract formation, corneal infiltration, glaucoma, giant papillary conjunctivitis, and symblepharon formation. Furthermore, in more than 60% of the patients, additional surgical intervention is needed.

Other glues have also been developed. Adhesive hemostats, based on fibrin, are usually constituted of fibrinogen, thrombin and factor XIII. Systems with fibrinogen and photosensitizers activated with light are also being tested. If adhesive hemostats have intrinsic properties which meet the requirements for a tissue adhesive, then autologous products (time consuming in an emergency) or severe treatments before clinical use are needed to avoid any contamination to the patient. An ideal sealant for corneal perforations should 1) not impair normal vision, 2) quickly restore the intraocular pressure (IOP), 3) maintain the structural integrity of the eye, 4) promote healing, 5) adhere to moist tissue surfaces, 6) possess solute diffusion properties which are molecular weight dependent and favorable for normal cornea function, 7) possess rheological properties that allow for controlled placement of the polymer on the wound, and 8) polymerize under mild conditions.

The use of sutures has limitations and drawbacks. First, suture placement itself inflicts trauma to corneal tissues, especially when multiple passes are needed. Secondly, although suture material has improved, sutures such as 10-0 nylon (which is the suture of choice in the cornea and elsewhere) can act as a nidus for infection and incite corneal inflammation and vascularization. With persistent inflammation and vascularization, the propensity for corneal scarring increases. Thirdly, corneal suturing often yields uneven healing and resultant regular and irregular astigmatism. Postoperatively, sutures are also prone to becoming loose and/or broken and require additional attention for prompt removal. Finally, effective suturing necessitates an acquired technical skill that can vary widely from surgeon to surgeon and can also involve prolonged operative time.

Cornea—Corneal Transplants

During a corneal transplant or penetrating keratoplasty surgery the diseased cornea is removed with a special round cutting tool called a trephine. The donor cornea is cut to a matching size. Then, the donor cornea is placed upon the eye and secured in place with approximately 16 sutures around the transplant to secure the new cornea in place. A sutureless procedure would be highly desirable because sutures are associated with the following drawbacks and others: (1) sutures provide a site for infection, (2) the sutured cornea takes 3 months to heal before the sutures need to be removed, and (3) the strain applied to the new cornea tissue from the sutures can distort the cornea. An ocular adhesive may also serve as an adjuvant to sutures and/or reduce the necessary number of sutures.

Cornea—Clear Corneal Incision

Clear corneal incisions in the temporal cornea offer several advantages with phacoemulsification. The major advantage associated with phacoemulsification is the reduction in size of the entrance wound. Smaller wounds require fewer sutures or even no sutures at all, minimizing induction of astigmatism, decreasing bleeding and subconjunctival hemorrhage, and speeding the recovery of visual acuity. See Agapitos, P. J. *Curr. Opin. Ophthalmol.* 1993, 4, 39-43 and Lyle, W. A.; Jin, G. J. J. *Cataract Refract. Surg.* 1996, 22, 1456-1460. Surgeons typically examine the clear corneal incisions at the completion of the procedure by inflating the anterior chamber with balanced salt solution and applying pressure to the anterior cornea to check for leakage from the wound. If there is some leakage, the wound may be hydrated with balanced saline solution to seal fully the wound. This is done by injecting balanced saline solution into the open stromal edges. Hydration forces the two edges of the wound together, creating a tight seal. The endothelial cell pump can then remove the fluid from both the anterior and posterior portions of the wound, further sealing the wound together. See Fine, I. H. *J. Cataract Refract. Surg.* 1991, 17 (*Suppl*), 672-676. These tests for fluid flow, however, make several assumptions, including that the eye will remain well pressurized during the early postoperative period, that the hydrated wound will not be rapidly deturgesced by the corneal endothelium, and that the absence of aqueous outflow from the wound correlates with the inability of surface fluid from the tear film to flow into the wound, possibly contaminating the aqueous humor and predisposing to infection. However, intraocular pressure is known to vary in the postoperative period, frequently dropping to less than 5 mm Hg, and telemetric intraocular pressure monitoring devices suggest that large fluctuations in intraocular pressure occur in individual eyes in response to blinking. See Shingleton, B. J.; Wadhwani, R. A.; O'Donoghue, M. W.; Baylus, S.; Hoey, H. *J. Cataract Refract. Surg.* 2001, 27, 524-527 and Percicot, C. L.; Schnell, C. R.; Debon, C.; Hariton, C. *J. Pharmacol. Toxicol. Methods* 1996, 36, 223-228.

In a recent study, optical coherence tomography (OCT) confirmed the morphology of clear corneal incision wounds was not constant but varied in response to changes in the intraocular pressure. See McDonnell, P. J.; Taban, M.; Sarayba, M.; Rao, B.; Zhang, J.; Schiffman, R.; Chen, Z. P. *Ophthalmology* 2003, 110, 2342-2348. When the eyes were well pressurized (20 mm Hg or higher), the chambers were deeply formed, and the wound edges were well apposed. Elevation of intraocular pressure up to 40 to 50 mm Hg did not result in any separation of the wound edges. As the intraocular pressure was reduced to 10 mm Hg and below, the wound edges progressively separated. The separation began at the internal aspect of the wound, with posterior migration of the posterior and peripheral wound leaflet. This separation resulted in a wedge-shaped gaping in the internal aspect of the incision. Coincident with this wound margin separation, the spontaneous flow of aqueous humor through the wound was observed, and the chamber became shallower. Elevating the intraocular pressure resulted in prompt closure of the corneal wound at its superficial margin, termination of fluid leakage from the wound, and deepening of the anterior chamber. India ink was also applied to the surface of the cornea and quickly became visible through the operating microscope within the clear corneal incisions. Histologic examination of the wounds confirmed partial penetration of India ink particles along the edges of the incisions in every cornea. These studies demonstrated that a transient reduction of intraocular pressure might result in poor wound apposition in clear corneal incisions, with the potential for fluid flow across the cornea and into the anterior chamber, with the attendant risk of endophthalmitis. See McDonnell, P. J.; Taban, M.; Sarayba, M.; Rao, B.; Zhang, J.; Schiffman, R.; Chen, Z. P. *Ophthalmology* 2003, 110, 2342-2348.

Nonetheless, a progressive increase in the percentage of surgeons preferring self-sealing clear corneal incisions over scleral tunnel incisions in the United States and Europe has occurred over the past decade. See Leaming, D. V. *J. Cataract Refract. Surg.* 1995, 21, 378-385 and Leaming, D. V. *J. Cataract Refract. Surg.* 2001, 27, 948-955. Some studies, however, reveal an increased incidence of postoperative endophthalmitis after clear corneal cataract incisions and a recent, retrospective, case-controlled study, reported that clear corneal incisions were a statistically significant risk factor for acute post-cataract surgery endophthalmitis when compared with scleral tunnel incisions. See John, M. E.; Noblitt, R. *Endophthalmitis. Scleral tunnel vs. clear corneal incision*; Slack, Inc.: Thorofare, N J, 2001; Colleaux, K. M.; Hamilton, W. K. *Can. J. Ophthalmol.* 2000, 35, 373-378; Nagaki, Y.; Hayasaka, S.; Kadoi, C.; Matsumoto, M.; Yanagisawa, S.; Watanabe, K.; Watanabe, K.; Hayasaka, Y.; Ikeda, N.; Sato, S.; Kataoka, Y.; Togashi, M.; Abe, T. *J. Cataract. Refract. Surg.* 2003, 29, 20-26; Stonecipher, K. G.; Parmley, V. C.; Jensen, H.; Rowsey, J. *J. Arch. Ophthalmol.* 1991, 109, 1562-1563; Lertsumitkul, S.; Myers, P. C.; O'Rourke, M. T.; Chandra, *J. Clin. Exp. Ophthalmol.* 2001, 29, 400-405; and Blake, A. C.; Holekamp, N. M.; Bohigian, G.; Thompson, P. A. *Am. J. Ophthalmol.* 2003, 136, 300-305. The visual outcome following severe endophthalmitis is always guarded. In a Western Australian Endophthalmitis Study more than half of the subjects suffered visual impairment, with 41% poorer than 20/200, 53% poorer than 20/125, and 58% poorer than 20/40. See Semmens, J. B.; Li, J.; Morlet, N.; Ng, *J. Clin. Exp. Ophthalmol.* 2003, 31, 213-219. Post-cataract endophthalmitis remains a potentially blinding complication of a sight-restoring procedure.

Refractive Surgery—Laser-Assisted In Situ Keratomileusis (LASIK)

Laser-assisted in situ keratomileusis is the popular refractive surgical procedure where a thin, hinged corneal flap is created by a microkeratome blade. This flap is then moved aside to allow an excimer laser beam to ablate the corneal stromal tissue with extreme precision for the correction of myopia (near-sightedness) and astigmatism. At the conclusion of the procedure, the flap is repositioned and allowed to heal. However, with trauma, this flap can become dislocated prior to healing, resulting in flap striae (folds) and severe visual loss. When this complication occurs, treatment involves prompt replacement of the flap and flap suturing. The use of sutures has limitations and drawbacks as discussed above. These novel adhesives could also play a useful role in the treatment of LASIK flap dislocations and striae (folds). These visually debilitating flap complications are seen not uncommonly following the popular procedure LASIK, and are currently treated by flap repositioning and suturing (which require considerable operative time and technical skill). A tissue adhesive could provide a more effective means to secure the flap.

Refractive Surgery—Lens Replacement

Cataracts or other diseases or injuries that lead to poorly functioning or damaged lens require the natural lens to be replaced. The optical properties of the normal eye lens are the consequence of a high concentration of proteins called "crystallins" forming a natural hydrogel. In vertebrate lenses, a range of differently sized protein assemblies, the alpha-, beta- and gamma-crystallins, are found creating a medium of high refractive index. The anatomical basis of accommodation includes the lens substance, lens capsule, zonular fibers, ciliary muscle and the elastic part of the choroid. Accommodation occurs through accurately controlled adjustments in the shape and thickness of the lens. The capsular bag is essential in transmitting the various extralenticular forces to the lens substance.

Modern cataract surgery can be done through a small incision (usually 2.5-3.5 mm). Once the incision is made, the anterior chamber is filled with a viscoelastic and the capsular bag is pricked with a needle. From this incision, a small continuous circular capsulorhexis (CCC) approximately 1.5 mm in diameter is performed using capsulorhexis forceps. Next endocapsular phacoemulsification is performed and the lens epithelial cells are removed by aspiration.

The normal function of the lens is to focus light onto the retina. Since removing the cataract leaves the eye without a lens to focus light, an artificial (intraocular) lens is commonly placed inside the eye. Most intraocular lenses are made of plastic, silicone, or acrylic compounds; have no moving parts; and last for the remainder of a person's life. These intraocular lens implants are held in place by the posterior capsule are not able to provide ocular accommodation. Refilling the lens capsule with in situ crosslinking materials described herein offers the potential to produce a synthetic hydrogel with mechanical properties similar to the lens of a twenty year old.

As such, the invention describes materials that reproduce the properties of the natural lens and these synthetic hydrogels maintain the integrity of the capsule to gain partial or full accommodation and restore vision to the patient. Alternatively, the dendritic polymers of the invention are incorporated in current IOL materials, such as PMMA, to alter hydrophilicity, water transport, refractive index, mechanical properties or biological response.

Retina—Retinal Holes

Techniques commonly used for the treatment of retinal holes, such as cryotherapy, diathermy and photocoagulation, are unsuccessful in the case of complicated retinal detachment, mainly because of the delay in the application and the weak strength of the chorioretinal adhesion. Cyanoacrylate retinopexy has been used in special cases. It has also been demonstrated that the chorioretinal adhesion is stronger and lasts longer than the earlier techniques. As noted previously with regard to corneal perforation treatment, the extremely rapid polymerization of cyanoacrylate glues (for example, risk of adhesion of the injector to the retina), the difficulty to use them in aqueous conditions and the toxicity are inconveniences and risks associated with this method. The polymerization can be slowed down by adding iophendylate to the monomers but still the reaction occurs in two to three seconds. Risks of retinal tear at the edge of the treated hole can also be observed because of the hardness of cyanoacrylate once polymerized.

Retina—Vitrectomy/Sclerotomy Incisions

The vitreous is a normally clear, gel-like substance that fills the center of the eye. It makes up approximately ⅔ of the eye's volume, giving it form and shape before birth. Certain problems affecting the back of the eye may require a vitrectomy, or surgical removal of the vitreous. During a vitrectomy, the surgeon creates small incisions/punctures in the eye (sclerotomies) for separate instruments. These incisions are placed in the pars plana of the eye, which is located just behind the iris but in front of the retina. The instruments which pass through these incisions include a light pipe, an infusion port, and the vitrectomy cutting device. Upon completion of pars plana vitrectomy, each sclerotomy site is closed with a single interrupted suture of 8-0 silk or 7-0 polyglycolic acid suture. After a vitrectomy, the eye is filled with fluid until the vitreous is replaced as the eye secretes aqueous and nutritive fluids.

Some of the most common eye conditions that require vitrectomy include 1) complications from diabetic retinopathy, such as retinal detachment or bleeding, 2) macular hole, 3) retinal detachment, 4) pre-retinal membrane fibrosis, 5) bleeding inside the eye (vitreous hemorrhage), 6) injury or infection, and 7) certain problems related to previous eye surgery.

Glaucoma—Filtering Bleb

Leaking filtering blebs after glaucoma surgery are difficult to manage and can lead to serious, vision-threatening complications. Filtering blebs can result in hypotony and shallowing of the anterior chamber, choroidal effusion, maculopathy, retinal, and choroidal folds, suprachoroidal hemorrhage, corneal decompensation, peripheral anterior synechiae, and cataract formation. A filtering bleb can also lead to the loss of bleb function and to the severe complications of endophthalmitis. The incidence of bleb leaks increases with the use of antimetabolites. Bleb leaks in eyes treated with 5-fluorouracil or mitomycin C may occur in as many as 20 to 40% of patients. Bleb leaks in eyes treated with antimetabolites may be difficult to heal because of thin avascular tissue and because of abnormal fibrovascular response. If the leak persists despite the use of conservative management, a 9-0 to 10-0 nylon or absorbable suture on a tapered vascular needle can be used to close the conjunctival wound. In a thin-walled or avascular bleb, a suture may not be advisable because it could tear the tissue and cause a larger leak. Fibrin adhesives have been used to close bleb leaks. The adhesive is applied to conjunctival wound simultaneously with thrombin to form a fibrin clot at the application site. The operative field must be dry during the application because fibrin will not adhere to wet tissue.

Cyanoacrylate glue may be used to close a conjuctival opening. To apply the glue, the surrounding tissue must be dried and a single drop of the cyanoacrylate is placed. The operative must be careful not to seal the applicator to the tissue or to seal surrounding tissue with glue given its quick reaction. A soft contact lens is then applied over the glue to decrease patient discomfort. However, this procedure can actually worsen the problem if the cyanoacrylate tears from the bleb and causes a larger wound.

Oculoplastics—Blepharoplasty Incisions

Blepharoplasty is an operation to remove excess skin, fat and muscle from around the eyes to correct droopy eyelids and bagginess under the eyes. It can be performed on the upper lids and lower lids, at the same time or separately. The operation may be done using either conventional or laser techniques. For surgery on the upper eyelids, cuts are made into the natural lines and creases in the lid, and into the laughter lines at the corner of the eye. For surgery on the lower eyelids, a cut is usually made just below the eyelashes. This means the scars run along the eye's natural folds, concealing them as much as possible. Excess fat, muscle and loose skin are removed, and the cut is closed using sutures. If only fat is being removed, sometimes the cut is made on the inside of the lower eyelid, leaving no visible scar. A tissue adhesive could provide a more effective means to secure the cuts made during surgery.

Gastrointestinal Anastomosis

The sealants and methods of the present invention should be useful in gastrointestinal anastomosis procedures. Gastrointestinal anastomosis is the technique of joining two pieces of bowel together. There are many techniques for gastro-intestinal anastomosis, including both mechanical stapled techniques and hand-sutured procedures. The technique may involve a simple end-end anastomosis of two pieces of jejunum, a more complex colo-anal anastomosis, or a biliary enteric join. One problem with techniques employing sutures or staples is that leakage may occur around the sutures or staples. See, for example, Bruce et al. Br. J. Surg. 88:1157-1168 (2001) reporting leakage rates of 5-8%. However, sealants and methods of the invention could be used to supplement the sutures or staples used in intestinal anastomoses, providing a better seal that reduces leakage. Compositions and procedures for proper sealing the consequences of a failed anastomosis are severe and frequently life-threatening. Although failures can be caused by myriad factors, including poor surgical technique (e.g., sutures that were not inserted correctly; knots that were tied too tightly rendering the ends ischaemic; or incorrect use of a staple gun), the sealants and methods of the invention should decrease or eliminate some of the causes of failed gastrointestinal anastomosis procedures.

Prostatectomy Urethral-Bladder Anastomosis

The sealants and methods of the present invention should be useful in prostatectomy urethral-bladder anastomosis procedures. Prostatectomy urethral-bladder anastomosis is the technique of joining together a patient's ureter and bladder after surgical removal of his prostate gland. Failures are caused by myriad factors, including poor surgical technique (e.g., sutures that were not inserted correctly; knots that were tied too tightly rendering the ends ischaemic). The sealants and methods of the invention should decrease or eliminate some of the causes of failed prostatectomy urethral-bladder anastomosis procedures.

Cartilage, Meniscus and Disk Repair

Cartilaginous tissues play important roles in contributing to load support and energy dissipation in the joints of the musculoskeletal system. These tissues include articular cartilage which is predominantly an avascular and alymphatic tissue with very low cell-density. As a result, articular cartilage has limited capacity for self-repair following injury or aging. Degeneration of cartilage in the meniscus, intervertebral disks, or joints can lead to severe and debilitating pain in patients. Injuries to these tissues are often retained for many years and may eventually lead to more severe secondary damage. See Moskowitz, R. W., *Osteoarthritis: diagnosis and medical/surgical management.* $2^{nd}$ ed.; W.B. Saunders Company: 1984. Today, more than one million knee, hip, and shoulder joint surgical procedures are performed annually in the United States as a consequence of trauma or a lifetime of wear and tear. See Praemer, A.; Furner, S.; Rice, D. P. Musculoskeletal Conditions in the United States, American Academy of Orthopaedic Surgeons: Rosemont, Ill., 1999. Despite the large number of patients suffering from cartilage degeneration, the only widely-available treatment options for cartilage degeneration are chronic administration of anti-inflammatory agents, total joint replacement, osteotomy, or allograft transplantation, each of which leads to mixed long-term results. The compositions and methods of the present invention should be useful in the treatment of such disorders and injuries.

Tissue Plane Applications

The materials of the invention can be applied to two planes of tissue and then these two tissues can be sealed together. Over time the sealant/hydrogel degrades as new tissue grows into the area. Applications include a number of cosmetic and tissue restoration surgeries. The sealant is used when the procedures involve significant tissue plane separation that may result in formation of seroma with associated complications, such as infection, e.g., general surgery procedures, such as mastectomies and lumpectomies, and plastic surgery procedures, such as abdominoplastys, rhytidectomy or rhinoplastys, mammaplasty and reconstruction, forehead lifts and buttocks lifts, as well as skin grafts, biopsy closure, cleft-palate reconstruction, hernia repair, lymph node resection, groin repair, Caesarean section, laparoscopic trocar repair, vaginal tear repair, and hand surgery.

Vascular and Cardiovascular Repair

The compositions and methods of the invention may be used for repairing, closing, and/or securing vascular and cardiovascular tissue. Representative procedures include coronary artery bypass grafts, coronary angioplasty, diagnostic cardia catheterization, carotid endarterectomy, and valve repair. An additional use of the sealant is for the repair of cardiac tissue after a myocardial infarction. The polymer would be applied to the infarcted tissue to provide structural support to the weakened tissue. For example, the material would act as a sleeve for the cardiac tissue.

Repair of Dura Tissue

Dura tissue is a fibrous membrane covering the brain and the spinal cord and lining the inner surface of the skull. Standard methods of dural repair involve the application of interrupted sutures and the use of dural replacement materials (duraplasty). This is a meticulous surgery and suffers from the limitation that pinholes produced by surgical needles can cause leakage. Moreover, intraoperative dehydration can shrink the dura creating a difficult closure since it is difficult to approximate the edges with sutures. In older patients, the dura is often more susceptiable to tearing when stretched and/or sutured because the dura can be thin and fragile. Adhesives such as fibrin have been explored for repair of dura tissue, but have had limited success. See "Glue in the Repair of Dural Defects in Craniofacial Resections," J. Latyngology and Otology 106: 356-57 (1992); Kjaergard et al., "Autologous Fibrin Glue Preparation and Clinical Use in Thoracic Surgery," Eur. J. Cardio-Thorc. Surg. 6: 52-54 (1992); Thompson et al., "Fibrin Glue: A Review of Its Preparation, Efficacy, and Adverse Effects as a Topical Hemostat," Drug Intelligence and Clinical Pharmacy 22: 946-52 (1988); and Brennan, "Fibrin Glue," Blood Reviews 5: 240-44 (1991). The sealants and methods of the present invention should be useful in repairing the dura after a craniotomy or laminectomy and prevent postoperative leakage of cerebrospinal fluid. See Preul et al. Neurosurgery 53:1189-1199 (2003) and Balance, C. A. in Some Points in the Surgery of the Brain and Its Membranes. London, Macmillan & Co.

Injection Site Wound

Many therapeutic agents are administered to a patient by injection. However, one complication of this procedure is that the tissue at the injection site can become infected or susceptible to poor healing. One clinical situation where infections are prone to occur is when a therapeutic agent is injected into the eye of a patient. This mode of administration is used in the treatment of age-related macular degeneration (AMD) and results in about 2% of patients suffering from infection or endophthalmitis.

Age-related macular degeneration is a disease that blurs the sharp, central vision needed for "straight-ahead" activities such as reading and driving. Specifically, AMD is a progressive disease of the retina where the light-sensing cells in the central area of vision (the macula) stop working and eventually die. The disease is caused by a combination of genetic and environmental factors, and it is most common in people who are age sixty and over. In fact, AMD is the leading cause of visual impairment in the elderly population. It is estimated that fifteen million people in the United States have AMD, with approximately two million new cases diagnosed annually. There are two types of AMD-wet and dry. Wet AMD occurs when abnormal blood vessels behind the retina start to grow under the macula. These new blood vessels tend to be very fragile and often leak blood and fluid. The blood and fluid raise the macula from its normal place at the back of the eye. Damage to the macula occurs rapidly and loss of central vision can occur quickly. On the other hand, dry AMD occurs when the light-sensitive cells in the macula slowly break down, gradually blurring central vision in the affected eye. Central vision is gradually lost. In this disease, Vascular Endothelial Growth Factor (VEGF) is a key growth factor, which promotes the new growth blood vessels. Currently, it is believed that that when the retinal pigment epithelial (RPE) cells begin to wither from lack of nutrition (i.e., ischemia), VEGF is up-regulated and new vessels are created. Yet, the vessels do not form properly and leaking results. This leakage causes scarring in the macula and eventual loss of central vision. To prevent or inhibit this neovascularization process, antiangiogenic drugs are given the patient. In most cases, the drugs are injected into the vitreous of the eyeball, then pass into the subretinal space where the vessels proliferate. These drugs include mucagenm squalamine lactate, combretastatin 4 prodrug, and avastin.

The sealants and methods of the present invention should be useful in sealing injection site wounds. Among the various possibilities, the injection can be given and then the sealant applied to the injection site, or alternatively the sealant can be applied and then the injection can be done through the sealant.

Therapeutic Use of Crosslinked Polyalkyleneimines

To date poly alkyleneimines (PAIs) have been used primarily as gene transfection agents with limited success. In general, large PAIs (25,000 molecular weight and higher) are more efficient at forming complexes and condensing with polynucleic acids, but their associated toxicity has also been reported to increase with increasing molecular weight. As a strategy to reduce this toxicity, polyalkylene glycols (PAGs), such as monomethoxy-polyethylene glycols, have been grafted to the PAIs in vitro before condensation with polynucleic acids. In a few cases, PAIs have been combined with difunctionally activated PEG in dilute solution to produce linear block copolymers of PAI and PAG, or in an emulsion polymerization process to produce small PAI/PAG microspheres. In both of these cases, the PAI/PAG block copolymers were synthesized in vitro for the purpose of condensing with polynucleic acids for gene transfection.

SUMMARY OF THE INVENTION

One aspect of the present invention generally relates to methods of sealing a wound or tissue plane or filling a void splace. In a preferred embodiment, the wound is an ophthalmic, pleural or dural wound. In certain instances, the compositions used to seal the wound or tissue plane comprises a polyalkyleneimine. In a preferred embodiment, the polyalkyleneimine is polyethyleneimine. Treatment of the polyethyleneimine with a cross-linking reagent causes the polyethyleneimine polymers to polymerize forming a seal. In certain instances, the cross-linking reagent is a polyethylene glycol having reactive terminal groups. In certain instances, the reactive terminal groups are activated esters, such as N-hydroxy succinimide ester. In certain instances, the reactive terminal groups are isocyanates. In certain instances, the polyethyleneimine has a lysine, cysteine, isocysteine or other nucleophilic group attached to the periphery of the polymer. In certain instances, the polyethyleneimine is mixed with a second polymer, such as a polyethylene glycol containing nucleophilic groups. In certain instances, the compositions used to seal the wound or tissue plane are formed by reacting a polyalkyleneimine bearing electrophilic groups with a cross-linking reagent containing nucleophilic groups. In certain instances, the electrophilic groups on the polyalkyleneimine are activated esters, such as N-hydroxy succinimide ester. In certain instances, the compositions used to seal the wound or tissue plane are formed by reacting a polyalkyleneimine bearing photopolymerizable groups with ultraviolet or visibile light. Compositions used to seal the wound which contain PEI or a derivative of PEI are found to adhere tightly to the tissue. Other aspects of the present invention relate to methods of filling a void of a patient or adhering tissue. In certain instances, the methods use a polyalkyleneimine. In a preferred embodiment, the polyalkyleneimine is polyethyleneimine. Another aspect of the present invention relates to a polymeric composition formed by exposing a polyalkyleneimine to an activated polyalkylene glycol. In certain instances, the composition is attached to mammalian tissue.

BRIEF DESCRIPTION OF FIGURES

FIG. 1a and FIG. 1b both depict poly alkyleneimines that may be reacted with electrophile-bearing polyalkylene glycols to form a hydrogel.

FIG. 4 depicts polyethylene glycols that may be reacted with nucleophile-bearing poly alkyleneimines to form a hydrogel, wherein variable w is an integer in the range of about 5 to about 200.

FIG. 5 depicts poly alkyleneimines that may be reacted with nucleophile-bearing polyalkylene glycols, e.g., PEG-$(NH_2)_2$, to form a hydrogel; wherein variables x, y, and z each represent an integer in the range of about 2 to about 200.

FIG. 7 depicts polyethylene glycols that may be reacted with electrophile-bearing poly alkyleneimines to form a hydrogel, wherein variable w is an integer in the range of about 5 to about 200.

FIG. 8 depicts poly alkyleneimines containing acrylate groups for use in photopolymerization procedures.

FIG. 9 depicts poly alkyleneimines containing methacrylate groups for use in photopolymerization procedures.

FIG. 12 depicts the results of experiments evaluating the ability of polyethyleneimine gels to adhere to eye tissue. In this figure, the term "PEG" refers to a polyethylene glycol polymer, "dendron" refers to Lys3Cys4, "TMXDI-1000" refers to O=C=N—C$(CH_3)_2$-(meta-phenyl)-C$(CH_3)_2$N(H)CO$_2$-(polyethylene glycol)-OC(O)N(H)C$(CH_3)_2$-(meta-phenyl)-C$(CH_3)_2$C=N=O, wherein the polyethylene glycol has a molecular weight of about 1000 g/mol, "TMXDI-1500" refers to O=C=N—C$(CH_3)_2$-(meta-phenyl)-C$(CH_3)_2$N(H)CO$_2$-(polyethylene glycol)-OC(O)N(H)C$(CH_3)_2$-(meta-phenyl)-C$(CH_3)_2$C=N=O wherein the polyethylene glycol has a molecular weight of about 1500 g/mol, "PEI-2000" refers to a polyethyleneimine having a molecular weight of about 2000 g/mol, and "PEI-1300" refers to a polyethyleneimine having a molecular weight of about 1300 g/mol.

FIG. 15 depicts three-dimension cross-linked polymer networks in which the polymerization occurs in an aqueous media. Scheme 1 indicates a polymer which swells, while Scheme 2 indicated a polymer which deswells or swells less than the polymer in scheme 1.

FIG. 32 depicts the percent change in set time and swelling of formulations containing (top) a single PEI solution with various inhibitors following 16-18 kGy of e-beam irradiation and (bottom) PEO separated from salts and buffers during 16-18 kGy of e-beam irradiation.

FIG. 37 depicts polyalkyleneimine [A] G1 DAB-PPI, a first generation PPI dendrimer with DAB (diaminobutane) as core; and [B] G2 DAB-PPI, a second generation PPI dendrimer with DAB (diaminobutane) as core).

FIG. 38 depicts table lists various PAI and activated PAG combinations (or derivatized PAG combinations) that can be used to make various hydrogels. In the table the following abbreviations are used: Polypropylene Glycol (PPG); Polyethylene Glycol (PEG); Amino Succinimidyl Glutarate (ASG); Succinimidy Propionic Acid (SPA); Succinimidy Glutarate (SG); Succinimidyl α-Methyl Butanoic Acid (SMB); Succinimidy 3-Methyl Glutarate (S3MG); Succinimidy 3,3-Dimethyl Glutarate (S3,3DMG); polyethyleneimine (PEI); First Generation polypropyleneimine dendrimer with diaminobutane core [G1-PPI(DAB)].

DETAILED DESCRIPTION OF THE INVENTION

Figure 1B:
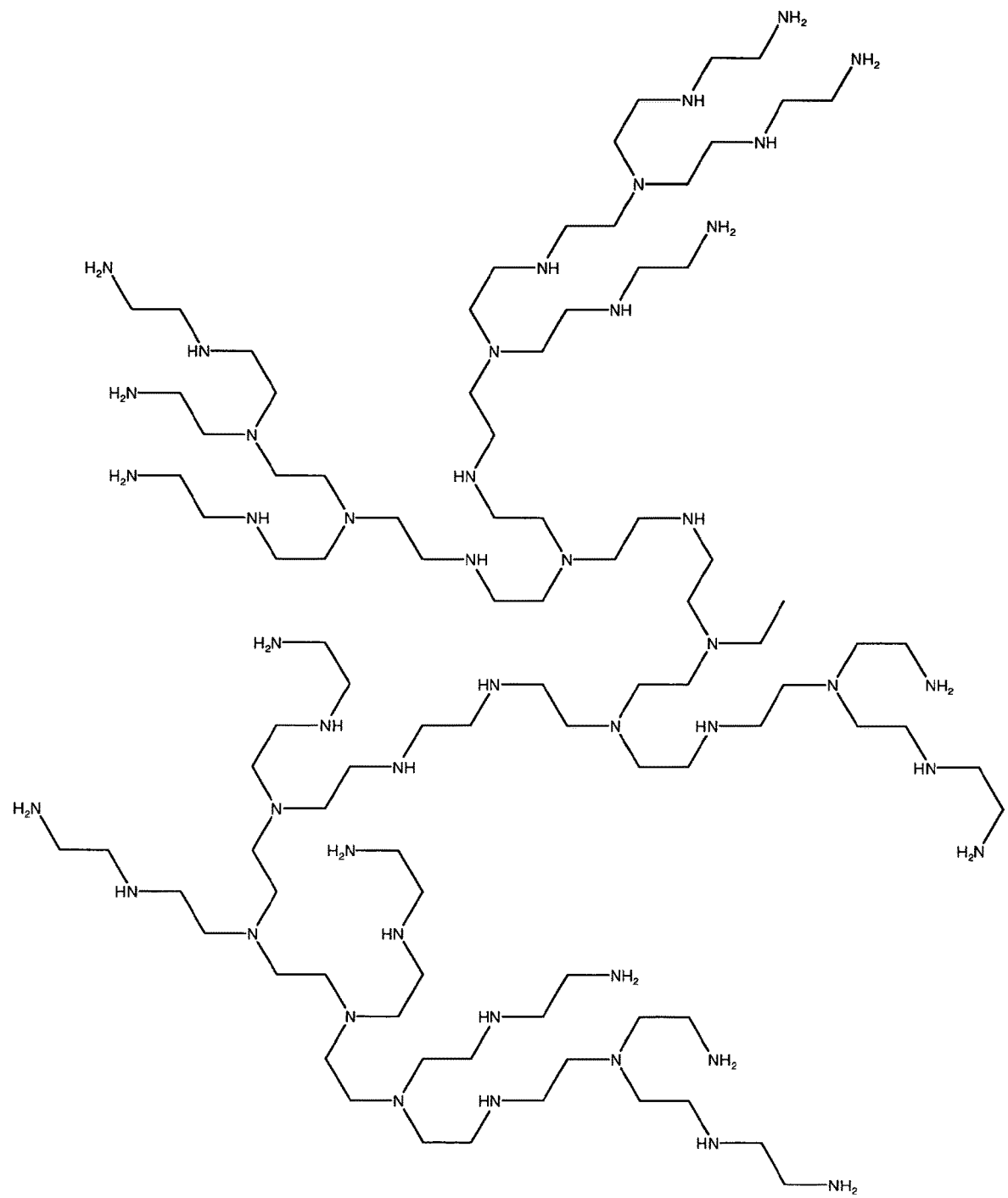
Figure 2:
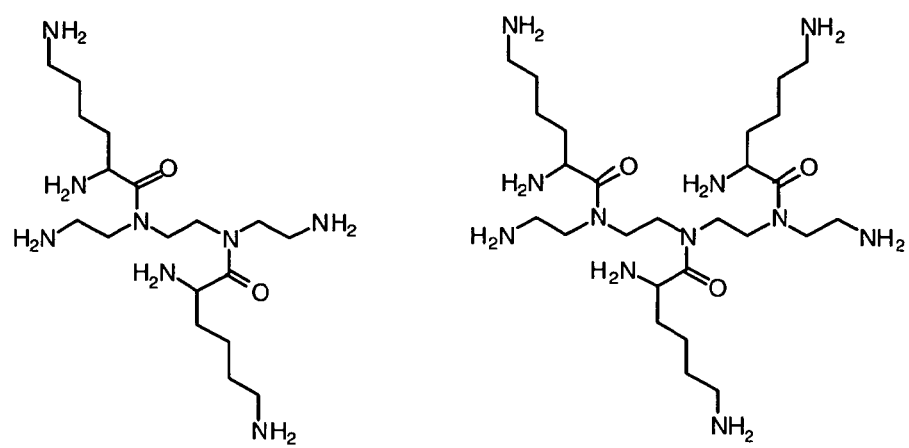
FIG. 2 depicts poly alkyleneimines that may be reacted with electrophile-bearing polyalkylene glycols to form a hydrogel.
Figure 3:
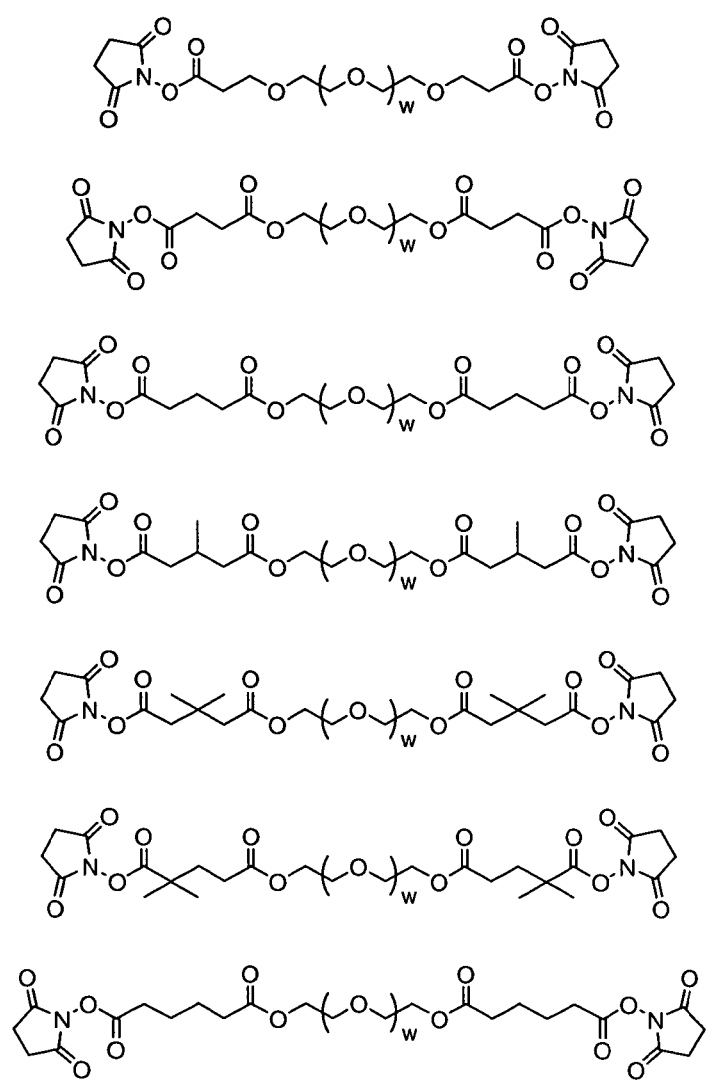
FIG. 3 depicts polyethylene glycols that may be reacted with nucleophile-bearing poly alkyleneimines to form a hydrogel, wherein variable w is an integer in the range of about 5 to about 200.
Figure 6:
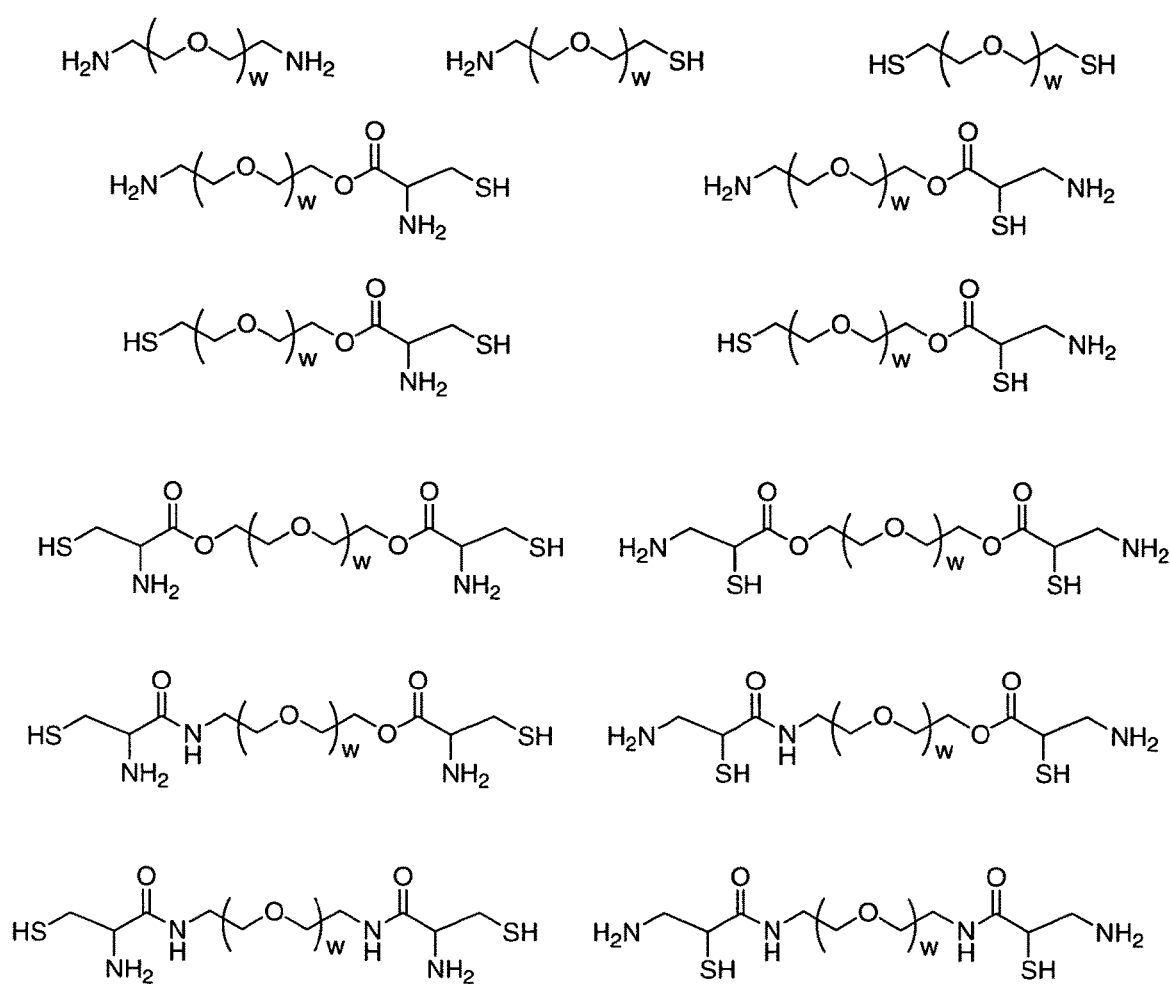
FIG. 6 depicts polyethylene glycols that may be reacted with electrophile-bearing poly alkyleneimines to form a hydrogel, wherein variable w is an integer in the range of about 5 to about 200.

The present invention generally relates to methods and compositions for sealing a wound, bonding a tissue, or filling a void. One aspect of the present invention features a method for sealing a wound using a polyalkyleneimine gel. The gel is prepared by reacting a polyalkyleneimine (PAI) with a cross-linking agent, such as an activated polyethylene glycol. The gels of the invention are amendable to a variety of clinical treatments, such as sealing or repairing ophthalmic wounds or incisions created during an ophthalmic surgery wounds/incisions created during general surgery, wounds/incisions in the dura, lung, vascular, or liver tissue, or for the repair of cartilage tissue. The gels of the invention are particularly useful for surgical procedures where the site of the wound is not easily accessible and/or when sutureless surgery is desirable. The polyalkyleneimine gels of the invention also offer the advantage that the secondary and tertiary amino groups of the gel can be converted to secondary and tertiary ammonium cations which may encourage cell attachment and cell ingrowth. In certain instances, the secondary and tertiary amines of the polyethyleneimine (PEI) can be converted to ammonium cations by placing the PEI in an aqueous solution.

General Depiction of PEI Chemistry

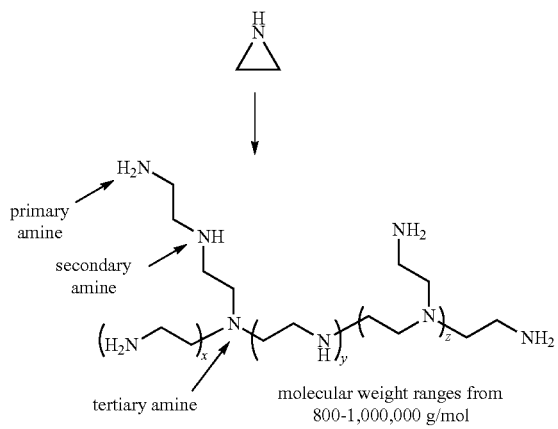

The polyalkyleneimine (PA) gels of the invention have superior adhesion properties. For example, reaction of polyethyleneimine (PEI) with an activated polyethylene glycol (PEG) provided a hydrogel that adhered to ocular tissue longer than a gel formed from a Lys3Cys4 dendron with the same activated polyethylene glycol (PEG). Although not to be bound by a particular theory, it is possible that the superior tissue-adhesion properties are due to two factors. First, the cationic properties of PEI promote interaction with, and possibly penetration within, an anionic tissue substrate, such as the stroma of the eye. See Rep. Prog. Phys. 61 (1998) 1325-1365. Cationic interactions could occur through the secondary and tertiary ammonium cations of the PEI backbone or through primary amino groups that did not react with the cross-linking reagent. Second, PEI contains a large number of functional groups per molecule, thus promoting an increased number of crosslinkable sites within the polymer network. The increased number of crosslinkable sites within the polymer network affords dense, interpenetrating networks between the hydrogel and the tissue surface. The number of free amino groups in the hydrogel can be controlled by varying the ratio of PEI to activated PEG. The ability to control the number of free amino groups is significant because greater cell ingrowth was observed in tissue ingrowth experiments using hydrogels that contained a larger percentage of PEI.

In addition to increased adhesion, we have found that as the molecular weight of the PEI increases from about 1,300 to about 2,000 g/mol the swelling of the resulting hydrogel decreases in certain instances. See FIG. 12. Thus, the molecular weight of the PEI may be adjusted in order to tune the swelling-effects of the resultant hydrogel.

A large variety of PAI derivatives are amenable to the present invention. For example, the amino groups of the PAI may be functionalized with a fatty acid, lower alkyl, an alkenyl, or alkynyl group. In addition, the amino groups or a portion of the amino groups may be functionalized to covalently or non-covalently carry or contain active agents, pharmaceutical agents, preservatives, radio isotopic ions, magnetically detectable ions, antibodies, medical contrast agents, colorants, dyes, or other visualization agents. In certain instances, about 1% to about 70% of the primary amines of the PEI are functionalized. The PAI derivatives may contain hydrolytically and/or enzymatically degradable linkages capable of releasing the functional derivatives, active agents, pharmaceutical agents, preservatives, radio isotopic ions, magnetically detectable ions, antibodies, colorants, dyes, or other visualization agents. Alternatively, a different nucleophile can be added to the PEI, such as a cysteine, isocysteine, thiol, or other such nucleophilic group. For example, a PEI can be modified such that all the primary amines are modified with a cysteine thus affording a PEI derivative which can form crosslinked gel/networks using the amine, thiol, or both the amine and thio. In certain instances, an ureido, urea, acetoacetoxy, RGD peptide, EDTA, or carbohydrate group may be bonded to one or more of the amino groups of the PEI. Representative carbohydrates include erythrose, threose, ribose, arabinose, xylose, lyxose, allose, altrose, glucose, mannose, gulose, idose, galactose, talose, sucrose, lactose, and the like. It is possible that the ureido group and urea group will impart adhesion partially via a cation/anion interaction. The acetoacetoxy group may adhere to tissue by making a metal complex on the surface of the tissue.

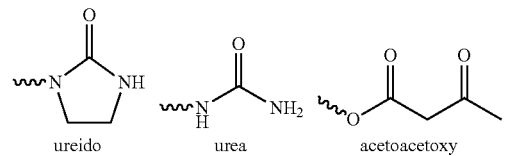

In certain instances, the PEI is functionalized so that both primary amino (—NH$_2$) groups and thiol (—SH) groups could react with electrophilic groups or a combination of them, such as an acrylate, succinimidyl ester, maleimide, ester, or aldehyde. The electrophilic groups can be attached to poly(alkyleneoxide) (e.g., PEG, PPG or PEG-PPG) polymers. Two or more electrophilic groups are required. Of course, the degree of PEI functionalization may be varied in order to obtain the desired physical properties of the resultant gel. In certain instances, only about 1% of the primary amino groups of the PEI are functionalized. In other instances, about 5% to about 25% of the primary amino groups of the PEI are functionalized. In other instances, about 25% to about 50% of the primary amino groups of the PEI are functionalized. In other instances, about 99% of the primary amino groups of the PEI are functionalized. In certain instances, one or more of the amino groups are reacted with an epoxide or acylating agent. In certain instances, one or more of the amino groups are reacted with an isocyanate, as shown below (see Partial Neutralization of Free Amines in Polyamines below).

Partial Neutralization of Free Amines in Polyamines
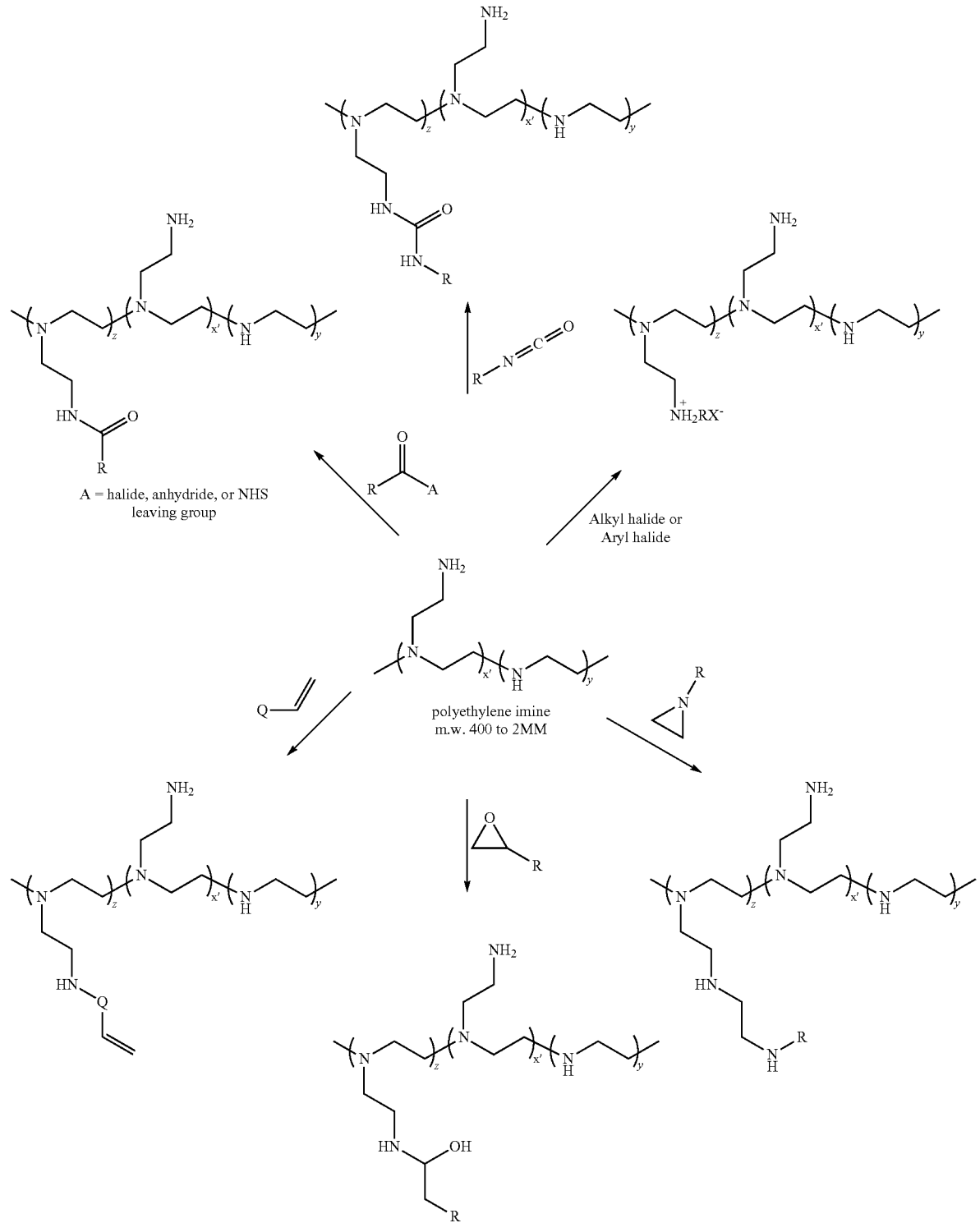
R = Alkyl, aryl or alkylaryl containing standard organic functional groups
Q = indicates connecting an olefin to the PEI with any of the illustrated reactions
X' = X-Z The molecular weight of the PEI may be adjusted to tune the physical properties of the gel formed by addition of the cross-linking agent. In certain instances, the PEI has a weight average molecular weight of about 400 g/mol to about 2,000,000 g/mol. In certain instances, the PEI has a weight average molecular weight of about 400 g/mol to about 1,000,000 g/mol. In certain instances, the PEI has a weight average molecular weight of about 400 g/mol to about 500,000 g/mol. In certain instances, the PEI has a weight average molecular weight of about 400 g/mol to about 100,000 g/mol. In certain instances, the PEI has a weight average molecular weight of about 400 g/mol to about 50,000 g/mol. In certain instances, the PEI has a weight average molecular weight of about 400 g/mol to about 10,000 g/mol. In certain instances, the PEI has a weight average molecular weight of about 400 g/mol to about 5,000 g/mol. In certain instances, the PEI has a weight average molecular weight of about 400 g/mol to about 2,000 g/mol.

In certain instances, the polyalkyleneimine has a weight average molecular weight of about 600 to about 10,000 Daltons, the polyalkylene glycol has a weight average molecular weight of about 500 to about 20,000 Daltons, and the molar ratio of the polyalkyleneimine to the polyalkylene glycol is within a molar range of about 0.025:1 to about 0.4:1. In certain instances, the hydrogel reaches equilibrium swelling in about 5 to about 30 hours. In certain instances, the hydrogel reaches equilibrium swelling in about 18 hours.

The polyalkyleneimine hydrogels of the invention are a significant advance over prior sealant systems because the poly alkyleneimines can incorporate primary, secondary and tertiary ammonium cations, which may encourage cell growth. Literature reports indicate that positive charge encourages soft tissue growth, while negative charge encourages hard tissue growth. See U.S. Pat. Nos. 4,988,358 and 5,092,883; both of which are hereby incorporated by reference. Notably, cell attachment is generally necessary to allow a cascade of events, such as cell spreading, the exhibition of normal morphological features, and tissue integration or tissue regeneration. It has also been suggested that the lack of cell attachment may induce many biological adverse reactions against foreign materials. Other PEG sealant systems may, in certain instances, act as a barrier between a first and second tissue, whereas the polyalkyleneimine polymers of the present invention, which may contain charged species, allows the hydrogel to contact two tissue surfaces, mechanically hold them together, and provide a suitable scaffold for cells to ingrow and eventually replace the hydrogel sealant. Alternatively, polyalkyleneimine polymers of the present invention may be used to coat one tissue surfaces, provide suitable conditions for the tissue to heal, and degrade on a similar time frame as healing. Another advantage of the present invention is that the primary, secondary and tertiary ammonium cations of the polyalkyleneimine hydrogels encourage deposition of other proteins to the hydrogel, thereby further facilitating cell attachment and ingrowth. Representative proteins that may be deposited include albumin, fibronectin, collagen, and the like.

Since prior sealant systems prepared by radical polymerization or nucleophile/electrophile addition chemistry of a first polyethylene glycol with a second polyethylene glycol or small organic compound commonly exhibit low protein adsorption and low cell attachment, 2-methacryloxy ethyltrimethyl ammonium chloride (a substituent with a quaternary amine) has been added to various sealant systems to encourage cell growth. For example, 2-methacryloxy ethyltrimethyl ammonium chloride has been added to PEG based sealants, PHEMA based sealants, and PEG-PPG based sealants to affect cell interaction and proliferation on the polymer substrate. See J. Cell. Physiol. 198 (2004) 133-143; Biomaterials 25 (2004) 3023-3028; BMC Biotechnology 4 (2004) 23; and J. Biomed. Mater. Res. 75A (2005) 295-307. Other approaches to preparing sealant systems containing charged species include adding an excess amount of the nucleophilic component in a nucleophile/electrophile cross-linking system, and then converting the nucleophilic moiety to a charged species. Although this approach produces charged species within the polymer, the mechanical and physical properties of the gel will be affected by changes in the ratio of electrophiles to nucleophiles. One alternative to sealant systems containing charged species is collagen-based sealant systems, which have shown medium to low amounts of tissue ingrowth after approximately 30 days. See U.S. Pat. No. 6,165,489; which is hereby incorporated by reference Many prior sealant systems are not optimal because the sealant system may degrade before appreciable healing or tissue ingrowth occurs. For example, tissue ingrowth often begins within one week after application of the sealant, and complete tissue ingrowth may occur within 28 days after application of the sealant in very porous systems. However, many prior sealant systems contain degradable linkages which can cause the hydrogels to degrade before appreciable tissue ingrowth occurs. Accordingly, in certain instances, the polyalkyleneimine hydrogel sealants of the invention maintain mechanical strength for at least about 7 days. In certain instances, the polyalkyleneimine hydrogel sealants of the invention maintain mechanical strength for at least about 20 days. This rate of degradation allows native tissue to ingrow and replace the hydrogel as it degrades.

Since charged species encourage tissue growth, polyalkyleneimines are advantageous because they allow for incorporation of a large number of charged species. The charged species are created by converting unreacted primary amines, and internal secondary and tertiary amines into ammonium cations under physiological conditions. Table 1 below illustrates the number of primary, secondary and tertiary amines contained in various crosslinkers based on a polymer system having eighteen primary amines. As illustrated in Table 1, the trilysine crosslinker contains only primary amines and a pendant carboxylate while a PPI (DAB)-G1 dendrimer adds 9 units of potential cationic charge with the addition of 9 tertiary amines. The $PEI_{800}$ adds 14 units of potentially charged species (i.e., 155% more charge) compared to the PPI(DAB)-G1 dendrimer, while the $PEI_{2000}$ adds 26% more potentially charged species than $PEI_{800}$. Finally, $PEI_{25000}$ adds 24% more potentially charged species than $PEI_{2000}$, owing to the increased number of secondary and tertiary amines. Since the number of secondary and tertiary amino groups increases with increasing molecular weight of the polyalkyleneimine, the polyalkyleneimine hydrogels of the invention can be tuned by incorporating crosslinkers with varying molecular weights, and hence charge density, in order to affect the tissue ingrowth and degradation properties of the hydrogel.

TABLE 1

| Crosslinker | 1° amines | 2° amines | 3° amines |
|---|---|---|---|
| $PEI_{25000}$ | 18 | 22 | 14 |
| $PEI_{2000}$ | 18 | 17 | 12 |
| $PEI_{800}$ | 18 | 14 | 9 |

TABLE 1-continued

| Crosslinker | 1° amines | 2° amines | 3° amines |
|---|---|---|---|
| PPI(DAB)-G1 | 18 | 0 | 9 |
| Trilysine | 18 | 0 | 0 |

Polyalkyleneimine hydrogel sealants offer an advantage over prior sealant systems because polyalkyleneimines, especially derivatized polyalkyleneimines, should have anti-microbial and antiviral activity. Recent reports indicate that both polyalkyleneimines and derivatives thereof have anti-microbial properties, while lacking activity against mammalian cells. See Biotechnol. Bioeng. 90 (2005) 715-722; Biotechnol. Bioeng. 83 (2003) 168-172; Biotechnology Letters 25 (2003) 1661-1665; Biotechnol. Prog. 18 (2002) 1082-1086; and Chem. Commun. (1999) 1585-1586; PNAS 103 (2006) 17667-17671. Thus, hydrogels prepared from polyalkyleneimines may help fight, inhibit, prevent or even eliminate the chance for infection when applied to the tissue of a patient. Since the presence of cationic groups, especially quaternary amines, may influence the antimicrobial properties of the hydrogel, the PAI, in certain instances, may be derivatized with one or more quaternary amines. In certain instances, the PAI may be derivatized with four or more quaternary amines. In certain instances, the PAI may be derivatized with ten or more quaternary amines. Since the presence of cationic groups and hydrophobic side chains, when combined, tend to confer better antimicrobial properties, the PAI, in certain instances, may be derivatize with one or more quaternary amines and one or more fatty acid, lower alkyl, alkenyl, or alkynyl groups.

Polyalkyleneimine hydrogel sealants offer the additional advantage that the amino groups of the polyalkyleneimine can act as a buffering agent. The ability to control the pH during preparation of the hydrogel is important because certain pHs are optimal for crosslinking of the components. In particular, the pH of a mixture of crosslinking components can affect the rate at which the crosslinking reaction takes places. In some instances, the desired pH can be achieved by adding a buffering agent, such as phosphates, carbonates, borates, and the like, to the solution containing the crosslinking components. However, when using poly alkyleneimines as a crosslinkable component, the primary, secondary, and tertiary amines act as buffering agents to provide some buffering capacity throughout a wide range of pHs. See Bioorganic Chemistry 22 (1994) 318-327. Moreover, as the crosslinkable component reacts, some of the amines are removed from solution, thereby reducing the pH. Since quick set-times can require higher pHs, it is advantageous to use a crosslinkable component which influences the pH so that the pH will lower to more physiological levels soon after mixing. This buffering feature of polalkyleneimines eliminates the need for a strong buffer to achieve the high pH-levels sometimes used in preparing a hydrogel. Notably, addition of strong buffers may not be desirable because such buffers may remain in the sealant and cause the patient's tissue to become irritated.

Using polyalkyleneimines as buffering agents and as a crosslinkable component provides an additional advantage in that an indicator within the formulation could be used to track the overall cure. In other words, as the formulation is mixed and begins to cure the pH changes and this change in pH may be monitored by a biologically acceptable pH indicator. The change in color could be a shift from one color to another or the appearance of color from an otherwise colorless formulation.

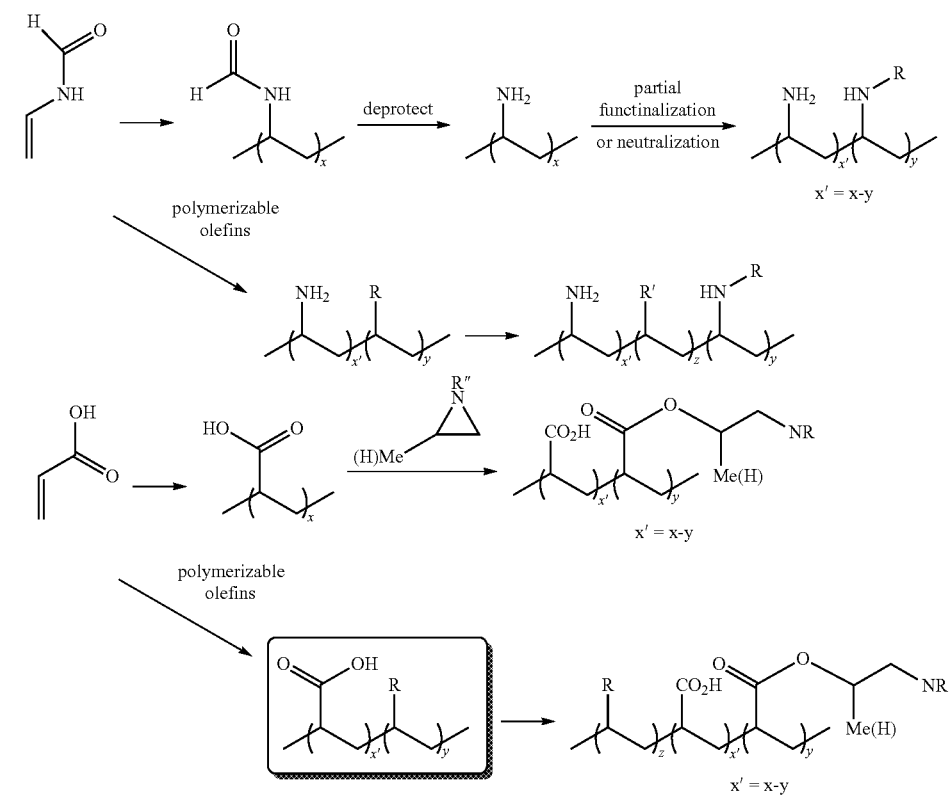

olefins = methyl methacrylate, butyl acrylate, vinyl acetate, ethyl acrylate, etc.

The methods of the invention are also amenable to other types of amine-containing polymers. For example, polymerization of acrylamide, followed by partial or complete conversion of the amide groups to amino groups, would provide a polyamine. Likewise, copolymerization of acrylamide with another monomeric olefin could be used to tune the properties of the resultant polyamine. Similarly, polymerization of acrylic acid, followed by partial or complete conversion of the carboxylic acids to amino groups, or partial or complete reaction of the carboxylic acid with an aziridine would provide a polyamine. As shown above, copolymerization of acrylic acid with an olefin, followed by conversion of the carboxylic acid to an amine-containing moeity would provide a polyamine. In certain instances, a polylysine or polylysine copolymer may be used in the methods of the present invention.

As described herein, the gels of the invention are formed by reacting a polyalkyleneimine with a cross-linking agent. A large number of cross-linking agents are amenable to the invention. In certain instances, the cross-linking agent is an activated polyethylene glycol. The activating group is preferably an electrophilic group. For example, in certain instances, the polyethylene glycol contains a N-hydroxy succinimide group at each end of the polymer. In certain instances, the succinimide is functionalized with a sulfonic acid moiety. In certain instances, the polyethylene glycol contains an aldehyde at each end of the polyethylene glycol. In certain instances the polyethylene glycol is a star, dendritic, or branched polymer with three or more activating groups.

In certain instances, the polyethylene glycol cross-linking agent contains two or more different electrophiles. The different electrophiles may have similar or dissimilar reactivities. The different electrophiles provide linkages having similar or dissimilar degradation rates imparting. The selection of electrophiles allows for control over the crosslinking reactions to form the hydrogels, the adhesive properties, and the degradation rate of the formed hydrogel. For example, a polyethylene glycol can be derivatized such that one end of the polyethylene glycol contains a SPA and another end contains a SG. In this example, both are activated esters, but the degradation rates of the two linkages are different. For example, a hydrogel prepared with only a PEG-SPA is generally stable at 37° C. for more than about four months, whereas a hydrogel prepared with PEG-SG is often stable for less than about one week. Notably, one hydrogel prepared from PEI and a PEG-SPA/SG having a 60:40 ratio of SPA:SG degraded in about a week.

In certain instances, the polyethylene glycol cross-linking agent contains a hydrophobic moiety. In certain instances, alkyl groups are installed between the polyethylene glycol and the terminal electrophilic groups of the cross-linking agent. In certain instances, the alkyl group contains about 4 to about 30 carbon atoms. In certain instances, the alkyl group contains about 5 to about 15 carbon atoms. In certain instances, the hydrophobic moiety is an aryl or aralkyl group. In certain instances, the alkyl moeity of the aralkyl group contains between 5-10 carbon atoms.

In certain instances, the polyethylene glycol cross-linking agent is represented by the generic formula (i) below, wherein w is an integer in the range of about 5 to 10,000, and n is an integer in the range of about 5 to about 30.

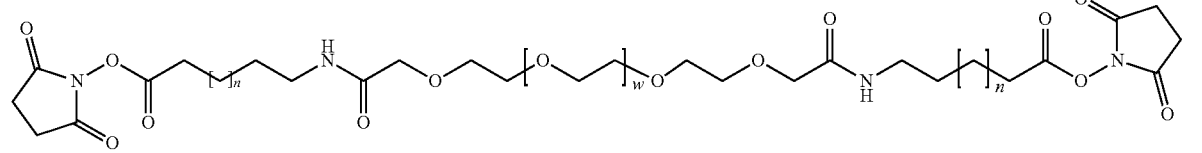

(i)

In certain instances, the polyethylene glycol cross-linking agent is represented by the generic formula (ii) below, wherein w is an integer in the range of about 5 to 10,000, and m is an integer in the range of about 1 to about 50.

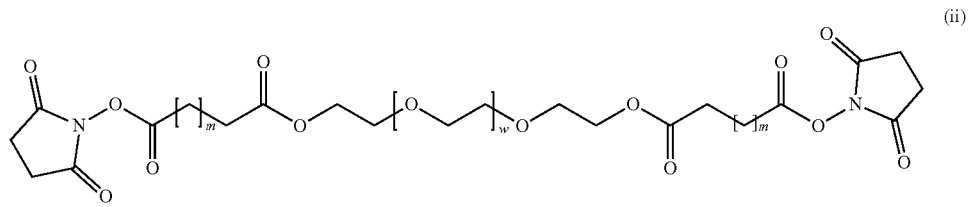

(ii)

In certain instances the hydrophobic moiety may be used as a foaming agent. The linkages between the polyethylene glycol and the hydrophobic moiety can be esters, amides, carbamates, carbonates, urea, urethane, and so forth.

A further embodiment of this invention is the use of a chemical peptide ligation reaction to create a crosslinked gel involving a dendritic polymer. In this reaction an aldehyde, aldehyde-acid or aldehyde-ester reacts with a cysteine-functionalized polymer to form a gel or crosslinked network. In certain instances, the dendritic polymers have nucleophilic groups, such as primary amino groups or thiol groups, which can react with electrophilic groups, such as an acrylate, succinimidyl ester, maleimide, ester aldehyde, or aldehyde on a small molecule. In certain instances, the dendritic polymer has nucleophilic groups capable of reacting with an activated diester of sebabic acid.

In certain instances, the polyethylene glycol contains a Michael acceptor at each end of the polyethylene glycol. In certain instances, the polyethylene glycol contains an isocyanate group at each end of the polyethylene glycol. For example, tetramethylxylene diisocyanate (TMXDI) may be used to render the PEG cross-linking agent more hydrophobic (See below). TMXDI can be utilized to assemble PEG and other diols into a prepolymer with a sterically hindered isocyanate as the terminal end of the prepolymer. One unique feature of TMXDI is that the isocyanate group is water stable for about 2-4 hours at 40° C. The water stability is likely due to the steric bulk attached directly to the isocyanate group. The water stability allows for the dissolution of the material in water, followed by a rapid reaction with amines in a cross-linking molecule such as a dendron, PEI, or polyvinyl amine, to name a few. In the example shown below, the dimethylolpropionic acid (DMPA) increases the water solubility of pre-polymers prepared with lower molecular weight PEGs.

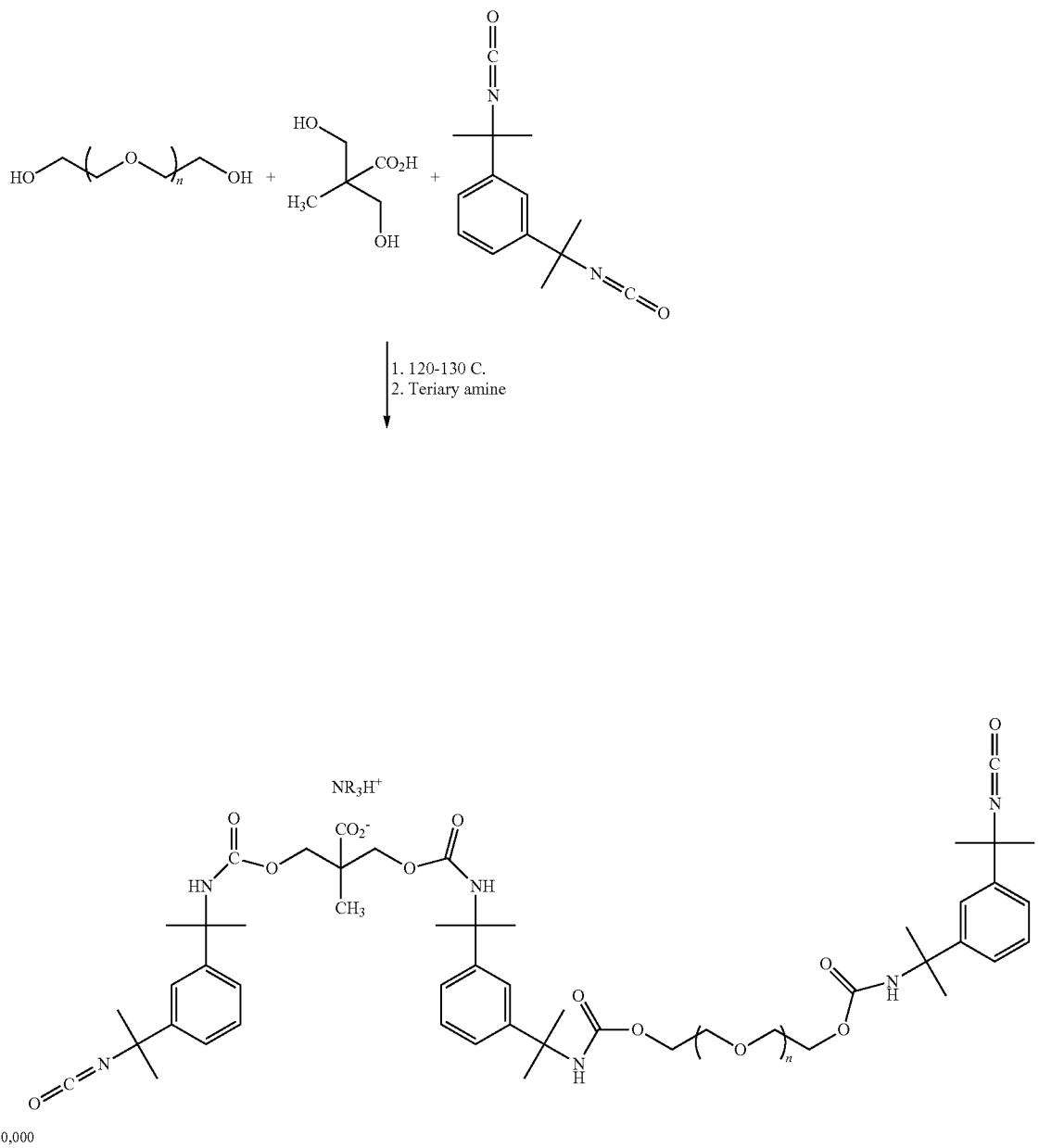

The basic TMXDI chemistry can be extended by substituting the DMPA with other diols. This will allow for the addition of other potential reactive functional groups, such as activated esters, epoxides, etc. As in the previous example, this chemistry is conducted such that the pre-polymers are terminated with isocyantates. Termination with isocyanates is accomplished using excess TMXDI.

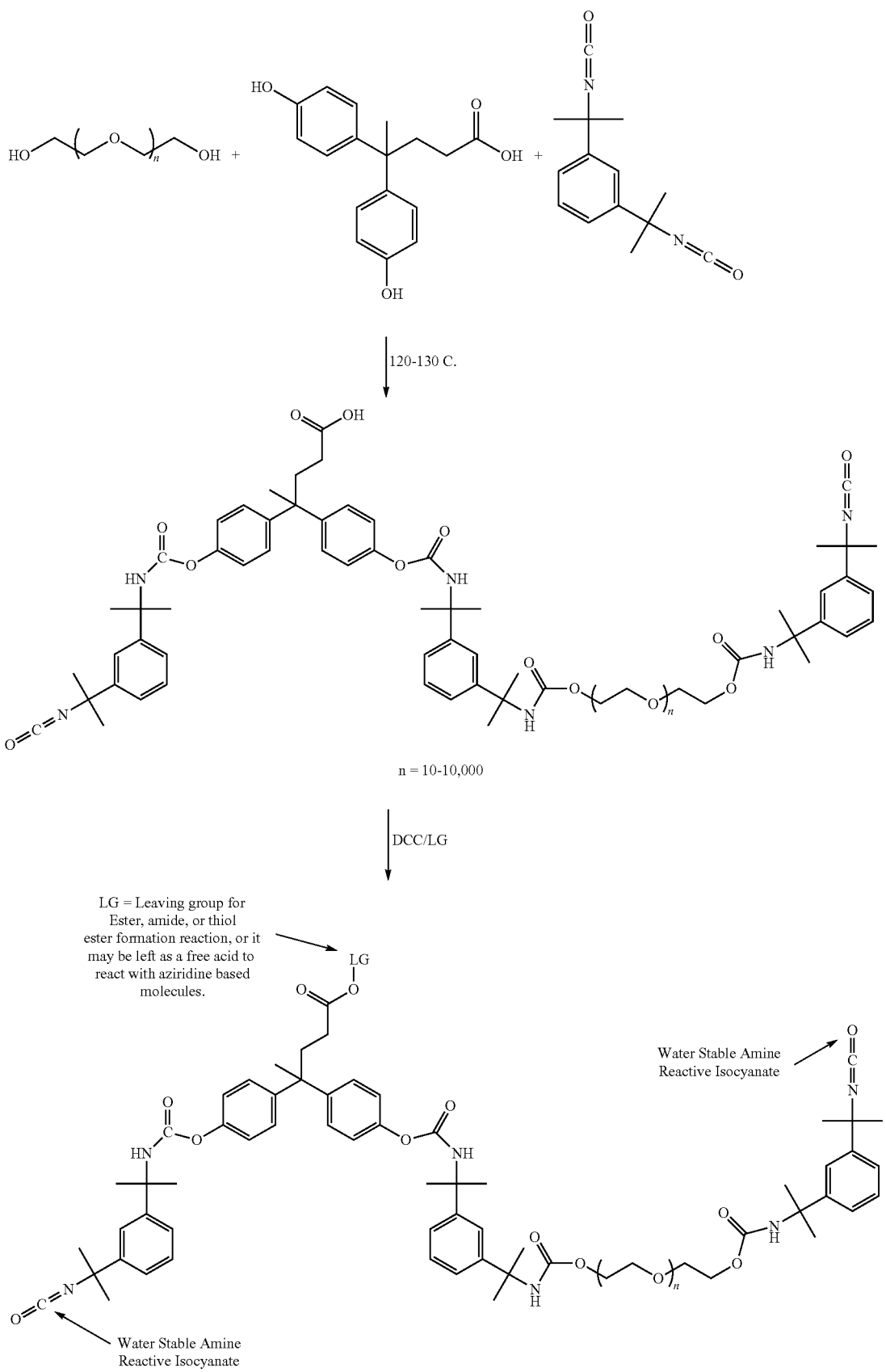

Synthesis of TMXDI pre-polymers with functionalizable diols and PEG will allow for integrating cross-linking while maintaining control over the molecular weight of the pre-polymers. The above bis-phenol derivative is shown merely for illustrative purposes; the diol can be any structure with a pending carboxylic acid. In a further embodiment, conducting the reaction with excess alcohol relative to the N=C=O groups will lead to hydroxyl-terminated pre-polymers.

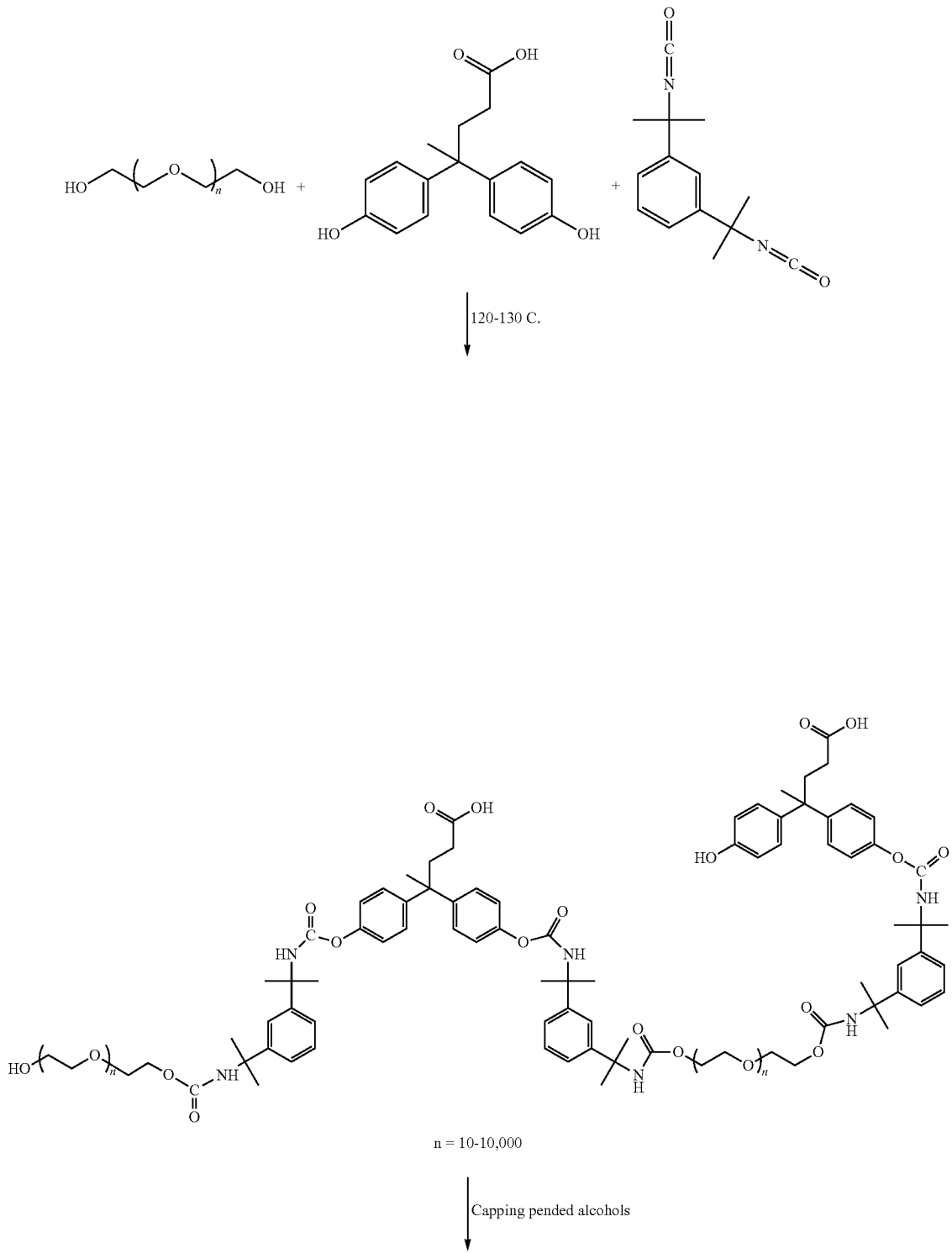

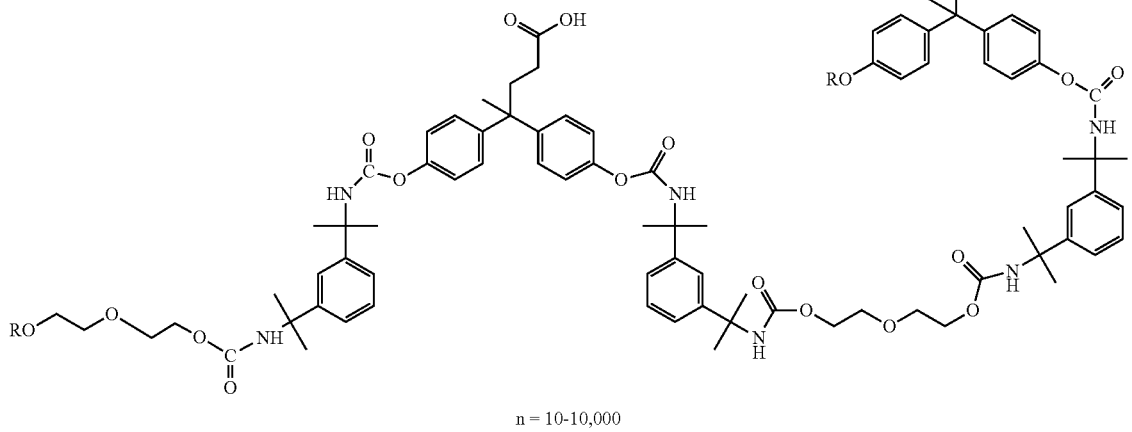

n = 10-10,000

↓ Adding Leaving Group (LG)

LG = Leaving group for ester, amide, or thiol ester formation reaction.

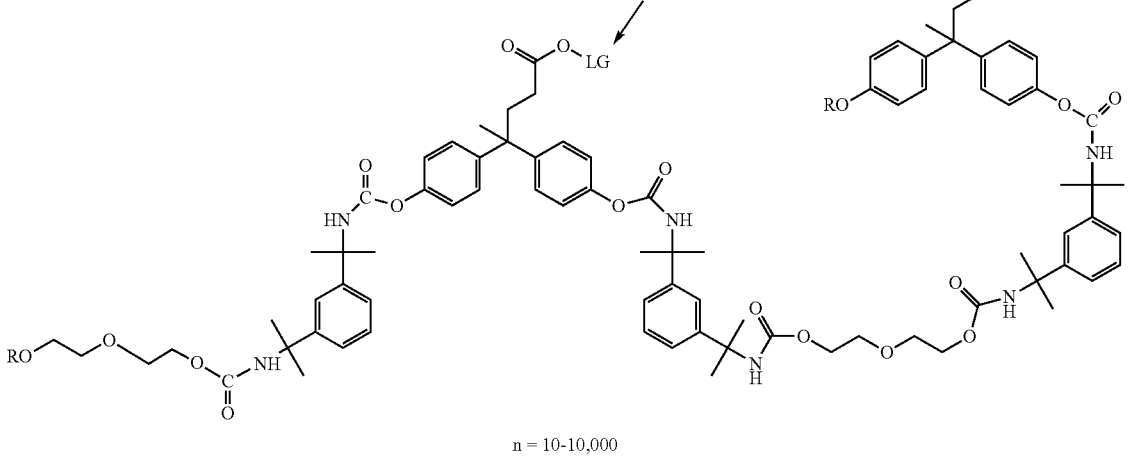

n = 10-10,000

The example above illustrates a typical diol prepolymer prepared using excess diol. In this situation, the goal is to consume the isocyanate groups, thereby leaving hydroxyl groups as the termination group. The functional groups in the backbone of the polymer can then be converted to activated esters. In addition, the terminal alcohols can be further converted to reactive groups.

Other diisocyanates, such as more reactive diisocyanates, can be used to form core materials which are hydroxyl-terminated. Following formation of the core molecule, the material can be reacted with TMXDI to yield a water-stable diisocyanate, as shown below. In certain instances, addition of alternative chain spacers via (1) preparation of an alcohol-terminated prepolymer with water-sensitive diisocyantes, then followed by (2) chain lengthening and termination with TMXDI (water-stable isocyanate) may be used. This process permits preparation of a polymer have a specific hydrophobicity.

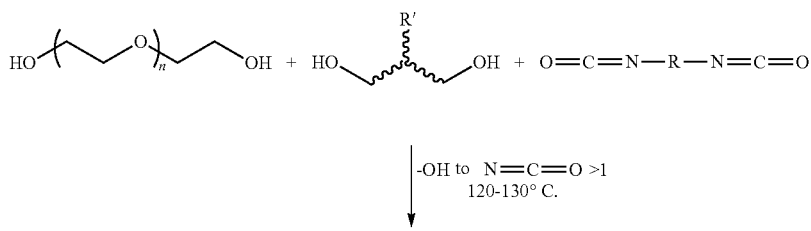

↓ -OH to N=C=O >1
120-130° C.

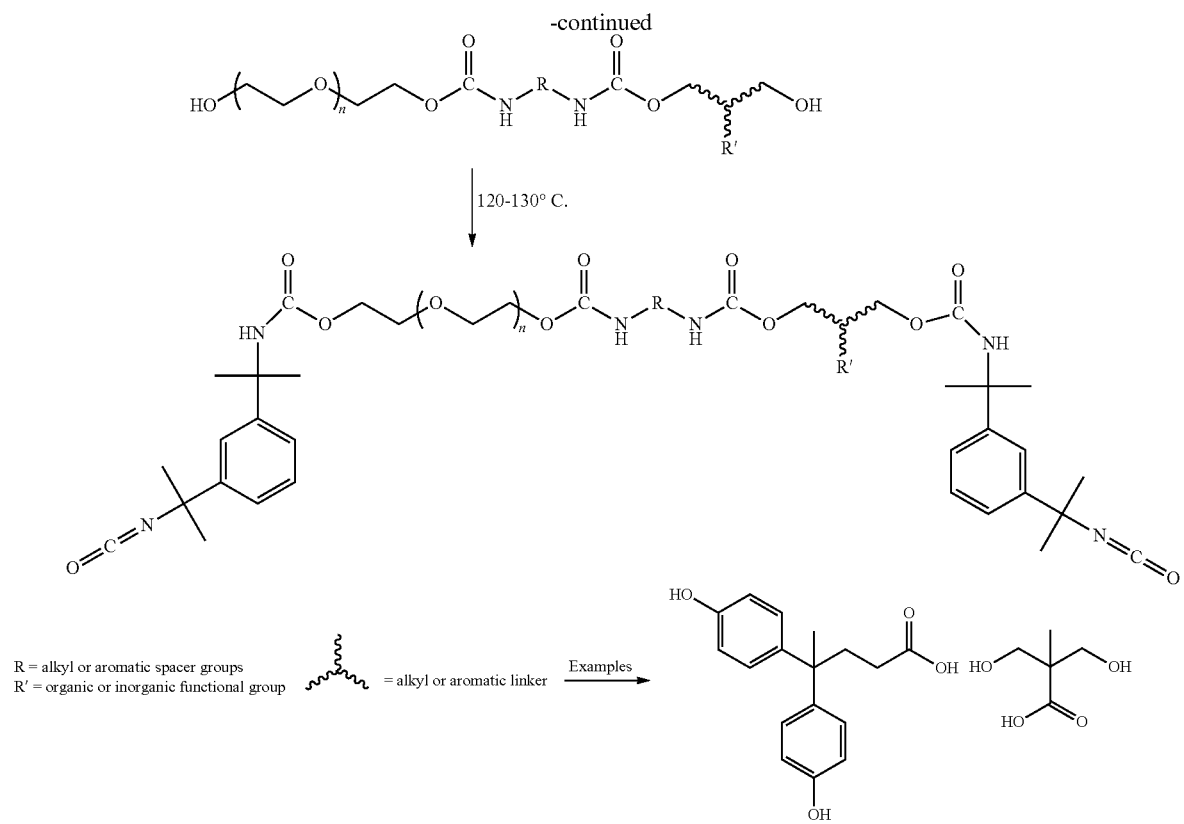

R = alkyl or aromatic spacer groups
R' = organic or inorganic functional group
= alkyl or aromatic linker In certain instances, the hydrophobicity of a polyethylene glycol is modified by reaction of a first diisocyanate in the presence of excess polyethylene glycol. The hydroxyl groups of the resultant polyethylene glycol conjugate may be converted to reactive functional groups.

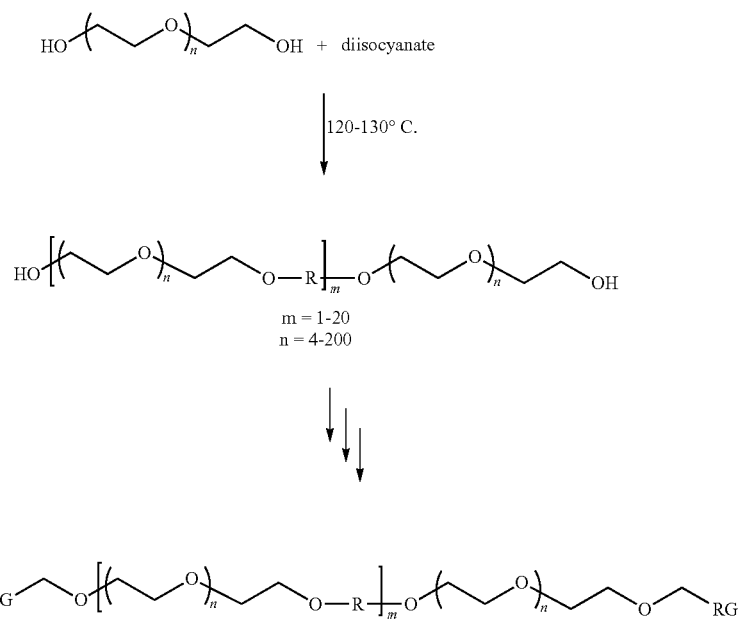

R = alkyl or aromatic group from the diisocyanate
RG = reactive group such as an activated ester or epoxide In certain aspects of the invention, the polarity of the cross-linker is tailored to control the amount of swelling that occurs in the resulting hydrogel. For example, water-reactive diisocyanates may be used to create a reactive cross-linker. This process entails reaction of unhindered diisocyanates with a PEG in the presence of a multifunctional alcohol, amine, or thiol. In certain instances, glycerin, triethanolamine, pentaerythitol, diethylene triamine, or 1, 3, 5-benzene triol can be utilized. The amount of multifunctional amine or alcohol will dictate the average number of reactive end groups per molecule.

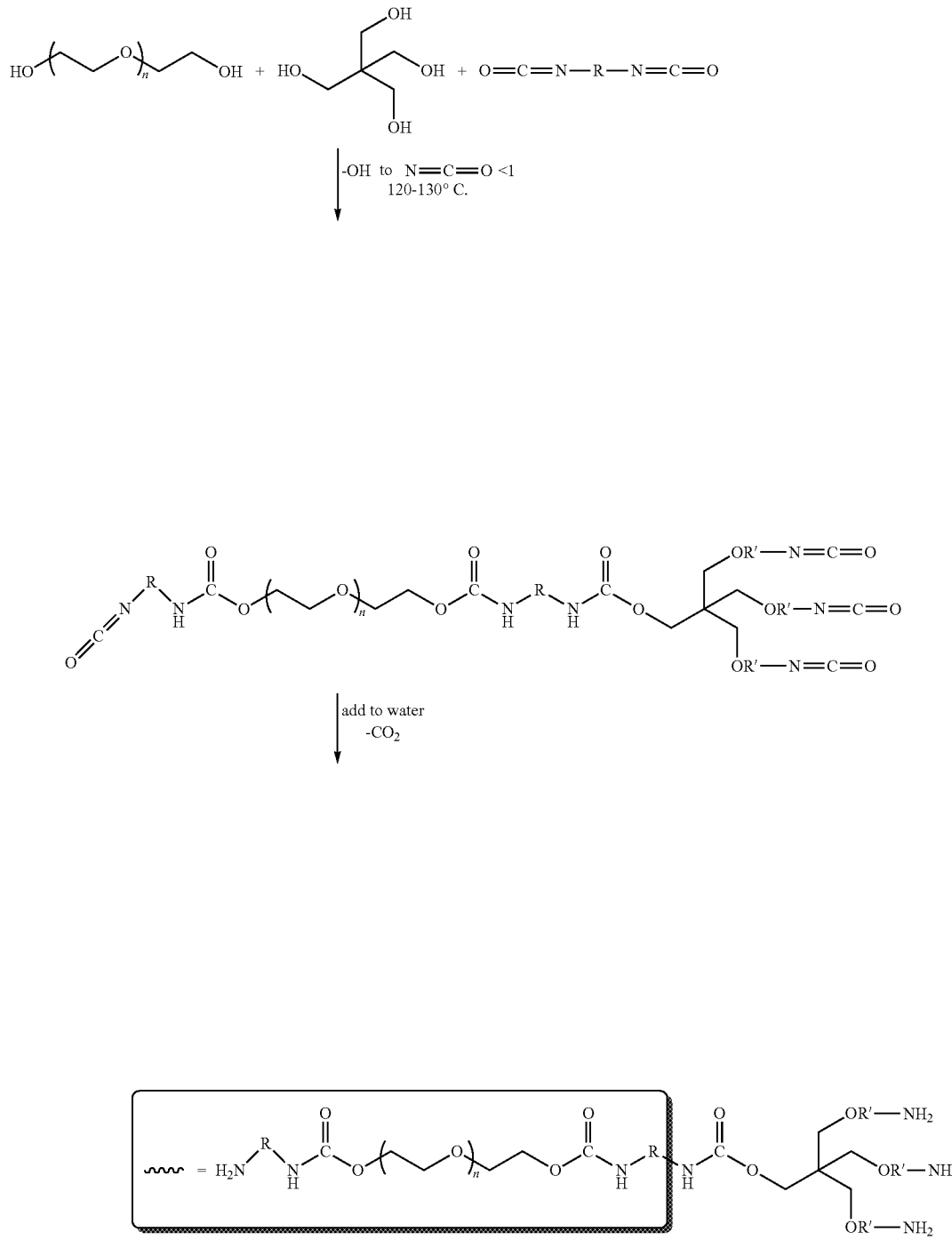

R = alkyl or aromatic spacer groups
R' = a combination of PEG, pentaerythritol, and diisocyanate to yield a multifunctional amine Further, increasing the amount of the highly branched alcohol, relative to the amount of the diisocyanate, will provide a compound having a larger number of amine end-groups.

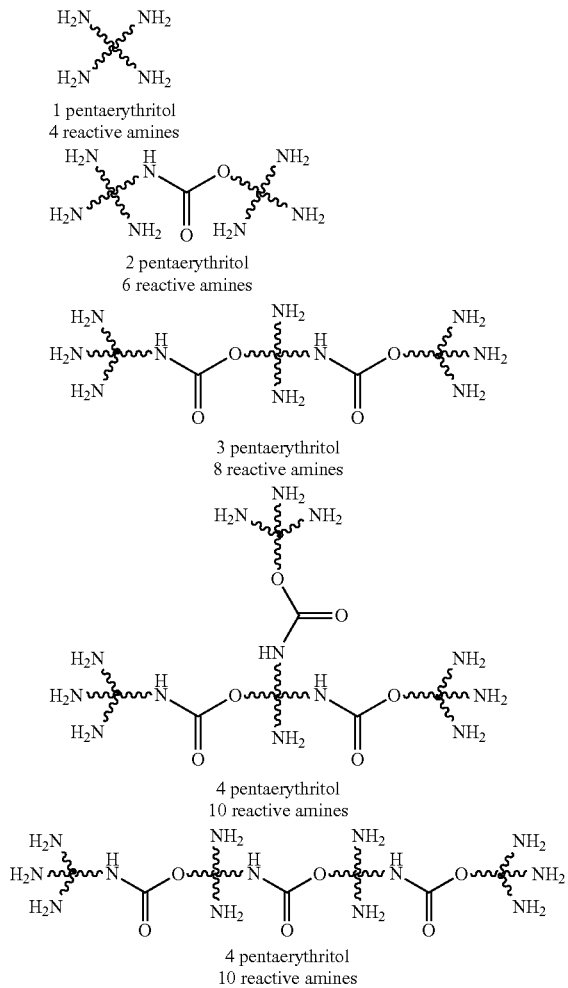

Figure 14:
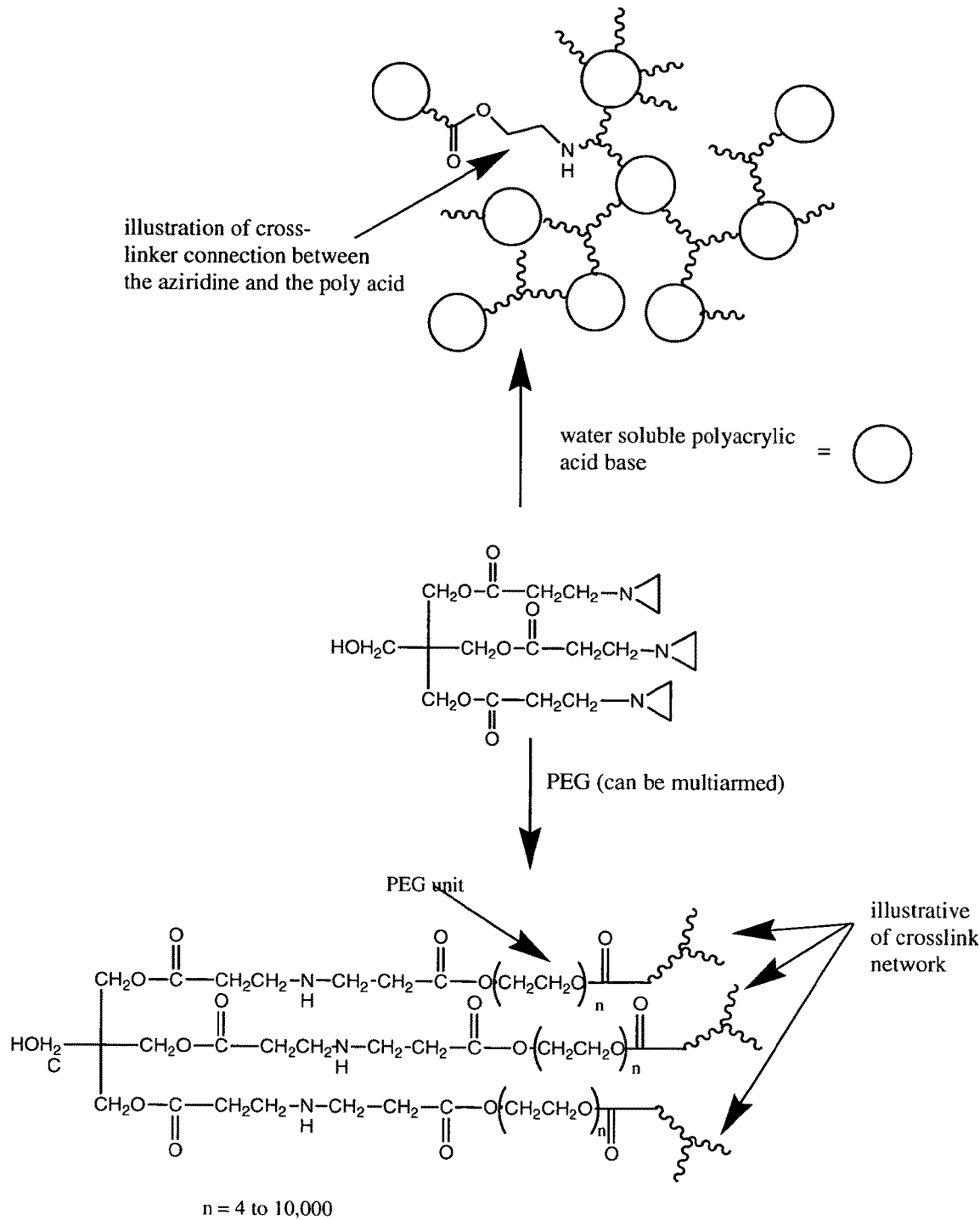
FIG. 14 depicts reaction of a polyaziridino cross-linking agent with a poly(carboxylic acid).

Another aspect of the invention relates to use of polyaziridino cross-linking reagents for cross-linking polymers containing a carboxylic acid group. This methodology takes advantage of the fact that aziridines are relatively water stable reactive functional groups. The aziridine will react rapidly with a free carboxylic acid group giving an amine linkage. Two basic approaches are illustrated in FIG. 14 with pentaerythitol-tris-(N-aziridinyl) propionate: (1) reaction of water soluble polymers with excess free carboxylic acid groups and (2) reaction with a PEG diacid. Noting, however, that the aziridine moiety may also react with free primary amines. Pentaerythitol-tris-(N-aziridinyl) propionate may be utilized for staged polymerization methodology. The amount of acid in the TMXDI prepolymers can be controlled to yield one acid group per molecule, and the aziridine can then be reacted with the prepolymers to yield a molecule with a controlled number of reactive isocyanate groups.

In certain instances, it is further conceivable to replace polyalkylene glycol crosslinkers with other water soluble synthetic biomaterials. For instance, a portion of the carboxylic acids of polyacrylic acid could be converted to N-hydroxy-succinimidyl ester derivatives. The resulting activated polymer would be mixed with a polyalkyleneimine cross-linking agent to form a hydrogel.

The adhesive compositions of the invention are applicable to sealing a large variety of wounds. For example, the sealants of the invention may be used in ophthalmic applications such as repair of corneal lacerations, retinal tears, corneal transplants, cataract procedures, corneal perforations, retinal holes, and filtering blebs. The crosslinkable sealants of the invention may also be useful for cardiovascular surgery, urinary tract surgery (nephrotomy closure, urethral repair, hypospadia repair), pulmonary surgery (sealing parenchymal & bronchial leaks, bronchopleural fistula repair, persistent air leak repairs), G.I. tract and stomach surgery (parotid cutaneous fistula, tracheo-oesophageal fistula, peptic ulcer repair), joint surgery (cartilage repair, meniscal repair), heart surgery (cardiac ventricular rupture repair), brain surgery (dural defect repairs), ear surgery (ear drum perforation), alveolar osteitis ("dry socket") and related post-surgical oral indications, and post-surgical drainage reduction (mastectomy, axillary dissection).

In cardiovascular surgery, the sealants can be used, for example, with needle holes, suture lines, diffuse and non-specific bleeding, anastomotic bleeding, friable tissue bleeding, aortic dissections, ventricular ruptures, and fistulas. The crosslinked hydrogels of the invention can be used as a patch to cover infracted tissue in a myocardial infarction to help reduce loss of tissue function. In certain instances, the crosslinked hydrogel is used for vascular applications where the prepared vascular patch, graft, or device contains site-specific angiogenesis factor(s), preferably by incorporating vascular endothelial growth factor and/or platelet derived growth factor into the vascular graft/patch or device. The vascular graft/patch may be used to bypass, replace, or repair a part of the diseased/dysfunctional blood vessel. In certain instances, the present invention provides a vascular device having site-specific angiogenesis factors comprising incorporating at least one vascular endothelial growth factor, or at least one platelet derived growth factor, or other angiogenesis factor, and combination thereof onto the medical device. In certain instances, the invention provides an implant comprising an angiogenesis antagonist for inhibiting undesired angiogenesis site-specifically, such as tumor, cancer, retinopathy, or the like. In certain instances, the vascular device having site-specific angiogenesis factor comprises at least one vascular endothelial growth factor. Vascular endothelial growth factor is a secreted angiogenic mitogen whose target cell specificity appears to be restricted to vascular endothelial cells. The resulting angiogenesis properties may also be induced using platelet derived growth factor, tissue treatment factor, and the like. The phrase "vascular endothelial growth factor" refers broadly to all members of the vascular endothelial growth factor family, which may comprise polynucleotides, polypeptides encoded by such polynucleotides that facilitate angiogenesis, and the like. U.S. Pat. No. 6,040,157 to Hu et al. (hereby incorporated by reference) discloses general characteristics and specific properties of vascular endothelial growth factor and is incorporated herein by reference. Notably, VEGF has at least four different forms of 121, 165, 189 and 206 amino acids due to alternative splicing, which are designated as VEGF121, VEGF165, VEGF189, and VEGF206, respectively. In certain instances, the growth factor is added to the hydrogel at the time of implantation. In certain instances, a method for incorporating the vascular endothelial growth factors comprises the step of impregnating the growth factors onto the tissue site, e.g., vascular graft, followed by treatment of the hydrogel.

The adhesive compositions of the invention may also be used in cosmetic applications. In certain instances, hydrogel adhesives are used in combination with a void filler, where the hydrogel precursors are injected under the skin. Alternatively, an adhesive composition may be applied as a topical cosmetic or therapeutic composition, used, e.g., in connection with creams, shampoos, soaps, sun screen, lotions to moisturize the tissue, and oils, for dermatological purposes, cleansing, and the like. The adhesive composition can also be used with agents such as rapamycin or analogs like everolimus or biolimus, which help minimize scaring after plastic surgery performed on the face, body, or other external skin area.

The adhesive compositions of the invention may also be used as a coating on or around non-degradable device implants to improve the device performance and/or reduce complications. For example, coating an implant with a polalkyleneimine hydrogel of the invention may reduce a patient's fibrotic response to the implant. In certain instances, the adhesive compositions of the invention may be used as a coating on breast implants.

Breast implant placement for augmentation, or breast reconstruction after mastectomy, is one of the most frequently performed cosmetic surgery procedures today. In 2002, over 300,000 women had breast implant surgery. Of these women, approximately 80,000 had breast reconstructions following a mastectomy due to cancer. Breast augmentation or reconstructive surgery involves the placement of a commercially available breast implant, which consists of a capsule filled with either saline or silicone, into the tissues underneath the mammary gland. Four different incision sites are used for breast implantation: axillary (armpit), periareolar (around the underside of the nipple), inframammary (at the base of the breast where it meets the chest wall) and transumbilical (around the belly button). The tissue is dissected away through the small incision, often with the aid of an endoscope (particularly for axillary and transumbilical procedures where tunneling from the incision site to the breast is required). A pocket for placement of the breast implant is created in either the subglandular or the subpectorial region. For subglandular implants, the tissue is dissected to create a space between the glandular tissue and the pectoralis major muscle that extends down to the inframammary crease. For subpectoral implants, the fibres of the pectoralis major muscle are carefully dissected to create a space beneath the pectoralis major muscle and superficial to the rib cage. Careful hemostasis is essential because it can contribute to complications such as capsular contractures. In fact, minimally invasive procedures (axillary, transumbilical approaches) generally must be converted to more open procedures, such as periareolar, if bleeding control is inadequate. Depending upon the type of surgical approach selected, the breast implant is often deflated and rolled up for placement in the patient. The implant can then be filled or expanded to the desired size once accurate positioning is achieved.

A significant percentage of women suffer from complications that frequently require repeat intervention to correct. The main complication relates to encapsulation of the breast prosthesis, thereby creating a periprosthetic shell (called capsular contracture) with up to 50% of patients reporting some dissatisfaction. Calcification can occur within the fibrous capsule adding to its firmness and complicating the interpretation of mammograms. Multiple causes of capsular contracture have been identified, including: infection, hematoma, foreign body reaction, migration of silicone gel molecules across the capsule and into the tissue, autoimmune disorders, genetic predisposition, and the surface characteristics of the prosthesis. Yet, abnormal fibroblast activity stimulated by a foreign body is a consistent observation. Capsular contracture can lead to a number of complications including implant malposition, unfavorable shape, and hardness. When the surrounding scar capsule begins to harden and contract, it results in discomfort, weakening of the shell, asymmetry, skin dimpling and malpositioning. True capsular contractures will occur in approximately 10% of patients after augmentation, and in 25% to 30% of reconstruction cases, with most patients reporting dissatisfaction with the aesthetic outcome. Scarring leading to asymmetries occurs in about 10% of breast augmentations and about 30% of breast reconstructions. Notably, scarring leading to asymmetry is the leading cause of revision surgery, and the formation of scar tissue is thought to be linked to chronic pain experienced by a significant number of patients. Other complications of breast augmentation surgery include late leaks, hematoma (approximately 1-6% of patients), seroma (2.5% of patients), hypertrophic scarring (2-5% of patients) and infections (about 1-4% of patients).

Current treatments to correct undesirable breast asymmetries include removal of the implant, capsulotomy (cutting or surgically releasing the capsule), capsulectomy (surgical removal of the fibrous capsule), or placing the implant in a different location (i.e., from subglandular to subpectoral). Ultimately, additional surgery (revisions, capsulotomy, removal, re-implantation) is required in over 20% of augmentation patients. Additional surgery is also required in over 40% of reconstruction patients, with scar formation and capsular contracture being the most common cause. Notably, procedures to break down the scar may not be sufficient, and approximately 8% of patients receiving breast augmentations and 25% of patients receiving breast reconstructions eventually have the implant removed. The adhesives of the present invention could be used as a coating for the breast implant in order to retard or reduce the extent of fibrosis.

The adhesives of the present invention could be used in combination with a degradable or nondegradable mesh to secure a tissue site. The combination of the mesh and the adhesive provides for improved strength. This protocol is particular useful when the area of tissue repair is large, such as a tissue plane or a hernie repair.

The sealants of the present invention can be used along with suture or staples to close or secure a wound. These wounds include those caused by trauma, surgical procedure, infection, or a health condition. When used in this manner, the sealant may provide a leak tight barrier for liquids or air.

The compositions of the invention can be injected or placed in vivo as a void filling composition or used as a sealant/adhesive when mixed with natural polymers such as collagen, hyaluronic acid, gelatin, heparin, fibrin and/or heparin sulfate. Voids of particular interest are the nasal airway, or an organ of the gastro-intestinal track, in order to arrest localized bleeding and/or promote healing following trauma, injury, or surgery.

In certain instances, a synthetic or natural polymer which may or may not be involved in the crosslinking reaction is added either before, during, and/or after mixing of the polalkyleneimine and the polymerization agent. The synthetic or natural polymers can enhance the mechanical properties, affect adhesion, alter the degradation rates, alter viscosity, and/or provide signaling to specific cells. Representative examples of natural polymers which can be added to the adhesive include collagen, hyaluronic acid, albumin, cellulose, elastin, fibrin, fibronectin, polylysine, and RGD containing peptides. Examples of synthetic polymers include poly(vinyl acetate), polyvinylpyrrolidone, poly(acrylic acid), poly(ethylene glycol), poly(propylene glycol)-poly(ethylene glycol) copolymer, and trimethylene carbonate. The synthetic or natural polymers to be added can be soluble in aqueous solution or can be insoluble in aqueous solution and dispersed throughout the adhesive/sealant to create a composite material.

In certain instances, a polyalkylene glycol containing nucleophilic groups is added to the polyalkyleneimine prior to mixing the polyalkyleneimine with a polyalkylene glycol containing electrophilic groups. In certain instances, a PEG is modified to contain amine groups and/or thiol groups. The modified PEG is mixed with the polyalkyleneimine, and then the polyalkyleneimine/modified-PEG solution is added to the PEG-electrophile solution to form the hydrogel. Incorporation of this third active component into the hydrogel can affect hydrogel properties. For example, the resultant hydrogel may swell more, be less mechanically strong, and/or degrade faster compared to a hydrogel prepared without a PEG containing nucleophilic groups.

In certain instances, a polyalkylene glycol containing nucleophilic groups is added to the polyalkyleneimine containing electrophilic groups. In certain instances, the polyalkylene glycol contains amino and/or thiol groups. In certain instances, the polyalkyleneimine contains an N-hydroxysuccinimide group optionally substituted with a sulfonic acid group.

In certain instances, the hydrogel formed by reaction of a polalkyleneimine and a polymerization agent is treated with an acrylate to form a photo-polymerization agent. Then, the photo-polymerization agent is treated with visible or ultraviolet light sufficient to polymerize the photo-polymerization agent.

In certain instances, a polyalkyleneimine containing a plurality of photopolymerizable groups, optionally in the presence of a polyalkylene glycol containing a plurality of photopolymerizable groups, is treated with visible light or ultraviolent light sufficient to polymerize the polalkyleneimine. In certain instances, the photopolymerizable group is an acrylate, such as methacrylate. In certain instances when visible light is used to polymerize the polyalkyleneimine, a photoinitator is admixed with the polyalkyleneimine. A large number of photoinitiators are known in the art and are amenable to the present invention. For example, eosin y is a photoinitiator that may be used with the polalkyleneimines described herein.

In instances where the adhesive and/or sealant serve as a scaffold for new tissue ingrowth, it can be important that the structure is porous. Control of the porosity in the adhesive will affect the time and rate at which new cells repopulate the tissue site. Pores sizes of about 10 to about 100 microns in diameter are preferred. Pores sizes of about 40 to about 80 microns in diameter are more preferred. One method to create a porous structure is to use two different buffers with the macromer (PEG and PEI, respectively) such that upon mixing the two solutions and formation of the adhesive an acid/base reaction occurs to generate $CO_2$ gas ($H_2CO_3$). For example, an acid (eg., HCl, acetic acid, formic, etc.) could be added to a solution containing a metal carbonate ($Na_2CO_3$, $CaCO_3$, etc.) or a metal bicarbonate ($NaHCO_3$, $KHCO_3$, etc.). Alternatively, during mixing of the PEG and PEI to form the sealant, turbulent mixing is used to create porous structure. Additional foaming agents such as polypropylene glycol/PEG block copolymers, alkylated PEGs, and other biphasic moieties are also contemplated. An additional concept described in the invention is the generation of a porous structure once the adhesive is at the wound/tissue site. For example, a dissolvable polymer, inorganic salt, nanosphere, or microsphere (PVA, PLA/PGA, collagen, microspheres, salt) is dispersed throughout the adhesive. In certain instances, the inorganic salt is a sodium salt, potassium salt, lithium salt, calcium salt, or magnesium salt. These polymers or objects degrade at a rate faster than the adhesive, and thus a porous structure is created over time. The term "porosity", and inflections thereof, as used with regard to a device of the present invention, will refer to a three-dimensional structure that permits or facilitates tissue ingrowth when placed within the body. Such three-dimensional structures include matrices such as open cells or channels, fibrous structures, textures having increased surface area, and the like.

Another aspect of the invention relates to a composition comprising a degradable scaffold and a hydrogel adhesive. In certain instances, the degradable scaffold comprises a biodegradable polymer. In certain instances, the degradable scaffold comprises poly(glycolic acid), poly(lactic acid), or copolymers thereof. In certain instances, the degradable scaffold comprises poly(lactic acid). In certain instances, the biodegradable polymer has a weight average molecular weight of about 500 g/mol to about 500,000 g/mol. In certain instances, the biodegradable polymer has a weight average molecular weight of about 500 g/mol to about 100,000 g/mol. In certain instances, the scaffold is placed in the wound site and the hydrogel adhesive is then applied to the wound. This approach provides that the tissue and the scaffold are secure in the wound site. Alternatively, the scaffold is coated with one component of the hydrogel adhesive, e.g., the polyalkyleneimine, the scaffold is placed in vivo, and then the second component of the hydrogel adhesive is added to form the hydrogel.

Another aspect of the invention relates to a method of repairing a wound, comprising the steps of applying a preformed hydrogel of the invention to the wound of a patient. The preformed hydrogel acts as a tissue filler for a wound site. The preformed hydrogel can also be used in combination with adhesive. In certain instances, the preformed hydrogel is placed in the tissue site and then the hydrogel adhesive is added. Alternatively, a hydrogel adhesive is applied to the wound site, the preformed hydrogel is added, and then the wound site is closed. In certain instances, a hydrogel adhesive is applied to the wound site, the preformed hydrogel is applied to the wound site, optionally adding more hydrogel adhesive, and then closing the wound.

In another aspect of the invention, the polymers, after being crosslinked, can also be seeded with cells and, then, used to repair damaged ophthalmic, orthopedic, cardiovascular or bone tissue. Alternatively, the polymers and cells can be mixed and then injected into the in vivo site and crosslinked in situ for tissue repair or replacement. The crosslinked polymers provide a three dimensional templates for new cell growth. The polymers of the invention can also be used for the encapsulation of or the covalent attachment of pharmaceutical agents/drugs such as bioactive peptides (e.g., growth factors), antibacterial compositions, antimicrobial compositions, and antinflammatory compounds to aid/enhance the closure and repair of the wound.

Another aspect of the invention relates to an optical lens comprising a polyalkyleneimine gel of the invention. The optical lens is prepared by reacting a polyalkyleneimine (PAI) with a cross-linking agent, such as an activated polyethylene glycol. In certain instances, a crosslinkable formulation is injected via a small opening into an empty lens-capsule bag. Subsequent crosslinking by a chemical reaction affords a hydrogel lens. Alternatively, the cross-linked hydrogel can be prepared, and then this preformed lens can be injected in the empty lens bag. In the latter case, the preformed lens can be pre-extracted to remove impurities.

Biologically Active Agents within the Dendritic Gel/Network

In certain instances, biologically active agents may be incorporated in the adhesive. Active agents amenable for use in the compositions of the present invention include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Pharmaceutically Acceptable Salts

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Sterilization Procedures

A variety of procedures are known in the art for sterilizing a chemical composition. Sterilization may be accomplished by chemical, physical, or irradiation techniques. Examples of chemical methods include exposure to ethylene oxide or hydrogen peroxide vapor. Examples of physical methods include sterilization by heat (dry or moist), retort canning, and filtration. The British Pharmacopoeia recommends heating at a minimum of 160° C. for not less than 2 hours, a minimum of 170° C. for not less than 1 hour and a minimum of 180° C. for not less than 30 minutes for effective sterilization. For examples of heat sterilization, see U.S. Pat. No. 6,136,326, which is hereby incorporated by reference. Passing the chemical composition through a membrane can be used to sterilize a composition. For example, the composition is filtered through a small pore filter such as a 0.22 micron filter which comprises material inert to the composition being filtered. In certain instances, the filtration is conducted in a Class 100,000 or better clean room. Examples of irradiation methods include gamma irradiation, electron beam irradiation, microwave irradiation, and irradiation using visible light. One preferred method is electron beam irradiation, as described in U.S. Pat. Nos. 6,743,858; 6,248,800; and 6,143,805, each of which is hereby incorporated by reference.

There are several sources for electron beam irradiation. The two main groups of electron beam accelerators are: (1) a Dynamitron, which uses an insulated core transformer, and (2) radio frequency (RF) linear accelerators (linacs). The Dynamitron is a particle accelerator (4.5 MeV) designed to impart energy to electrons. The high energy electrons are generated and accelerated by the electrostatic fields of the accelerator electrodes arranged within the length of the glass-insulated beam tube (acceleration tube). These electrons, traveling through an extension of the evacuation beam tube and beam transport (drift pipe) are subjected to a magnet deflection system in order to produce a "scanned" beam, prior to leaving the vacuum enclosure through a beam window. The dose can be adjusted with the control of the percent scan, the beam current, and the conveyor speed. In certain instances, the electron-beam radiation employed may be maintained at an initial fluence of at least about 2 µCurie/cm$^2$, at least about 5 µCurie/cm$^2$, at least about 8 µCurie/cm$^2$, or at least about 10 Curie/cm$^2$. In certain instances, the electron-beam radiation employed has an initial fluence of from about 2 to about 25 µCurie/cm$^2$. In certain instances, the electron-beam dosage is from about 5 to 50 kGray, or from about 15 to about 20 kGray with the specific dosage being selected relative to the density of material being subjected to electron-beam radiation as well as the amount of bioburden estimated to be therein. Such factors are well within the skill of the art.

The composition to be sterilized may be in any type of at least partially electron beam permeable container such as glass or plastic. In embodiments of the present invention, the container may be sealed or have an opening. Examples of glass containers include ampules, vials, syringes, pipettes, applicators, and the like. The penetration of electron beam irradiation is a function of the packaging. If there is not enough penetration from the side of a stationary electron beam, the container may be flipped or rotated to achieve adequate penetration. Alternatively, the electron beam source can be moved about a stationary package. In order to determine the dose distribution and dose penetration in product load, a dose map can be performed. This will identify the minimum and maximum dose zone within a product.

Procedures for sterilization using visible light are described in U.S. Pat. No. 6,579,916, which is hereby incorporated by reference. The visible light for sterilization can be generated using any conventional generator of sufficient power and breadth of wavelength to effect sterilization. Generators are commercially available under the tradename PureBright® in-line sterilization systems from PurePulse Technologies, Inc. 4241 Ponderosa Ave, San Diego, Calif. 92123, USA. The PureBright® in-line sterilization system employs visible light to sterilize clear liquids at an intensity approximately 90000 times greater than surface sunlight. If the amount of UV light penetration is of concern, conventional UV absorbing materials can be used to filter out the UV light.

In a preferred embodiment, the composition is sterilized to provide a Sterility Assurance Level (SAL) of at least about $10^{-3}$. The Sterility Assurance Level measurement standard is described, for example, in ISO/CD 14937, the entire disclosure of which is incorporated herein by reference. In certain embodiments, the Sterility Assurance Level may be at least about $10^{-4}$, at least about $10^{-5}$, or at least about $10^{-6}$.

As discussed above, in certain embodiments of the present invention, one or more of the compositions, reagents, or components of a kit has been sterilized. The sterilization may be achieved using gamma radiation, e-beam radiation, dry heat sterilization, ethylene oxide sterilization, or a combination of any of them. The compositions, reagents, or components of the kits can be sterilized in an aqueous solution or neat.

In certain embodiments a compound of formula Ia, formula Ib, or formula III (as described herein) has been sterilized by e-beam radiation between 2 and 40 kGy.

In certain embodiments a compound of formula Ia, formula Ib, or formula III has been sterilized by e-beam radiation between 3-20 kGy.

In certain embodiments a compound of formula Ia, formula Ib, or formula III has been sterilized by e-beam radiation between 5-12 kGy.

In certain embodiments a compound of formula Ia, formula Ib, or formula III has been diluted in aqueous solution, optionally buffered; and said aqueous solution has been sterilized by e-beam radiation between 2 and 40 kGy.

In certain embodiments a compound of formula Ia, formula Ib, or formula III has been diluted in aqueous solution, optionally buffered; and said aqueous solution has been sterilized by e-beam radiation between 3-20 kGy.

In certain embodiments a compound of formula Ia, formula Ib, or formula III has been diluted in aqueous solution, optionally buffered; and said aqueous solution has been sterilized by e-beam radiation between 5-12 kGy.

In certain embodiments of the present invention, a method further comprises the step of sterilizing a compound of formula Ia, formula Ib, or formula III with e-beam radiation. In certain embodiments, said e-beam radiation is between 2 and 40 kGy. In certain embodiments, said e-beam radiation is between 3 and 20 kGy. In certain embodiments, said e-beam radiation is between 5 and 12 kGy. In certain embodiments, said sterilization is carried out below 30° C. In certain embodiments, said sterilization is carried out below 20° C. In certain embodiments, said sterilization is carried out below 10° C. In certain embodiments, said sterilization is carried out below 0° C.

Delivery Systems

Figure 10:
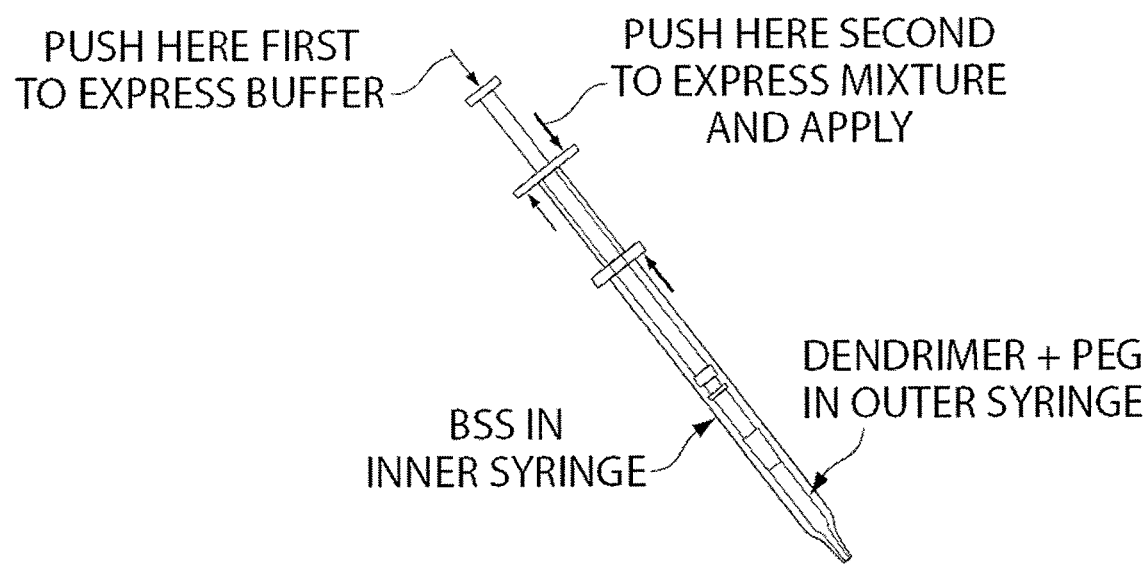
FIG. 10 depicts a double-acting, single-barrel syringe.
Figure 11:
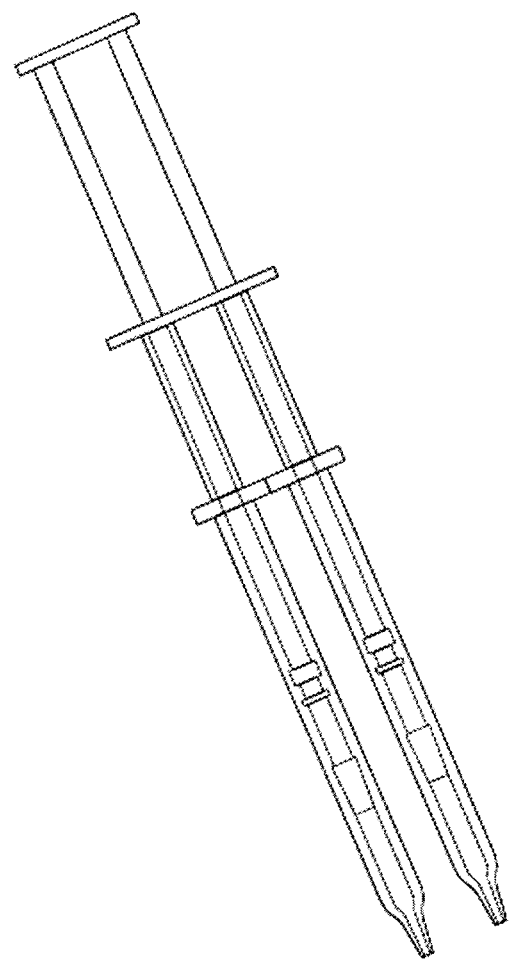
FIG. 11 depicts a double-barrel syringe.
Figure 13:
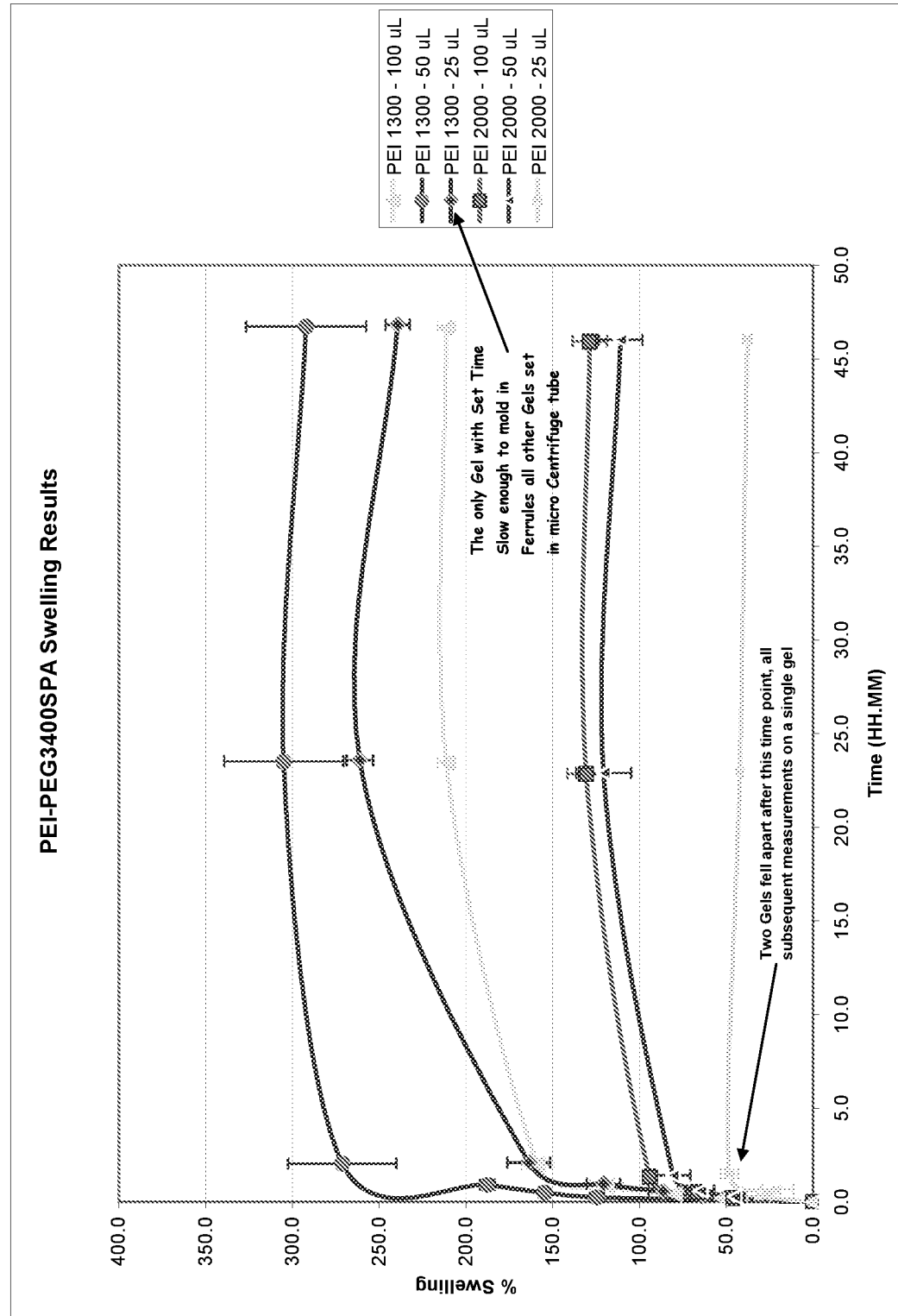
FIG. 13 depicts the impact of swelling with change in molecular weight and ratio of PEI in hydrogels prepared with PEG-SPA. Increasing the molecular weight decreased the swelling. For PEI 2000, increasing the amount of PEG-SPA relative to PEI decreased the swelling of the gels.

The materials used to form the sealant of the present invention may be delivered to the wound of a patient using a large number of known delivery devices. For example, the delivery system may be a single-barrel syringe system. In certain instances, the single-barrel syringe is a double acting, single-barrel syringe system as displayed in FIG. 10. In certain situations, a double- or multi-barrel syringe system, as displayed in FIG. 11, may be preferable. In instances where the polymerizable polyalkyleneimine is mixed with a polymerization agent prior to delivering the solution to the wound of a patient, a delivery device that flows two or more streams of liquid in a mixing chamber may be preferable. Alternatively, a delivery device that mixes two solids and two liquids and then separately flows these streams of liquid to a mixing chamber may be advantageous. In certain instances, delivery may be assisted with machines, compressed air or gases, and the like. Of course, variations may be made in the size of the delivery device, the length of the delivery device, and/or the use of machines to aid in delivery.

In certain instances, a delivery system is used to deliver the sealant-forming materials to the wound of a patient, wherein at least two dry, reactive components are stored together in a dry state and introduced into a liquid component(s) at the time of use to form a mixture that forms a hydrogel.

In certain instances, it may be advantageous the mix the components used to form the hydrogel by static mixing device such as a tortuous path mixing element. As an example, both components could be dissolved in aqueous solution prior to use. Once mixed, the solutions would polymerize in a predetermined amount of time. For example, the two components could be mixed (without gelation) prior to applying the mixture to a patient. The pH of the mixing solution may be adjusted in order to slow or prevent crosslinking of hydrogel components. Once the components used to form the hydrogel are mixed, the resultant solution may be contacted with a frit or resin designed to raise or lower the pH to a level suitable for crosslinking.

Another aspect of the invention relates to a method of preparing a hydrogel, comprising the steps of combining an aqueous solution of a first component, and a neat form of a second component to give a mixture; and applying the mixture to a tissue site. In certain embodiments, the present invention relates to the aforementioned method, wherein said step of combining to give said mixture occurs shortly before said step of applying. In certain embodiments, the present invention relates to the aforementioned method, wherein said step of combining to give said mixture occurs less than about 30 minutes before said step of applying. In certain embodiments, the present invention relates to the aforementioned method, wherein said step of combining to give said mixture occurs less than about 20 minutes before said step of applying. In certain embodiments, the present invention relates to the aforementioned method, wherein said step of combining to give said mixture occurs less than about 10 minutes before said step of applying. In certain embodiments, the present invention relates to the aforementioned method, wherein said step of combining to give said mixture occurs less than about 5 minutes before said step of applying.

Another aspect of the invention relates to a method of controlling the polymerization of a two component hydrogel system through combining the two components in an aqueous solution in one container with a final solution pH in a range unsuitable for crosslinking, and expressing the solution through an ion exchange resin to either lower or raise the pH of the solution to a range suitable for crosslinking.

Another aspect of the invention relates to a method of controlling the polymerization of a two component hydrogel system through combining an aqueous solution of the first component with a neat form of the second component with a final solution pH in a range unsuitable for crosslinking, and expressing the solution through an ion exchange resin to either lower or raise the pH of the solution to a range suitable for crosslinking.

For example, PEG-NHS and a PEI could be mixed during packaging and dissolved prior to use in a buffer designed to provide a solution with a pH of about 6. The solution is mixed, and then the solution is contacted with a resin embedded in the delivery device. The resin would raise the pH to about 7 for initiate crosslinking.

Another aspect of the invention relates to one the methods described herein for sealing a wound, filling a void, augmenting soft tissue, or adhering tissue, wherein the components are PEG-NHS and PEI Mw2000, the initial pH of the solution containing the combined components is below approximately pH 7, and the ion exchange resin is an anion exchange resin (including but not limited to MTO-Dowex M43, Dowex 66, or Dowex 1X2-200)

Another aspect of the invention relates to a method of controlling the polymerization of a two component hydrogel system through combining the two components in an aqueous solution in one container with a final solution pH in a range unsuitable for crosslinking, and expressing the solution through an frit/resin coated/loaded with an acidic or basic media to lower or raise the pH of the solution to a range suitable for crosslinking.

Another aspect of the invention relates to a method of controlling the polymerization of a two component hydrogel system through combining the two components in an aqueous solution in one container with a final solution pH in a range unsuitable for crosslinking, and contacting the solution with an applicator loaded with with either an acidic or basic media to lower or raise the pH of the solution to a range suitable for crosslinking.

It is appreciated that the above methods may be optimized by modifying, inter alia, the size and shape of the instrument that that delivers the solution suitable for crossliking. For example, the diameter and/or length of the crosslinking-solution holding chamber can be altered, or the diameter and/or length of the chamber housing the frit/resin loaded with an acidic or basic media can be altered. Similarly, the applicator tip of the delivery instrument can be perament or disposable. The delivery instrument may be constructed so that the adhesive is applied as a spray, mist, or liquid. In certain instances, the delivery instrument is a single or double barrel syringe. Further, it is appreciated that the above methods may involve air-assisted delivery the cross-linking solution. In certain instances, the above methods may employ a brush or sponge to delivery the hydrogel to the tissue.

Pharmaceutical Agents

A large number of pharmaceutical agents are known in the art and are amenable for use in the pharmaceutical compositions of the invention. The term "pharmaceutical agent" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful pharmaceutical agents include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

More specifically, non-limiting examples of useful pharmaceutical agents include the following therapeutic categories: analgesics, such as nonsteroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard aklylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor para-sympathomimetics, sympatholytics, alpha-blocker sympatholytics, beta-blocker sympatholytics, sympathomimetics, and adrenergic agonist sympathomimetics; cardiovascular agents, such as antianginals, beta-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, beta-blocker anti-gluacoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful pharmaceutical agents from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) *vinca* alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA) (enteric coated ASA); (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I anti-arrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) α-blocker antihypertensives, such as prazosin; (46) angiotensin-converting enzyme inhibitor (ACE inhibitor) antihypertensives, such as captopril and enalapril; (47) 3-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydro-chlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) .beta.-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid antiinflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D compounds, such as calcitriol.

In addition to the foregoing, the following less common drugs may also be used: chlorhexidine; estradiol cypionate in oil; estradiol valerate in oil; flurbiprofen; flurbiprofen sodium; ivermectin; levodopa; nafarelin; and somatropin. Further, the following drugs may also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-la; lenograstim (G-CSF); olanzapine; recombinant thyroid stimulating hormone (r-TSH); and topotecan.

Further still, the following intravenous products may be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-.beta. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents such as antifungals, anti-virals, antiseptics and antibiotics.

Alternatively, the pharmaceutical agent may be a radiosensitizer, such as metoclopramide, sensamide or neusenamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); LIX (made by Terrapin); or the like. Preferably, the biologically active substance is selected from the group consisting of peptides, poly-peptides, proteins, amino acids, polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other anti-neoplastics such as paclitaxel, antibiotics, anti-virals, antifungals, anti-inflammatories, and anticoagulants.

The biologically active substances are used in amounts that are therapeutically effective. While the effective amount of a biologically active substance will depend on the particular material being used, amounts of the biologically active substance from about 1% to about 65% may be desirable. Lesser amounts may be used to achieve efficacious levels of treatment for certain biologically active substances.

Methods of Controlling Swelling in a Hydrogel

Figure 16:
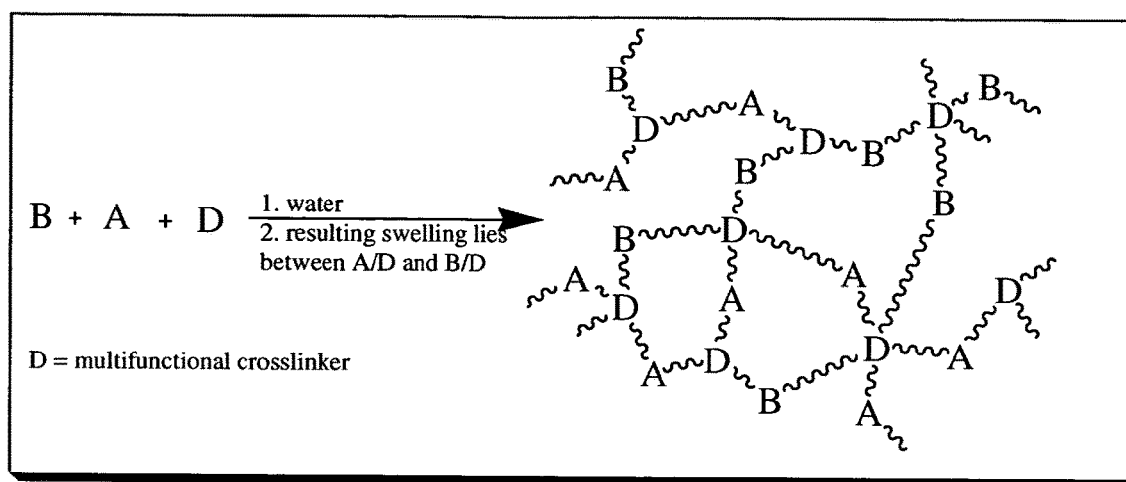
FIG. 16 depicts polymer formation with a combination of A and B with D to form a hydrogel with intermediate swelling characteristics.

Another aspect of the present invention relates to a method of controlling swelling in hydrogel polymers by reacting two difunctional macromomers (pre-polymers) in the presence of multifunctional cross-linking molecules. The ability to control the swelling is accomplished by preparing two or more difunctional molecules with distinctly different swelling characteristic when reacted separately with the multifunctional cross-linker. For example, the one difunctional molecule (A) will be hydrophobic in character, such that the resulting polymer would deswell (lose water) upon formation of a hydrogel, while the second difunctional molecule (B) will swell (uptake water) upon the formation of a hydrogel (See FIG. 15). Preparing a polymer via the reaction of A and B in the presence of a cross-linker (D) will result in a polymer that has swelling characteristics between the two endpoint polymers (See FIG. 16). The ratio of A to B will determine the extent of swelling in the final product. In fact, the correct ratio of A to B will at times result in a polymer which does not swell or deswell. Note: A and B denote a hydrophobic difunctional material (yielding a highly swellable hydrogel) and hydrophilic material (yielding a low swelling hydrogel), respectively.

Figure 17:
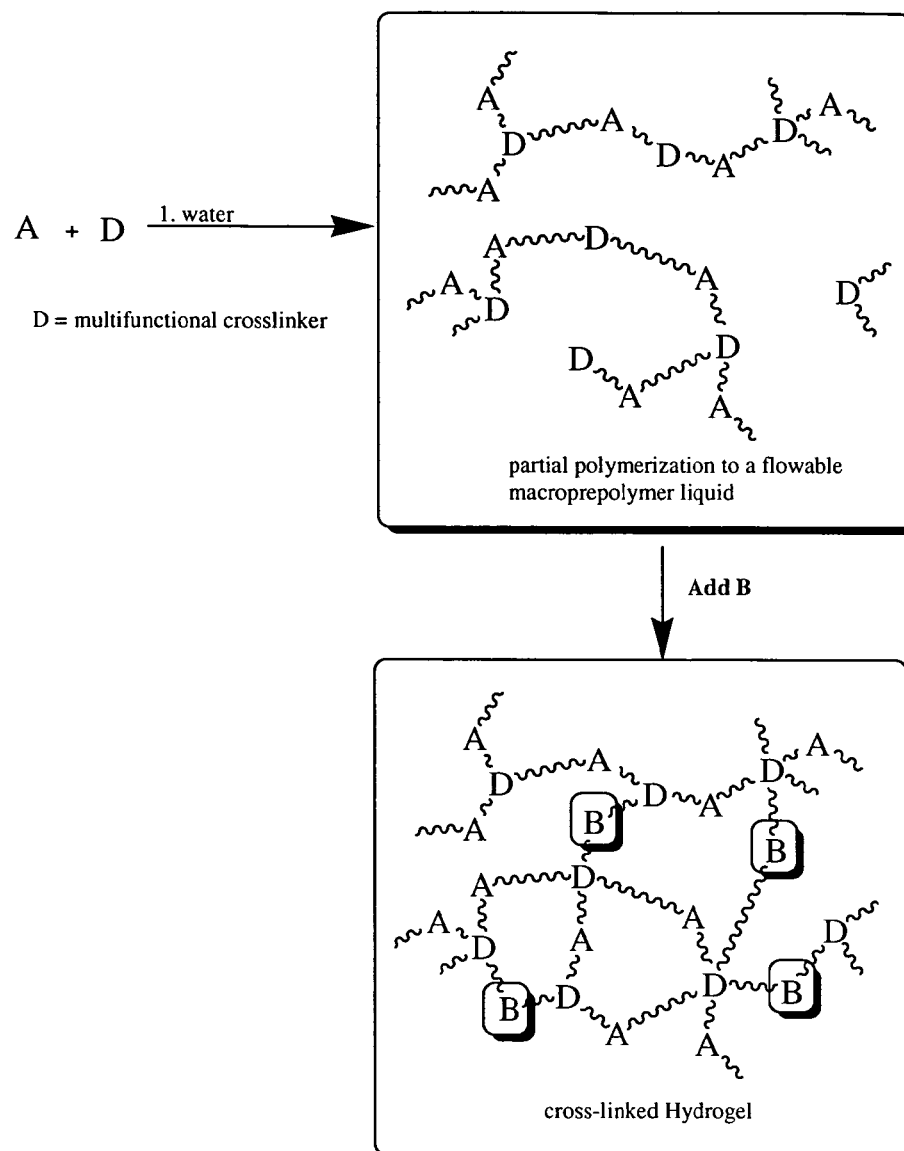
FIG. 17 depicts partial or staged polymerization. One goal is to polymerize A or B in the presence of Excess D to yield a flowable water stable macro-prepolymer. Upon application, A or B is added to the macro-prepolymer to complete the polymerization to form a highly cross linked hydrogel.

In addition to the discovery of a method to control swelling, a method to form hydrogels has been discovered in which a difunctional molecule can be reacted with a cross-linker to yield a viscous macro-prepolymer, which is stable in solution for extended periods of time. The addition of a second prepolymer is then added to more completely cross-link the polymer to form a hydrogel (See FIG. 17). This is significant because as hydrophobicity of A increases, it becomes more difficult to dissolve the material. This increased amount of time/effort required in order to be dissolve the material can be a significant disadvantage when the material needs to be dissolved just prior to use.

Figure 18:
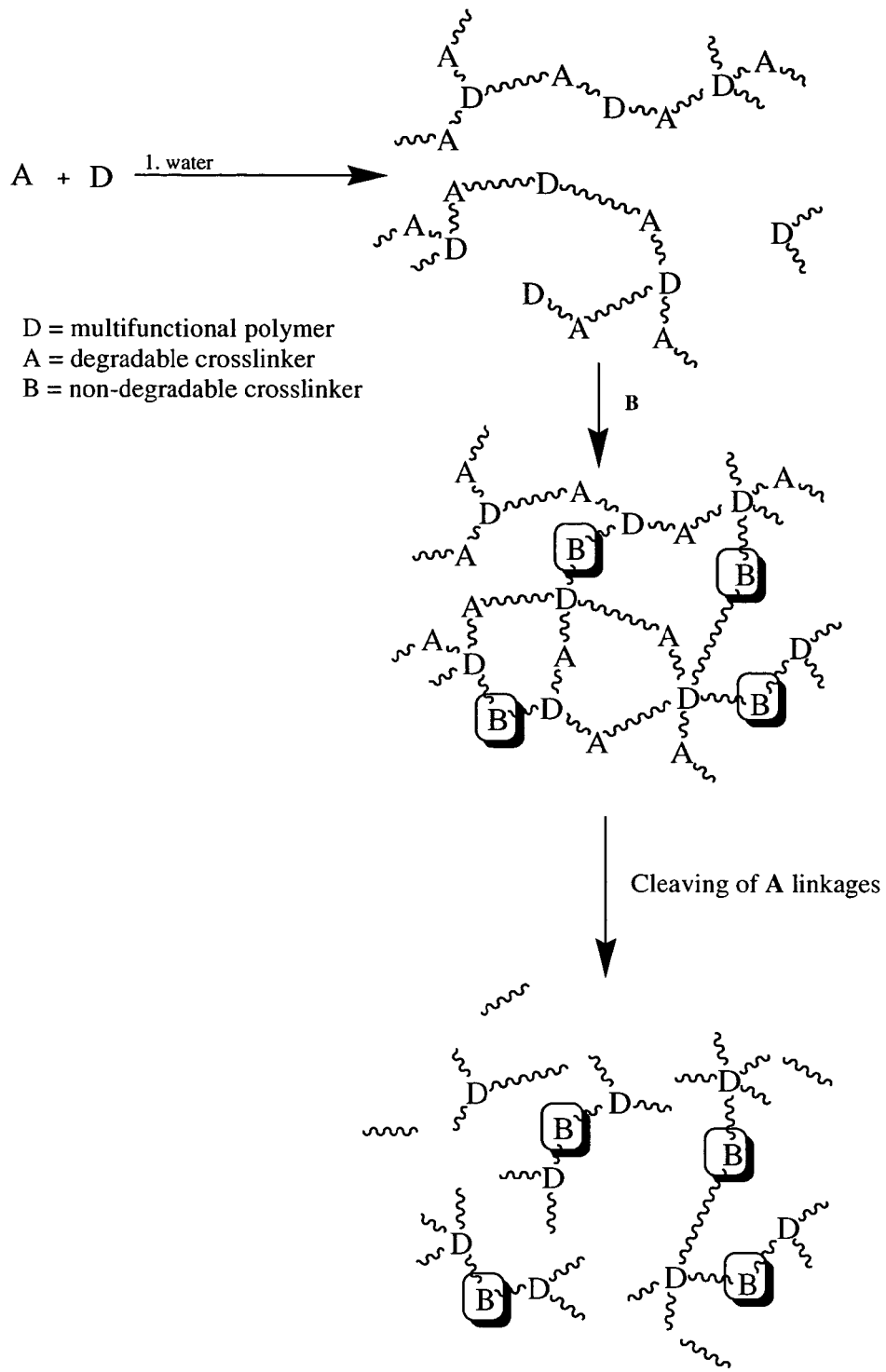
FIG. 18 depicts formation of a macro-prepolymer between A and D, networking the polymer via the addition of B, then breaking up the network by cleaving the bond between A and D.

The ability to make a cross-linked hydrogel with more than one difunctional molecule to the cross-linker can allow one to utilize one molecule with significantly different coupling chemistry and degradation chemistry. This will allow for not only assembly of the polymer, but also for disassembly of the polymer. One novel aspect is that one portion of the network can be broken to yield high molecular weight flowable materials that can be removed from their intended place of use (See FIG. 18).

Figure 19:
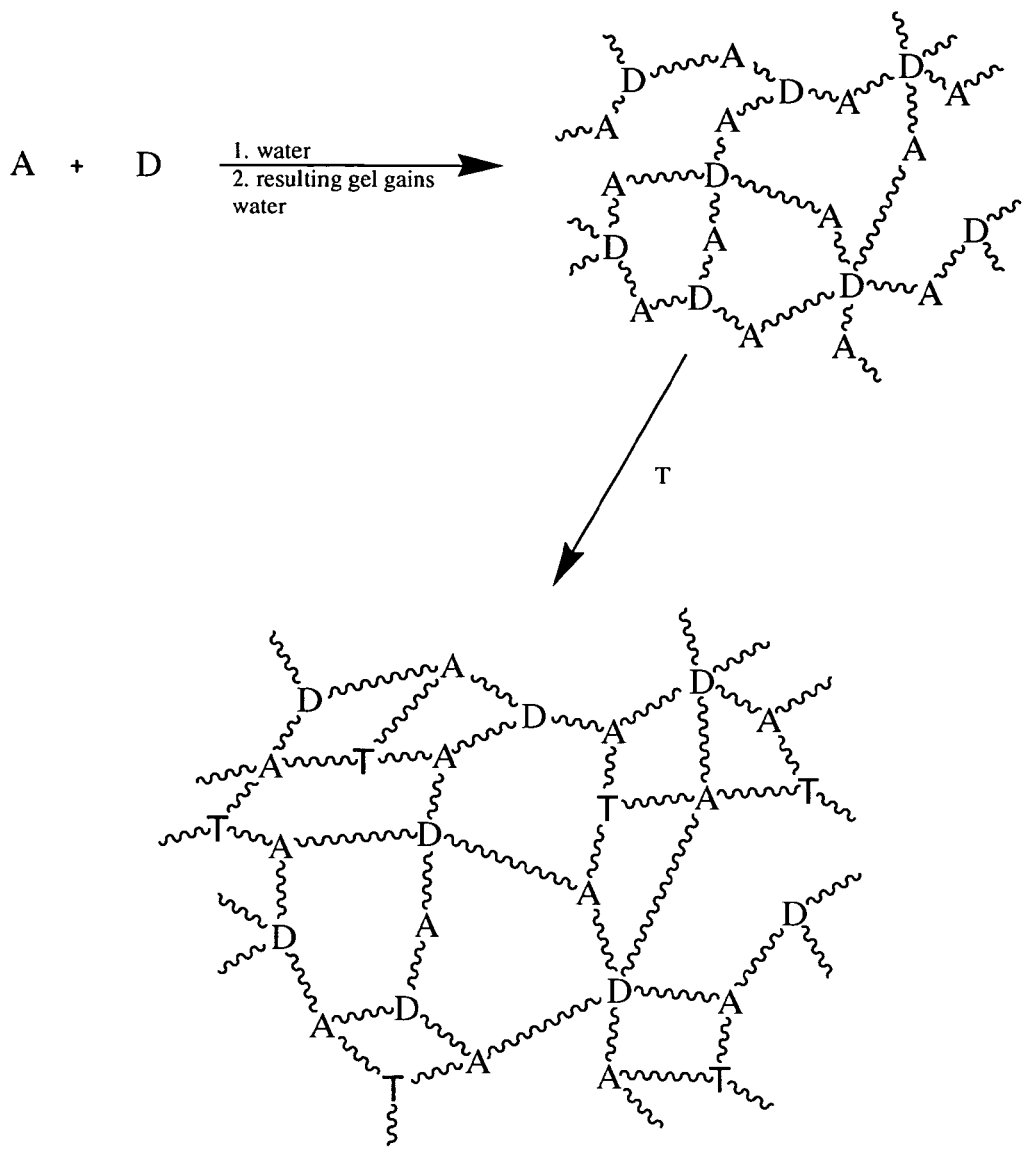
FIG. 19 depicts gel formation with two cross-linkers which utilized unique chemistries to form the cross-links. Then, addition of aziridine-containing molecules affords additional cross-linking to the existing gel or imparts additional cross-linking during the initial polymerization.

FIG. 19 illustrates the use of two different cross-linkers which crosslink a normally difunctional reactive molecule via a pendent acid group. In this case, a polyethylene glycol prepolymer is prepared containing two isocyanate groups, which can be reacted with an amine-based cross-linker. In certain instances, the prepolymer contains a normally, unreactive carboxylic acid group. This methodology takes advantage of the pendent acid group by reacting it with a multifunctional aziridine.

Figure 20:
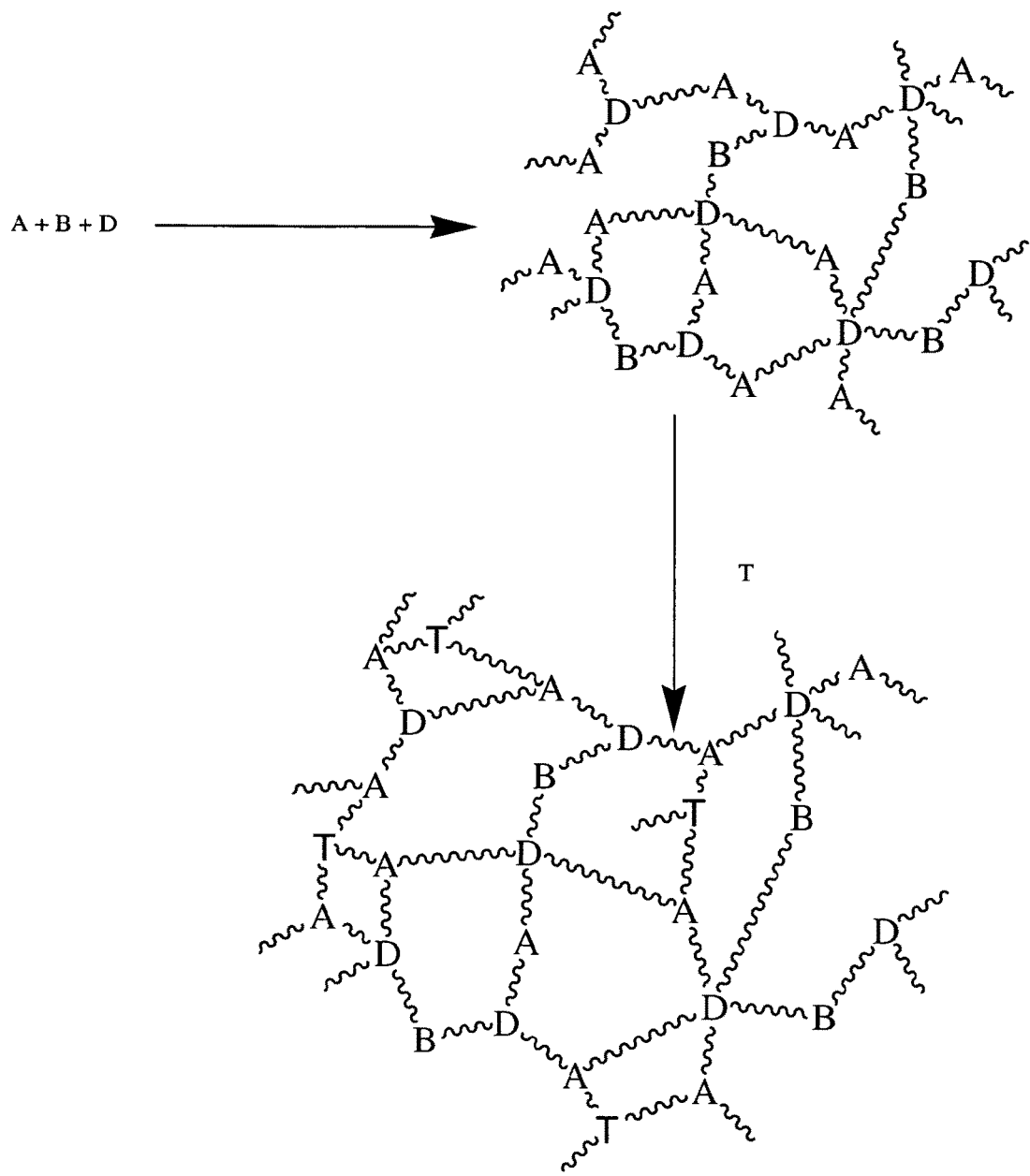
FIG. 20 depicts use of a multifunctional aziridine to form another cross-link connection between PEG units.

FIG. 20 illustrates an example in which a mixed A/B polymer is additionally crosslinked in the same manner shown in FIG. 19. The methodology in FIG. 20 allows one to manage hydrophobicity and the extent of crosslinking. Note that the level of aziridine-based crosslinkers can be adjusted to vary the ultimate cross-linking density, and therefore the swelling characteristics of the resulting hydrogel.

General Procedures for the Eye Surgeries Involving a Central Corneal Wound

An enucleated human eye (NC Eye Bank) is placed under a surgical microscope with the cornea facing upwards. The corneal epithelium is scraped with a 4.1 mm keratome blade, and then a 2.75 mm keratome blade is used to incise the central cornea. Next the keratome blade is used to form the 4.1 mm linear or stellate laceration. The wound is closed with either 3 interrupted 10-0 nylon sutures or the photo-crosslinkable or self-gelling crosslinkable biodendritic copolymer. Next, a 25 gauge butterfly needle connected to a syringe pump (kdScientific, Model 100 series) is inserted into the scleral wall adjacent to an ocular muscle. In order to measure the wound leaking pressures, the eye is connected to a cardiac transducer via a 20 gauge needle which is inserted 1 cm through the optic nerve. The needle is held in place with surgical tape. The pressure is then recorded. The syringe pump dispensed buffered saline solution (at a rate of 15-20 mL/hr) into the eye while the pressure is simultaneously read on the cardiac transducer. The syringe pump rate is maintained to achieve a continuous 1 mm Hg increase in pressure. The leak pressure is recorded as the pressure at which fluid was observed to leak from the eye under the surgical microscope.

General Procedures for Eye Surgeries Involving a Clear Corneal Wound

An enucleated human eye is secured under the operating microscope so that the cornea is oriented upwards, facing the microscope. A cardiac transducer(Hewlett-Packard, Palo Alto, Calif.) is primed and attached a 20-gauge needle (Sherwood Medical, St. Louis, Mo.) to the end of the saline tubing leading from the transducer. The needle is inserted into the optic nerve approximately 1 cm into the globe. It is not necessary to tie the needle and optic nerve together in order to secure the needle. If the optic nerve has been cut very short, the wound may leak. Eye Bank eyes with little to no optic nerve should not be used. Next, insert a 24-gauge butterfly needle on a saline filled 10-cc syringe (Becton Dickinson & Co., Rutherford, N.J.) connected to a syringe pump (KdScientific Model 100) into the anterior chamber through the peripheral cornea. Unless the eyes are very fresh, remove the epithelium by scraping with a blade edge and wipe with Opticel sponges (Wilson Ophthalmic Corp., Mustang, Okla.). A 3.0 mm dual beveled, angled slit knife (Alcon, Ft. Worth, Tex.) is used to make a 3.0 mm clear corneal linear incision (perpendicular to the plane of the cornea) 90 degrees from the orientation of the butterfly needle. Place the cardiac monitor on an arterial pressure setting and adjusted to zero mm Hg. Wipe the wound with an Opticel sponge to dry wound. If desired, the edges of the wound can be marked with a pen such as a Devon Skin Marker and Ruler, Regular tip #150 (Tyco Healthcare, Japan). Apply the mixed polymer to the dried wound as advised. Wait for the polymer to cure the advised amount of time. For the suture group, use one interrupted 10-0 nylon suture to close the 3.0 mm clear corneal linear incision using a needle holder and 0.12 forceps. Apply fluoroscein dye using Fluorets strip (Chavvin) to the polymer or wound itself and the surrounding area. Slowly inject saline into the eye via a syringe pump at a rate of 8 mL/hour to slowly increase the IOP as measured by the transducer. Use the cardiac transducer to monitor the IOP of the repaired eyes as done in similar experiments described in the literature. A Tonopen (Medtronic Solan, Jacksonville, Fla.) can be used to confirm the concordance of the transducer readings at low pressure readings. Check for signs of leakage through the corneal wound or around the polymer sealant. Record the IOP reading from the transducer when leaking through the wound or around the wound (i.e. the leaking pressure) is observed. Qualitatively observe the adherence of the polymer to the enucleated eye following the procedure.

General Procedure for Securing a LASIK Flap

LASIK (laser-assisted in situ keratomileusis) is the popular refractive surgical procedure where a thin, hinged corneal flap is created by a microkeratome blade. This flap is then moved aside to allow an excimer laser beam to ablate the corneal stromal tissue with extreme precision for the correction of myopia (near-sightedness) and astigmatism. At the conclusion of the procedure, the flap is then repositioned and allowed to heal. However, with trauma, this flap can become dislocated prior to healing, resulting in flap striae (folds) and severe visual loss. When this complication occurs, treatment involves prompt replacement of the flap and flap suturing. The use of sutures has limitations and drawbacks as discussed above. For the LASIK flap study, hinged corneal flaps were created using the Hansatome microkeratome system on four human donor eyebank eyes. Flap adherence is tested with dry Merocel sponges and tying forceps. Biodendrimer tissue adhesive is applied to the entire flap edge and then polymerized with an argon laser beam. The biodendrimer sealant successfully sealed the flap.

General Procedure for Eye Surgery Involving a Corneal Transplant

An enucleated human eye (NC Eye Bank) or pig eye is placed under a surgical microscope with the cornea facing upwards. A 5.5 mm central corneal trephination is made in an enucleated eye and then this newly formed button will then be autografted back to the original eye. For the biodendrimer sealant formulations, 20 µL sealant is applied to the wound edges to secure the autograft after 8 or 16 sutures were put into place. Leaking/bursting pressures for all eyes is determined as done for the corneal laceration studies. Evidence of major wound leakage or wound dehiscence is used as endpoints for bursting pressure studies. Fluorescein dye will be applied to the wound and the surrounding area using a Fluorets strip (Chavvin) to look for wound leakage. The use of 8 or 16 sutures affords a wound that leaks at less than 15 mm Hg. The crosslinkable polymer system is applied to the wound.

Methods of the Invention

One aspect of the present invention relates to a method of sealing a wound of a patient, comprising the steps of:

applying an effective amount of a polymerization agent to a wound of a patient, and exposing said polymerization agent to a compound of formula III sufficient to polymerize said polymerization agent, wherein said polymerization agent is a compound of formula Ia or formula Ib; and formula Ia is represented by:

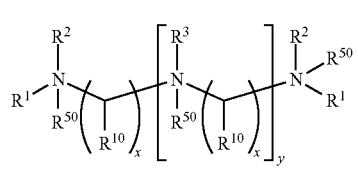

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —X$^1$—[C($R^4$)$_2$]$_d$N($R^5$)C(O)N($R^5$)$_2$, —X$^1$—[C($R^4$)$_2$]$_d$OC(O)CH$_2$C(O)—alkyl,

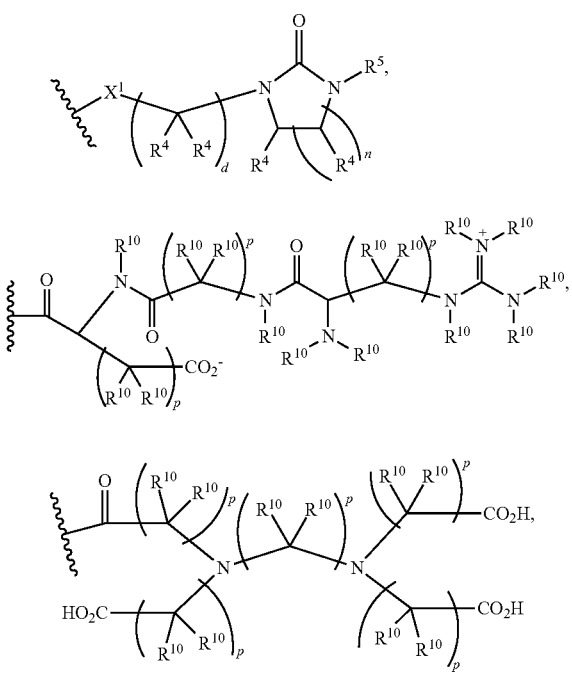

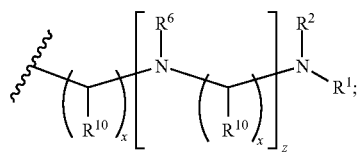

or a carbohydrate radical;

$R^3$ represents independently for each occurrence H or

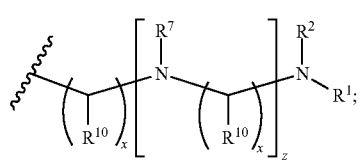

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

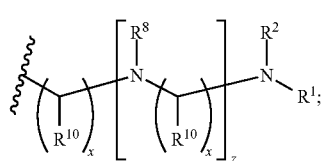

$R^7$ represents independently for each occurrence H or

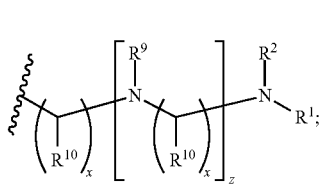

$R^8$ represents independently for each occurrence H or

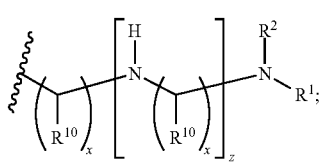

$R^9$ represents independently for each occurrence H or

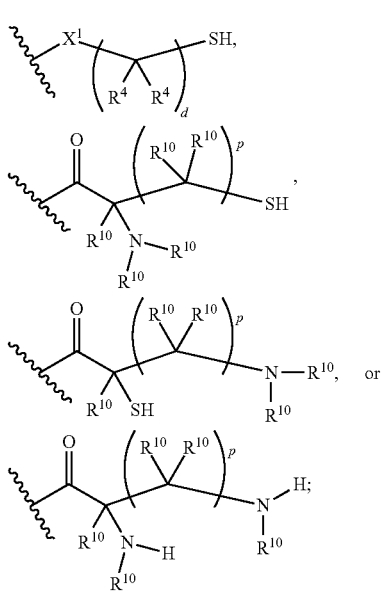

$R^{10}$ represents independently for each occurrence H or $(C_1\text{-}C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$, d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

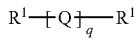

wherein

Q represents independently for each occurrence

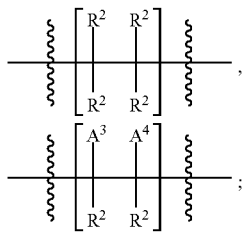

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence $-CO_2R^4$;

$A^2$ represents independently for each occurrence H or $-CO_2R^4$;

$A^3$ represents independently for each occurrence $-N(R^1)(R^{50})(R^3)$;

$A^4$ represents independently for each occurrence H, alkyl, aryl, $-CO_2R^4$, or $-OC(O)R^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, $-C(O)NH_2$, $-X^1-[C(R^5)_2]_dN(R^5)C(O)NH_2$,

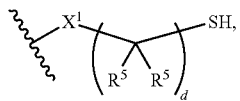

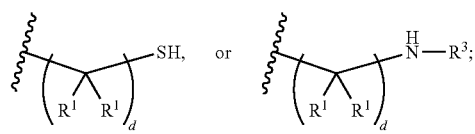

$R^4$ represents independently for each occurrence H, alkyl, aryl, aralkyl,

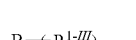

$R^5$ represents independently for each occurrence H or alkyl;

$X^1$ represents independently for each occurrence a bond or $-C(O)-$;

d represents independently for each occurrence 1, 2, 3, 4, 5, 6, 7, or 8;

p represents independently for each occurrence 1, 2, 3, 4, or 5; and q is an integer from about 50 to about 100,000; and formula III is represented by:

$$B-(R^{1-III})_{2,3,or 4} \quad III$$

wherein $R^{1-III}$ represents independently for each occurrence $-(C(R^{2-III})_2)_fC(O)R^{3-III}$, $-C(O)(C(R^{2-III})_2)_fC(O)R^{3-III}$, $-(C(R^{2-III})_2)_fR^{4-III}$, $-C(O)(C(R^{2-III})_2)_fR^{4-III}$, $-(C(R^{2-III})_2)_fC(O)N(R^{5-III})-[A^{4-III}]_t-C(O)-R^{3-III}$, $-(C(R^{2-III})_2)_fCO_2-[A^{4-III}]_t-C(O)-R^{3-III}$,

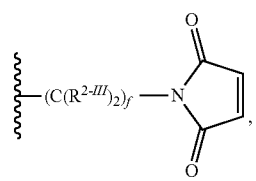

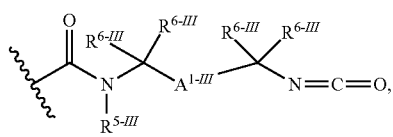

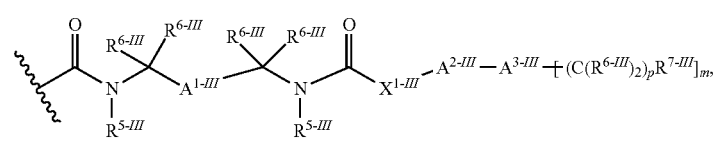

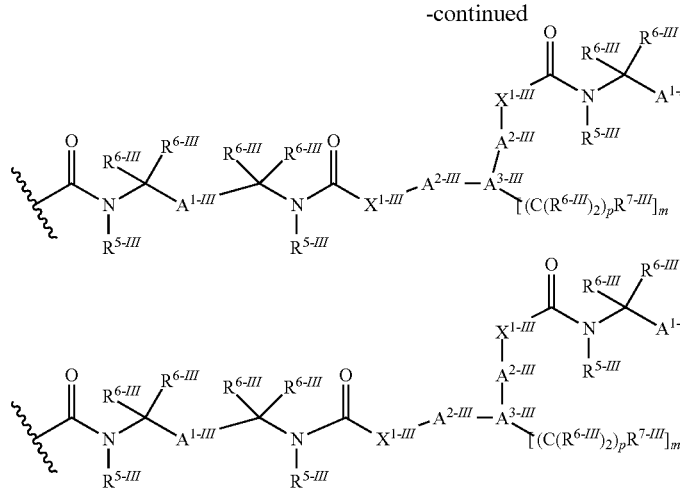

$R^{2-III}$ a represents independently for each occurrence H, alkyl, or halogen;

$R^{3-III}$ represents independently for each occurrence H, alkyl, fluoroalkyl, chloroalkyl, —CH$_2$NO$_2$,

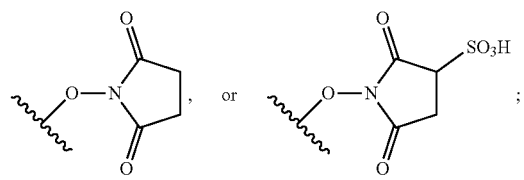 [SMILES: *ON1C(=O)CCC1=O ; *ON1C(=O)CC(S(=O)(=O)O)C1=O]

;

$R^{4-III}$ represents independently for each occurrence —N=C=O, —N=C=S,

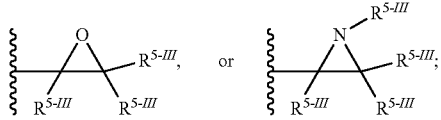

;

$R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O,

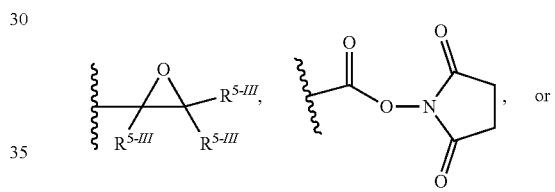

$R^{8-III}$ represents independently for each occurrence

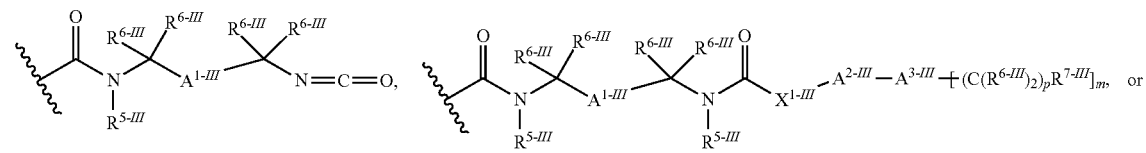

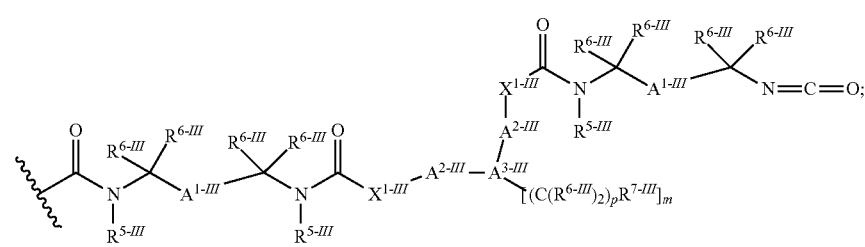

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

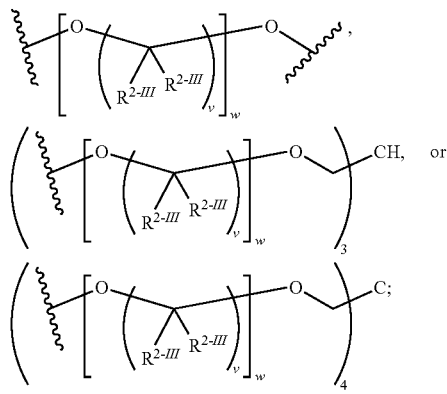

$X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

Another aspect of the present invention relates to a method of augmenting soft tissue or filling a void of a patient, comprising the steps of:

applying an effective amount of a polymerization agent to soft tissue or a void of a patient, and exposing said polymerization agent to a compound of formula III sufficient to polymerize said polymerization agent, wherein said polymerization agent is a compound of formula Ia or formula Ib; and formula Ia is represented by:

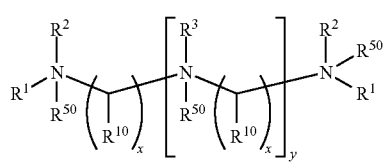

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, $-C(O)$-alkyl, $-C(O)N(R^5)_2$, $-X^1-[C(R^4)_2]_d N(R^5)C(O)N(R^5)_2$, $-X^1-[C(R^4)_2]_d OC(O)CH_2 C(O)$-alkyl,

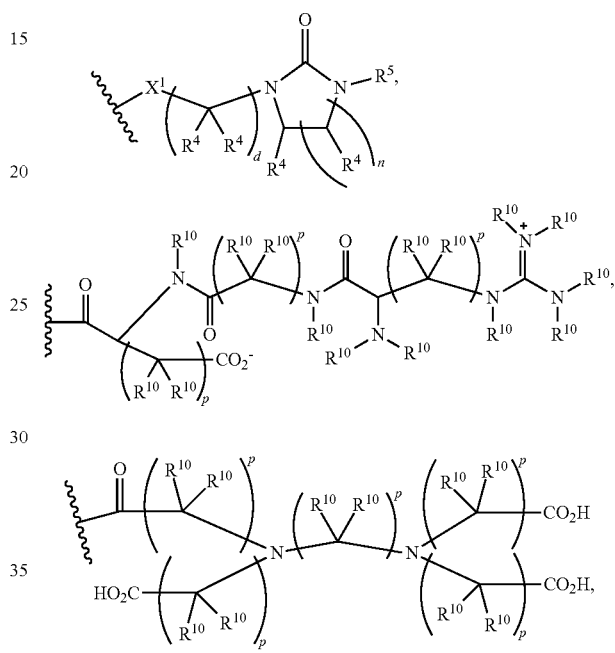

or a carbohydrate radical;

$R^3$ represents independently for each occurrence H or

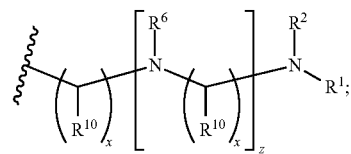

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

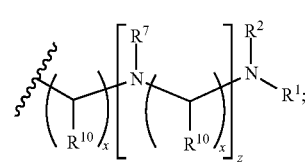

$R^7$ represents independently for each occurrence H or

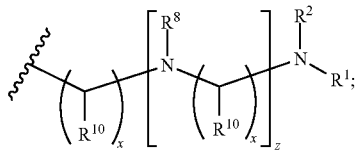

$R^8$ represents independently for each occurrence H or

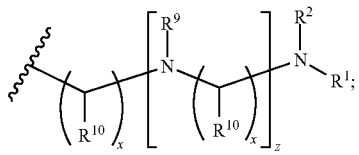

$R^9$ represents independently for each occurrence H or

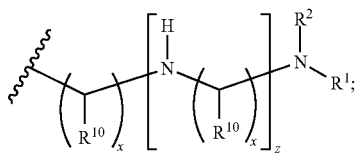

$R^{10}$ represents independently for each occurrence H or $(C_1-C_3)$alkyl;
$X^1$ represents independently for each occurrence a bond or —C(O)—;
$A^1$ represents independently for each occurrence H, —C(O)NH$_2$, —X$^1$—[C(R$^4$)$_2$]$_d$N(R$^5$)C(O)NH$_2$,

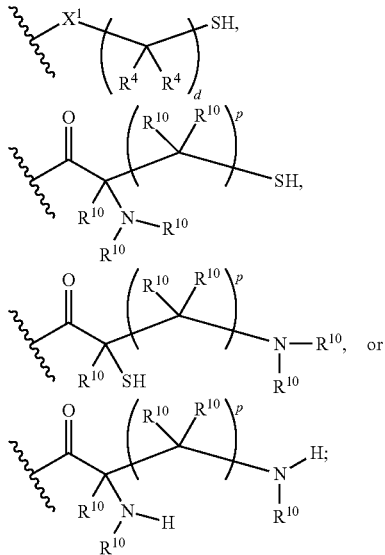

d represents independently for each occurrence 1, 2, 3, 4, 5, 6, 7, or 8;
n represents independently for each occurrence 1, 2, 3, or 4;
p represents independently for each occurrence 1, 2, 3, 4, or 5;

x represents independently for each occurrence 1, 2, 3, 4, or 5;
y is an integer in the range of 1 to about 40,000;
z represents independently for each occurrence an integer in the range of 0 to about 20,000; and
provided at least about 5% of $R^1$ is $A^1$, and the sum of y and z is less than about 50,000; formula Ib is represented by:

wherein
Q represents independently for each occurrence

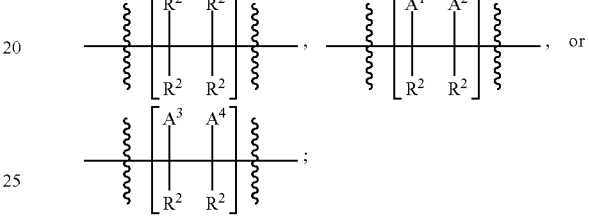

$R^{50}$ independently for each occurrence is an electron pair or a substituent selected from the group consisting of H, alkyl, and aralkyl; when an instance of $R^{50}$ represents a substituent a pharmaceutically acceptable counterion is present;
$A^1$ represents independently for each occurrence —CO$_2$R$^4$;
$A^2$ represents independently for each occurrence H or —CO$_2$R$^4$.
$A^3$ represents independently for each occurrence —N(R$^1$)(R$^{50}$)(R$^3$);
$A^4$ represents independently for each occurrence H, alkyl, aryl, —CO$_2$R$^4$, or —OC(O)R$^4$;
$R^1$ represents independently for each occurrence H, alkyl or polymerization initiator;
$R^2$ represents independently for each occurrence H, alkyl, aryl, or aralkyl;
$R^3$ represents independently for each occurrence H, alkyl, aryl, aralkyl, acyl, —C(O)NH$_2$, —X$^1$—[C(R$^5$)$_2$]$_d$N(R$^5$)C(O)NH$_2$,

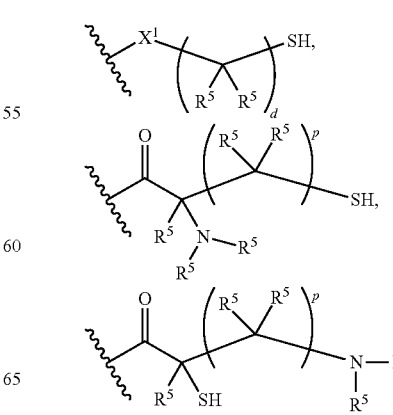

-continued

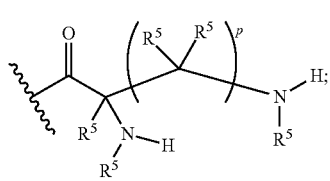

$R^4$ represents independently for each occurrence H, alkyl, aryl, aralkyl,

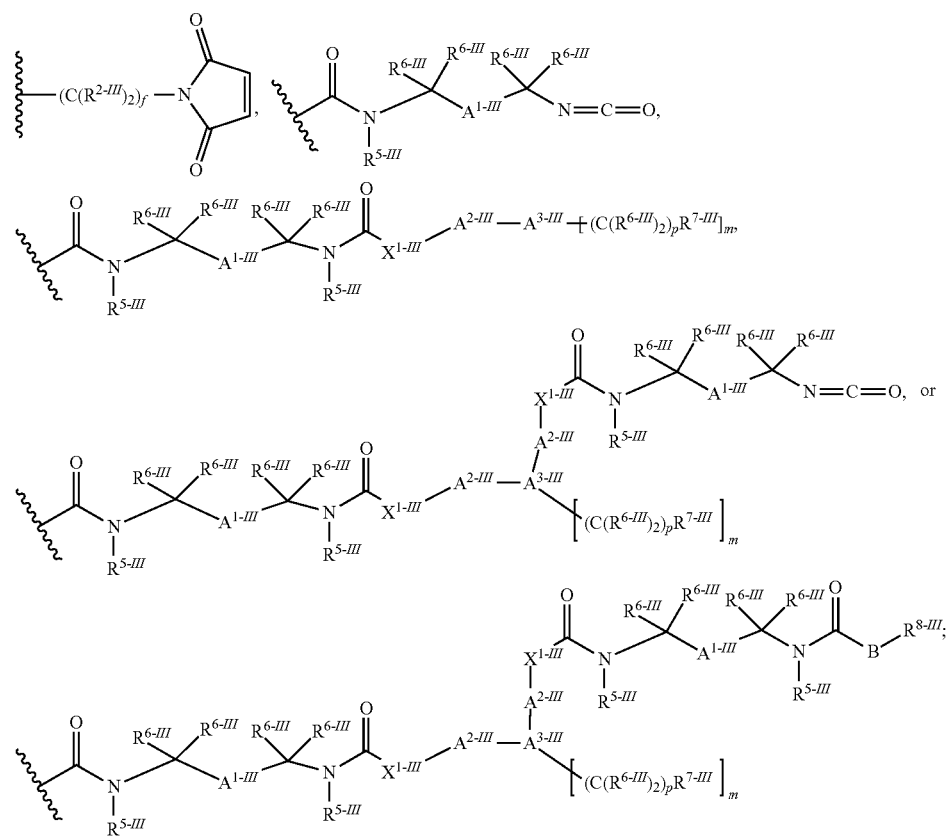

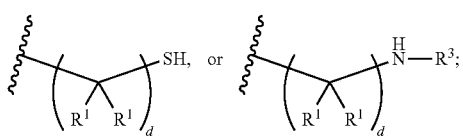

$R^5$ represents independently for each occurrence H or alkyl;

$X^1$ represents independently for each occurrence a bond or —C(O)—;

d represents independently for each occurrence 1, 2, 3, 4, 5, 6, 7, or 8;

p represents independently for each occurrence 1, 2, 3, 4, or 5; and q is an integer from about 50 to about 100,000; and formula III is represented by:

$$B{+}(R^{1\text{-}III})_{2,\ 3,\ or\ 4} \qquad III$$

wherein
$R^{1\text{-}III}$ represents independently for each occurrence —(C($R^{2\text{-}III}$)$_2$)$_f$C(O)$R^{3\text{-}III}$, —C(O)(C($R^{2\text{-}III}$)$_2$)$_f$C(O)$R^{3\text{-}III}$, —(C($R^{2\text{-}III}$)$_2$)$_f$$R^{4\text{-}III}$, —C(O)(C($R^{2\text{-}III}$)$_2$)$_f$$R^{4\text{-}III}$, —(C($R^{2\text{-}III}$)$_2$)$_f$C(O)N($R^{5\text{-}III}$)-[$A^{4\text{-}III}$]$_t$—C(O)—$R^{3\text{-}III}$, —(C($R^{2\text{-}III}$)$_2$)$_f$CO$_2$-[$A^{4\text{-}III}$]$_t$—C(O)—$R^{3\text{-}III}$, $R^{2\text{-}III}$ represents independently for each occurrence H, alkyl, or halogen;

$R^{3\text{-}III}$ represents independently for each occurrence H, alkyl, fluoroalkyl, chloroalkyl, —CH$_2$NO$_2$,

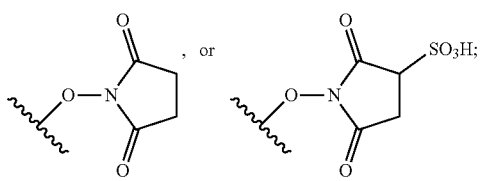 [SMILES: *ON1C(=O)CCC1=O ; *ON1C(=O)CC(S(=O)(=O)O)C1=O]

$R^{4\text{-}III}$ represents independently for each occurrence —N=C=O, —N=C=S,

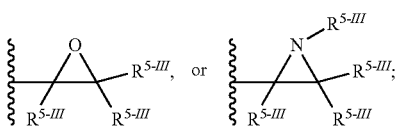

$R^{5-III}$ represents independently for each occurrence H, alkyl, or aralkyl;

$R^{6-III}$ represents independently for each occurrence H or $(C_1\text{-}C_6)$alkyl;

$R^{7-III}$ represents independently for each occurrence —$CO_2H$, —$(C(R^{6-III})_2)_p N{=}C{=}O$,

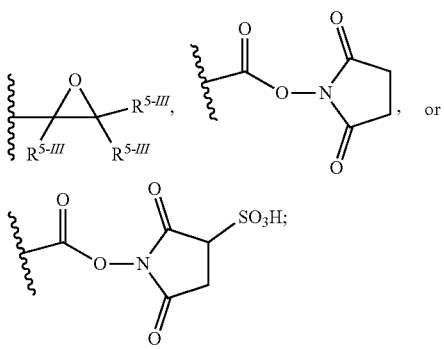

$R^{8-III}$ represents independently for each occurrence

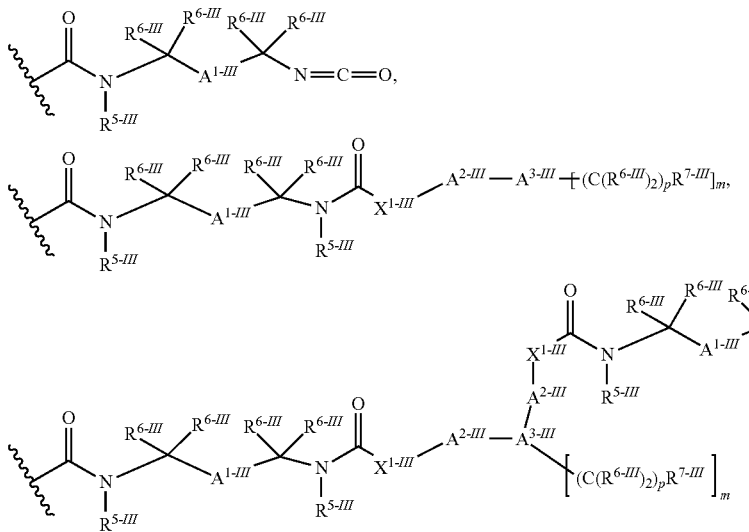

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

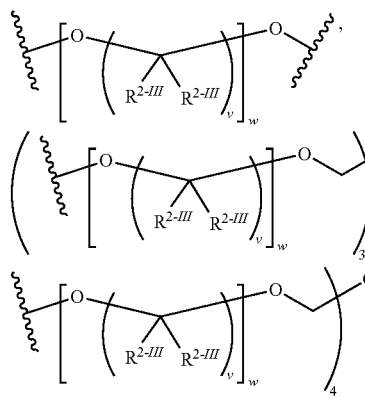

$X^{1-III}$ represents independently for each occurrence O or —$N(R^{5-III})$—;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

Another aspect of the present invention relates to a method of adhering tissue of a patient, comprising the steps of:

applying an effective amount of a polymerization agent to a first tissue of a patient, exposing said polymerization agent to a compound of formula III to form an adhesive composition, and contacting said adhesive composition with a second tissue of a patient, wherein the amount of said compound of formula III is sufficient to polymerize said polymerization agent and said polymerization agent is a compound of formula Ia or formula Ib; and formula Ia is represented by:

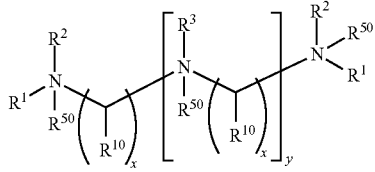

Ia wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —$X^1$—[C($R^4$)$_2$]$_d$N($R^5$)C(O)N($R^5$)$_2$, —$X^1$—[C($R^4$)$_2$]$_d$OC(O)CH$_2$C(O)—alkyl,

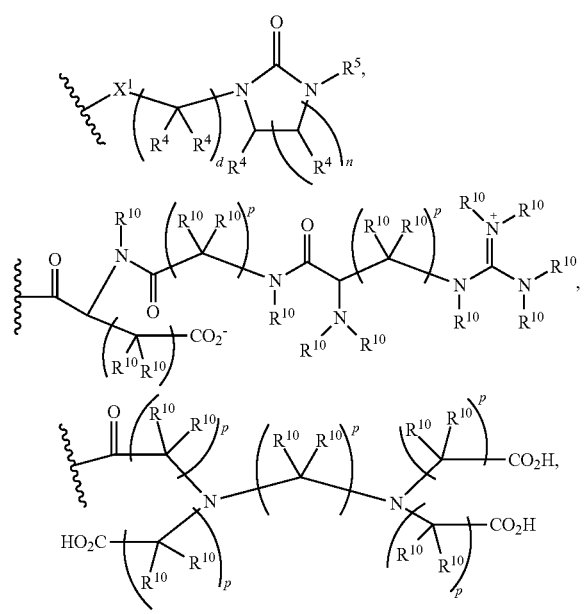

or a carbohydrate radical;

$R^3$ represents independently for each occurrence H or

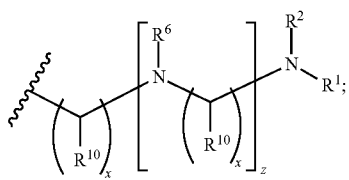

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

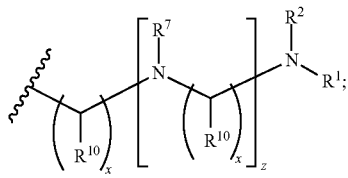

$R^7$ represents independently for each occurrence H or

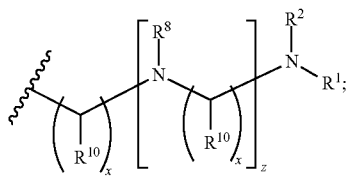

$R^8$ represents independently for each occurrence H or

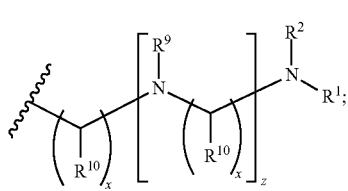

$R^9$ represents independently for each occurrence H or

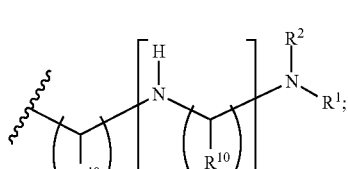

$R^{10}$ represents independently for each occurrence H or ($C_1$-$C_3$)alkyl;

$X^1$ represents independently for each occurrence a bond or —C(O)—;

$A^1$ represents independently for each occurrence H, —C(O)NH$_2$, —$X^1$—[C($R^4$)$_2$]$_d$N($R^5$)C(O)NH$_2$,

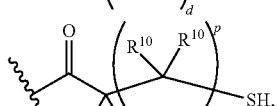

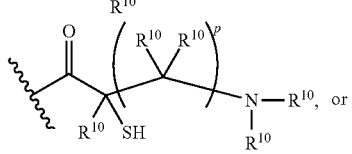

-continued

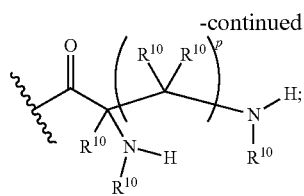

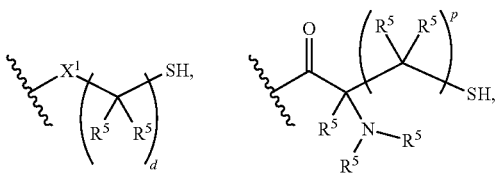

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

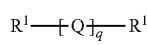   Ib wherein

Q represents independently for each occurrence

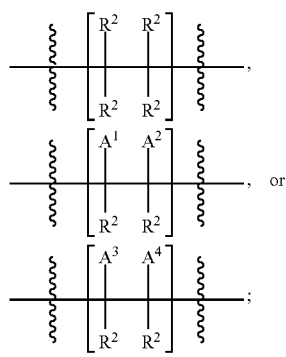

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —$CO_2R^4$;

$A^2$ represents independently for each occurrence H or —$CO_2R^4$;

$A^3$ represents independently for each occurrence —$N(R^1)(R^{50})(R^3)$;

$A^4$ represents independently for each occurrence H, alkyl, aryl, —$CO_2R^4$, or —$OC(O)R^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —$C(O)NH_2$, —$X^1$—$[C(R^5)_2]_dN(R^5)C(O)NH_2$,

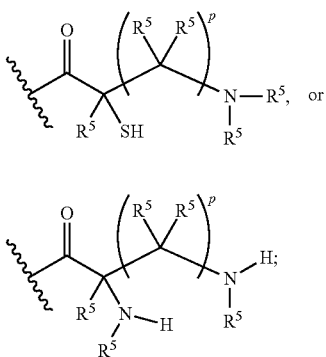

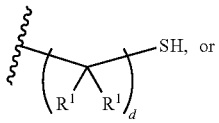

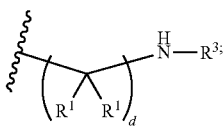

$R^5$ represents independently for each occurrence H or alkyl;

$X^1$ represents independently for each occurrence a bond or —C(O)—;

d represents independently for each occurrence 1, 2, 3, 4, 5, 6, 7, or 8;

p represents independently for each occurrence 1, 2, 3, 4, or 5; and q is an integer from about 50 to about 100,000; and formula III is represented by:

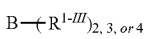   III wherein $R^{1-III}$ represents independently for each occurrence —(C$(R^{2-III})_2)_jC(O)R^{3-III}$, —C(O)(C$(R^{2-III})_2)_kC(O)R^{3-III}$, —(C$(R^{2-III})_2)_jR^{4-III}$, —C(O)(C$(R^{2-III})_2)_kR^{4-III}$, —(C$(R^{2-III})_2)_jC(O)N(R^{5-III})$-[$A^{4-III}]_t$—C(O)—$R^{3-III}$, —(C$(R^{2-III})_2)_jCO_2$-[$A^{4-III}]_t$-C(O)—$R^{3-III}$,

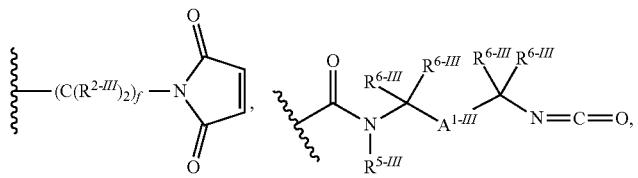

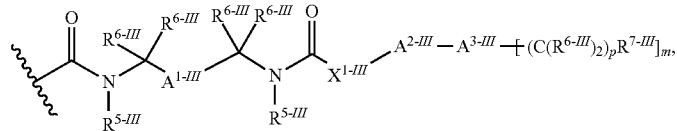

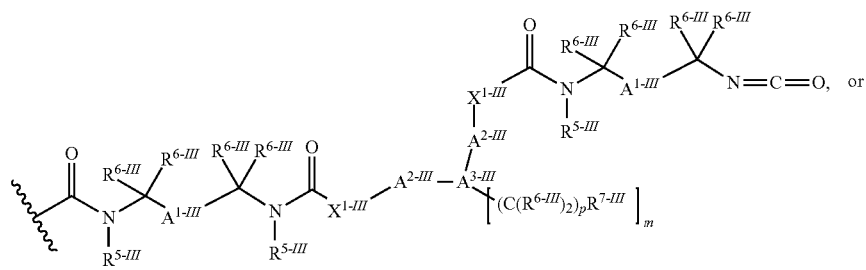

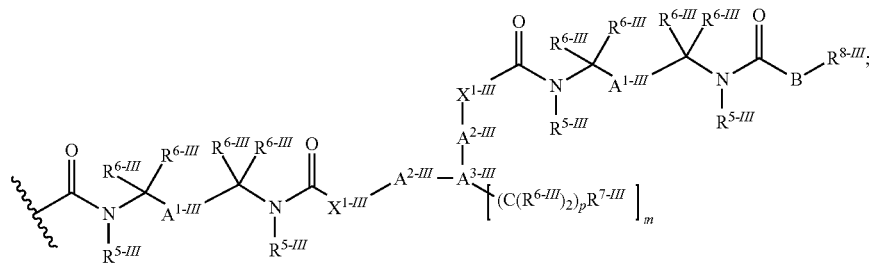

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$,

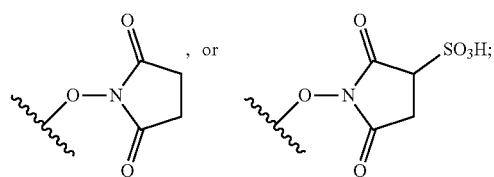 [SMILES: *ON1C(=O)CCC1=O ; *ON1C(=O)CC(S(=O)(=O)O)C1=O]

$R^{4-III}$ represents independently for each occurrence —N=C=O, —N=C=S,

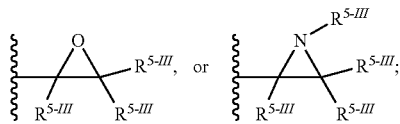

$R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O,

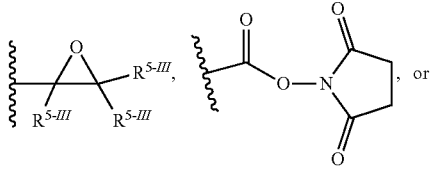

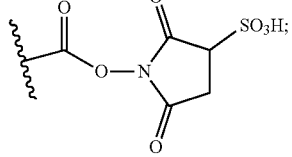

$R^{8-III}$ represents independently for each occurrence

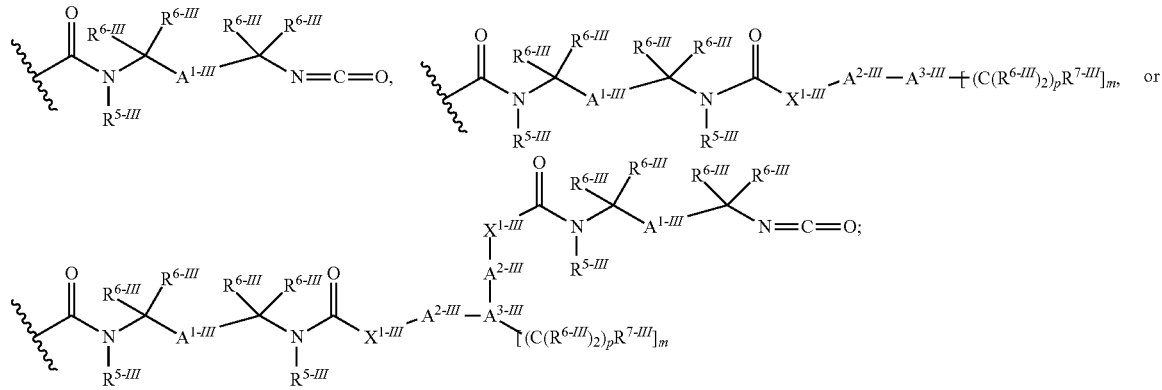

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

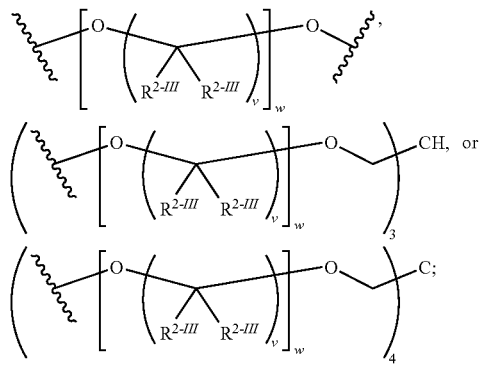

$X^{1-III}$ represents independently for each occurrence O or —N($R^{5-III}$)—;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

In certain instances, the present invention relates to the aforementioned method, wherein f and k each represent independently for each occurrence 1, 2, 3, 4, 5, 6, 7, 8, or 9.

In certain instances, the present invention relates to the aforementioned method, wherein said polymerization agent is a compound of formula Ia.

In certain instances, the present invention relates to the aforementioned method, wherein said polymerization agent is a compound of formula Ia, $R^{10}$ is H, and x is 2 or 3.

In certain instances, the present invention relates to the aforementioned method, wherein said polymerization agent is a compound of formula Ia, $R^{10}$ is H, x is 2 or 3, at least about ½ of $R^1$ are H, and at least about ½ of $R^2$ are H.

In certain instances, the present invention relates to the aforementioned method, wherein said polymerization agent is a compound of formula Ia, $R^{10}$ is H, x is 2 or 3, at least about ½ of $R^1$ are H, at least about ½ of $R^2$ are H, and the sum of y and z is an integer in the range of about 20 to about 500.

In certain instances, the present invention relates to the aforementioned method, wherein said polymerization agent is a compound of formula Ia, $R^{10}$ is H, x is 2 or 3, at least about 90% of $R^1$ are $A^1$, and $A^1$ represents independently for each occurrence H,

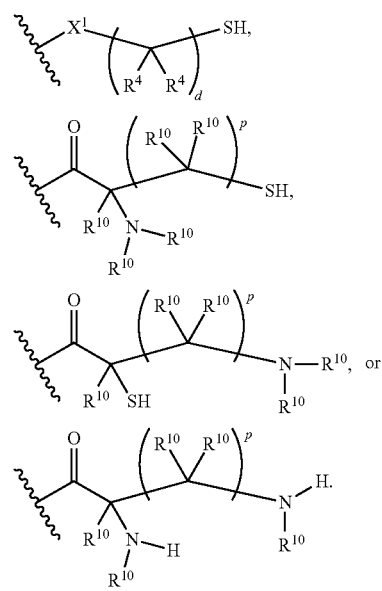

In certain instances, the present invention relates to the aforementioned method, wherein said polymerization agent is a compound of formula Ia, $R^{10}$ is H, x is 2 or 3, at least about 90% of $R^1$ and $R^2$ are $A^1$, and $A^1$ represents independently for each occurrence H,

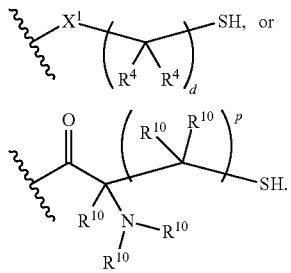

In certain instances, the present invention relates to the aforementioned method, wherein said polymerization agent is a compound of formula Ia, $R^{10}$ is H, x is 2 or 3, at least about 95% of $R^1$ and $R^2$ are H, and the sum of y and z is an integer in the range of about 20 to about 500.

In certain instances, the present invention relates to the aforementioned method, wherein said polymerization agent is a compound of formula Ia, $R^{10}$ is H, and x is 3 or 4.

In certain instances, the present invention relates to the aforementioned method, wherein said polymerization agent is a compound of formula Ia, $R^{10}$ is H, x is 3 or 4, and at least about 95% of $R^1$ and $R^2$ are H.

In certain instances, the present invention relates to the aforementioned method, wherein said polymerization agent is $NH_2(CH_2)_2N(H)(CH_2)_4N(H)(CH_2)_2NH_2$.

In certain instances, the present invention relates to the aforementioned method, wherein said polymerization agent is $NH_2(CH_2)_3N(H)(CH_2)_4N(H)(CH_2)_3NH_2$.

In certain instances, the present invention relates to the aforementioned method, wherein said polymerization agent is a compound of formula Ib.

In certain instances, the present invention relates to the aforementioned method, wherein said polymerization agent is a compound of formula Ib, and $A^3$ is —N(H)$R^3$.

In certain instances, the present invention relates to the aforementioned method, wherein said polymerization agent is a compound of formula Ib, $A^3$ is —N(H)$R^3$, and $R^1$ and $R^3$ are H.

In certain instances, the present invention relates to the aforementioned method, wherein said polymerization agent is a compound of formula Ib, $A^3$ is —N(H)$R^3$, $R^1$ and $R^3$ are H, and x is 0.

In certain instances, the present invention relates to the aforementioned method, wherein said polymerization agent is a compound of formula Ib, and $A^1$ is —$CO_2R^4$.

In certain instances, the present invention relates to the aforementioned method, wherein said polymerization agent is a compound of formula Ib, $A^1$ is —$CO_2R^4$, $R^4$ is

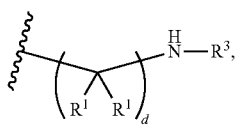

and $R^1$ and $R^3$ are H.

In certain instances, the present invention relates to the aforementioned method, wherein said polymerization agent is a compound of formula Ib, $A^1$ is —$CO_2R^4$, $R^4$ is

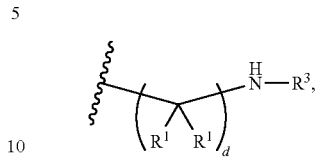

$R^1$ and $R^3$ are H, and x is 0.

In certain instances, the present invention relates to the aforementioned method, wherein w is independently for each occurrence an integer in the range of about 50 to about 250.

In certain instances, the present invention relates to the aforementioned method, wherein w is independently for each occurrence an integer in the range of about 60 to about 90.

In certain instances, the present invention relates to the aforementioned method, wherein $R^{1-III}$ is —(C($R^{2-III}$)$_2$)$_k$C(O)$R^3$ or —C(O)(C($R^{2-III}$)$_2$)$_k$C(O)$R^{3-III}$, $R^{2-III}$ is H, and $R^{3-III}$ is

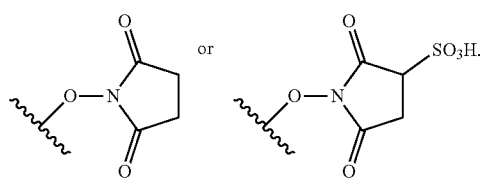 [SMILES: *ON1C(=O)CCC1=O ; "or" ; *ON1C(=O)CC(S(=O)(=O)O)C1=O]

In certain instances, the present invention relates to the aforementioned method, wherein $R^{1-III}$ is —(C($R^{2-III}$)$_2$)$_k$C(O)$R^{3-III}$ or —C(O)(C($R^{2-III}$)$_2$)$_k$C(O)$R^{3-III}$, $R^{2-III}$ is H, and $R^{3-III}$ is

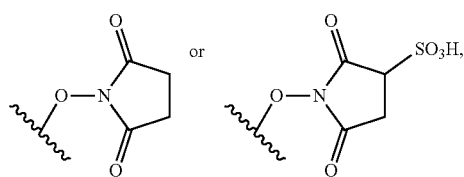 [SMILES: *ON1C(=O)CCC1=O ; *ON1C(=O)CC(S(=O)(=O)O)C1=O]

B is

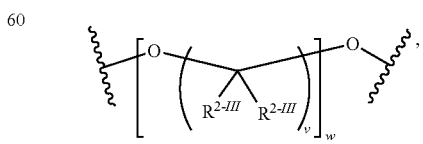

and v is 2.

In certain instances, the present invention relates to the aforementioned method, $R^{1-III}$ is $-(C(R^{2-III})_2)_kC(O)R^{3-III}$ or $-C(O)(C(R^{2-III})_2)_kC(O)R^{3-III}$, $R^{2-III}$ is H, $R^{3-III}$ is

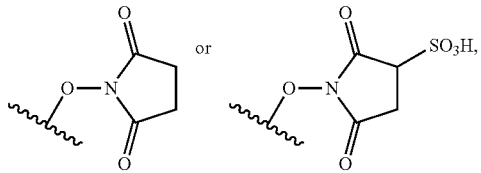 [SMILES: *ON1C(=O)CCC1=O ; "or" ; *ON1C(=O)CC(S(=O)(=O)O)C1=O]

B is

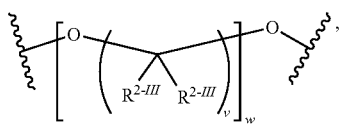

v is 2, and w is independently for each occurrence an integer in the range of about 15-90.

In certain instances, the present invention relates to the aforementioned method, wherein $R^{1-III}$ is $-(C(R^{2-III})_2)_kC(O)R^{3-III}$ or $-C(O)(C(R^{2-III})_2)_kC(O)R^{3-III}$, $R^{2-III}$ is H, $R^{3-III}$ is

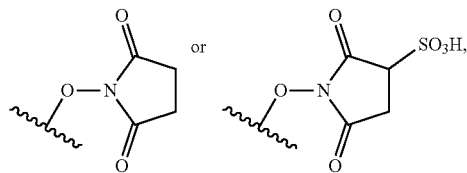 [SMILES: *ON1C(=O)CCC1=O ; *ON1C(=O)CC(S(=O)(=O)O)C1=O]

B is

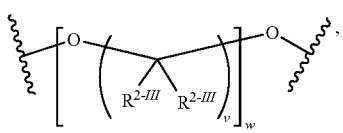

and v is 2.

In certain instances, the present invention relates to the aforementioned method, wherein $R^{1-III}$ is $-(C(R^{2-III})_2)_kC(O)R^{3-III}$ or $-C(O)(C(R^{2-III})_2)_kC(O)R^{3-III}$, $R^{2-III}$ is H, $R^{3-III}$ is

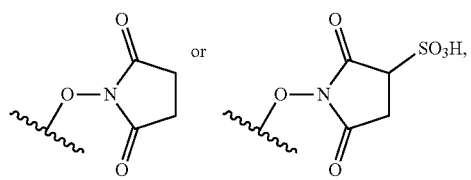 [SMILES: *ON1C(=O)CCC1=O ; *ON1C(=O)CC(S(=O)(=O)O)C1=O]

B is

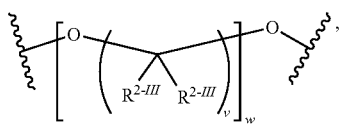

v is 2, and w is independently for each occurrence an integer in the range of about 15-90, B is

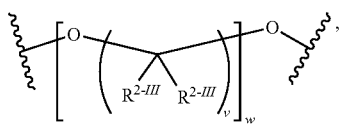

v is 2, said polymerization agent is a compound of formula Ia, $R^{10}$ is H, x is 2, at least about ½ of $R^1$ are H, and at least about ½ of $R^2$ are H.

In certain instances, the present invention relates to the aforementioned method, wherein $R^{1-III}$ is $-(CH_2)_3C(O)R^{3-III}$, $R^{3-III}$ is

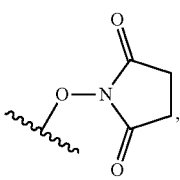 [SMILES: *ON1C(=O)CCC1=O]

B is

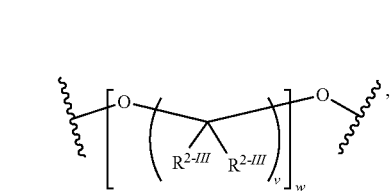

In certain instances, the present invention relates to the aforementioned method, wherein $R^{1-III}$ is $-C(O)(CH_2)_2C(O)R^{3-III}$ or $-C(O)(CH_2)_3C(O)R^{3-III}$, $R^{3-III}$ is

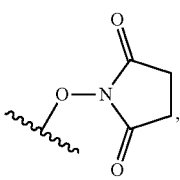 [SMILES: *ON1C(=O)CCC1=O]

B is
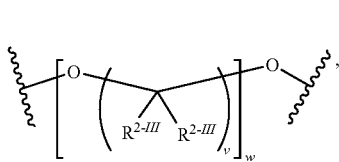
and v is 2.
In certain instances, the present invention relates to the aforementioned method, wherein formula III is
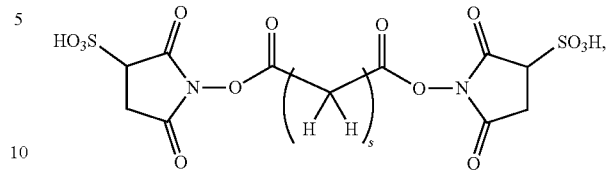
and s is an integer in the range of about 1-20 inclusive.
In certain instances, the present invention relates to the aforementioned method, wherein $R^{1\text{-}III}$ represents independently for each occurrence
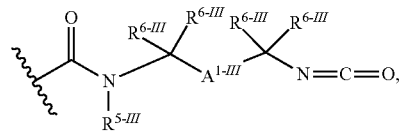
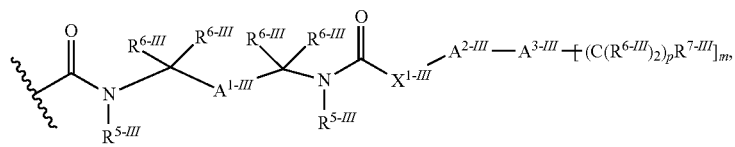
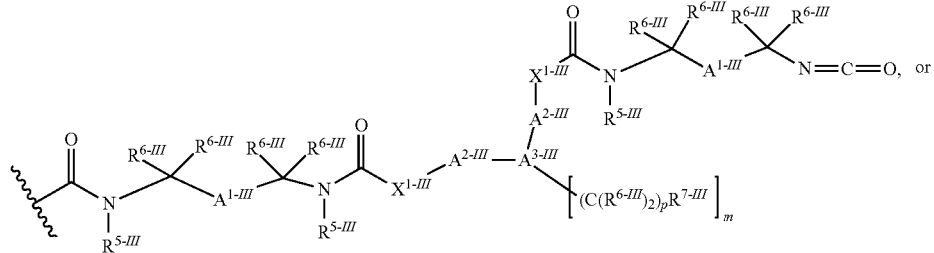
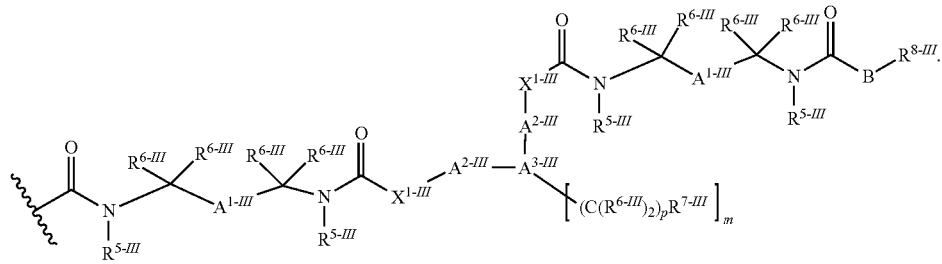

In certain instances, the present invention relates to the aforementioned method, wherein, B is

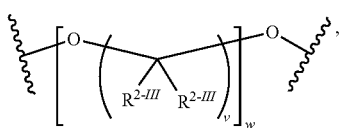

$R^{2\text{-}III}$ is H, and $A^{1\text{-}III}$ is aryl diradical.

In certain instances, the present invention relates to the aforementioned method, wherein, B is

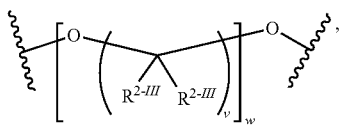

$R^{2\text{-}III}$ is H, and $A^{1\text{-}III}$ is optionally substituted phenyl diradical.

In certain instances, the present invention relates to the aforementioned method, wherein, B is

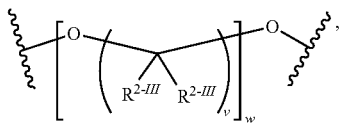

$R^{2\text{-}III}$ is H, $A^{2\text{-}III}$ is a bond, and $A^{3\text{-}III}$ is alkyl diradical.

In certain instances, the present invention relates to the aforementioned method, wherein, B is

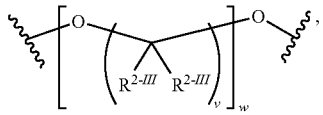

$R^{2\text{-}III}$ is H, $A^{2\text{-}III}$ is a bond, $A^{3\text{-}III}$ is alkyl diradical, and $R^{7\text{-}III}$ is

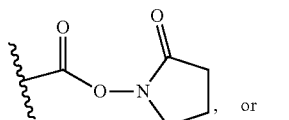, or

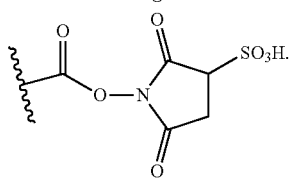

In certain instances, the present invention relates to the aforementioned method, wherein, B is

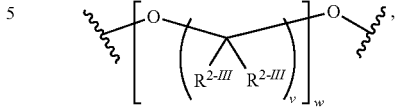

$R^{2\text{-}III}$ is H, $A^{2\text{-}III}$ is aryl diradical, $A^{3\text{-}III}$ is aralkyl diradical, and $R^{7\text{-}III}$ is

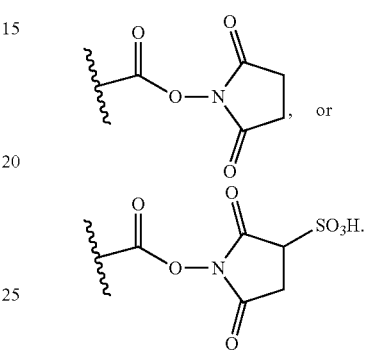

In certain instances, the present invention relates to the aforementioned method, wherein, B is

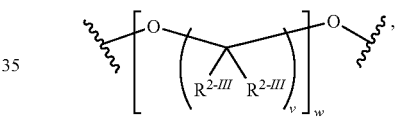

$R^{2\text{-}III}$ is H, $A^{2\text{-}III}$ is optionally substituted phenyl diradical, $A^{3\text{-}III}$ is optionally substituted benzyl diradical, and $R^{7\text{-}III}$ is

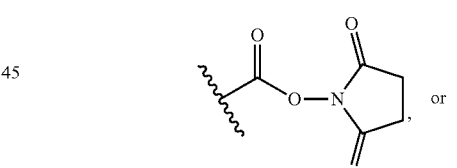, or

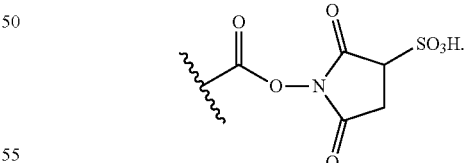

In certain instances, the present invention relates to the aforementioned method, wherein, B is

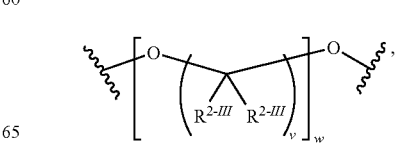

$R^{2-III}$ is H, v is 2, and $R^{1-III}$ is

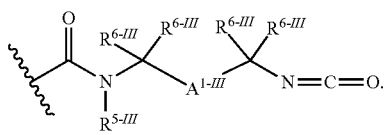

In certain instances, the present invention relates to the aforementioned method, wherein, B is

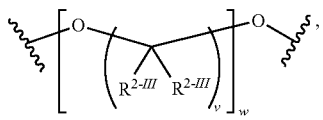

$R^{2-III}$ is H, v is 2, $R^{1-III}$ is

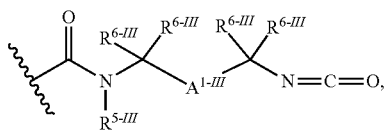

$R^{6-III}$ is $(C_1-C_4)$alkyl, and $A^{1-III}$ is aryl diradical.

In certain instances, the present invention relates to the aforementioned method, wherein, B is

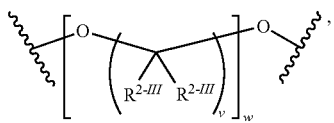

$R^{2-III}$ is H, v is 2, $R^{1-III}$ is

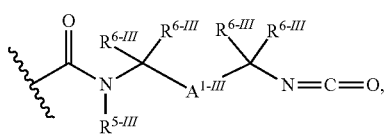

$R^{6-III}$ is $(C_1-C_4)$alkyl, and $A^{1-III}$ is optionally substituted phenyl diradical.

In certain instances, the present invention relates to the aforementioned method, wherein, B is

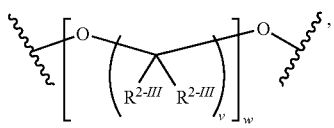

$R^{2-III}$ is H, v is 2, $R^{1-III}$ is

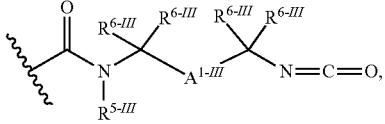

$R^{6-III}$ is methyl, and $A^{1-III}$ is phenyl diradical.

In certain instances, the present invention relates to the aforementioned method, wherein, B is

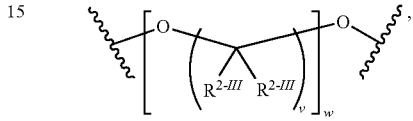

$R^{2-III}$ is H, v is 2, $R^{1-III}$ is

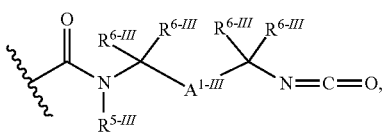

$R^{6-III}$ is methyl, $A^{1-III}$ is phenyl diradical, said polymerization agent is a compound of formula Ia, $R^{10}$ is H, x is 2, at least about ½ of $R^1$ are H, and at least about ½ of $R^2$ are H.

In certain embodiments, the present invention relates to the aforementioned method, wherein said polymerization agent is a compound of formula Ia, said compound of formula Ia has a weight average molecular weight of about 600 to about 10,000 Daltons, said compound of formula III has a weight average molecular weight of about 500 to about 20,000 Daltons, and the molar ratio of said compound of formula Ia to said compound of formula III is about 0.025:1 to about 0.4:1.

In certain embodiments, the present invention relates to the aforementioned method, wherein $R^{1-III}$ is $-(C(R^{2-III})_2)_fC(O)N(R^{5-III})-[A^{4-III}]_tC(O)-R^{3-III}$, $A^{4-III}$ is an alkyl diradical, t and f are 1, $R^{2-III}$ and $R^{5-III}$ are hydrogen, and R is

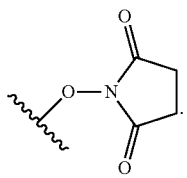 [SMILES: *ON1C(=O)CCC1=O]

In certain embodiments, the present invention relates to the aforementioned method, further comprising the step of sterilizing said polymerization agent.

In certain embodiments, the present invention relates to the aforementioned method, further comprising the step of sterilizing said compound of formula III.

In certain embodiments, the present invention relates to the aforementioned method, wherein said sterilizing is performed by treatment with ethylene oxide, hydrogen peroxide, heat, gamma irradiation, electron beam irradiation, microwave irradiation, or visible light irradiation.

In certain embodiments, the present invention relates to the aforementioned method, said said polymerization agent and said compound of formula III have a sterility assurance level of at least about $10^{-3}$.

In certain embodiments, the present invention relates to the aforementioned method, said polymerization agent and said compound of formula III have a sterility assurance level of at least about 10-6.

In certain embodiments, the present invention relates to the aforementioned method, wherein said patient is a primate, bovine, equine, feline, or canine.

In certain embodiments, the present invention relates to the aforementioned method, wherein said patient is a human.

In certain embodiments, the present invention relates to the aforementioned method, wherein said wound is an ophthalmic wound.

In certain embodiments, the present invention relates to the aforementioned method, wherein said wound is a wound to the cornea of an eye.

In certain embodiments, the present invention relates to the aforementioned method, wherein said wound is an epithelial defect, corneal incision, corneal laceration, corneal perforation, corneal ulceration, retinal hole, filtering bleb, corneal transplant, trabeculectomy incision, sclerotomy incision, blepharoplasty, or skin incision.

In certain embodiments, the present invention relates to the aforementioned method, wherein said wound is an epithelial defect, corneal incision, corneal laceration, corneal perforation, or corneal ulceration.

In certain embodiments, the present invention relates to the aforementioned method, wherein said wound is a corneal incision or corneal laceration.

In certain embodiments, the present invention relates to the aforementioned method, wherein said wound is a located in the dura.

In certain embodiments, the present invention relates to the aforementioned method, wherein said wound is a located in the lung tissue.

In certain embodiments, the present invention relates to the aforementioned method, wherein said wound is a tissue plane.

In certain embodiments, the present invention relates to the aforementioned method, wherein said wound is in a vein or artery.

In certain embodiments, the present invention relates to the aforementioned method, wherein said wound is less than about 25 mm long.

In certain embodiments, the present invention relates to the aforementioned method, wherein said wound is less than about 15 mm long.

In certain embodiments, the present invention relates to the aforementioned method, wherein said wound is less than about 10 mm long.

In certain embodiments, the present invention relates to the aforementioned method, wherein said wound is less than about 5 mm long.

In certain embodiments, the present invention relates to the aforementioned method, wherein said void is less than about 15 mm in diameter.

In certain embodiments, the present invention relates to the aforementioned method, wherein said void is less than about 10 mm in diameter.

In certain embodiments, the present invention relates to the aforementioned method, wherein said void is less than about 5 mm in diameter.

In certain embodiments, the present invention relates to the aforementioned method, wherein said first tissue and said second tissue are independently selected from the group consisting of skin, muscle, blood vessel, tendon, cartilage, ligament, liver, kidney, lung, heart, intestinal tissue, stomach, and corneal tissue.

In certain embodiments, the present invention relates to the aforementioned method, wherein said polymerization agent is sterile.

Another aspect of the present invention relates to a method of sealing a wound of a patient, comprising the steps of:

exposing an effective amount of a polymerization agent to a compound of formula III to form an adhesive composition, and applying said adhesive composition to a wound of a patient, wherein said polymerization agent is a compound of formula Ia or formula Ib; and formula Ia is represented by:

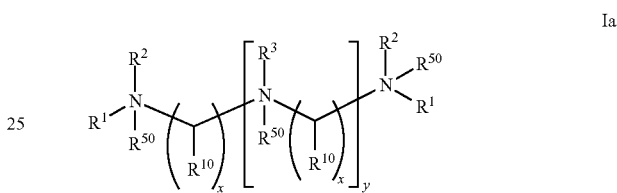

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)O[C(R^4)_2]N(R^5)_2$, —C(O)N(R^5)[C(R^4)_2]_dN(R^5)_2$, —C(O)N(R^5)_2$, —X^1—[C(R^4)_2]_dN(R^5)C(O)N(R^5)_2$, —X^1—[C(R^4)_2],N(R^5)C(O)N(R^5)_2$, —X^1—[C(R^4)_2]_dOC(O)CH_2C(O)-alkyl,

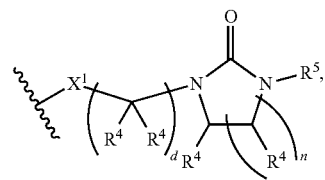

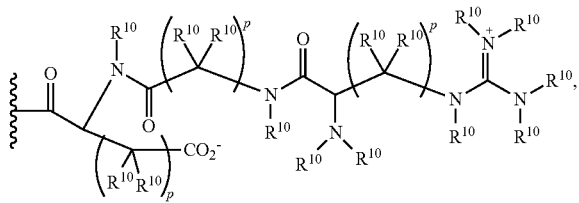

-continued

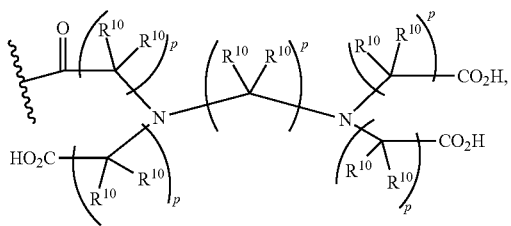

or a carbohydrate radical;

$R^3$ represents independently for each occurrence H or

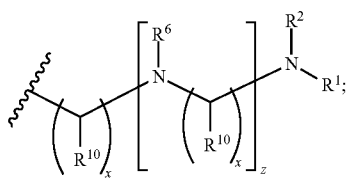

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

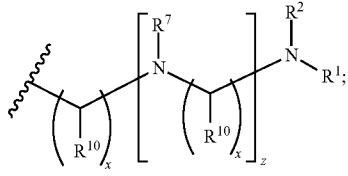

$R^7$ represents independently for each occurrence H or

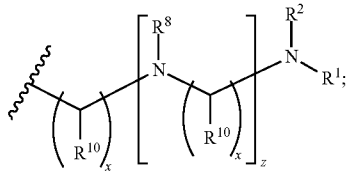

$R^8$ represents independently for each occurrence H or

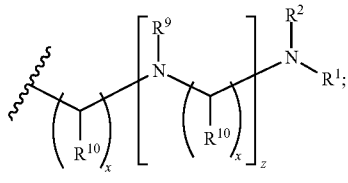

$R^9$ represents independently for each occurrence H or

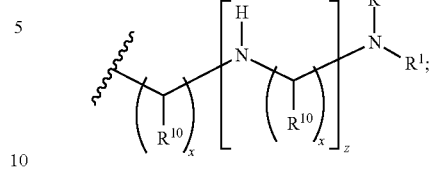

$R^{10}$ represents independently for each occurrence H or $(C_1$-$C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$,

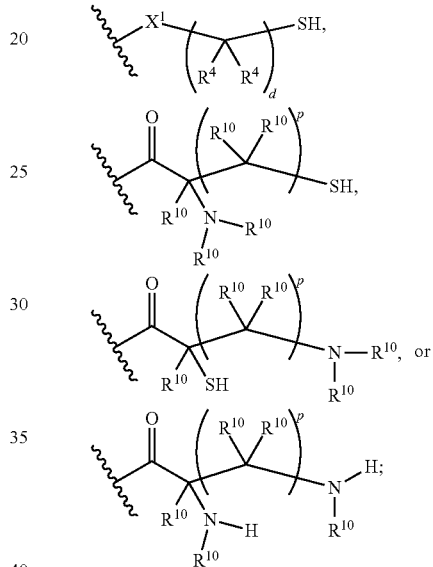

d represents independently for each occurrence 1, 2, 3, 4, 5, 6, 7, 8, 9, or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

$$R^1\!-\!\!\left(Q\right)_{\!q}\!\!-\!R^1 \qquad \text{Ib}$$

wherein

Q represents independently for each occurrence

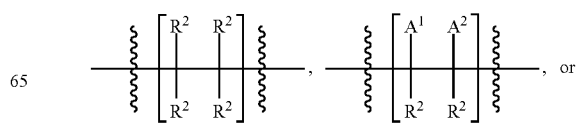, or

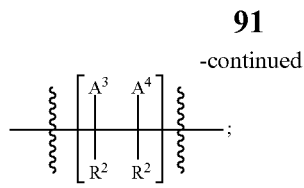

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —CO$_2$R$^4$;

$A^2$ represents independently for each occurrence H or —CO$_2$R$^4$;

$A^3$ represents independently for each occurrence —N(R$^1$)(R$^{50}$)(R$^3$);

$A^4$ represents independently for each occurrence H, alkyl, aryl, —CO$_2$R$^4$, or —OC(O)R$^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —C(O)NH$_2$, —X$^1$—[C(R$^5$)$_2$]$_d$N(R$^5$)C(O)NH$_2$,

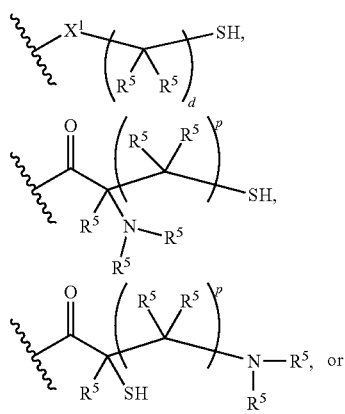

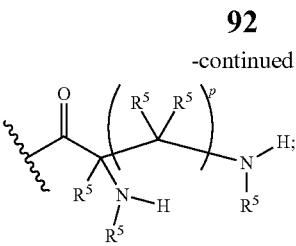

$R^4$ represents independently for each occurrence H, alkyl, aryl, aralkyl,

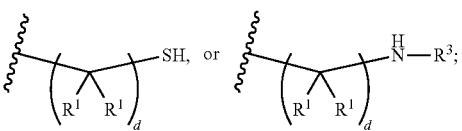

$R^5$ represents independently for each occurrence H or alkyl;

$X^1$ represents independently for each occurrence a bond or —C(O)—;

d represents independently for each occurrence 1, 2, 3, 4, 5, 6, 7, 8, 9, or 10;

p represents independently for each occurrence 1, 2, 3, 4, or 5; and q is an integer from about 50 to about 100,000; and formula III is represented by:

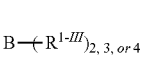

III wherein $R^{1\text{-}III}$ represents independently for each occurrence —(C(R$^{2\text{-}III}$)$_2$)$_j$C(O)R$^{3\text{-}III}$, —C(O)(C(R$^{2\text{-}III}$)$_2$)$_k$C(O)R$^{3\text{-}III}$, —(C(R$^{2\text{-}III}$)$_2$)$_j$R$^{4\text{-}III}$, —C(O)(C(R$^{2\text{-}III}$)$_2$)$_k$R$^{4\text{-}III}$, —(C(R$^{2\text{-}III}$)$_2$)$_j$C(O)N(R$^{5\text{-}III}$)-[A$^{4\text{-}III}$]$_t$—C(O)—R$^{3\text{-}III}$, —(C(R$^{2\text{-}III}$)$_2$)$_j$CO$_2$-[A$^{4\text{-}III}$]$_t$-C(O)—R$^{3\text{-}III}$,

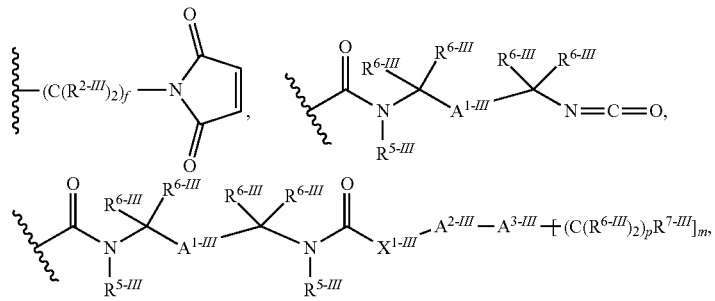

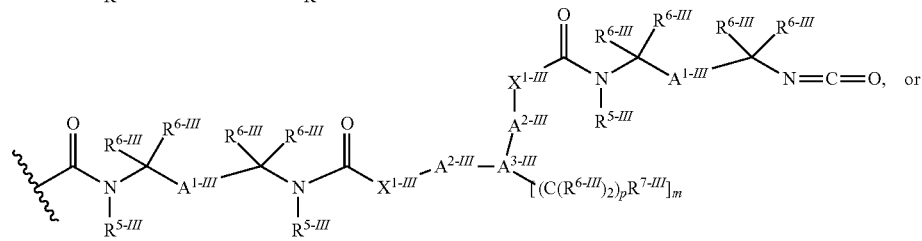

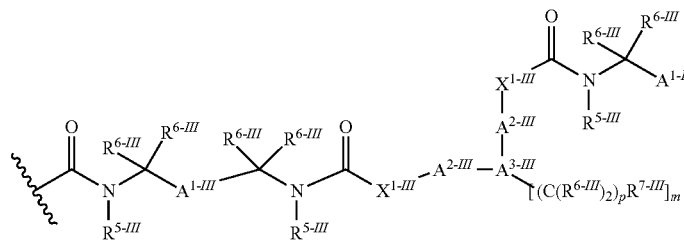

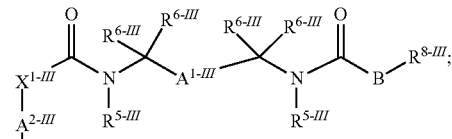

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$,

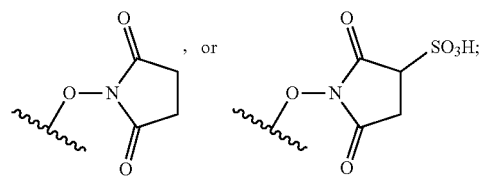 [SMILES: *ON1C(=O)CCC1=O ; *ON1C(=O)CC(S(=O)(=O)O)C1=O]

$R^{4-III}$ represents independently for each occurrence —N=C=O, —N=C=S,

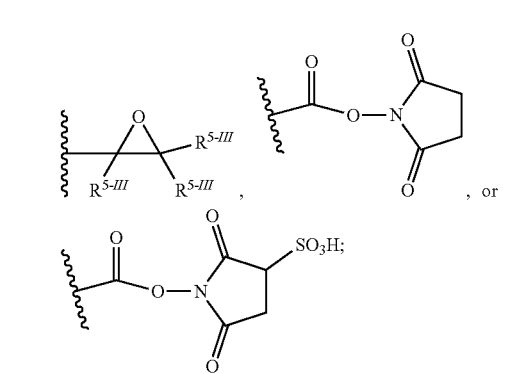

$R^{8-III}$ represents independently for each occurrence

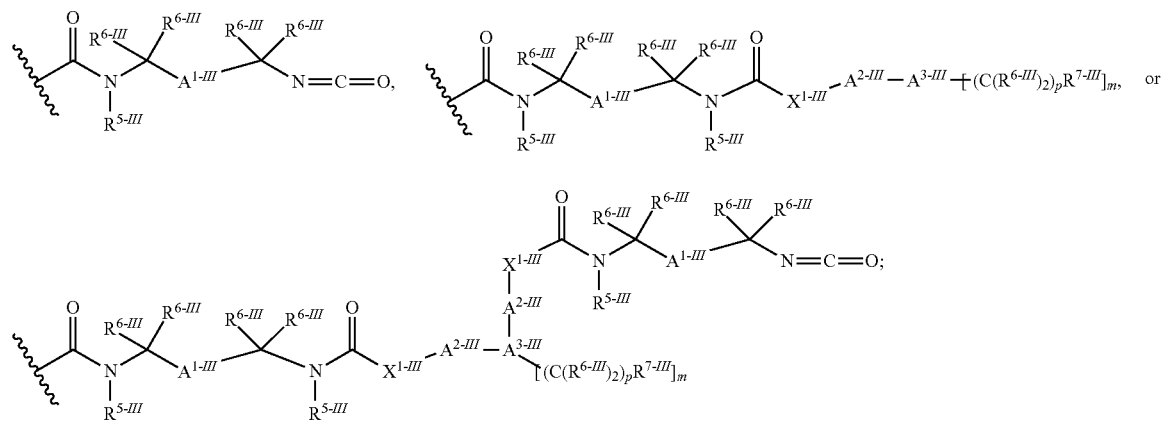

$R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O, $A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

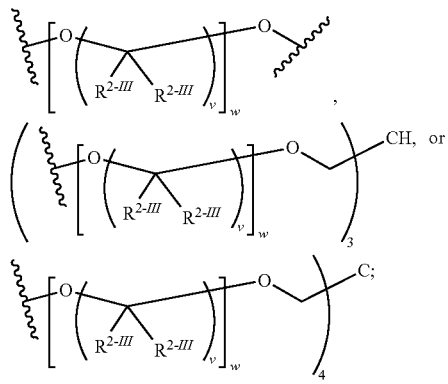

, $X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

Another aspect of the present invention relates to a method of augmenting soft tissue or filling a void of a patient, comprising the steps of:

exposing an effective amount of a polymerization agent to a compound of formula III to form an adhesive composition, and applying said adhesive composition to soft tissue or a void of a patient, wherein said polymerization agent is a compound of formula Ia or formula Ib; and formula a is represented by:

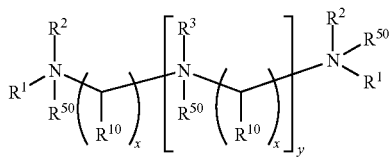

Ia wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, $-C(O)$-alkyl, $-C(O)O$ $[C(R^4)_2]_dN(R^5)_2$, $-C(O)N(R^5)[C(R^4)_2]_dN(R^5)_2$, $-C(O)N$ $(R^5)_2$, $-X^1-[C(R^4)_2]_dN(R^5)C(O)N(R^5)_2$, $-X^1-$ $[C(R^4)_2]_dN(R^5)C(O)N(R^5)_2$, $-X^1-[C(R^4)_2]_dOC(O)CH_2C$ (O)-alkyl,

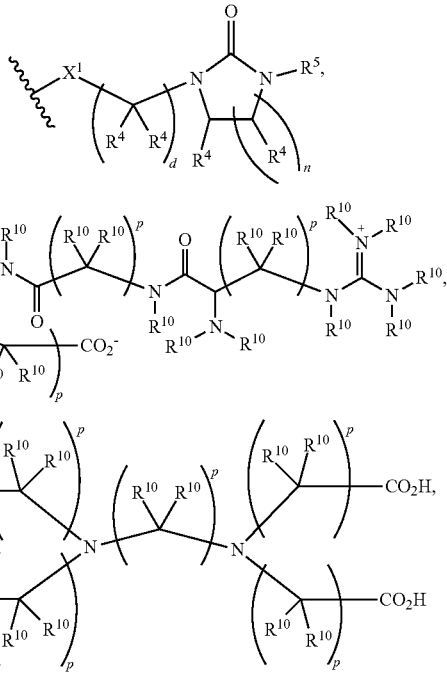

or a carbohydrate radical;

$R^3$ represents independently for each occurrence H or

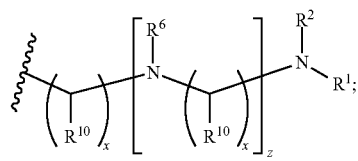

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

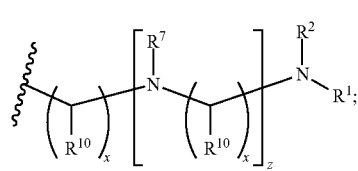

$R^7$ represents independently for each occurrence H or

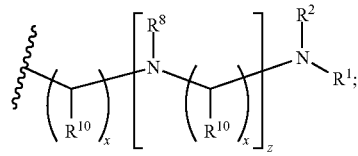

$R^8$ represents independently for each occurrence H or

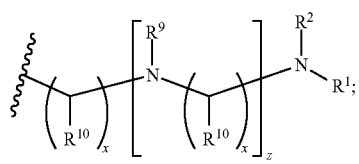

$R^9$ represents independently for each occurrence H

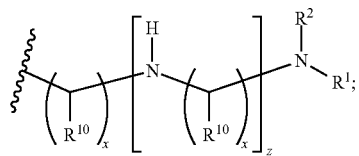

$R^{10}$ represents independently for each occurrence H or $(C_1-C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$,

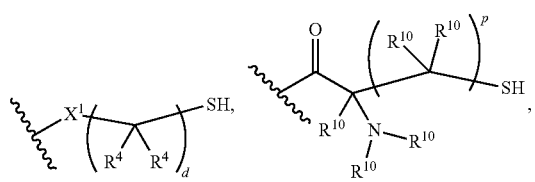

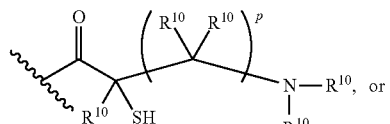

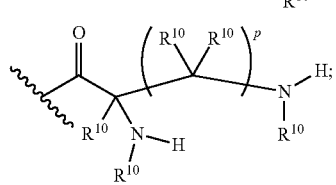

d represents independently for each occurrence 1, 2, 3, 4, 5, 6, 7, 8, 9, or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

Ib

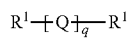

wherein

Q represents independently for each occurrence

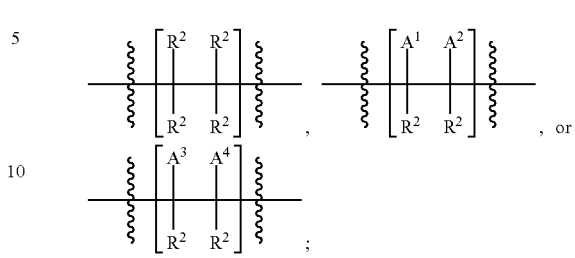

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —CO$_2$R$^4$;

$A^2$ represents independently for each occurrence H or —CO$_2$R$^4$;

$A^3$ represents independently for each occurrence —N(R$^1$)(R$^{50}$)(R$^3$);

$A^4$ represents independently for each occurrence H, alkyl, aryl, —CO$_2$R$^4$, or —OC(O)R$^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —C(O)NH$_2$, X$^1$—[C(R$^5$)$_2$]$_d$N(R$_5$)C(O)NH$_2$,

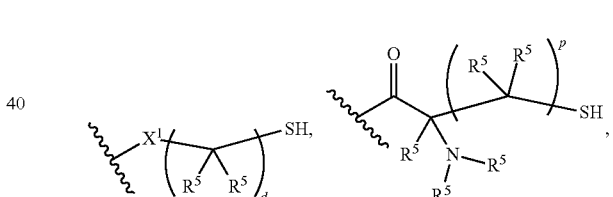

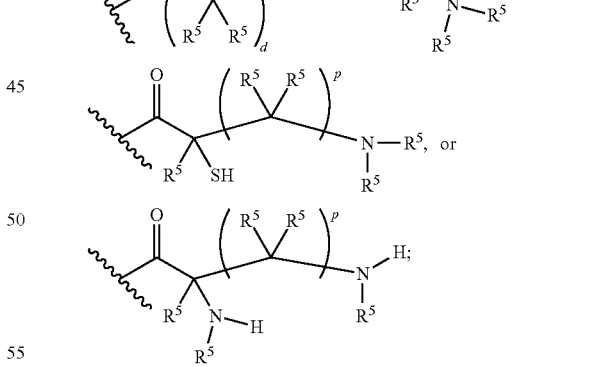

$R^4$ represents independently for each occurrence H, alkyl, aryl, aralkyl,

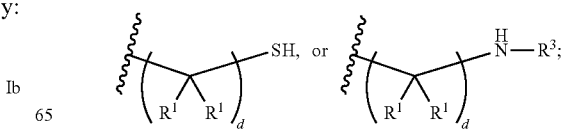

$R^5$ represents independently for each occurrence H or alkyl;

$X^1$ represents independently for each occurrence a bond or —C(O)—;

d represents independently for each occurrence 1, 2, 3, 4, 5, 6, 7, 8, 9 or 10;

p represents independently for each occurrence 1, 2, 3, 4, or 5; and q is an integer from about 50 to about 100,000; and formula III is represented by:

$$B-(R^{1-III})_{2, 3, or 4} \quad\quad III$$

wherein $R^{1-III}$ represents independently for each occurrence —(C($R^{2-III}$)$_2$)$_f$C(O)$R^{3-III}$, —C(O)(C($R^{2-III}$)$_2$)$_k$C(O)$R^{3-III}$, —(C($R^{2-III}$)$_2$)$_f$$R^{4-III}$, —C(O)(C($R^{2-III}$)$_2$)$_k$$R^{4-III}$, —(C($R^{2-III}$)$_2$)$_f$C(O)N($R^{5-III}$)-[$A^{4-III}$]$_t$—C(O)—$R^{3-III}$, —(C($R^{2-III}$)$_2$)$_f$CO$_2$-[$A^{4-III}$]$_t$—C(O)—$R^{3-III}$,

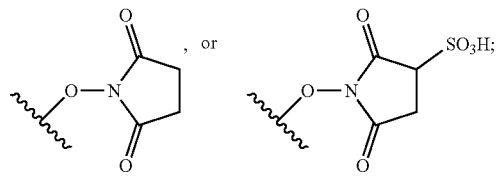 [SMILES: *ON1C(=O)CCC1=O ; "or" ; *ON1C(=O)CC(S(=O)(=O)O)C1=O]

$R^{4-III}$ represents independently for each occurrence —N=C=O, —N=C=S,

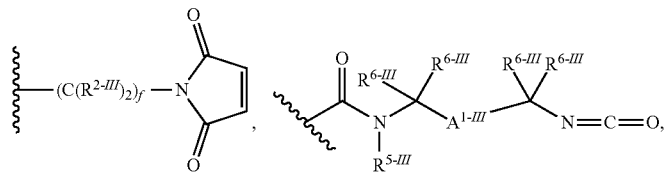

$R^{5-III}$ represents independently for each occurrence H, alkyl, or aralkyl;

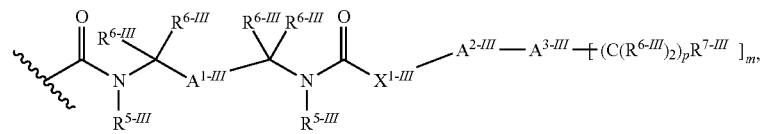

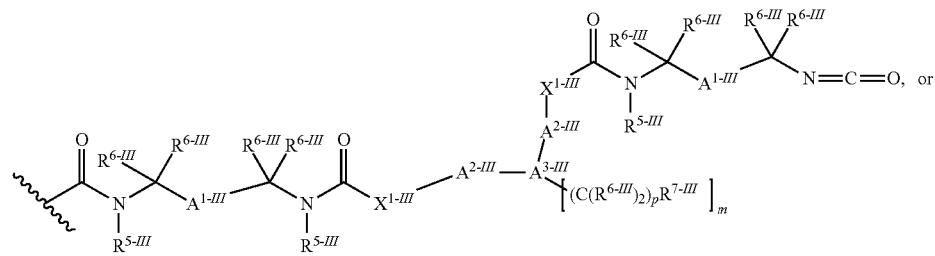

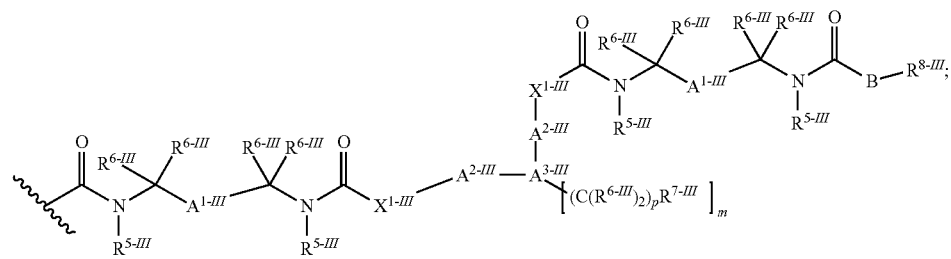

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$, $R^{6-III}$ represents independently for each occurrence H or (C$_1$-C$_6$)alkyl;

$R^{7-III}$ represents independently for each occurrence —CO$_2$H, —(C($R^{6-III}$)$_2$)$_p$N=C=O,

101

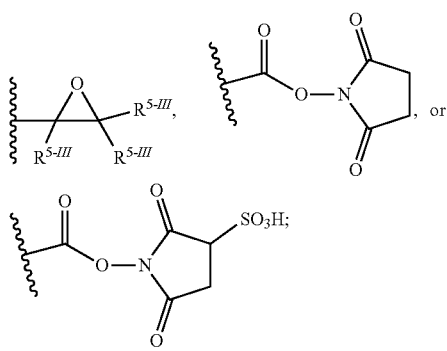

$R^{8-III}$ represents independently for each occurrence

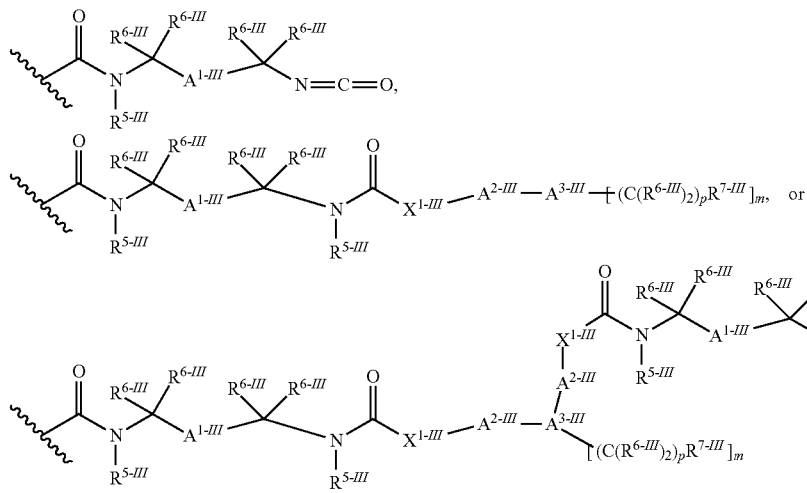

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

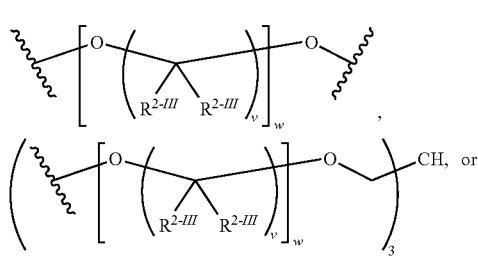

102

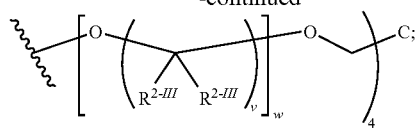

$X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

Another aspect of the present invention relates to a method of adhering tissue of a patient, comprising the steps of:

exposing an effective amount of a polymerization agent to a compound of formula III to form an adhesive composition, applying said adhesive composition to a first tissue of a patient to form an adhesive tissue, and contacting said adhesive tissue with a second tissue of a patient, wherein said polymerization agent is a compound of formula Ia or formula Ib; and formula a is represented by:

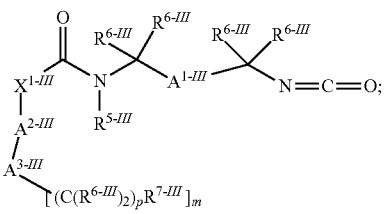

Ia wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)O[C(R$^4$)$_2$]$_d$N(R$^5$)$_2$, —C(O)N(R$^5$)[C(R$^4$)$_2$]$_d$N(R$^5$)$_2$, —C(O)N(R$^5$)$_2$, —X$^1$—[C(R$^4$)$_2$]$_d$N(R$^5$)C(O)N(R$^5$)$_2$, —X$^1$—[C(R$^4$)$_2$]$_d$N(R$^5$)C(O)N(R$^5$)$_2$, —X$^1$—[C(R$^4$)$_2$]$_d$OC(O)CH$_2$C(O)-alkyl,

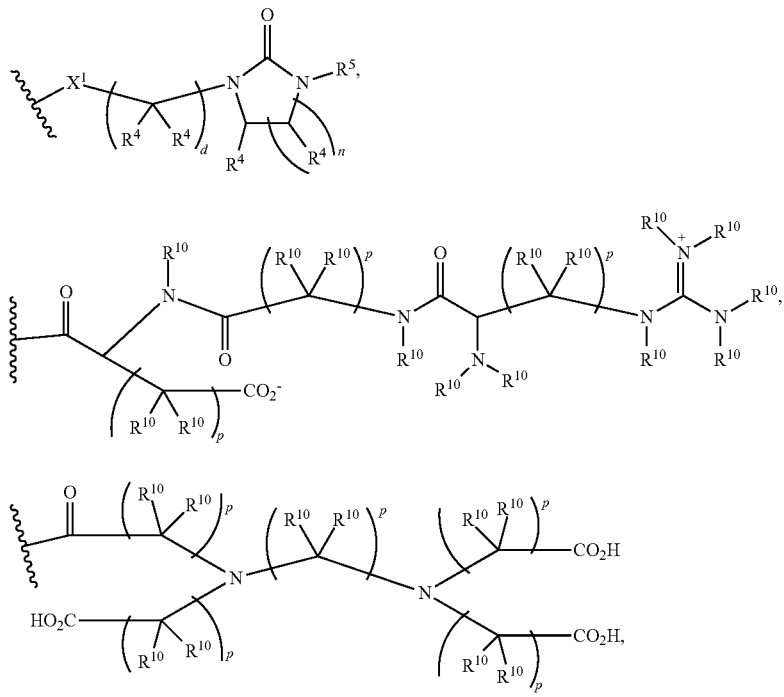

or a carbohydrate radical;

$R^3$ represents independently for each occurrence H or

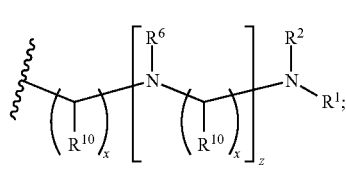

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

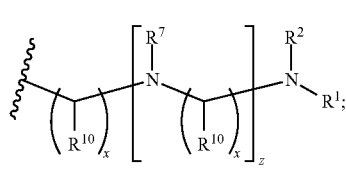

$R^7$ represents independently for each occurrence H or

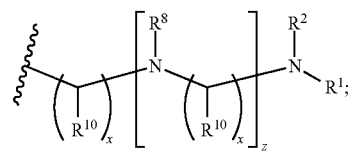

$R^8$ represents independently for each occurrence H or

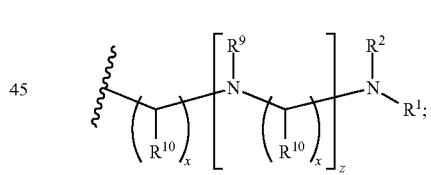

$R^9$ represents independently for each occurrence H or

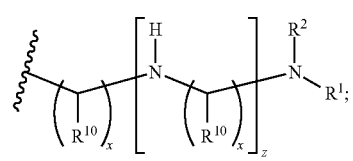

$R^{10}$ represents independently for each occurrence H or $(C_1-C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$,

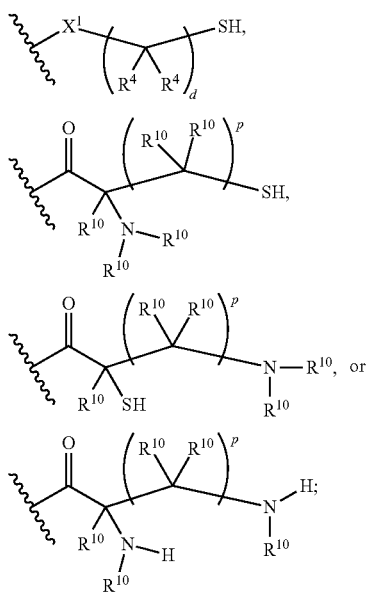

d represents independently for each occurrence 1, 2, 3, 4, 5, 6, 7, 8, 9, or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

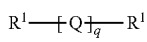

Ib wherein

Q represents independently for each occurrence

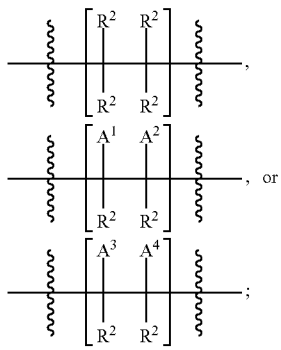

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —$CO_2R^4$;

$A^2$ represents independently for each occurrence H or —$CO_2R^4$;

$A^3$ represents independently for each occurrence —N($R^1$)($R^{50}$)($R^3$);

$A^4$ represents independently for each occurrence H, alkyl, aryl, —$CO_2R^4$, or —OC(O)$R^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —C(O)$NH_2$, —$X^1$—[C($R^5$)$_2$]$_d$N($R^5$)C(O)$NH_2$,

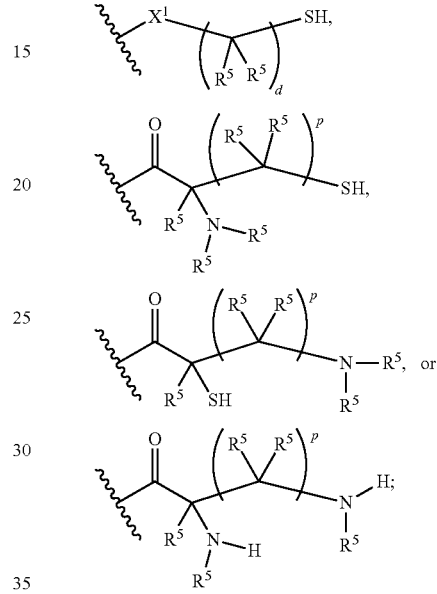

$R^4$ represents independently for each occurrence H, alkyl, aryl, aralkyl,

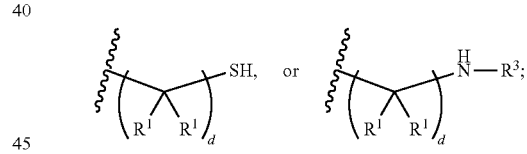

$R^5$ represents independently for each occurrence H or alkyl;

$X^1$ represents independently for each occurrence a bond or —C(O)—;

d represents independently for each occurrence 1, 2, 3, 4, 5, 6, 7, 8, 9 or 10;

p represents independently for each occurrence 1, 2, 3, 4, or 5; and q is an integer from about 50 to about 100,000; and formula III is represented by:

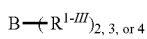

III wherein $R^{1-III}$ represents independently for each occurrence —(C($R^{2-III}$)$_2$)$_x$C(O)$R^{3-III}$, —C(O)(C($R^{2-III}$)$_2$)$_k$C(O)$R^{3-III}$, —(C($R^{2-III}$)$_2$)$_x$$R^{4-III}$, —C(O)(C($R^{2-III}$)$_2$)$_k$$R^{4-III}$, —(C($R^{2-III}$)$_2$)C(O)N($R^{5-III}$)-[$A^{4-III}$]$_t$—C(O)—$R^{3-III}$, —(C($R^{2-III}$)$_2$)$_x$$CO_2$-[$A^{4-III}$]$_t$-C(O)—$R^{3-III}$,

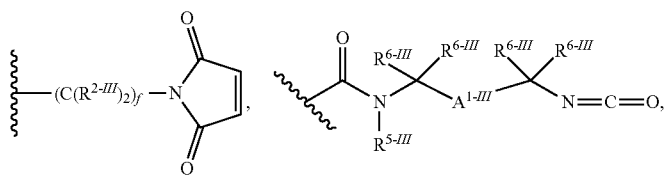

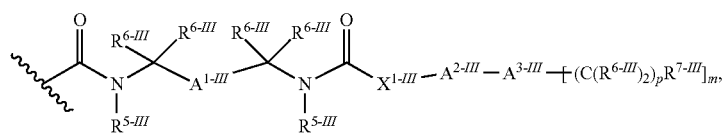

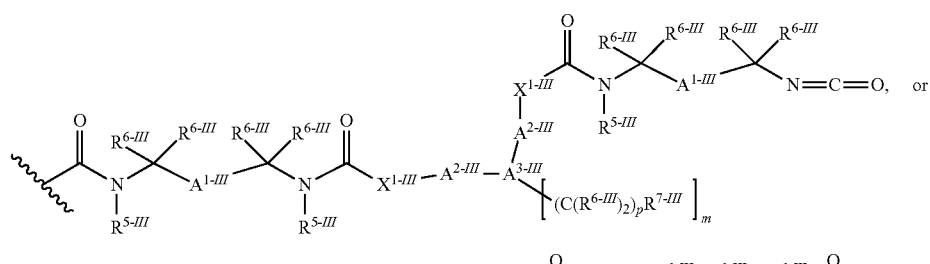

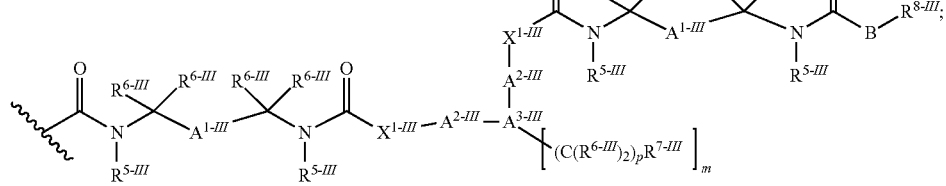

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$,

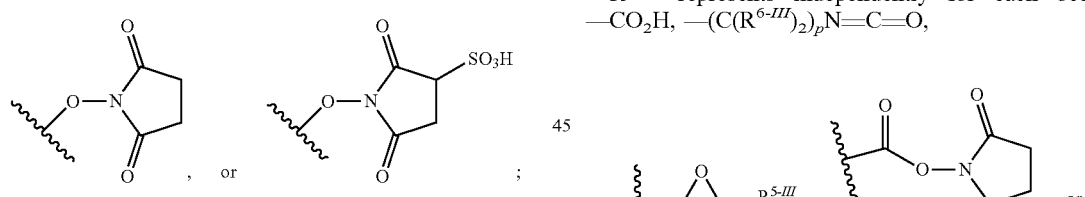

$R^{4-III}$ represents independently for each occurrence —N=C=O, —N=C=S,

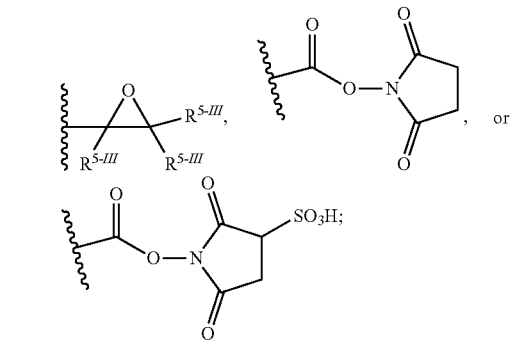

$R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O, $R^{8-III}$ represents independently for each occurrence

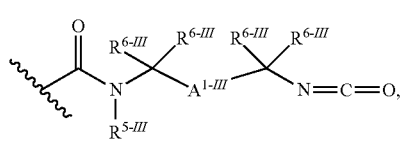

-continued

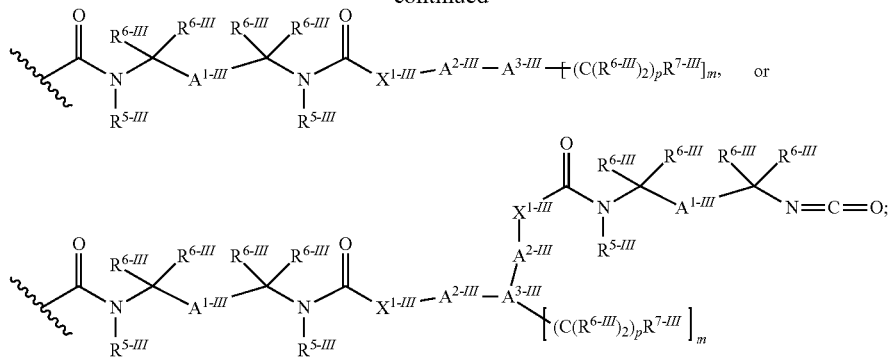

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

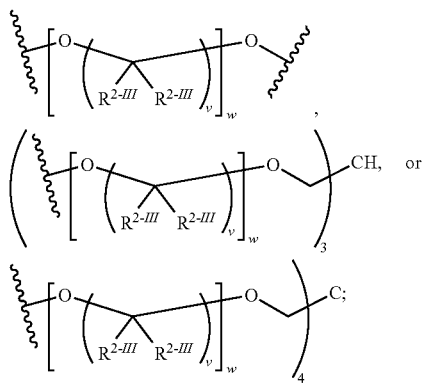

$X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

In certain instances, the present invention relates to the aforementioned method, wherein f and k each represent independently for each occurrence 1, 2, 3, 4, 5, 6, 7, 8, or 9.

In certain instances, the present invention relates to the aforementioned method, wherein said polymerization agent is a compound of formula Ia.

In certain instances, the present invention relates to the aforementioned method, wherein said polymerization agent is a compound of formula Ia, d represents independently for each occurrence 1, 2, 3, 4, 5, 6, 7, or 8.

In certain instances, the present invention relates to the aforementioned method, wherein said polymerization agent is a compound of formula Ia, $R^1$ and $R^2$ represent independently for each occurrence $A^1$, alkyl, alkenyl, alkynyl, $-C(O)$-alkyl, $-C(O)N(R^5)_2$, $X^1-[C(R^4)_2]_dN(R^5)C(O)N(R^5)_2$, $-X^1-[C(R^4)_2]_dOC(O)CH_2C(O)$-alkyl,

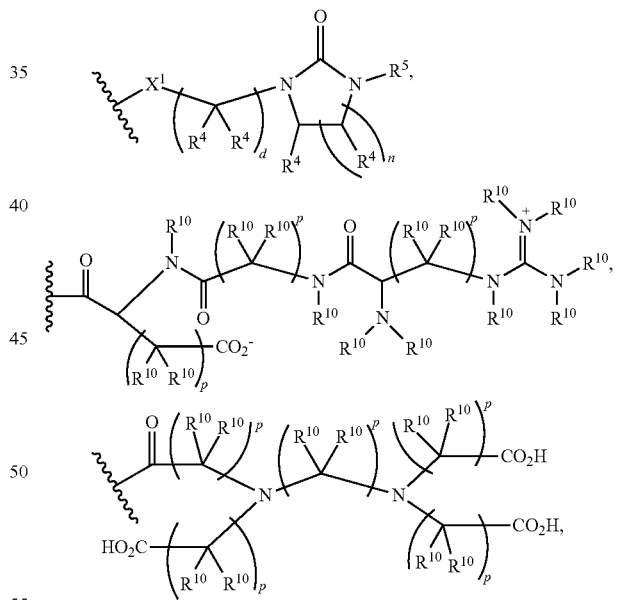

or a carbohydrate radical.

In certain instances, the present invention relates to the aforementioned method, wherein said polymerization agent is a compound of formula Ia, $R^{10}$ is H, and x is 2 or 3.

In certain instances, the present invention relates to the aforementioned method, wherein said polymerization agent is a compound of formula Ia, $R^{10}$ is H, x is 2 or 3, at least about ½ of $R^1$ are H, and at least about ½ of $R^2$ are H.

In certain instances, the present invention relates to the aforementioned method, wherein said polymerization agent is a compound of formula Ia, $R^{10}$ is H, x is 2 or 3, at least about ½ of R¹ are H, at least about ½ of R² are H, and the sum of y and z is an integer in the range of about 20 to about 500.

In certain instances, the present invention relates to the aforementioned method, wherein said polymerization agent is a compound of formula Ia, $R^{10}$ is H, x is 2 or 3, at least about 90% of $R^1$ are $A^1$, and $A^1$ represents independently for each occurrence H,

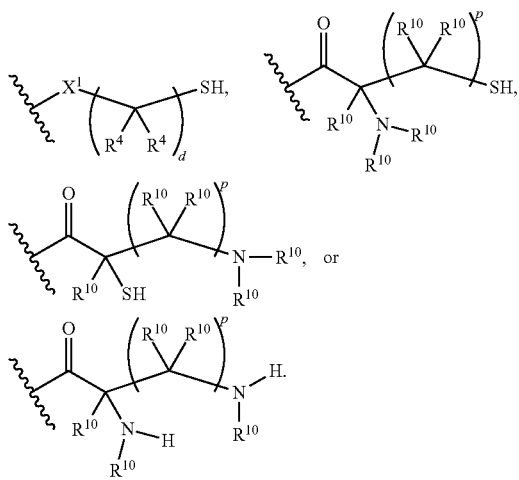

In certain instances, the present invention relates to the aforementioned method, wherein said polymerization agent is a compound of formula Ia, $R^{10}$ is H, x is 2 or 3, at least about 90% of $R^1$ and $R^2$ are $A^1$, and $A^1$ represents independently for each occurrence H,

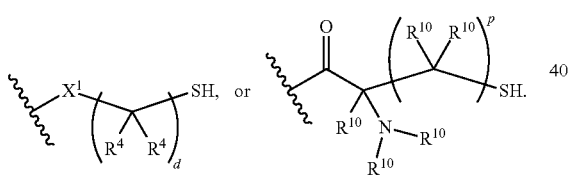

In certain instances, the present invention relates to the aforementioned method, wherein said polymerization agent is a compound of formula Ia, $R^{10}$ is H, x is 2 or 3, at least about 95% of $R^1$ and $R^2$ are H, and the sum of y and z is an integer in the range of about 20 to about 500.

In certain instances, the present invention relates to the aforementioned method, wherein said polymerization agent is a compound of formula Ia, $R^1$ is H, and x is 3 or 4.

In certain instances, the present invention relates to the aforementioned method, wherein said polymerization agent is a compound of formula Ia, $R^1$ is H, x is 3 or 4, and at least about 95% of $R^1$ and $R^2$ are H.

In certain instances, the present invention relates to the aforementioned method, wherein said polymerization agent is $NH_2(CH_2)_2N(H)(CH_2)_4N(H)(CH_2)_2NH_2$.

In certain instances, the present invention relates to the aforementioned method, wherein said polymerization agent is $NH_2(CH_2)_3N(H)(CH_2)_4N(H)(CH_2)_3NH_2$.

In certain instances, the present invention relates to the aforementioned method, wherein said polymerization agent is a compound of formula Ib.

In certain instances, the present invention relates to the aforementioned method, wherein said polymerization agent is a compound of formula Ib, d represents independently for each occurrence 1, 2, 3, 4, 5, 6, 7, or 8.

In certain instances, the present invention relates to the aforementioned method, wherein said polymerization agent is a compound of formula Ib, and $A^3$ is $-N(H)R^3$.

In certain instances, the present invention relates to the aforementioned method, wherein said polymerization agent is a compound of formula Ib, $A^3$ is $-N(H)R^3$, and R, and $R^3$ are H.

In certain instances, the present invention relates to the aforementioned method, wherein said polymerization agent is a compound of formula Ib, $A^3$ is $-N(H)R^3$, $R^1$ and $R^3$ are H, and x is 0.

In certain instances, the present invention relates to the aforementioned method, wherein said polymerization agent is a compound of formula Ib, and $A^1$ is $-CO_2R^4$.

In certain instances, the present invention relates to the aforementioned method, wherein said polymerization agent is a compound of formula Ib, $A^1$ is $-CO_2R^4$, $R^4$ is

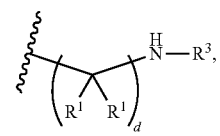

and $R^1$ and $R^3$ are H.

In certain instances, the present invention relates to the aforementioned method, wherein said polymerization agent is a compound of formula Ib, $A^1$ is $-CO_2R^4$, $R^4$ is

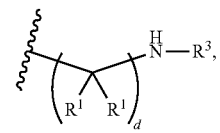

$R^1$ and $R^3$ are H, and x is 0.

In certain instances, the present invention relates to the aforementioned method, wherein w is independently for each occurrence an integer in the range of about 50 to about 250.

In certain instances, the present invention relates to the aforementioned method, wherein w is independently for each occurrence an integer in the range of about 60 to about 90.

In certain instances, the present invention relates to the aforementioned method, wherein $R^{1-III}$ is $-(C(R^{2-III})_2)_kC(O)R^3$ or $-C(O)(C(R^{2-III})_2)_kC(O)R^{3-III}$, $R^{2-III}$ is H, and $R^{3-III}$ is

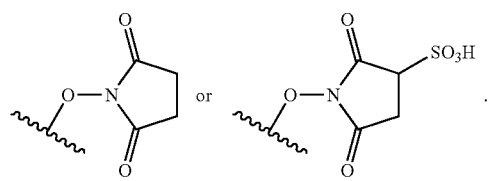 [SMILES: *ON1C(=O)CCC1=O ; *ON1C(=O)CC(S(=O)(=O)O)C1=O]

In certain instances, the present invention relates to the aforementioned method, wherein $R^{1-III}$ is $-(C(R^{2-III})_2)_kC$ (O)$R^{3\text{-}III}$ or —C(O)(C($R^{2\text{-}III}$)$_2$)$_k$C(O)$R^{3\text{-}III}$, $R^{2\text{-}III}$ is H, $R^{3\text{-}III}$ is

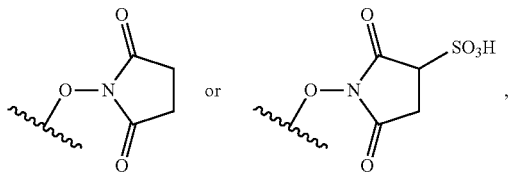 [SMILES: *ON1C(=O)CCC1=O ; *ON1C(=O)CC(S(=O)(=O)O)C1=O]

B is

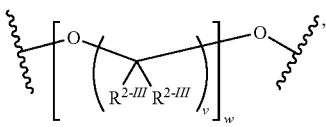

and v is 2.

In certain instances, the present invention relates to the aforementioned method, $R^{1\text{-}III}$ is —(C($R^{2\text{-}III}$)$_2$)$_j$C(O)$R^{3\text{-}III}$ or —C(O)(C($R^{2\text{-}III}$)$_2$)$_k$C(O)$R^{3\text{-}III}$, $R^{2\text{-}III}$ is H, $R^{3\text{-}III}$ is

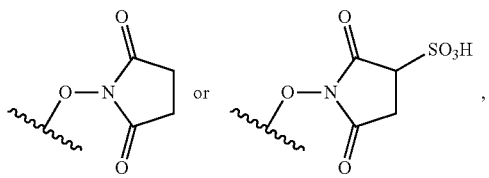 [SMILES: *ON1C(=O)CCC1=O ; *ON1C(=O)CC(S(=O)(=O)O)C1=O]

B is

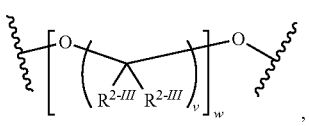

v is 2, and w is independently for each occurrence an integer in the range of about 15-90.

In certain instances, the present invention relates to the aforementioned method, $R^{1\text{-}III}$ is —(C($R^{2\text{-}III}$)$_2$)$_j$C(O)$R^{3\text{-}III}$ or —C(O)(C($R^{2\text{-}III}$)$_2$)$_k$C(O)$R^{3\text{-}III}$, $R^{2\text{-}III}$ is H, $R^{3\text{-}III}$ is

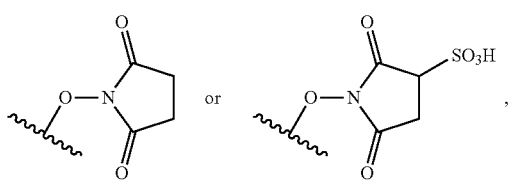 [SMILES: *ON1C(=O)CCC1=O ; *ON1C(=O)CC(S(=O)(=O)O)C1=O]

B is

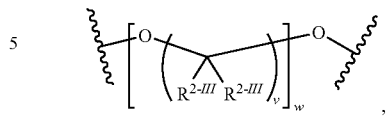

and v is 2.

In certain instances, the present invention relates to the aforementioned method, wherein $R^{1\text{-}III}$ is —(C($R^{2\text{-}III}$)$_2$)$_j$C(O)$R^{3\text{-}III}$ or —C(O)(C($R^{2\text{-}III}$)$_2$)$_k$C(O)$R^{3\text{-}III}$, $R^{2\text{-}III}$ is H, $R^{3\text{-}III}$ is

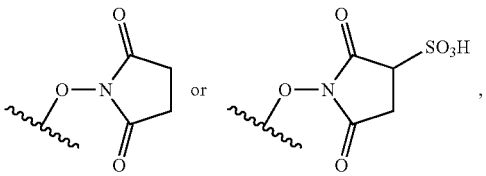 [SMILES: *ON1C(=O)CCC1=O ; *ON1C(=O)CC(S(=O)(=O)O)C1=O]

B is

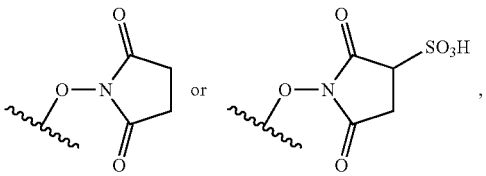 [SMILES: *ON1C(=O)CCC1=O ; *ON1C(=O)CC(S(=O)(=O)O)C1=O]

v is 2, and w is independently for each occurrence an integer in the range of about 15-90, B is

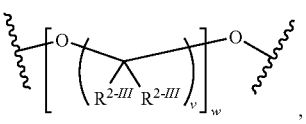

v is 2, said polymerization agent is a compound of formula Ia, $R^{10}$ is H, x is 2, at least about ½ of $R^1$ are H, and at least about ½ of $R^2$ are H.

In certain instances, the present invention relates to the aforementioned method, wherein $R^{1\text{-}III}$ is —(CH$_2$)$_3$C(O)$R^{3\text{-}III}$, $R^{3\text{-}III}$ is

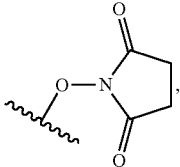 [SMILES: *ON1C(=O)CCC1=O]

B is

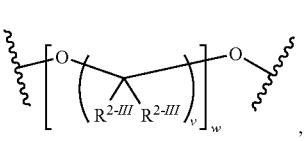

and v is 2.

In certain instances, the present invention relates to the aforementioned method, wherein $R^{1\text{-}III}$ is —C(O)(CH$_2$)$_2$C(O)R$^{3\text{-}III}$ or —C(O)(CH$_2$)$_3$C(O)R$^{3\text{-}III}$, R$^{3\text{-}III}$ is

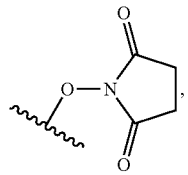 [SMILES: *ON1C(=O)CCC1=O]

B is

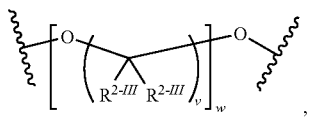

and v is 2.

In certain instances, the present invention relates to the aforementioned method, wherein formula III is

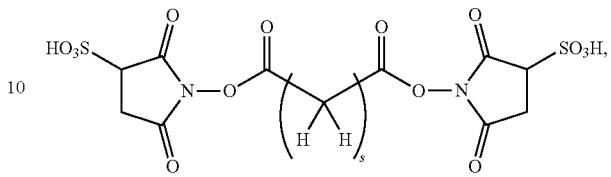

and s is an integer in the range of about 1-20 inclusive.

In certain instances, the present invention relates to the aforementioned method, wherein $R^{1\text{-}III}$ represents independently for each occurrence

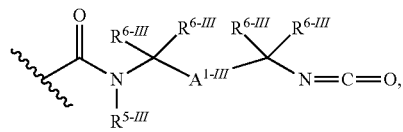

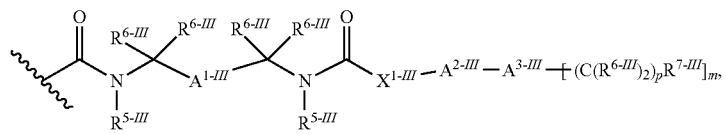

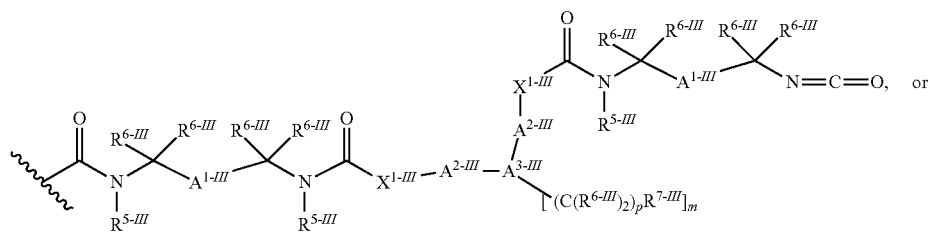

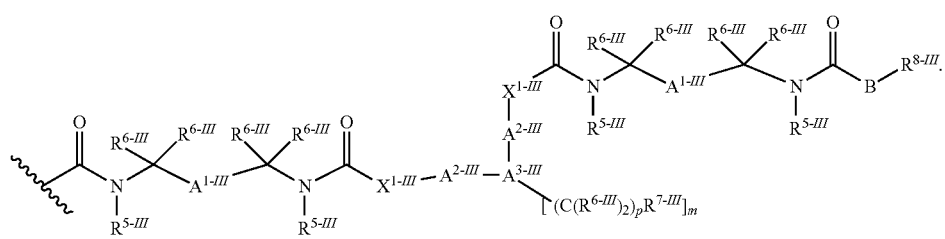

In certain instances, the present invention relates to the aforementioned method, wherein, B is

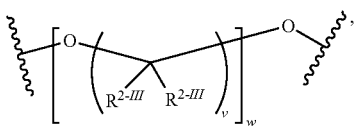

$R^{2-III}$ is H, and $A^{1-III}$ is aryl diradical.

In certain instances, the present invention relates to the aforementioned method, wherein, B is

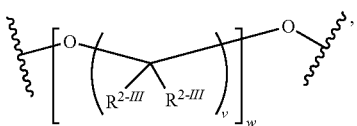

$R^{2-III}$ is H, and $A^{1-III}$ is optionally substituted phenyl diradical.

In certain instances, the present invention relates to the aforementioned method, wherein, B is

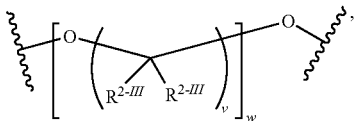

$R^{2-III}$ is H, $A^{2-III}$ is a bond, and $A^{3-III}$ is alkyl diradical.

In certain instances, the present invention relates to the aforementioned method, wherein, B is

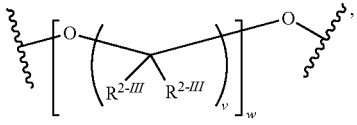

$R^{2-III}$ is H, $A^{2-III}$ is a bond, $A^{3-III}$ is alkyl diradical, and $R^{7-III}$ is

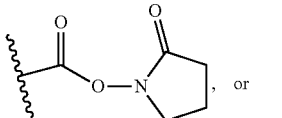, or

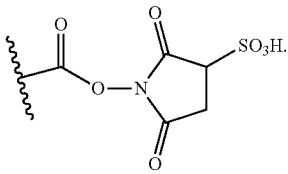

In certain instances, the present invention relates to the aforementioned method, wherein, B is

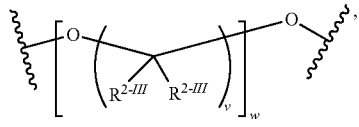

$R^{2-III}$ is H, $A^{2-III}$ is aryl diradical, $A^{3-III}$ is aralkyl diradical, and $R^{7-III}$ is

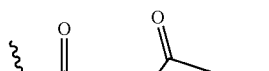, or

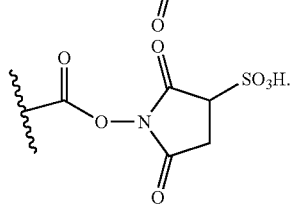

In certain instances, the present invention relates to the aforementioned method, wherein, B is

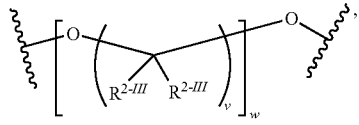

$R^{2-III}$ is H, $A^{2-III}$ is optionally substituted phenyl diradical, $A^{3-III}$ is optionally substituted benzyl diradical, and $R^{7-III}$ is

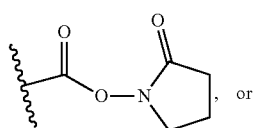, or

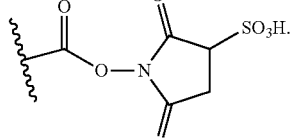

In certain instances, the present invention relates to the aforementioned method, wherein, B is

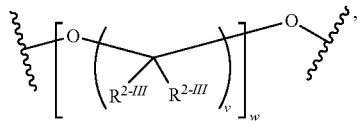

$R^{2-III}$ is H, v is 2, and $R^{1-III}$ is

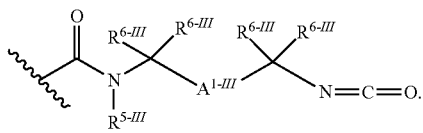

In certain instances, the present invention relates to the aforementioned method, wherein, B is

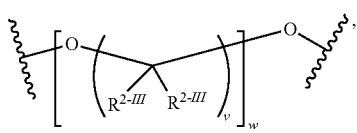

$R^{2-III}$ is H, v is 2, $R^{1-III}$ is

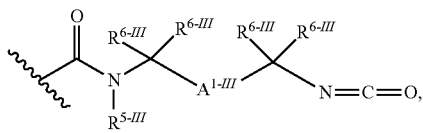

$R^{6-III}$ is $(C_1-C_4)$alkyl, and $A^{1-III}$ is aryl diradical.

In certain instances, the present invention relates to the aforementioned method, wherein, B is

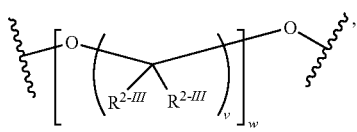

$R^{2-III}$ is H, v is 2, $R^{1-III}$ is

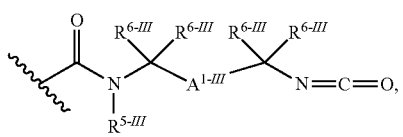

$R^{6-III}$ is $(C_1-C_4)$alkyl, and $A^{1-III}$ is optionally substituted phenyl diradical.

In certain instances, the present invention relates to the aforementioned method, wherein, B is

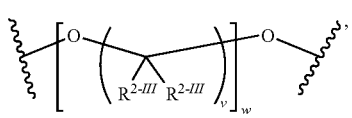

$R^{2-III}$ is H, v is 2, $R^{1-III}$ is

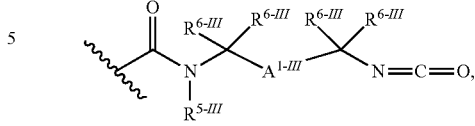

$R^{6-III}$ is methyl, and $A^{1-III}$ is phenyl diradical.

In certain instances, the present invention relates to the aforementioned method, wherein, B is

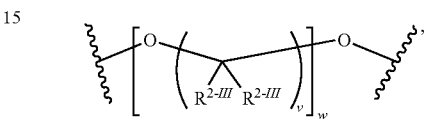

$R^{2-III}$ is H, v is 2, $R^{1-III}$ is

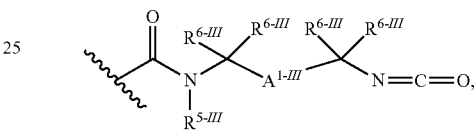

$R^{6-III}$ is methyl, $A^{1-III}$ is phenyl diradical, said polymerization agent is a compound of formula Ia, $R^{10}$ is H, x is 2, at least about ½ of $R^1$ are H, and at least about ½ of $R^2$ are H.

In certain embodiments, the present invention relates to the aforementioned method, wherein said polymerization agent is a compound of formula Ia, said compound of formula Ia has a weight average molecular weight of about 600 to about 10,000 Daltons, said compound of formula III has a weight average molecular weight of about 500 to about 20,000 Daltons, and the molar ratio of said compound of formula Ia to said compound of formula III is about 0.025:1 to about 0.4:1.

In certain embodiments, the present invention relates to the aforementioned method, wherein $R^{1-III}$ is —$(C(R^{2-III})_2)_f C(O)N(R^{5-III})$-$[A^{4-III}]_f$-$C(O)$—$R^{3-III}$, $A^{4-III}$ is an alkyl diradical, t and f are 1, $R^{2-III}$ and $R^{5-III}$ are hydrogen, and $R^{3-III}$ is

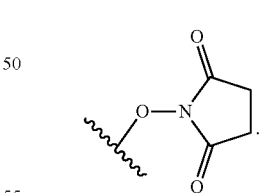

In certain embodiments, the present invention relates to the aforementioned method, further comprising the step of sterilizing said polymerization agent.

In certain embodiments, the present invention relates to the aforementioned method, further comprising the step of sterilizing said compound of formula III.

In certain embodiments, the present invention relates to the aforementioned method, wherein said sterilizing is performed by treatment with ethylene oxide, hydrogen peroxide, heat, gamma irradiation, electron beam irradiation, microwave irradiation, or visible light irradiation.

In certain embodiments, the present invention relates to the aforementioned method, said polymerization agent and said compound of formula III have a sterility assurance level of at least about $10^{-3}$.

In certain embodiments, the present invention relates to the aforementioned method, said polymerization agent and said compound of formula III have a sterility assurance level of at least about $10^{-6}$.

In certain embodiments, the present invention relates to the aforementioned method, wherein said patient is a primate, bovine, equine, feline, or canine.

In certain embodiments, the present invention relates to the aforementioned method, wherein said patient is a human.

In certain embodiments, the present invention relates to the aforementioned method, wherein said wound is an ophthalmic wound.

In certain embodiments, the present invention relates to the aforementioned method, wherein said wound is a wound to the cornea of an eye.

In certain embodiments, the present invention relates to the aforementioned method, wherein said wound is an epithelial defect, corneal incision, corneal laceration, corneal perforation, corneal ulceration, retinal hole, filtering bleb, corneal transplant, trabeculectomy incision, sclerotomy incision, blepharoplasty, or skin incision.

In certain embodiments, the present invention relates to the aforementioned method, wherein said wound is an epithelial defect, corneal incision, corneal laceration, corneal perforation, or corneal ulceration.

In certain embodiments, the present invention relates to the aforementioned method, wherein said wound is a corneal incision or corneal laceration.

In certain embodiments, the present invention relates to the aforementioned method, wherein said wound is a located in the dura.

In certain embodiments, the present invention relates to the aforementioned method, wherein said wound is a located in the lung tissue.

In certain embodiments, the present invention relates to the aforementioned method, wherein said wound is a tissue plane.

In certain embodiments, the present invention relates to the aforementioned method, wherein said wound is in a vein or artery.

In certain embodiments, the present invention relates to the aforementioned method, wherein said wound is less than about 25 mm long.

In certain embodiments, the present invention relates to the aforementioned method, wherein said wound is less than about 15 mm long.

In certain embodiments, the present invention relates to the aforementioned method, wherein said wound is less than about 10 mm long.

In certain embodiments, the present invention relates to the aforementioned method, wherein said wound is less than about 5 mm long.

In certain embodiments, the present invention relates to the aforementioned method, wherein said void is less than about 15 mm in diameter.

In certain embodiments, the present invention relates to the aforementioned method, wherein said void is less than about 10 mm in diameter.

In certain embodiments, the present invention relates to the aforementioned method, wherein said void is less than about 5 mm in diameter.

In certain embodiments, the present invention relates to the aforementioned method, wherein said first tissue and said second tissue are independently selected from the group consisting of skin, muscle, blood vessel, tendon, cartilage, ligament, liver, kidney, lung, heart, intestinal tissue, stomach, and corneal tissue.

In certain embodiments, the present invention relates to the aforementioned method, wherein said polymerization agent is sterile.

Another aspect of the present invention relates to a method, comprising the step of:

applying an effective amount of a polymerization agent and a compound of formula III to the skin of a patient sufficient to polymerize said polymerization agent, wherein said polymerization agent is a compound of formula Ia or formula Ib; and formula Ia is represented by:

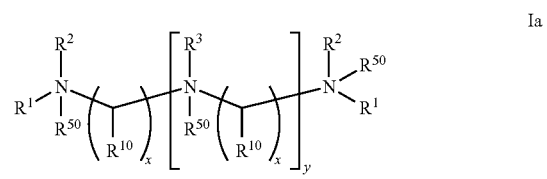

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —$X^1$—[C($R^4$)$_2$]$_d$N($R^5$)C(O)N($R^5$)$_2$, —$X^1$—[C($R^4$)$_2$]$_d$OC(O)CH$_2$C(O)-alkyl,

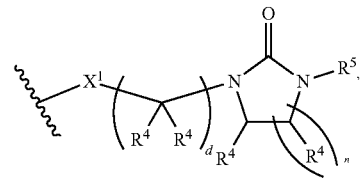

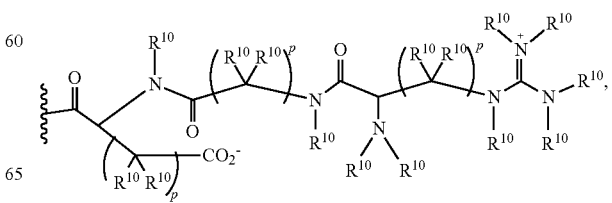

-continued

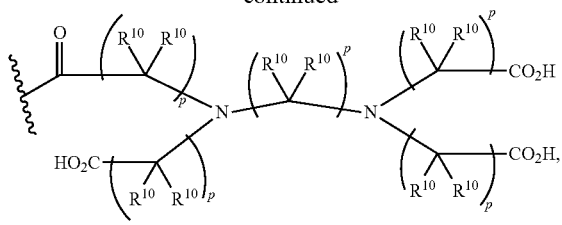

or a carbohydrate radical;

$R^3$ represents independently for each occurrence H or

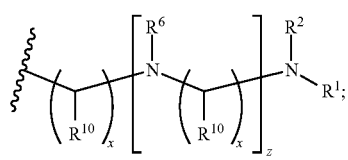

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

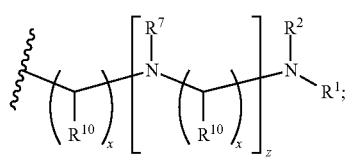

$R^7$ represents independently for each occurrence H or

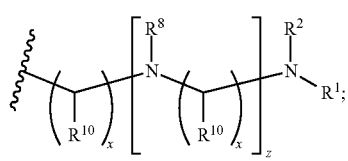

$R^8$ represents independently for each occurrence H or

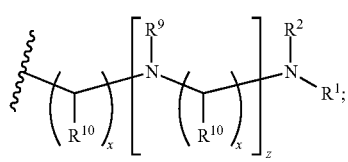

$R^9$ represents independently for each occurrence H or

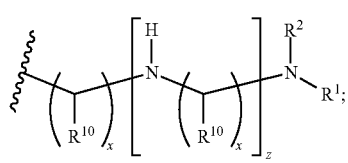

$R^{10}$ represents independently for each occurrence H or $(C_1\text{-}C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$,

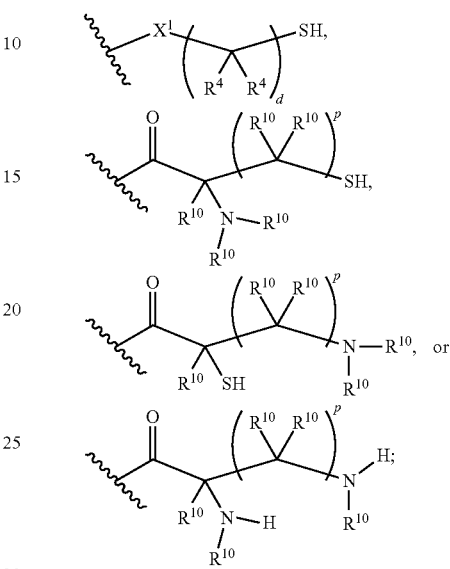

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

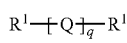

Ib wherein

Q represents independently for each occurrence

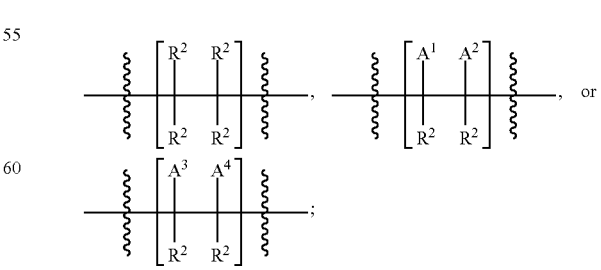

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence $-CO_2R^4$;

$A^2$ represents independently for each occurrence H or $-CO_2R^4$;

$A^3$ represents independently for each occurrence $-N(R^1)(R^{50})(R^3)$;

$A^4$ represents independently for each occurrence H, alkyl, aryl, $-CO_2R^4$, or $-OC(O)R^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, $-C(O)NH_2$, $-X^1-[C(R^5)_2]_dN(R^5)C(O)NH_2$,

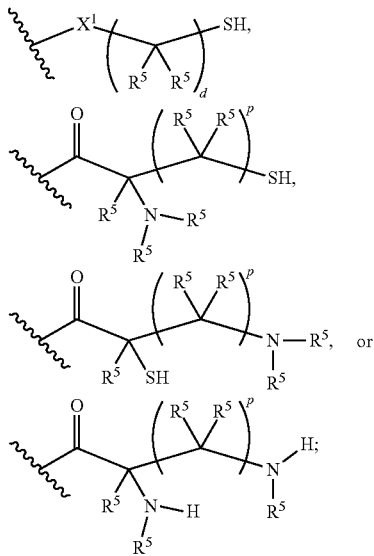

$R^4$ represents independently for each occurrence H, alkyl, aryl, aralkyl,

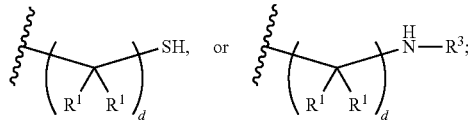

$R^5$ represents independently for each occurrence H or alkyl;

$X^1$ represents independently for each occurrence a bond or $-C(O)-$;

d represents independently for each occurrence 1, 2, 3, 4, 5, 6, 7, or 8;

p represents independently for each occurrence 1, 2, 3, 4, or 5; and q is an integer from about 50 to about 100,000; and t represents independently for each occurrence 2, 3, 4, 5, or 6; and formula III is represented by:

$$B-(R^{1-III})_{2, 3, \text{ or } 4} \quad \text{III}$$

wherein $R^{1-III}$ represents independently for each occurrence $-(C(R^{2-III})_2)_fC(O)R^{3-III}$, $-C(O)(C(R^{2-III})_2)_kC(O)R^{3-III}$, $-(C(R^{2-III})_2)_fR^{4-III}$, $-C(O)(C(R^{2-III})_2)_kR^{4-III}$, $-(C(R^{2-III})_2)_fC(O)N(R^{5-III})-[A^{4-III}]_t-C(O)-R^{3-III}$, $-(C(R^{2-III})_2)_fCO_2-[A^{4-III}]_t-C(O)-R^{3-III}$,

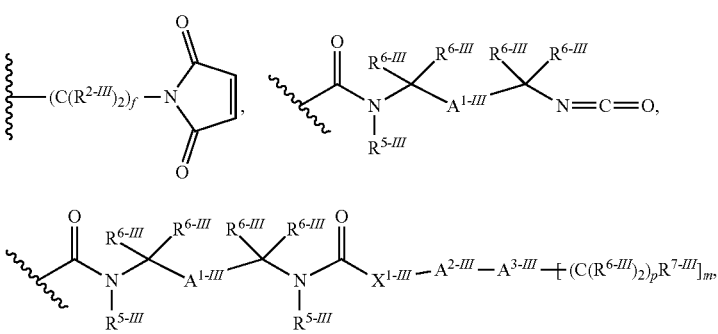

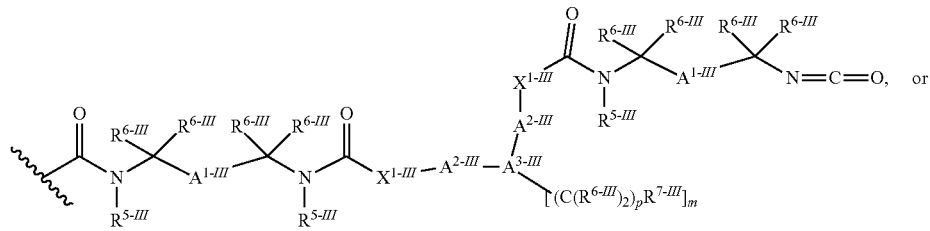

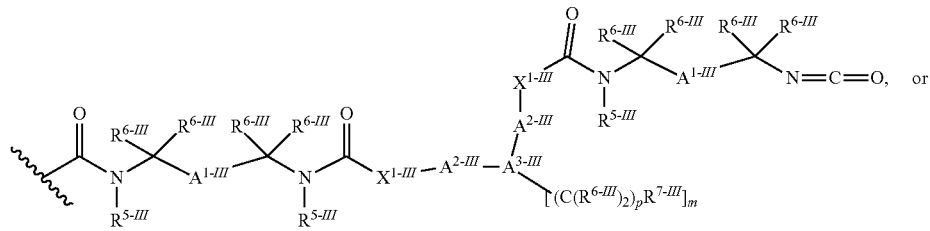

-continued

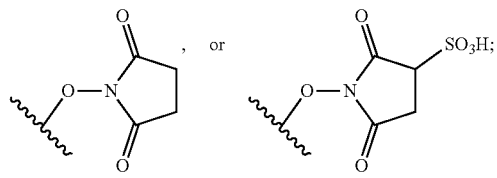 [SMILES: *ON1C(=O)CCC1=O ; *ON1C(=O)CC(S(=O)(=O)O)C1=O]
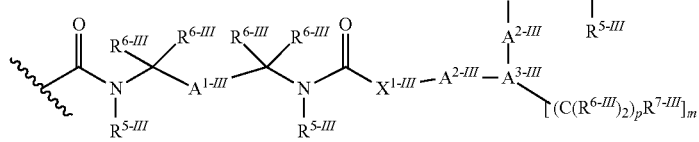

$R^{2\text{-}III}$ represents independently for each occurrence H, alkyl, or halogen;

$R^{3\text{-}III}$ represents independently for each occurrence H, alkyl, fluoroalkyl, chloroalkyl, —CH$_2$NO$_2$,

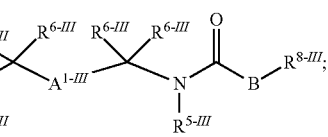

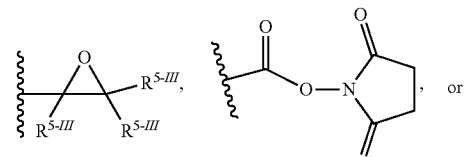

$R^{4\text{-}III}$ represents independently for each occurrence —N=C=O, —N=C=S,

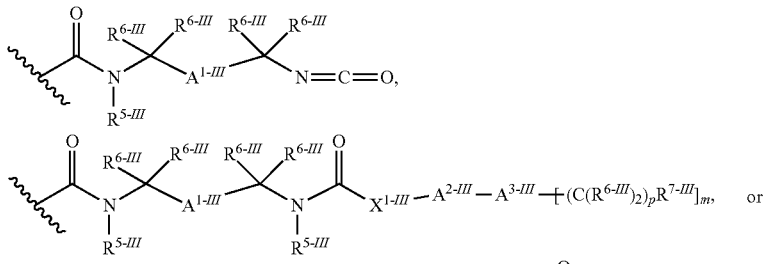

$R^{5\text{-}III}$ represents independently for each occurrence H, alkyl, or aralkyl;

$R^{6\text{-}III}$ represents independently for each occurrence H or (C$_1$-C$_6$)alkyl;

$R^{7\text{-}III}$ represents independently for each occurrence —CO$_2$H, —(C(R$^{6\text{-}III}$)$_2$)$_p$N=C=O,

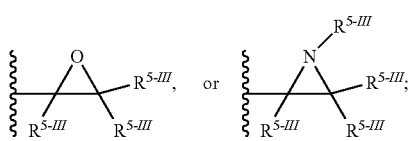

$R^{8\text{-}III}$ represents independently for each occurrence

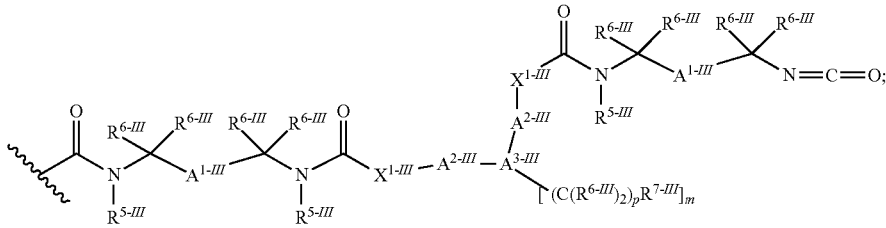

$A^{1\text{-}III}$ and $A^{3\text{-}III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2\text{-}III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4\text{-}III}$ represents independently for each occurrence an alkyl diradical, cycloalkyl diradical, aryl diradical, or aralkyl diradical;

B represents independently for each occurrence alkyl diradical, heteroalkyl diradical, or

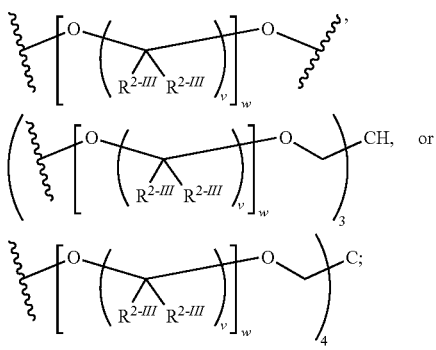

$X^{1-III}$ represents independently for each occurrence O or —N($R^{5-III}$)—;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

In certain instances, the present invention relates to the aforementioned method, wherein f and k each represent independently for each occurrence 1, 2, 3, 4, 5, 6, 7, 8, or 9.

In certain instances, the present invention relates to the aforementioned method, further comprising the step of inserting a needle through the hydrogel and into the patient.

In certain instances, the present invention relates to the aforementioned method, wherein said needle is a syringe needle.

In certain instances, the present invention relates to the aforementioned method, wherein said needle is inserted into the eye of a patient suffering from age-related macular degeneration.

Another aspect of the present invention relates to a method, comprising the step of: injecting into a patient an effective amount of a polymerization agent and a compound of formula III sufficient to polymerize said polymerization agent, wherein said polymerization agent is a compound of formula Ia or formula Ib; and formula Ia is represented by:

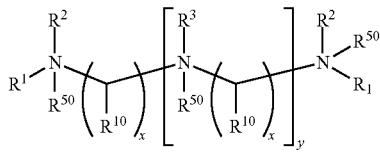

Ia wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —$X^1$—[C($R^4$)$_2$]$_d$N($R^5$)C(O)N($R^5$)$_2$, —$X^1$—[C($R^4$)$_2$]$_d$OC(O)CH$_2$C(O)—alkyl,

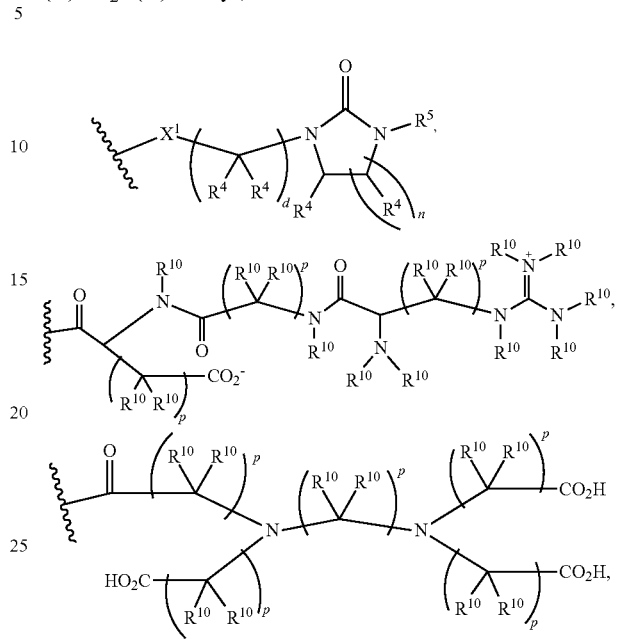

or a carbohydrate radical;

$R^3$ represents independently for each occurrence H or

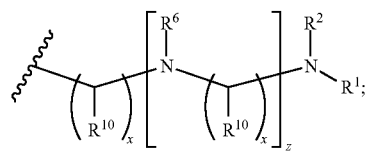

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

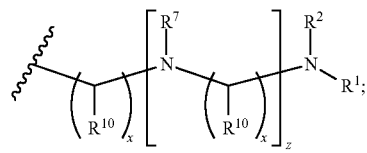

$R^7$ represents independently for each occurrence H or

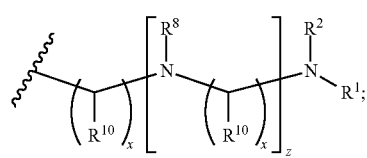

$R^8$ represents independently for each occurrence H or

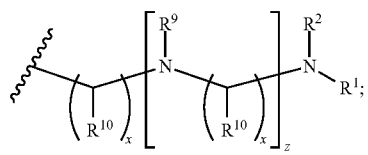

$R^9$ represents independently for each occurrence H or

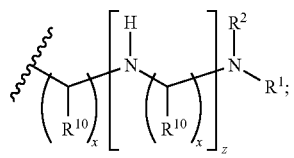

$R^{10}$ represents independently for each occurrence H or $(C_1\text{-}C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$,

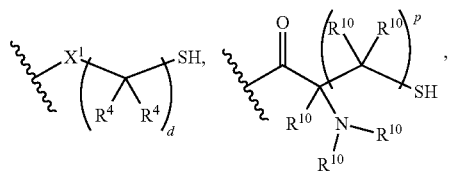

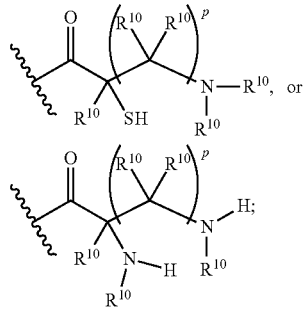

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of R$^1$ is A$^1$, and the sum of y and z is less than about 50,000; formula Ib is represented by:

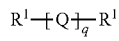

Ib wherein

Q represents independently for each occurrence

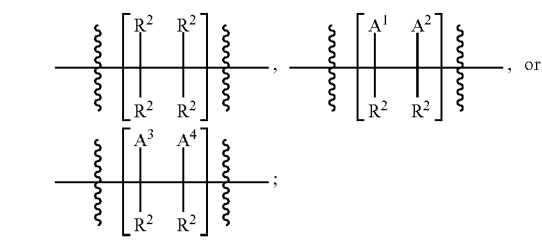

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —CO$_2$R$^4$;

$A^2$ represents independently for each occurrence H or —CO$_2$R$^4$;

$A^3$ represents independently for each occurrence —N(R$^1$)(R$^{50}$)(R$^3$);

$A^4$ represents independently for each occurrence H, alkyl, aryl, —CO$_2$R$^4$, or —OC(O)R$^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —C(O)NH$_2$, —X$^1$—[C(R$^5$)$_2$]$_d$N(R$^5$)C(O)NH$_2$,

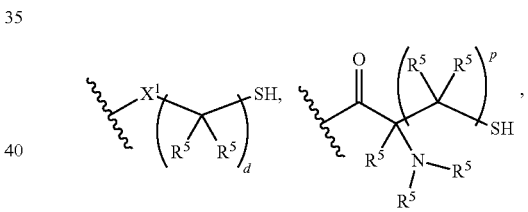

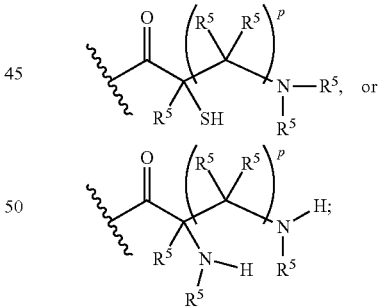

$R^4$ represents independently for each occurrence H, alkyl, aryl, aralkyl,

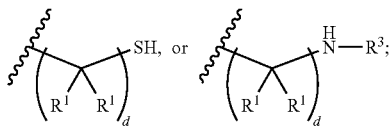

$R^5$ represents independently for each occurrence H or alkyl;

$X^1$ represents independently for each occurrence a bond or —C(O)—;

d represents independently for each occurrence 1, 2, 3, 4, 5, 6, 7, or 8;

p represents independently for each occurrence 1, 2, 3, 4, or 5; and q is an integer from about 50 to about 100,000; and formula III is represented by:

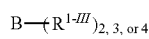

III wherein $R^{1\text{-}III}$ represents independently for each occurrence —(C($R^{2\text{-}III}$)$_2$)$_f$C(O)$R^{3\text{-}III}$, —C(O)(C($R^{2\text{-}III}$)$_2$)$_k$C(O)$R^{3\text{-}III}$, —(C($R^{2\text{-}III}$)$_2$)$_f R^{4\text{-}III}$, —C(O)(C($R^{2\text{-}III}$)$_2$)$_k R^{4\text{-}III}$, —(C($R^{2\text{-}III}$)$_2$)$_f$C(O)N($R^{5\text{-}III}$)-[$A^{4\text{-}III}$]$_t$—C(O)—$R^{3\text{-}III}$, —(C($R^{2\text{-}III}$)$_2$)$_f$CO$_2$-[$A^{4\text{-}III}$]$_t$-C(O)-$R^{3\text{-}III}$, $R^{4\text{-}III}$ represents independently for each occurrence —N=C=O, —N=C=S,

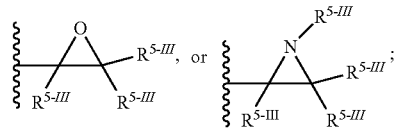

$R^{5\text{-}III}$ represents independently for each occurrence H, alkyl, or aralkyl;

$R^{6\text{-}III}$ represents independently for each occurrence H or ($C_1$-$C_6$)alkyl;

$R^{7\text{-}III}$ represents independently for each occurrence —CO$_2$H, —(C($R^{6\text{-}III}$)$_2$)$_p$N=C=O,

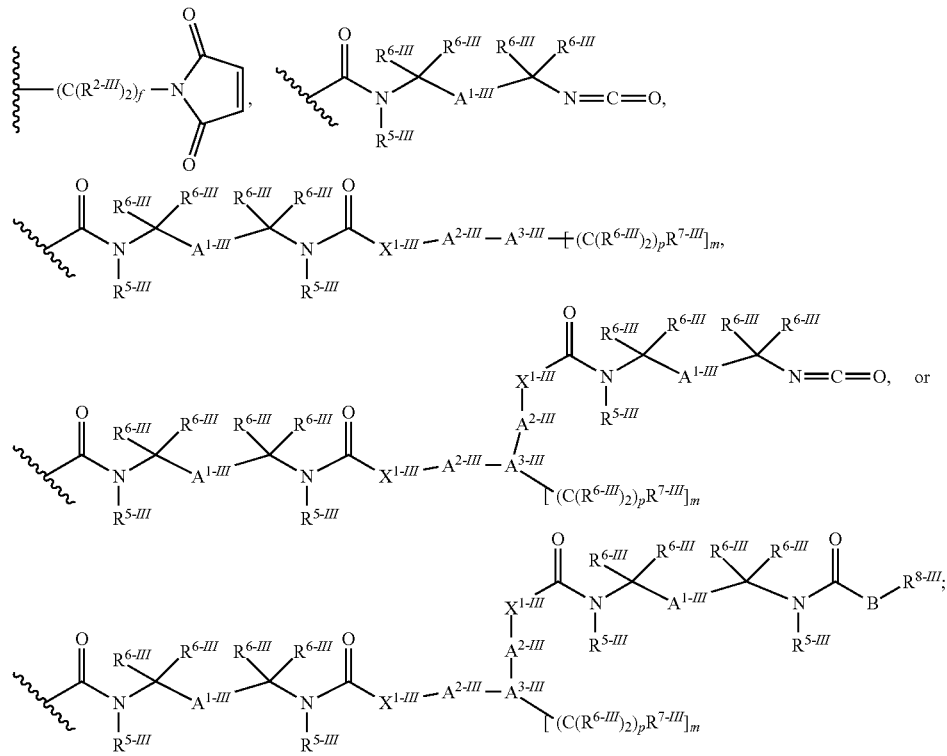

$R^{2\text{-}III}$ represents independently for each occurrence H, alkyl, or halogen;

$R^{3\text{-}III}$ represents independently for each occurrence H, alkyl, fluoroalkyl, chloroalkyl, —CH$_2$NO$_2$,

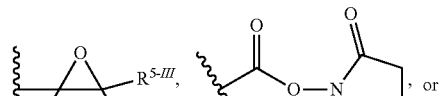

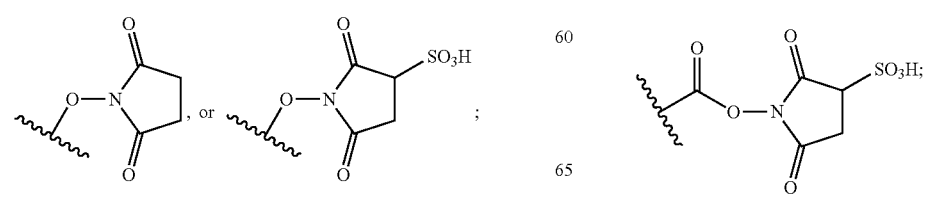

$R^{8-III}$ represents independently for each occurrence

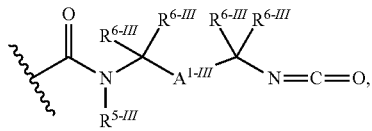
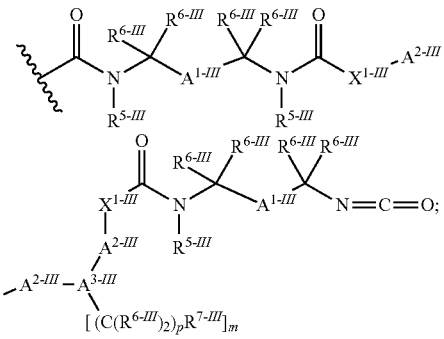
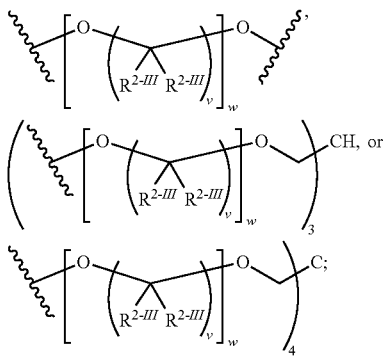

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or $X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

In certain instances, the present invention relates to the aforementioned method, wherein f and k each represent independently for each occurrence 1, 2, 3, 4, 5, 6, 7, 8, or 9.

In certain embodiments, the present invention relates to the aforementioned method, wherein said polymerization agent and said compound of formula III are injected under the skin of a patient.

Another aspect of the present invention relates to a method of coating a medical implant, comprising the step of:

applying to a medical implant an effective amount of a polymerization agent and a compound of formula III sufficient to polymerize said polymerization agent, wherein said polymerization agent is a compound of formula Ia or formula Ib; and formula Ia is represented by:

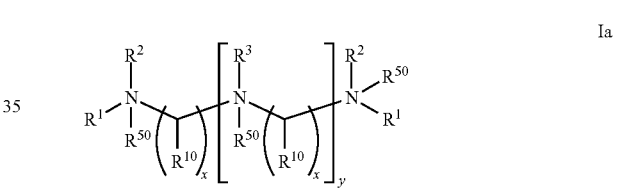

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, $-C(O)$-alkyl, $-C(O)N(R^5)_2$, $-X^1-[C(R^4)_2]_dN(R^5)C(O)N(R^5)_2$, $-X^1-[C(R^4)_2]_dOC(O)CH_2C(O)-$alkyl,

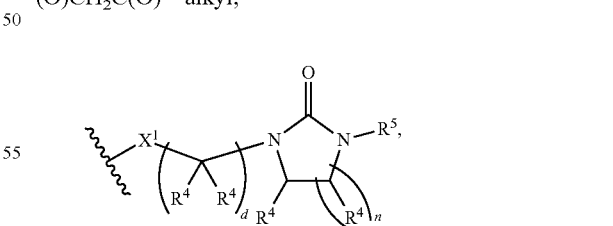
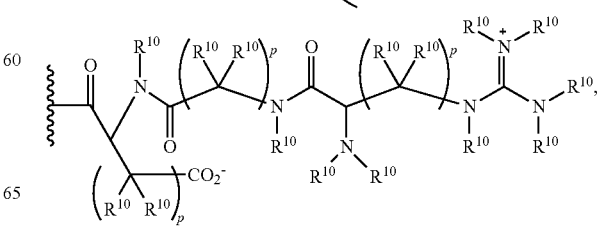

-continued

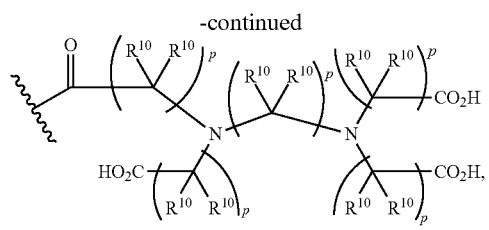

or a carbohydrate radical;

R³ represents independently for each occurrence H or

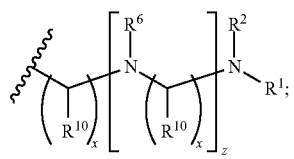

R⁴ represents independently for each occurrence H, alkyl, alkoxyl, halogen, aryl, or aralkyl;

R⁵ represents independently for each occurrence H, alkyl, aryl, or aralkyl;

R⁶ represents independently for each occurrence H or

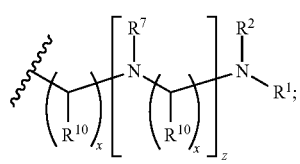

R⁷ represents independently for each occurrence H or

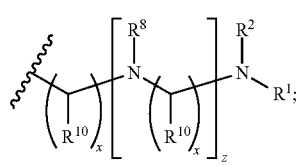

R⁸ represents independently for each occurrence H or

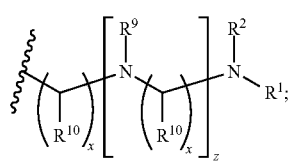

R⁹ represents independently for each occurrence H or

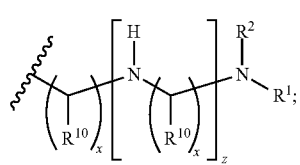

R¹⁰ represents independently for each occurrence H or ($C_1$-$C_3$)alkyl;

X¹ represents independently for each occurrence a bond or —C(O)—;

A¹ represents independently for each occurrence H, —C(O)NH$_2$, —X¹—[C(R⁴)$_2$]$_d$N(R⁵)C(O)NH$_2$,

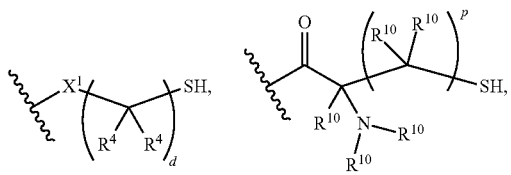

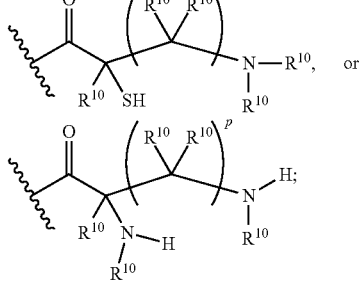

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of R¹ is A¹, and the sum of y and z is less than about 50,000; formula Ib is represented by:

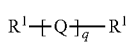

Ib wherein

Q represents independently for each occurrence

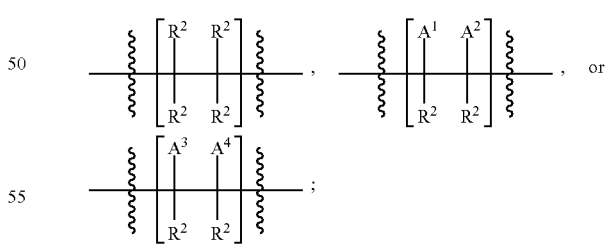

R⁵⁰ independently for each occurrence is an electron pair or a substituent selected from the group consisting of H, alkyl, and aralkyl; when an instance of R⁵⁰ represents a substituent a pharmaceutically acceptable counterion is present;

A¹ represents independently for each occurrence —CO$_2$R⁴;

A² represents independently for each occurrence H or —CO$_2$R⁴;

$A^3$ represents independently for each occurrence —N($R^1$)($R^{50}$)($R^3$);

$A^4$ represents independently for each occurrence H, alkyl, aryl, —$CO_2R^4$, or —$OC(O)R^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —C(O)$NH_2$, $X^1$—[C($R^5$)$_2$]$_d$N($R^5$)C(O)$NH_2$,

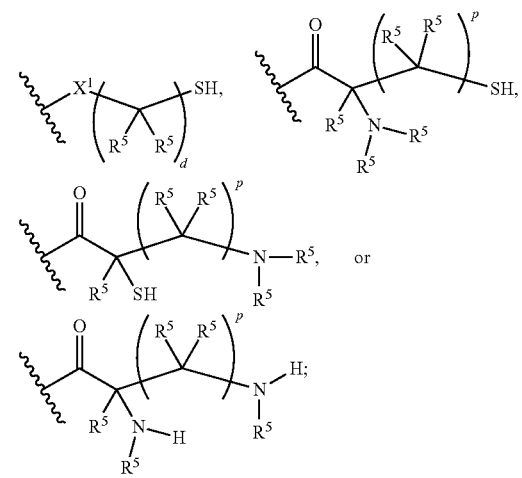

$R^4$ represents independently for each occurrence H, alkyl, aryl, aralkyl,

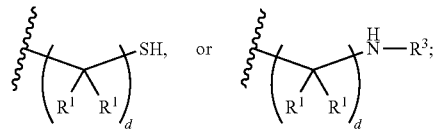

$R^5$ represents independently for each occurrence H or alkyl;

$X^1$ represents independently for each occurrence a bond or —C(O)—;

d represents independently for each occurrence 1, 2, 3, 4, 5, 6, 7, or 8;

p represents independently for each occurrence 1, 2, 3, 4, or 5; and q is an integer from about 50 to about 100,000; and formula III is represented by:

$$B\text{—}(R^{1\text{-}III})_{2,\,3,\,or\,4} \qquad III$$

wherein $R^{1\text{-}III}$ represents independently for each occurrence —(C($R^{2\text{-}III}$)$_2$)$_f$C(O)$R^{3\text{-}III}$, —C(O)(C($R^{2\text{-}III}$)$_2$)$_k$C(O)$R^{3\text{-}III}$, —(C($R^{2\text{-}III}$)$_2$)$_f R^{4\text{-}III}$, —C(O)(C($R^{2\text{-}III}$)$_2$)$_k R^{4\text{-}III}$, —(C($R^{2\text{-}III}$)$_2$)$_f$C(O)N($R^{5\text{-}III}$)-[$A^{4\text{-}III}$]$_t$—C(O)—$R^{3\text{-}III}$, —(C($R^{2\text{-}III}$)$_2$)$_f CO_2$-[$A^{4\text{-}III}$]$_t$-C(O)—$R^{3\text{-}III}$,

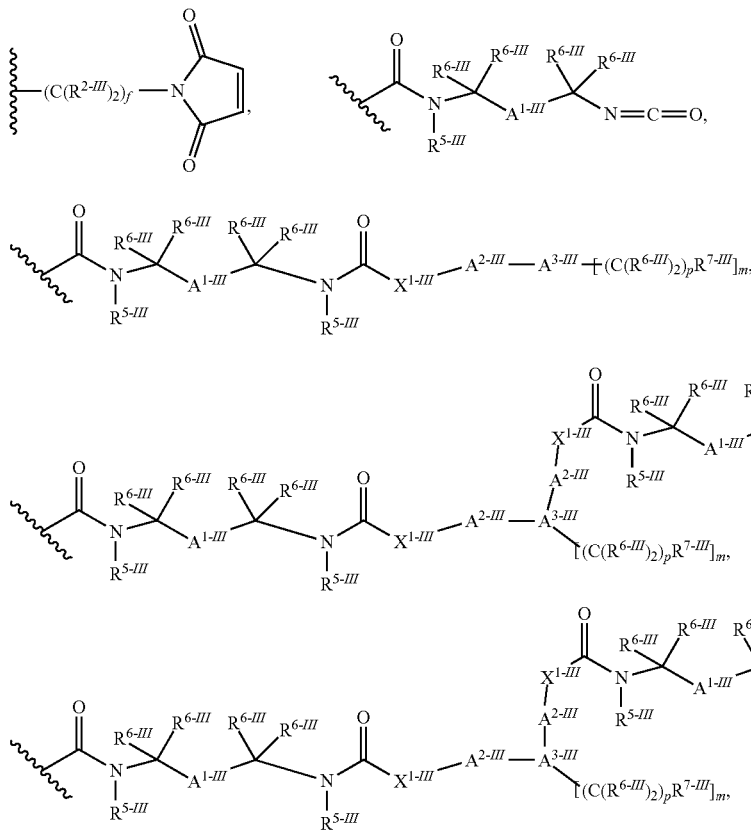

$R^{2-III}$ represents independently for each occurrence H, alkyl, or halogen;

$R^3$ represents independently for each occurrence H, alkyl, fluoroalkyl, chloroalkyl, —CH$_2$NO$_2$,

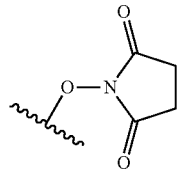 or 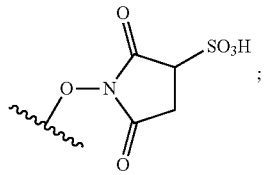 ;

$R^{4-III}$ represents independently for each occurrence —N=C=O, —N=C=S,

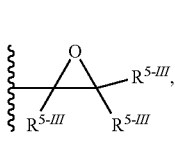 or 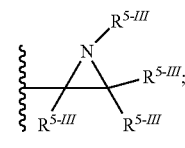 ;

$R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O,

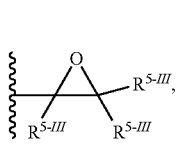 , 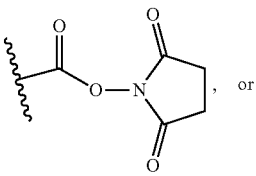 , or

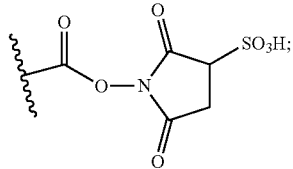 ;

$R^{8-III}$ represents independently for each occurrence

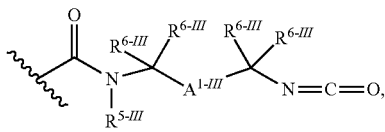

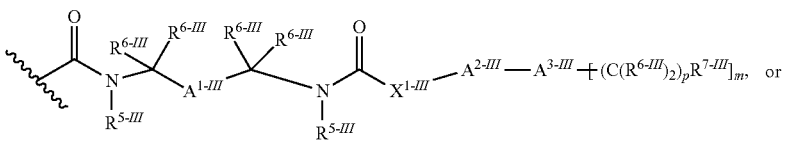 or

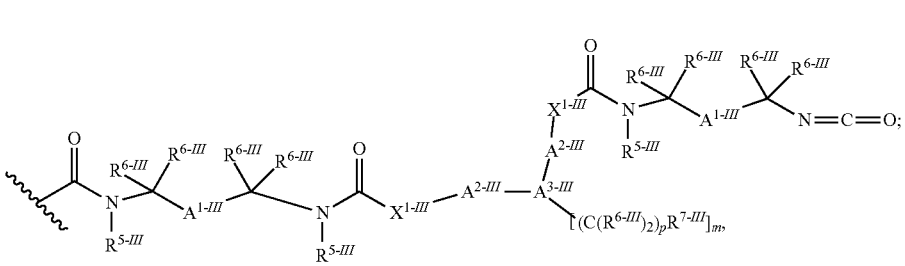

$A^{1-III}$ and $A^{3-III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{2-III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

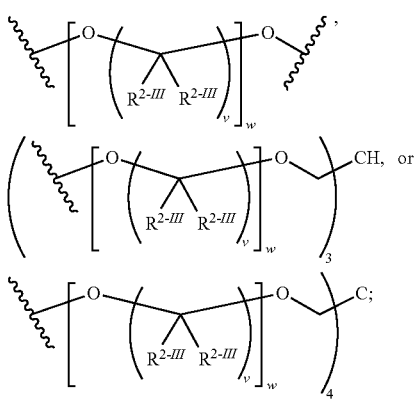

$X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

In certain instances, the present invention relates to the aforementioned method, wherein f and k each represent independently for each occurrence 1, 2, 3, 4, 5, 6, 7, 8, or 9.

In certain embodiments, the present invention relates to the aforementioned method, wherein said medical implant is a breast implant.

In certain embodiments, the present invention relates to any of the aforementioned methods, wherein $R^{1-III}$ represents independently for each occurrence $-(C(R^{2-III})_2)_fC(O)N(R^{5-III})-[A^{4-III}]_t-C(O)-R^{3-III}$ or $-(C(R^{2-III})_2)_fCO_2-[A^{4-III}]_t-C(O)-R^{3-III}$.

In certain embodiments, the present invention relates to any of the aforementioned methods, wherein $R^{1-III}$ is $-(C(R^{2-III})_2)_fC(O)N(R^{5-III})-[A^{4-III}]_t-C(O)-R^{3-III}$, $A^{4-III}$ is an alkyl diradical, t is 1, $R^{2-III}$ is H, and $R^{3-III}$ represents independently for each occurrence

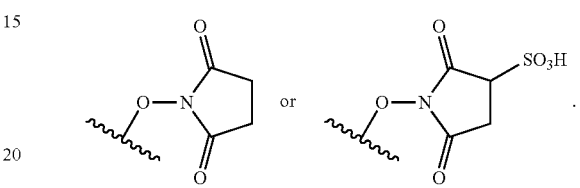

In certain embodiments, the present invention relates to any of the aforementioned methods, wherein $R^{1-III}$ is $-(C(R^{2-III})_2)_fC(O)N(R^{5-III})-[A^{4-III}]_t-C(O)-R^{3-III}$, $A^{4-III}$ is an alkyl diradical, t is 1, $R^{2-III}$ is H, $R^{3-III}$ represents independently for each occurrence

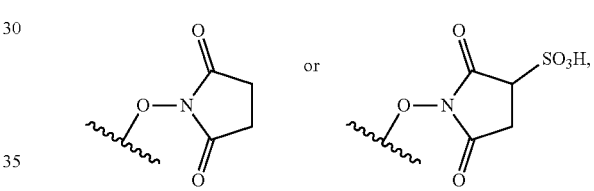

and B is

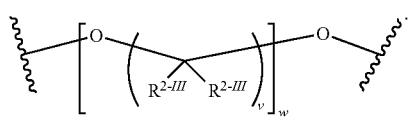

In certain embodiments, the present invention relates to any of the aforementioned methods, wherein said compound of formula III is one of the following:

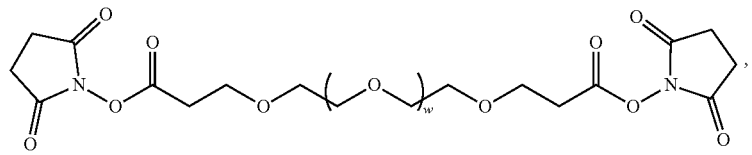

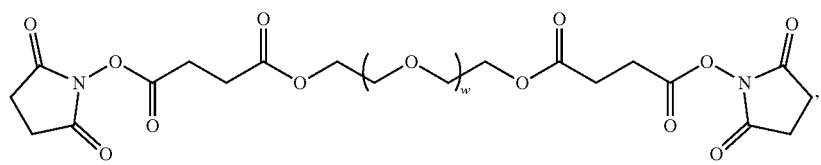

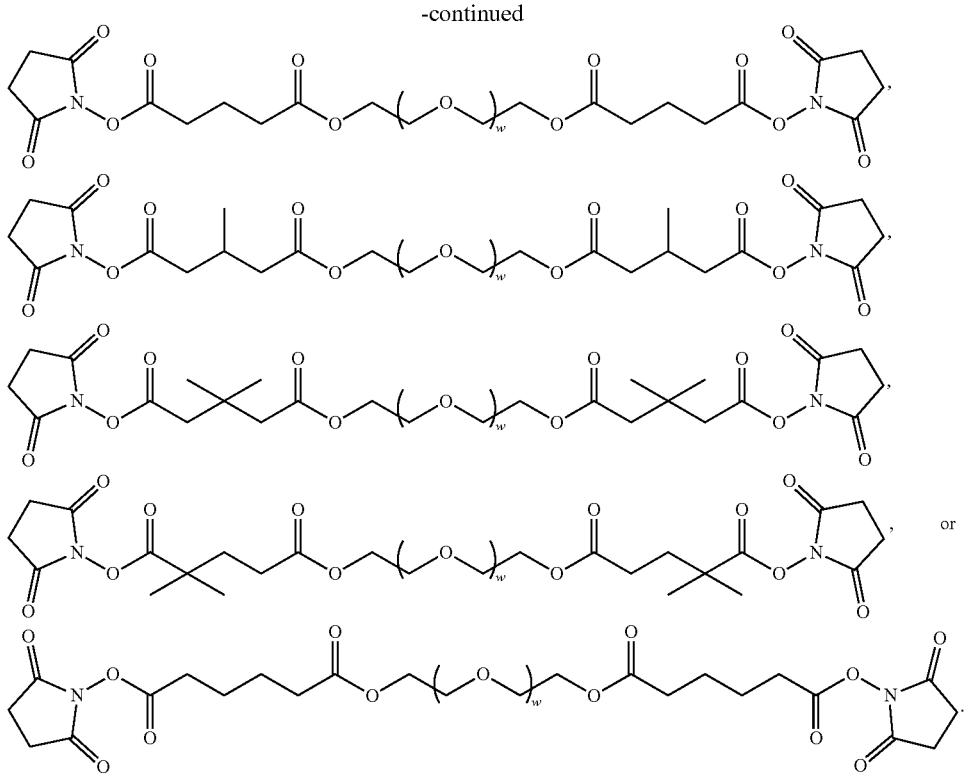

In certain embodiments, the present invention relates to any of the aforementioned methods, further comprising the step of exposing said compound of formula III to a compound $$B\text{-}(R^1)_t \quad\quad IV$$

wherein, $R^1$ represents independently for each occurrence —C(R$^2$)$_2$)$_j$C(O)—X—R$^3$, —C(O)(C(R$^2$)$_2$)$_k$C(O)—X—R$^3$, or —R$^3$, $R^2$ represents independently for each occurrence H, alkyl, or halogen;

$R^3$ represents independently for each occurrence

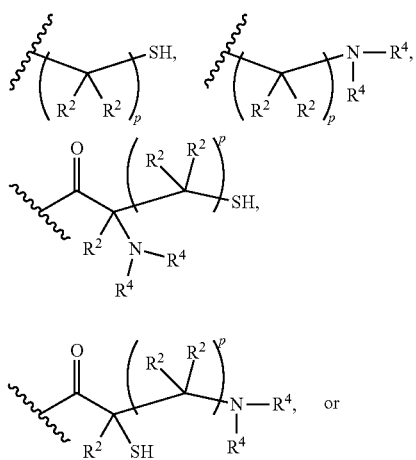

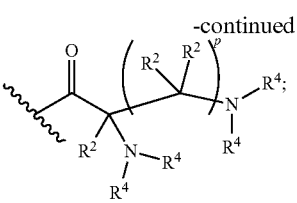

$R^4$ represents independently for each occurrence H, alkyl, aryl, aralkyl,

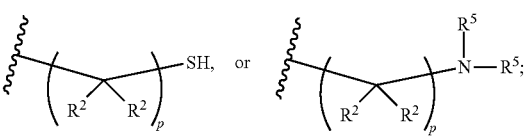

$R^5$ represents independently for each occurrence H or alkyl;

$X^1$ represents independently for each occurrence O or —N(R$^5$)—;

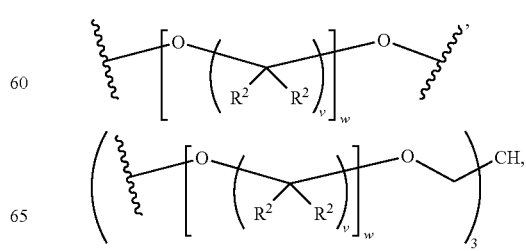

147

-continued

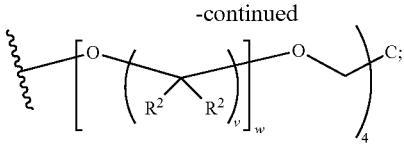

f and k each are independently selected for each occurrence from the group consisting of 1-25 inclusive;

p represents independently for each occurrence 1, 2, 3, 4, or 5;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

In certain instances, the present invention relates to the aforementioned method, wherein f and k each represent independently for each occurrence 1, 2, 3, 4, 5, 6, 7, 8, or 9.

In certain embodiments, the present invention relates to the aforementioned method, further comprising the step of mixing said compound of formula IV with said polymerization agent prior to exposing said compound of formula IV to said compound of formula III.

In certain embodiments, the present invention relates to any of the aforementioned methods, further comprising the step of:

exposing a gel to a compound of formula V to form a photo-polymerization agent, and treating said photo-polymerization agent with ultraviolet light or visible light sufficient to polymerize said photo-polymerization agent; wherein said gel is the product formed by exposing said polymerization agent to a compound of formula III, and said compound of formula V is represented by:

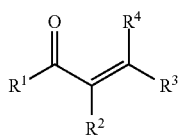

wherein,

R$^1$ is halogen,

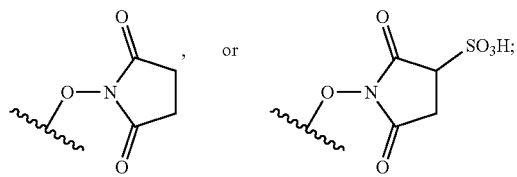 [SMILES: *ON1C(=O)CCC1=O ; *ON1C(=O)CC(S(=O)(=O)O)C1=O]

and

R$^2$, R$^3$, and R$^4$ each represent independently for each occurrence H, alkyl, aryl, or aralkyl.

In certain embodiments, the present invention relates to the aforementioned method, wherein R$^2$ is H or alkyl, and R$^3$ and R$^4$ are H.

In certain embodiments, the present invention relates to the aforementioned method, wherein R$^2$ is H or alkyl, R$^3$ and R$^4$ are H, and R$^1$ is chloride.

In certain embodiments, the present invention relates to the aforementioned method, wherein said photo-polymerization agent is treated with ultraviolet light sufficient to polymerize said photo-polymerization agent.

148

In certain embodiments, the present invention relates to the aforementioned method, wherein said photo-polymerization agent is treated with visible light, and said method further comprises the step of exposing said photo-polymerization agent to a photoinitiator.

In certain embodiments, the present invention relates to the aforementioned method, wherein said photoinitiator is eosin y.

In certain embodiments, the present invention relates to the aforementioned method, further comprising the step of sterilizing said polymerization agent.

In certain embodiments, the present invention relates to the aforementioned method, further comprising the step of sterilizing said compound of formula III.

In certain embodiments, the present invention relates to the aforementioned method, wherein said sterilizing is performed by treatment with ethylene oxide, hydrogen peroxide, heat, gamma irradiation, electron beam irradiation, microwave irradiation, or visible light irradiation.

In certain embodiments, the present invention relates to the aforementioned method, said said polymerization agent and said compound of formula III have a sterility assurance level of at least about 10$^{-3}$.

In certain embodiments, the present invention relates to the aforementioned method, said polymerization agent and said compound of formula III have a sterility assurance level of at least about 10$^{-6}$.

In certain embodiments, the present invention relates to the aforementioned method, wherein said patient is a primate, bovine, equine, feline, or canine.

In certain embodiments, the present invention relates to the aforementioned method, wherein said patient is a human.

In certain embodiments, the present invention relates to the aforementioned method, wherein said wound is an ophthalmic wound.

In certain embodiments, the present invention relates to the aforementioned method, wherein said wound is a wound to the cornea of an eye.

In certain embodiments, the present invention relates to the aforementioned method, wherein said wound is an epithelial defect, corneal incision, corneal laceration, corneal perforation, corneal ulceration, retinal hole, filtering bleb, corneal transplant, trabeculectomy incision, sclerotomy incision, blepharoplasty, or skin incision.

In certain embodiments, the present invention relates to the aforementioned method, wherein said wound is an epithelial defect, corneal incision, corneal laceration, corneal perforation, or corneal ulceration.

In certain embodiments, the present invention relates to the aforementioned method, wherein said wound is a corneal incision or corneal laceration.

In certain embodiments, the present invention relates to the aforementioned method, wherein said wound is a located in the dura.

In certain embodiments, the present invention relates to the aforementioned method, wherein said wound is a located in the lung tissue.

In certain embodiments, the present invention relates to the aforementioned method, wherein said wound is a tissue plane.

In certain embodiments, the present invention relates to the aforementioned method, wherein said wound is in a vein or artery.

In certain embodiments, the present invention relates to the aforementioned method, wherein said wound is less than about 25 mm long.

In certain embodiments, the present invention relates to the aforementioned method, wherein said wound is less than about 15 mm long.

In certain embodiments, the present invention relates to the aforementioned method, wherein said wound is less than about 10 mm long.

In certain embodiments, the present invention relates to the aforementioned method, wherein said wound is less than about 5 mm long.

In certain embodiments, the present invention relates to the aforementioned method, wherein said void is less than about 15 mm in diameter.

In certain embodiments, the present invention relates to the aforementioned method, wherein said void is less than about 10 mm in diameter.

In certain embodiments, the present invention relates to the aforementioned method, wherein said void is less than about 5 mm in diameter.

In certain embodiments, the present invention relates to the aforementioned method, wherein said first tissue and said second tissue are independently selected from the group consisting of skin, muscle, blood vessel, tendon, cartilage, ligament, liver, kidney, lung, heart, intestinal tissue, stomach, and corneal tissue.

In certain embodiments, the present invention relates to the aforementioned method, wherein said polymerization agent is sterile.

Another aspect of the present invention relates to a method of sealing a wound of a patient, comprising the steps of:

applying an effective amount of a polymerization agent to a wound of a patient, and exposing said polymerization agent to a compound of formula III sufficient to polymerize said polymerization agent, wherein said polymerization agent is a polymer having one or more monomeric units represented by formula Ie; and formula Ie is represented by:

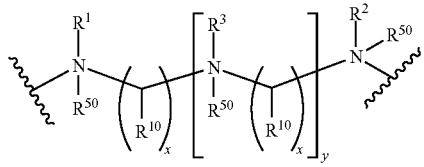

Ie wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —X$^1$—[C($R^4$)$_2$]$_d$N($R^5$)C(O)N($R^5$)$_2$, —X$^1$—[C($R^4$)$_2$]$_d$OC(O)CH$_2$C(O)—alkyl,

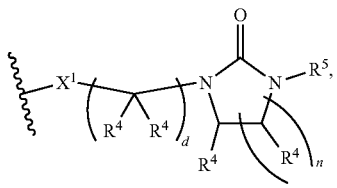

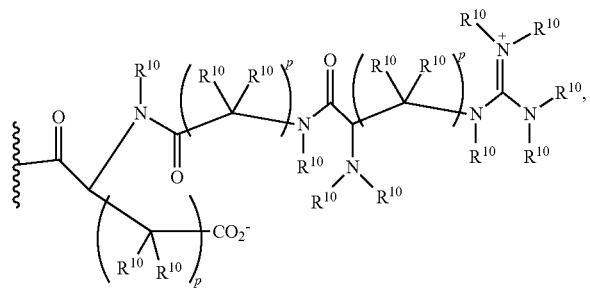

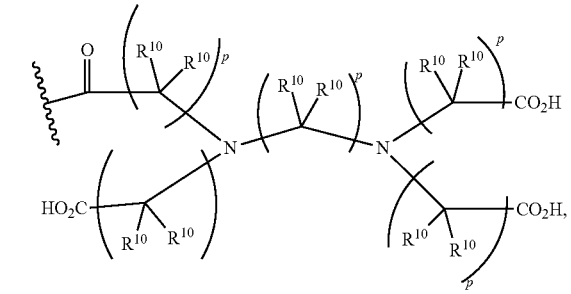

or a carbohydrate radical;

$R^3$ represents independently for each occurrence H or

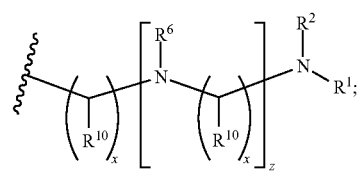

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

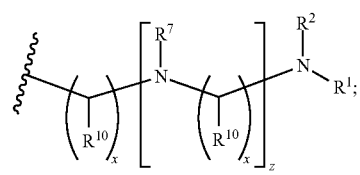

$R^7$ represents independently for each occurrence H or

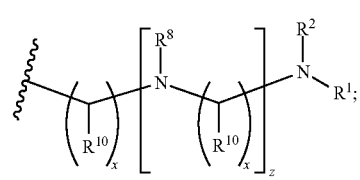

$R^8$ represents independently for each occurrence H or

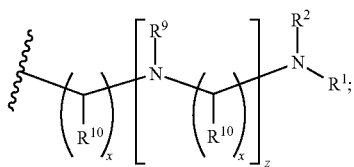

$R^9$ represents independently for each occurrence H or

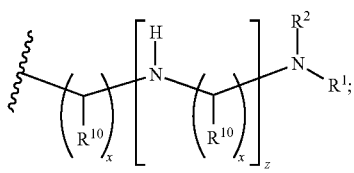

$R^{10}$ represents independently for each occurrence H or $(C_1\text{-}C_3)$alkyl;
$X^1$ represents independently for each occurrence a bond or —C(O)—;
$A^1$ represents independently for each occurrence H, —C(O)NH$_2$, —X$^1$—[C(R$^4$)$_2$]$_d$N(R$^5$)C(O)NH$_2$,

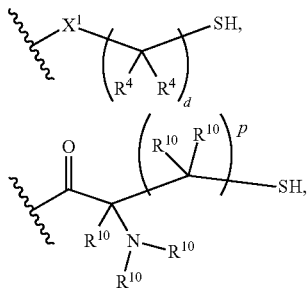

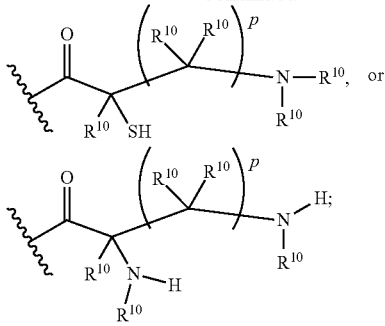

d represents independently for each occurrence 1, 2, 3, 4, 5, 6, 7, or 8;
n represents independently for each occurrence 1, 2, 3, or 4;
p represents independently for each occurrence 1, 2, 3, 4, or 5;
x represents independently for each occurrence 1, 2, 3, 4, or 5;
y is an integer in the range of 1 to about 40,000;
z represents independently for each occurrence an integer in the range of 0 to about 20,000; and
provided at least about 5% of $R^1$ is $A^1$, and the sum of y and z is less than about 50,000; and
formula III is represented by:

$$B\text{—}(R^{1\text{-}III})_{2,\,3,\,or\,4} \qquad III$$

wherein
$R^{1\text{-}III}$ represents independently for each occurrence —(C(R$^{2\text{-}III}$)$_2$)$_f$C(O)R$^{3\text{-}III}$, —C(O)(C(R$^{2\text{-}III}$)$_2$)$_k$C(O)R$^{3\text{-}III}$, —(C(R$^{2\text{-}III}$)$_2$)$_f$R$^{4\text{-}III}$, —C(O)(C(R$^{2\text{-}III}$)$_2$)$_k$R$^{4\text{-}III}$, —(C(R$^{2\text{-}III}$)$_2$)$_f$C(O)N(R$^{5\text{-}III}$)-[A$^{4\text{-}III}$]$_t$—C(O)—R$^{3\text{-}III}$, —(C(R$^{2\text{-}III}$)$_2$)$_f$CO$_2$-[A$^{4\text{-}III}$]$_t$-C(O)—R$^{3\text{-}III}$,

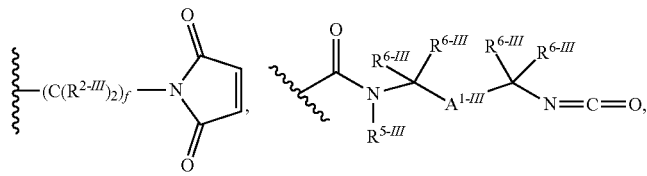

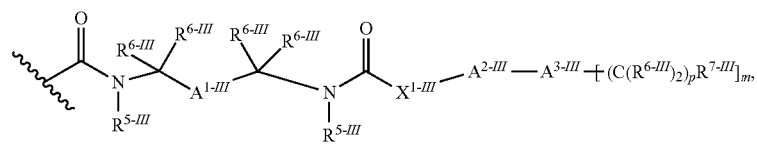

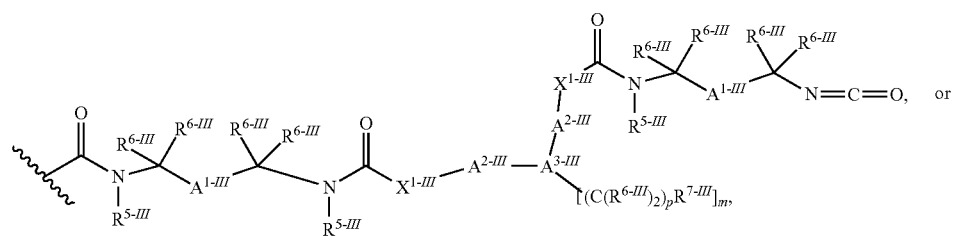

-continued

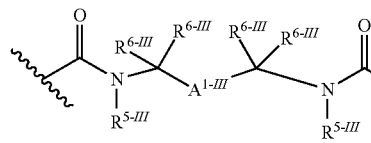
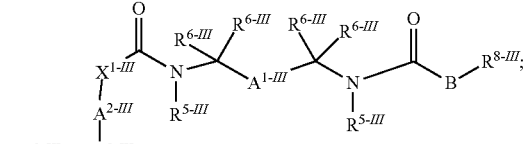

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$,

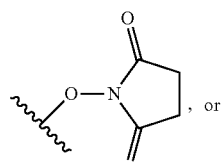, or

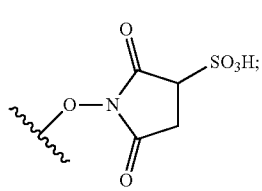

$R^{4-III}$ represents independently for each occurrence —N=C=O, —N=C=S,

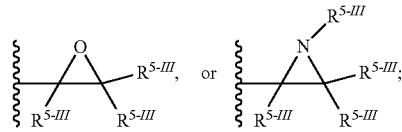

$R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O,

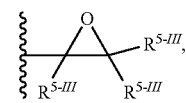

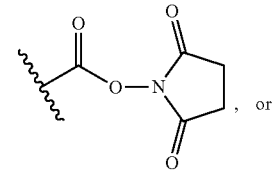, or

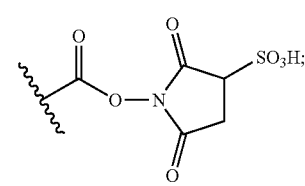

$R^{8-III}$ represents independently for each occurrence

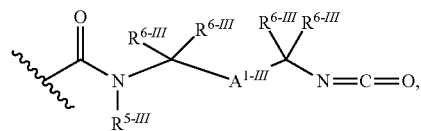

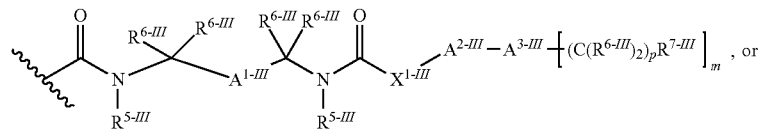, or

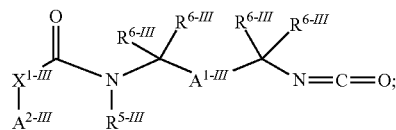

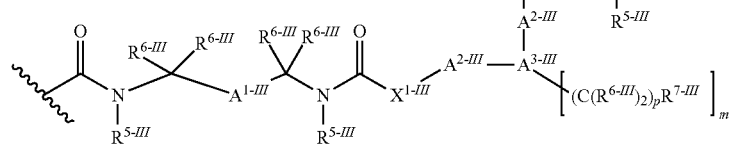

$A^{1-III}$ and $A^{3-III}$ represent independently for each occurrence alkyl, heteroalkyl, cycloalkyl, heterocycloalkyl, alkenyl, alkynyl, aryl, heteroaryl, aralkyl, or heteroaralkyl;

$A^{2-III}$ represents independently for each occurrence a bond, alkyl, heteroalkyl, cycloalkyl, heterocycloalkyl, alkenyl, alkynyl, aryl, heteroaryl, aralkyl, or heteroaralkyl;

$A^{4-III}$ represents independently for each occurrence an alkyl diradical, cycloalkyl diradical, aryl diradical, or aralkyl diradical;

B represents independently for each occurrence alkyl diradical, heteroalkyl diradical, or

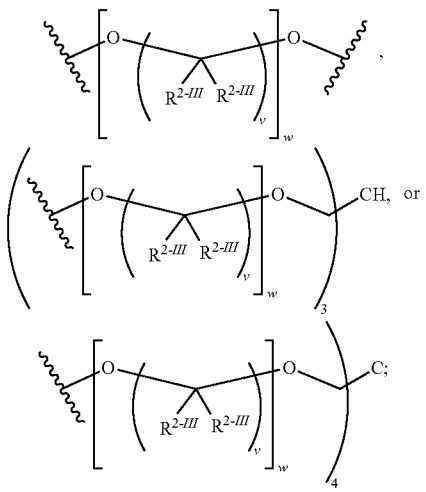

$X^{1-III}$ represents independently for each occurrence O or $-N(R^{5-III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and x and y each represent independently for each occurrence 1, 2, 3, 4, 5, 6, 7, 8, or 9.

In certain instances, the present invention relates to the aforementioned method, wherein $R^{10}$ is H, and x is 2 or 3.

In certain instances, the present invention relates to the aforementioned method, wherein $R^{10}$ is H, x is 2 or 3, at least about ½ of $R^1$ are H, and at least about ½ of $R^2$ are H.

In certain instances, the present invention relates to the aforementioned method, wherein $R^{10}$ is H, x is 2 or 3, at least about ½ of $R^1$ are H, at least about ½ of $R^2$ are H, and the sum of y and z is an integer in the range of about 20 to about 500.

In certain instances, the present invention relates to the aforementioned method, wherein $R^{10}$ is H, x is 2 or 3, at least about 90% of $R^1$ are $A^1$, and $A^1$ represents independently for each occurrence H,

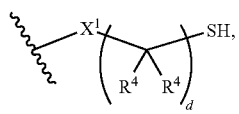

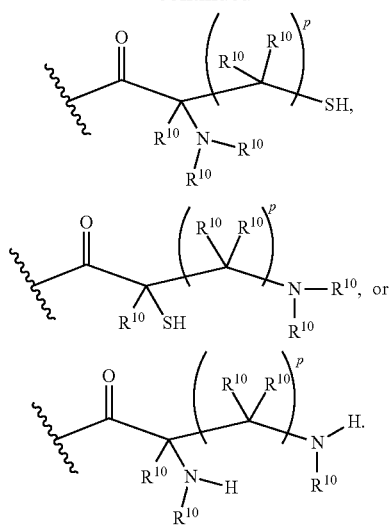

In certain instances, the present invention relates to the aforementioned method, wherein $R^{10}$ is H, x is 2 or 3, at least about 90% of $R^1$ and $R^2$ are $A^1$, and $A^1$ represents independently for each occurrence H,

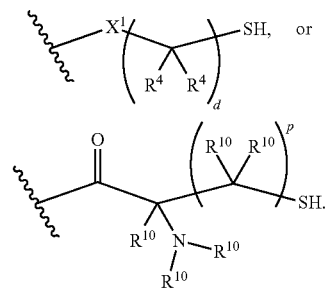

In certain instances, the present invention relates to the aforementioned method, wherein $R^{10}$ is H, x is 2 or 3, at least about 95% of $R^1$ and $R^2$ H; and the sum of y and z is an integer in the range of about 20 to about 500.

In certain instances, the present invention relates to the aforementioned method, wherein w is independently for each occurrence an integer in the range of about 50 to about 250.

In certain instances, the present invention relates to the aforementioned method, wherein w is independently for each occurrence an integer in the range of about 60 to about 90.

In certain instances, the present invention relates to the aforementioned method, wherein $R^{1-III}$ is $-(C(R^{2-III})_2)_xC(O)R^{3-III}$ or $-C(O)(C(R^{2-III})_2)_yC(O)R^{3-III}$, $R^{2-III}$ is H, and $R^{3-III}$ is

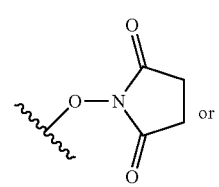

-continued

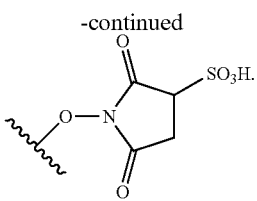

In certain instances, the present invention relates to the aforementioned method, wherein $R^1$ is $-(C(R^{2-III})_2)_xC(O)R^{3-III}$ or $-C(O)(C(R^{2-III})_2)_yC(O)R^{3-III}$, $R^{2-III}$ is H, $R^{3-III}$ is

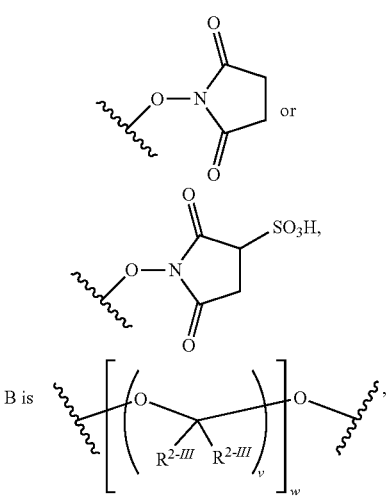

B is

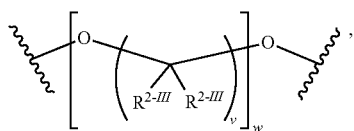

and v is 2.

In certain instances, the present invention relates to the aforementioned method, $R^{1-III}$ is $-(C(R^{2-III})_2)_xC(O)R^{3-III}$ or $-C(O)(C(R^{2-III})_2)_yC(O)R^{3-III}$, $R^{2-III}$ is H, $R^{3-III}$ is

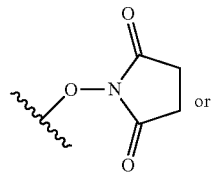

B is v is 2, and w is independently for each occurrence an integer in the range of about 15-90.

In certain instances, the present invention relates to the aforementioned method, $R^{1-III}$ is $(C(R^{2-III})_2)_xC(O)R^{3-III}$ or $-C(O)(C(R^{2-III})_2)_yC(O)R^{3-III}$, $R^{2-III}$ is H, $R^{3-III}$ is

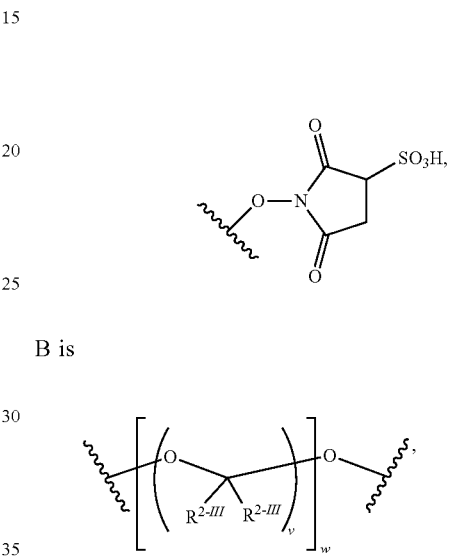

B is

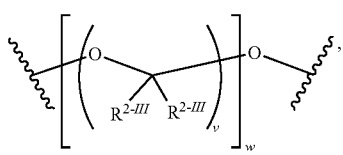

v is 2, and w is independently for each occurrence an integer in the range of about 15-90, B is v is 2, $R^{10}$ is H, x is 2, at least about ½ of $R^1$ are H, and at least about ½ of $R^2$ are H.

In certain instances, the present invention relates to the aforementioned method, wherein, formula III is

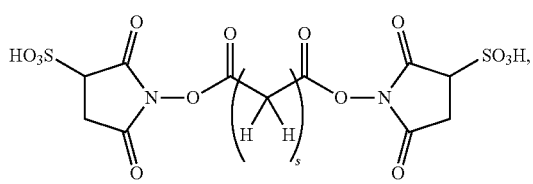

and s is an integer in the range of about 1-20 inclusive.

In certain instances, the present invention relates to the aforementioned method, wherein $R^{1-III}$ represents independently for each occurrence

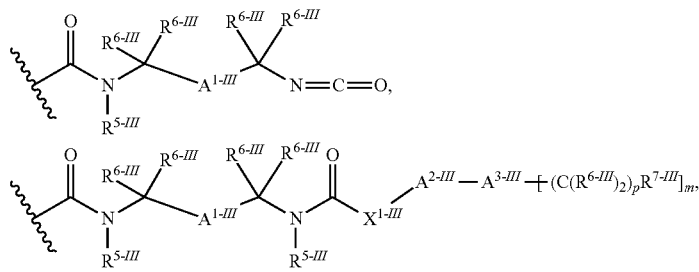

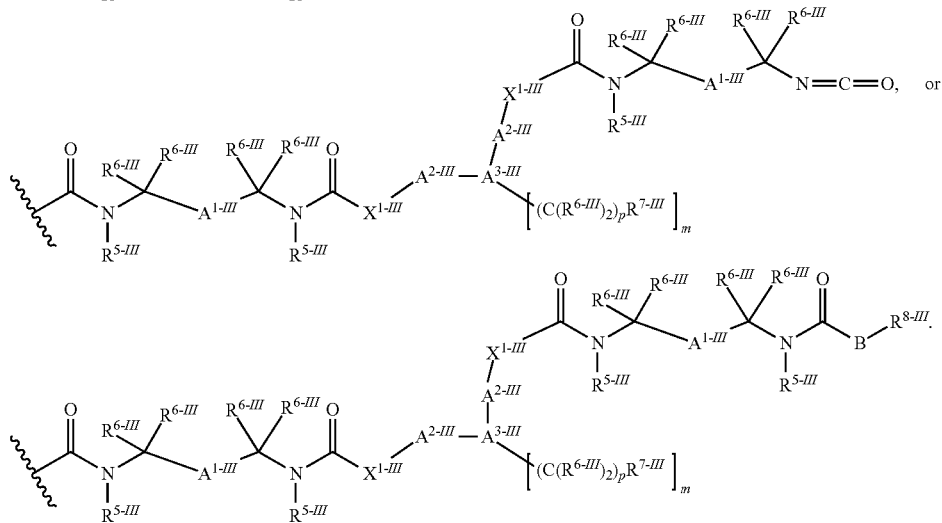

In certain instances, the present invention relates to the aforementioned method, wherein, B is

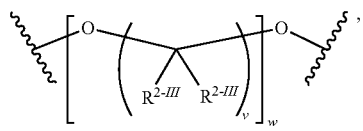

$R^{2-III}$ is H, and $A^{1-III}$ is aryl.

In certain instances, the present invention relates to the aforementioned method, wherein, B is

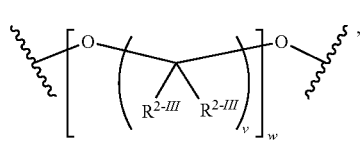

$R^{2-III}$ is H, and $A^{1-III}$ is optionally substituted phenyl.

In certain instances, the present invention relates to the aforementioned method, wherein B is

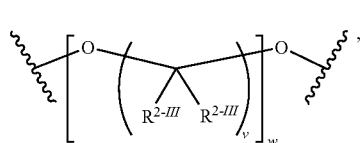

$R^{2-III}$ is H, $A^{2-III}$ is a bond, and $A^{3-III}$ is alkyl.

In certain instances, the present invention relates to the aforementioned method, wherein, B is

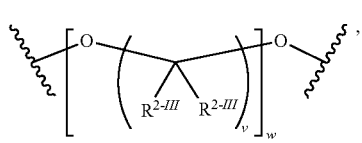

$R^{2-III}$ is H, $A^{2-III}$ is a bond, $A^{3-III}$ is alkyl, and $R^{7-III}$ is

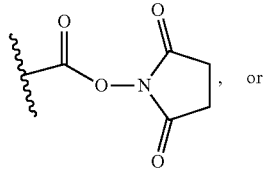

, or

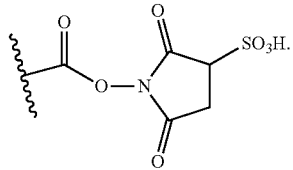

In certain instances, the present invention relates to the aforementioned method, wherein, B is

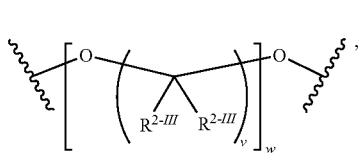

$R^{2\text{-}III}$ is H, $A^{2\text{-}III}$ is aryl, $A^{3\text{-}III}$ is aralkyl, and $R^{7\text{-}III}$ is

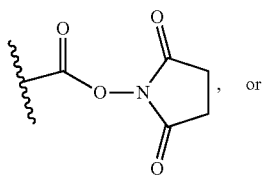, or

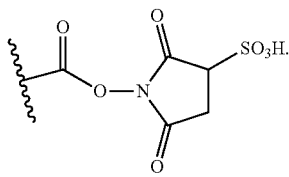

In certain instances, the present invention relates to the aforementioned method, wherein, B is

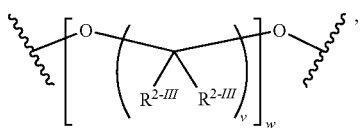

$R^{2\text{-}III}$ is H, $A^{2\text{-}III}$ is optionally substituted phenyl, $A^{3\text{-}III}$ is optionally substituted benzyl, and $R^{7\text{-}III}$ is

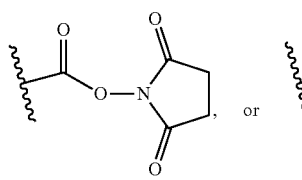, or 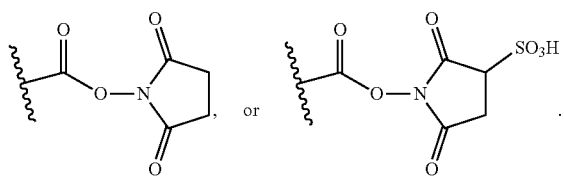 [SMILES: *C(=O)ON1C(=O)CCC1=O ; *C(=O)ON1C(=O)CC(S(=O)(=O)O)C1=O].

In certain instances, the present invention relates to the aforementioned method, wherein, B is

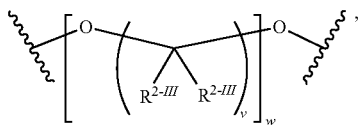

$R^{2\text{-}III}$ is H, v is 2, and $R^{1\text{-}III}$ is

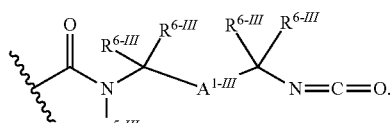

In certain instances, the present invention relates to the aforementioned method, wherein, B is

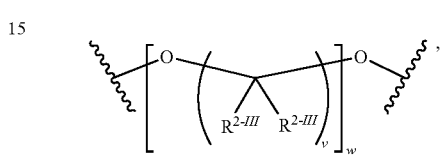

$R^{2\text{-}III}$ is H, v is 2, $R^{1\text{-}III}$ is

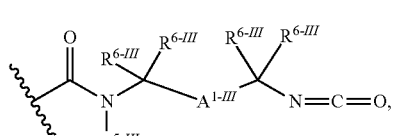

$R^{6\text{-}III}$ is $(C_1\text{-}C_4)$alkyl, and $A^{1\text{-}III}$ is aryl.

In certain instances, the present invention relates to the aforementioned method, wherein, B is

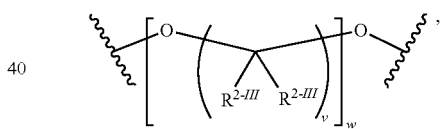

$R^{2\text{-}III}$ is H, v is 2, $R^{1\text{-}III}$ is

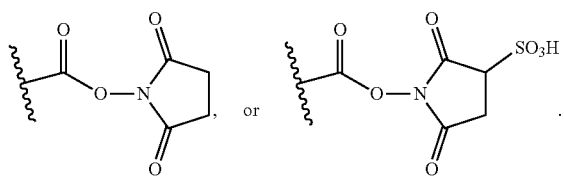 [SMILES: *C(=O)ON1C(=O)CCC1=O ; *C(=O)ON1C(=O)CC(S(=O)(=O)O)C1=O]

$R^{6\text{-}III}$ is $(C_1\text{-}C_4)$alkyl, and $A^{1\text{-}III}$ is optionally substituted phenyl.

In certain instances, the present invention relates to the aforementioned method, wherein, B is

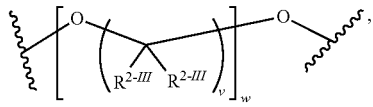

$R^{2-III}$ is H, v is 2, $R^{1-III}$ is

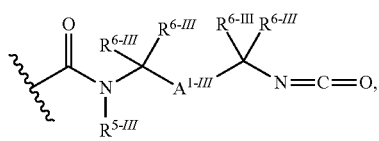

$R^{6-III}$ is methyl, and $A^{1-III}$ is phenyl.

In certain instances, the present invention relates to the aforementioned method, wherein, B is

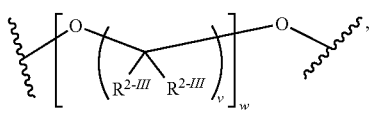

$R^{2-III}$ is H, v is 2, $R^{1-III}$ is

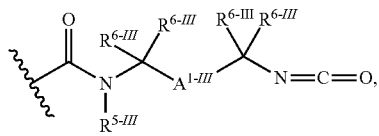

$R^{6-III}$ is methyl, $A^{1-III}$ is phenyl, $R^{10}$ is H, x is 2, at least about ½ of $R^1$ are H, and at least about ½ of $R^2$ are H.

In certain embodiments, the present invention relates to the aforementioned method, wherein $R^{1-III}$ is $-(C(R^{2-III})_2)_fC(O)N(R^{5-III})-[A^{4-III}]_t-C(O)-R^{3-III}$, $A^{4-III}$ is an alkyl diradical, t and f are 1, $R^{2-III}$ and $R^{5-III}$ are hydrogen, and $R^{3-III}$ is

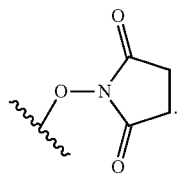 [SMILES: *ON1C(=O)CCC1=O]

Another aspect of the present invention relates to a method of sealing a wound of a patient, comprising the steps of: exposing an effective amount of a polymerization agent to a compound of formula III to form an adhesive composition, and applying said adhesive composition to a wound of a patient, wherein said polymerization agent is a polymer having one or more monomeric units represented by formula Ie; and formula Ie is represented by:

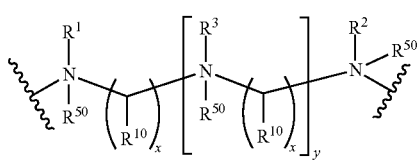

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, $-C(O)$-alkyl, $-C(O)N(R^5)_2$, $-X^1-[C(R^4)_2]_dN(R^5)C(O)N(R^5)_2$, $-X^1-[C(R^4)_2]_dOC(O)CH_2C(O)$—alkyl

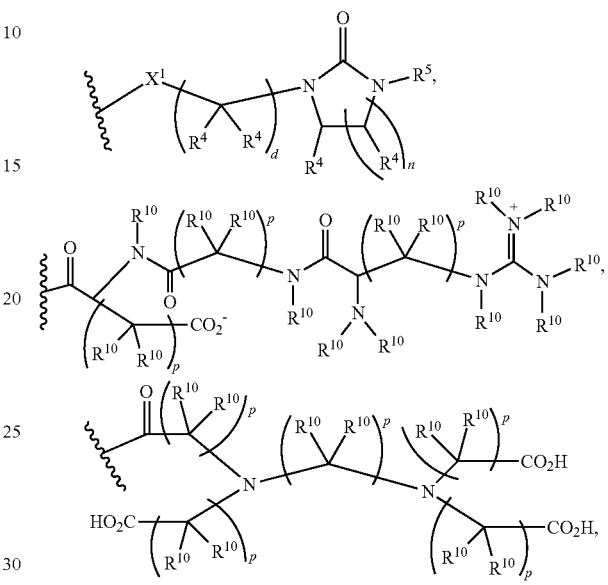

or a carbohydrate radical;

$R^3$ represents independently for each occurrence H or

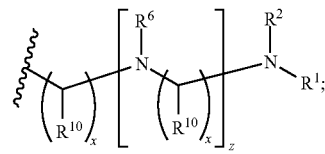

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

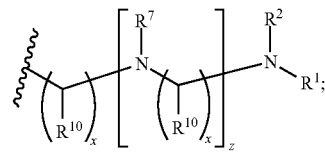

$R^7$ represents independently for each occurrence H or

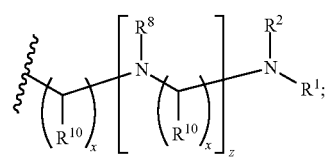

R[8] represents independently for each occurrence H or

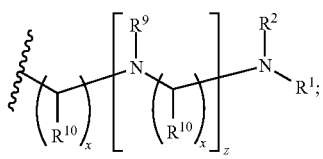

R[9] represents independently for each occurrence H or

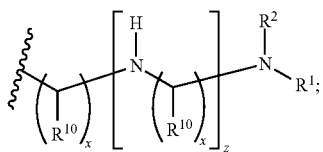

R[10] represents independently for each occurrence H or (C$_1$-C$_3$)alkyl;

X[1] represents independently for each occurrence a bond or —C(O)—;

A[1] represents independently for each occurrence H, —C(O)NH$_2$, —X[1]—[C(R[4])$_2$]$_d$N(R[5])C(O)NH$_2$,

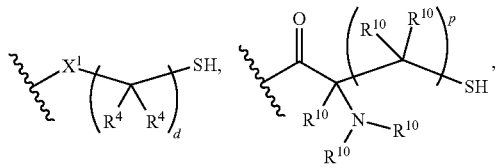

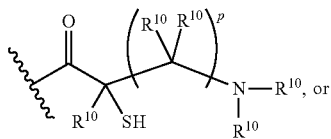

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of R[1] is A[1], and the sum of y and z is less than about 50,000; and formula III is represented by:

$$B-(R^{1-III})_{2,\,3,\,or\,4} \qquad \text{III}$$

wherein

R[1-III] represents independently for each occurrence —(C(R[2-III])$_2$)$_f$C(O)R[3-III], —C(O)(C(R[2-III])$_2$)$_y$C(O)R[3-III], —(C(R[2-III])$_2$)$_x$R[4-III], —C(O)(C(R[2-III])$_2$)$_x$R[4-III], —(C(R[2-III])$_2$)$_f$C(O)N(R[5-III])-[A[4-III]]$_t$—C(O)—R[3-III], —(C(R[2-III])$_2$)$_f$CO$_2$-[A[4-III]]$_t$-C(O)—R[3-III],

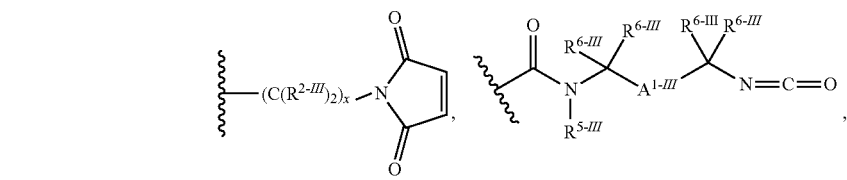

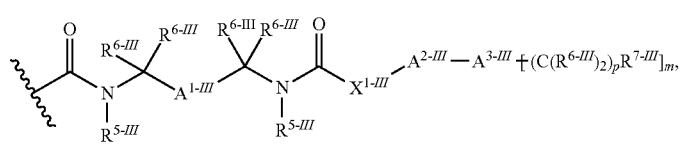

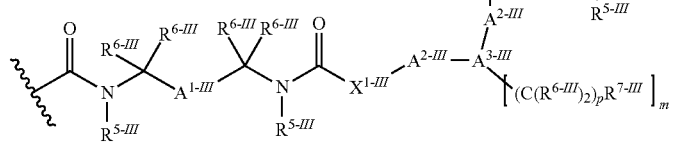

-continued

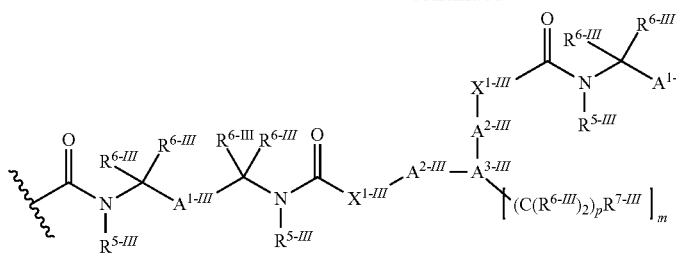

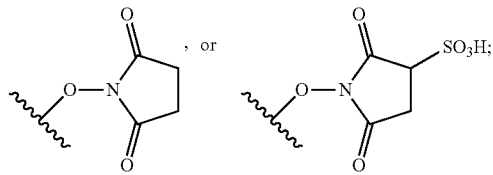 [SMILES: *ON1C(=O)CCC1=O ; "," ; *ON1C(=O)CC(S(=O)(=O)O)C1=O]

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$,

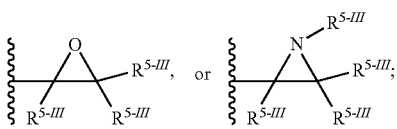, or $R^{4-III}$ represents independently for each occurrence —N=C=O, —N=C=S,

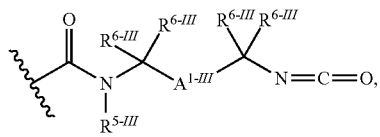, or $R^{5-III}$ represents independently for each occurrence H, alkyl, or aralkyl;

$R^{6-III}$ represents independently for each occurrence H or (C$_1$-C$_6$)alkyl;

$R^{7-III}$ represents independently for each occurrence —CO$_2$H, —(C(R$^{6-III}$)$_2$)$_p$N=C=O,

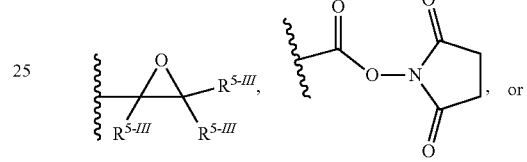, or

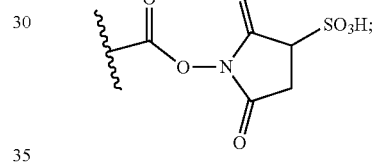

$R^8$ represents independently for each occurrence

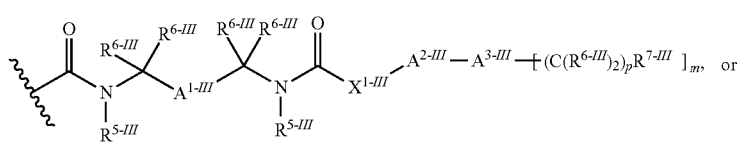

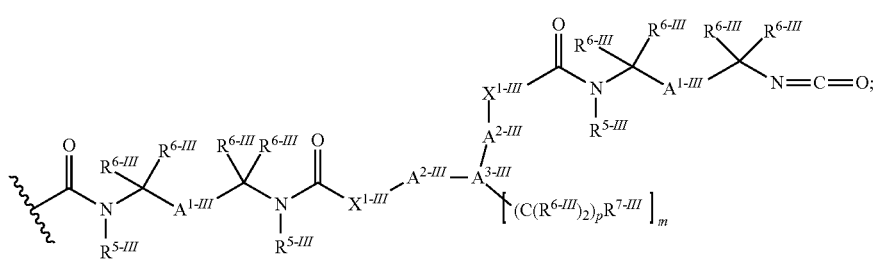

$A^{1\text{-}III}$ and $A^{3\text{-}III}$ represent independently for each occurrence alkyl, heteroalkyl, cycloalkyl, heterocycloalkyl, alkenyl, alkynyl, aryl, heteroaryl, aralkyl, or heteroaralkyl;

$A^{2\text{-}III}$ represents independently for each occurrence a bond, alkyl, heteroalkyl, cycloalkyl, heterocycloalkyl, alkenyl, alkynyl, aryl, heteroaryl, aralkyl, or heteroaralkyl;

$A^{4\text{-}III}$ represents independently for each occurrence an alkyl diradical, cycloalkyl diradical, aryl diradical, or aralkyl diradical;

B represents independently for each occurrence alkyl diradical, heteroalkyl diradical, or

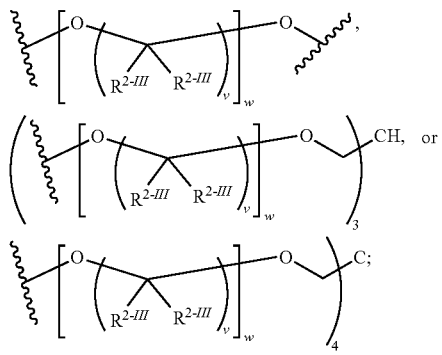

$X^{1\text{-}III}$ represents independently for each occurrence O or $-N(R^{5\text{-}III})-$;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and x and y each represent independently for each occurrence 1, 2, 3, 4, 5, 6, 7, 8, or 9.

In certain instances, the present invention relates to the aforementioned method, wherein $R^{10}$ is H, and x is 2 or 3.

In certain instances, the present invention relates to the aforementioned method, wherein $R^{10}$ is H, x is 2 or 3, at least about ½ of $R^1$ are H, and at least about ½ of $R^2$ are H.

In certain instances, the present invention relates to the aforementioned method, wherein $R^{10}$ is H, x is 2 or 3, at least about ½ of $R^1$ are H, at least about ½ of $R^2$ are H, and the sum of y and z is an integer in the range of about 20 to about 500.

In certain instances, the present invention relates to the aforementioned method, wherein $R^{10}$ is H, x is 2 or 3, at least about 90% of $R^1$ are $A^1$, and $A^1$ represents independently for each occurrence H,

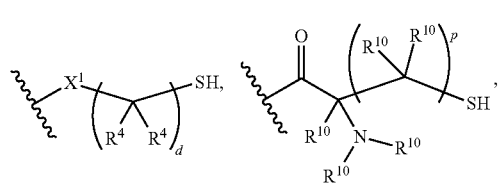

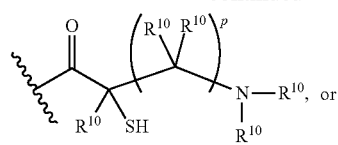

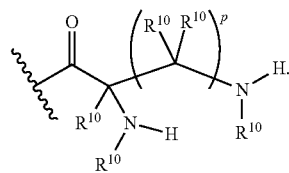

In certain instances, the present invention relates to the aforementioned method, wherein $R^{10}$ is H, x is 2 or 3, at least about 90% of $R^1$ and $R^2$ are $A^1$, and $A^1$ represents independently for each occurrence H,

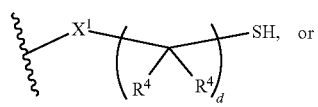

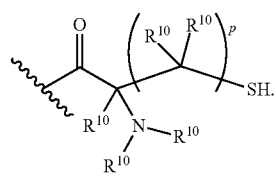

In certain instances, the present invention relates to the aforementioned method, wherein $R^{10}$ is H, x is 2 or 3, at least about 95% of $R^1$ and $R^2$ are H; and the sum of y and z is an integer in the range of about 20 to about 500.

In certain instances, the present invention relates to the aforementioned method, wherein w is independently for each occurrence an integer in the range of about 50 to about 250.

In certain instances, the present invention relates to the aforementioned method, wherein w is independently for each occurrence an integer in the range of about 60 to about 90.

In certain instances, the present invention relates to the aforementioned method, wherein $R^{1\text{-}III}$ is $-(C(R^{2\text{-}III})_2)_xC(O)R^3$ or $-C(O)(C(R^{2\text{-}III})_2)_yC(O)R^{3\text{-}III}$, $R^{2\text{-}III}$ is H, and $R^{3\text{-}III}$ is

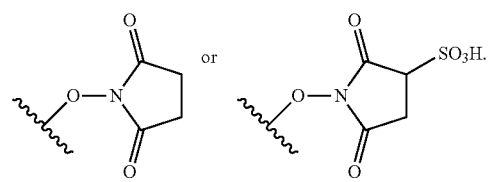 [SMILES: *ON1C(=O)CCC1=O ; *ON1C(=O)CC(S(=O)(=O)O)C1=O]

In certain instances, the present invention relates to the aforementioned method, wherein $R^1$ is $-(C(R^{2-III})_2)_xC(O)R^{3-III}$ or $-C(O)(C(R^{2-III})_2)_yC(O)R^{3-III}$, $R^{2-III}$ is H, $R^{3-III}$ is

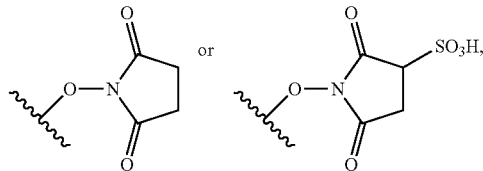 [SMILES: *ON1C(=O)CCC1=O ; *ON1C(=O)CC(S(=O)(=O)O)C1=O]

B is

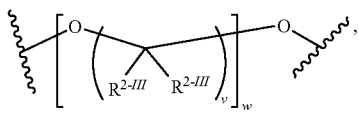

and v is 2.

In certain instances, the present invention relates to the aforementioned method, $R^{1-III}$ is $-(C(R^{2-III})_2)_xC(O)R^{3-III}$ or $-C(O)(C(R^{2-III})_2)_yC(O)R^{3-III}$, $R^{2-III}$ is

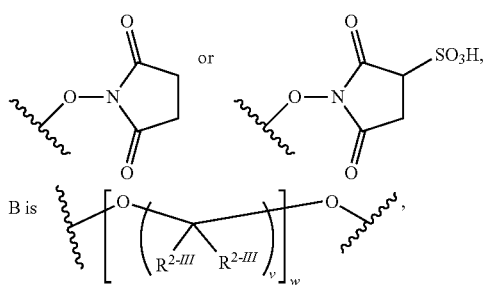

v is 2, and w is independently for each occurrence an integer in the range of about 15-90.

In certain instances, the present invention relates to the aforementioned method, $R^{1-III}$ is $-(C(R^{2-III})_2)_xC(O)R^{3-III}$ or $-C(O)(C(R^{2-III})_2)_yC(O)R^{3-III}$, $R^{2-III}$ is H, $R^{3-III}$ is

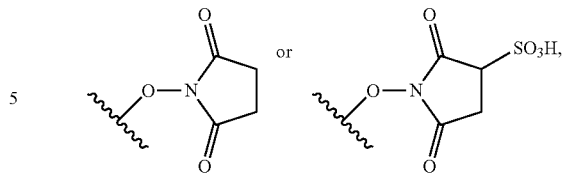

B is

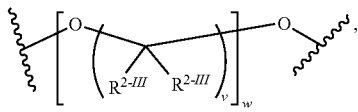

v is 2, and w is independently for each occurrence an integer in the range of about 15-90, B is

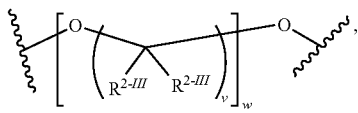

v is 2, $R^{10}$ is H, x is 2, at least about ½ of $R^1$ are H, and at least about ½ of $R^2$ are H.

In certain instances, the present invention relates to the aforementioned method, wherein, formula III is

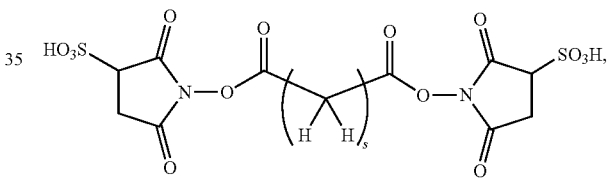

and s is an integer in the range of about 1-20 inclusive.

In certain instances, the present invention relates to the aforementioned method, wherein $R^{1-III}$ represents independently for each occurrence

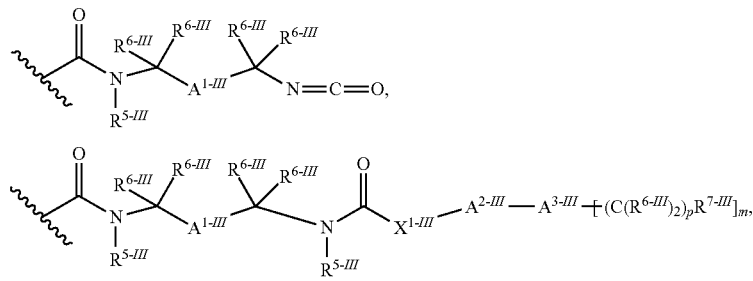

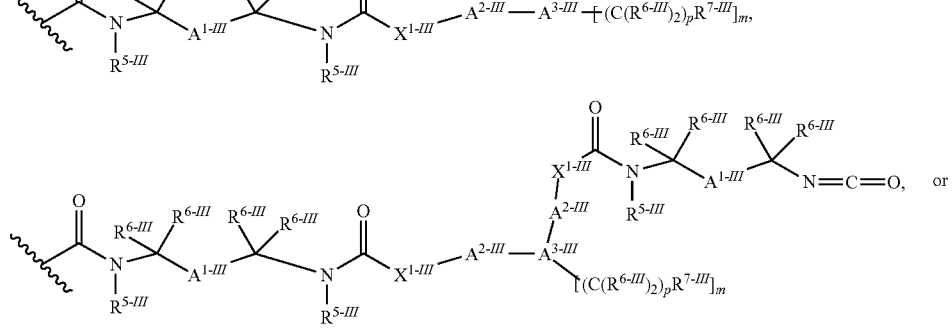

-continued

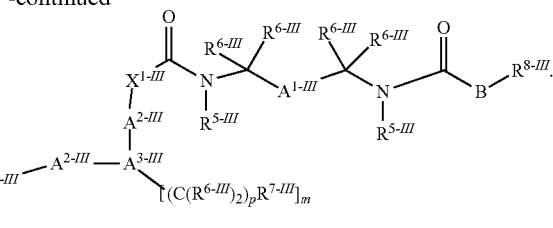

In certain instances, the present invention relates to the aforementioned method, wherein, B is

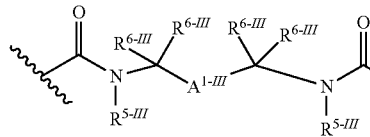

$R^{2-III}$ is H, and $A^{1-III}$ is aryl.

In certain instances, the present invention relates to the aforementioned method, wherein, B is

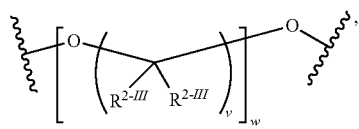

$R^{2-III}$ is H, and $A^{1-III}$ is optionally substituted phenyl.

In certain instances, the present invention relates to the aforementioned method, wherein, B is

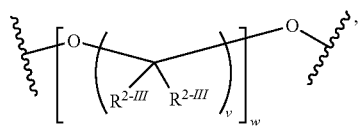

$R^{2-III}$ is H, $A^{2-III}$ is a bond, and $A^{3-III}$ is alkyl.

In certain instances, the present invention relates to the aforementioned method, wherein, B is

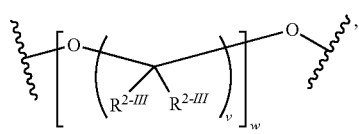

$R^{2-III}$ is H, $A^{2-III}$ is a bond, $A^{3-III}$ is alkyl, and $R^{7-III}$ is

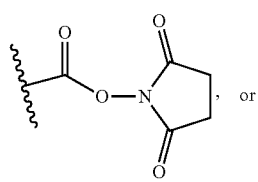, or

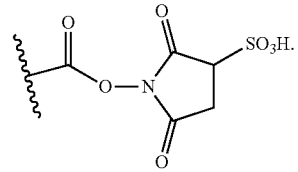

In certain instances, the present invention relates to the aforementioned method, wherein, B is

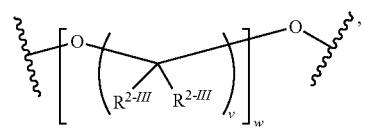

$R^{2-III}$ is H, $A^{2-III}$ is aryl, $A^{3-III}$ is aralkyl, and $R^{7-III}$ is

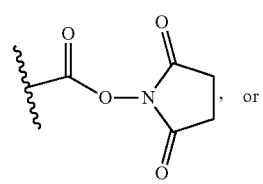, or

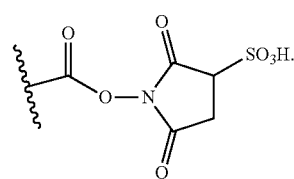

In certain instances, the present invention relates to the aforementioned method, wherein, B is

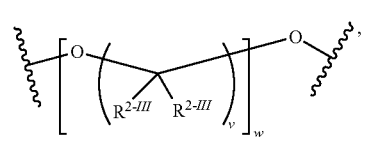

$R^{2\text{-}III}$ is H, $A^{2\text{-}III}$ is optionally substituted phenyl, $A^{3\text{-}III}$ is optionally substituted benzyl, and $R^{7\text{-}III}$ is

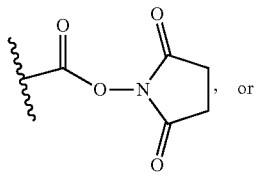, or

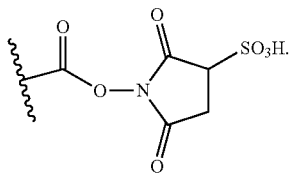

In certain instances, the present invention relates to the aforementioned method, wherein, B is

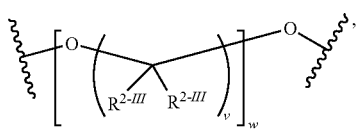

$R^{2\text{-}III}$ is H, v is 2, and $R^{1\text{-}III}$ is

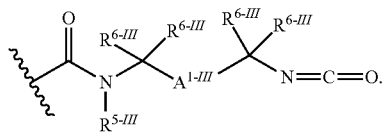

In certain instances, the present invention relates to the aforementioned method, wherein, B is

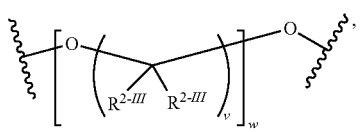

$R^{2\text{-}III}$ is H, v is 2, $R^{1\text{-}III}$ is

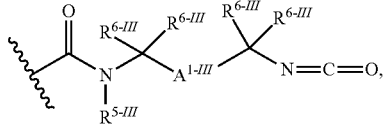

$R^{6\text{-}III}$ is $(C_1\text{-}C_4)$alkyl, and $A^{1\text{-}III}$ is aryl.

In certain instances, the present invention relates to the aforementioned method, wherein, B is

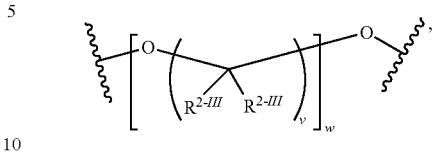

$R^{2\text{-}III}$ is H, v is 2, $R^{1\text{-}III}$ is

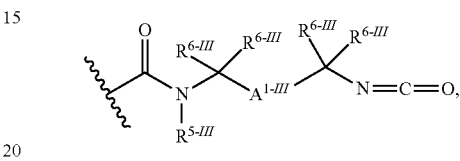

$R^{6\text{-}III}$ is $(C_1\text{-}C_4)$alkyl, and $A^{1\text{-}III}$ is optionally substituted phenyl.

In certain instances, the present invention relates to the aforementioned method, wherein, B is

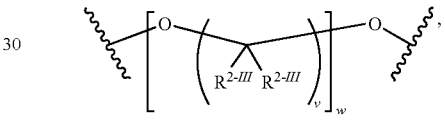

$R^{2\text{-}III}$ is H, v is 2, $R^{1\text{-}III}$ is

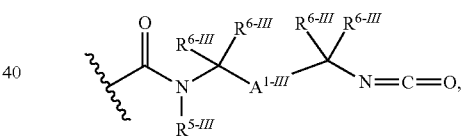

$R^{6\text{-}III}$ is methyl, and $A^{1\text{-}III}$ is phenyl.

In certain instances, the present invention relates to the aforementioned method, wherein, B is

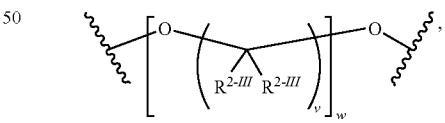

$R^{2\text{-}III}$ is H, v is 2, $R^{1\text{-}III}$ is

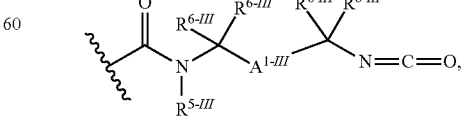

$R^{6\text{-}III}$ is methyl, $A^{1\text{-}III}$ is phenyl, $R^{10}$ is H, x is 2, at least about ½ of R are H, and at least about ½ of $R^2$ are H.

In certain embodiments, the present invention relates to the aforementioned method, wherein $R^{1\text{-}III}$ is $-(C(R^{2\text{-}III})_2)_fC(O)N(R^{5\text{-}III})\text{-}[A^{4\text{-}III}]_t\text{-}C(O)-R^{3\text{-}III}$, $A^{4\text{-}III}$ is an alkyl diradical, t and f are 1, $R^{2\text{-}III}$ and $R^{5\text{-}III}$ are hydrogen, and $R^{3\text{-}III}$ is In certain embodiments, the present invention relates to any of the aforementioned methods, further comprising the step of dissolving in an optionally buffered sterile aqueous solution a compound of formula Ia, Ib, or III to produce a mixture.

In certain embodiments, the present invention relates to any of the aforementioned methods, further comprising the step of dissolving in an optionally buffered sterile aqueous solution a polymer having one or more monomeric units represented by formula Ic.

In certain embodiments, the present invention relates to the aforementioned method, further comprising the step of sterilizing said mixture using e-beam radiation; and wherein said e-beam radiation is from about 2-40 kGy.

In certain embodiments, the present invention relates to the aforementioned method, further comprising the step of sterilizing said mixture using e-beam radiation; and wherein said e-beam radiation is from about 3-20 kGy.

In certain embodiments, the present invention relates to the aforementioned method, further comprising the step of sterilizing said mixture using e-beam radiation; and wherein said e-beam radiation is from about 5-12 kGy.

In certain embodiments, the present invention relates to any of the aforementioned methods, further comprising the step of dissolving in an optionally buffered sterile aqueous solution an antioxidant, and a compound of formula Ia, Ib, or III.

In certain embodiments, the present invention relates to any of the aforementioned methods, further comprising the step of dissolving in an optionally buffered sterile aqueous solution an antioxidant, and a polymer having one or more monomeric units represented by formula Ie.

In certain embodiments, the present invention relates to the aforementioned method, further comprising the step of sterilizing said mixture using e-beam radiation; and wherein said e-beam radiation is from about 2-40 kGy.

In certain embodiments, the present invention relates to the aforementioned method, further comprising the step of sterilizing said mixture using e-beam radiation; and wherein said e-beam radiation is from about 3-20 kGy.

In certain embodiments, the present invention relates to the aforementioned method, further comprising the step of sterilizing said mixture using e-beam radiation; and wherein said e-beam radiation is from about 5-12 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 50 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 50 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 25 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 25 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 10 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 10 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 5 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 5 wt % of said mixture; and wherein said e-beam radiation is from about 2-40 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 50 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 50 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ta or Ib constitutes from about 0.01 wt % to about 25 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 25 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 10 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 10 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ta or Ib constitutes from about 0.01 wt % to about 5 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 5 wt % of said mixture; and wherein said e-beam radiation is from about 3-20 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 50 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 50 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 25 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 25 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 10 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 10 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a compound of formula Ia or Ib to produce a mixture; and sterilizing said mixture using e-beam radiation; wherein said compound of formula Ia or Ib constitutes from about 0.01 wt % to about 5 wt % of said mixture; and wherein said e-beam radiation is from about 5-12 kGy.

In certain embodiments, the present invention relates to any of the aforementioned methods, further comprising the steps of dissolving in an optionally buffered sterile aqueous solution a polymer having one or more monomeric units represented by formula Ie to produce a mixture; and sterilizing said mixture using e-beam radiation; wherein said polymer constitutes from about 0.01 wt % to about 5 wt % of said mixture; and wherein said e-beam radiation is from about 5-12 kGy.

Another aspect of the present invention relates to a method of sealing a wound of a patient, comprising the steps of:

applying an effective amount of a polymerization agent to a wound of a patient, and exposing said polymerization agent to visible light or ultraviolet light sufficient to polymerize said polymerization agent, wherein said polymerization agent is a compound of formula I, formula III, or a mixture thereof; or a pharmaceutically acceptable salt of any of them; and formula I is represented by:

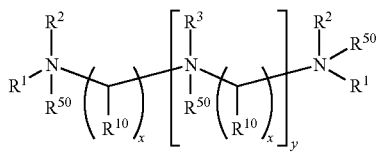

I wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —$X^1$—[C($R^4$)$_2$]$_d$N($R^5$)C(O)N($R^5$)$_2$, —$X^1$—[C($R^4$)$_2$]$_d$OC(O)CH$_2$C(O)—alkyl,

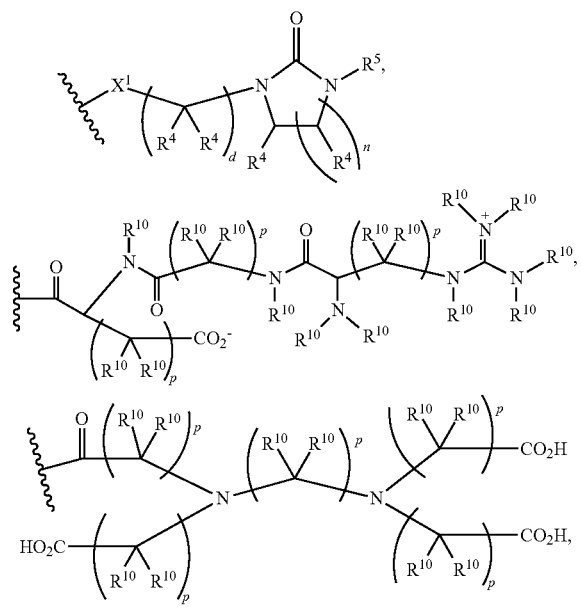

or a carbohydrate radical;

$R^3$ represents independently for each occurrence H or

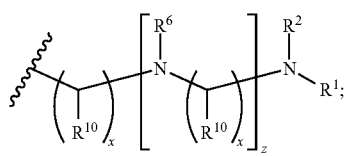

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

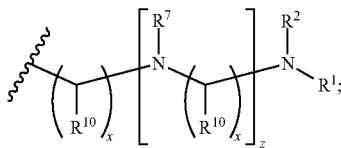

$R^7$ represents independently for each occurrence H or

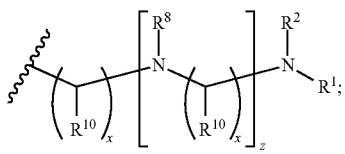

$R^8$ represents independently for each occurrence H or

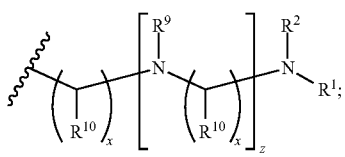

$R^9$ represents independently for each occurrence H or

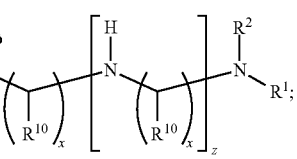

$R^{10}$ represents independently for each occurrence H or ($C_1$-$C_3$)alkyl;

$X^1$ represents independently for each occurrence a bond or —C(O)—;

$A^1$ represents independently for each occurrence

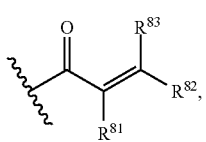

wherein $R^{81}$, $R^{82}$, and $R^{83}$ each represent independently for each occurrence H, alkyl, aryl, or aralkyl;

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; and formula III is represented by:

III wherein $R^1$ represents independently for each occurrence —(C$(R^2)_2$)$_x$C(O)—X—$R^3$, —C(O)(C($R^2$)$_2$)$_k$C(O)—X—$R^3$, or —$R^3$;

$R^2$ represents independently for each occurrence H, alkyl, or halogen;

$R^3$ represents

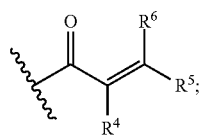

$R^4$, $R^5$, and $R^6$ each represent independently for each occurrence H, alkyl, aryl, or aralkyl;

X represents independently for each occurrence O or —N($R^5$)—.

B is

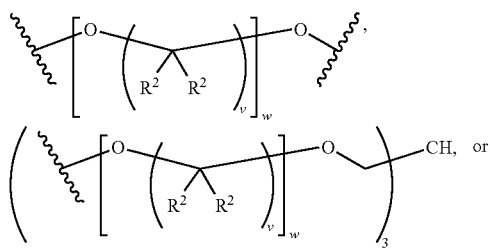

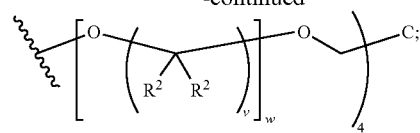

f and k each are independently selected for each occurrence from the group consisting of 1-25 inclusive;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

Another aspect of the present invention relates to a method of augmenting soft tissue or filling a void of a patient, comprising the steps of:

applying an effective amount of a polymerization agent to soft tissue or a void of a patient, and exposing said polymerization agent to visible light or ultraviolet light sufficient to polymerize said polymerization agent, wherein said polymerization agent is a compound of formula I, formula III, or a mixture thereof; or a pharmaceutically acceptable salt of any of them; and formula I is represented by:

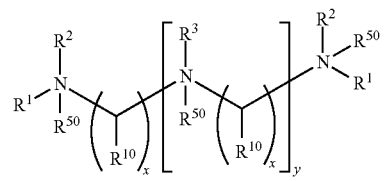

I wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —$X^1$—[C($R^4$)$_2$]$_d$N($R^5$)C(O)N($R^5$)$_2$, —$X^1$—[C($R^4$)$_2$]$_d$OC(O)CH$_2$C(O)—alkyl,

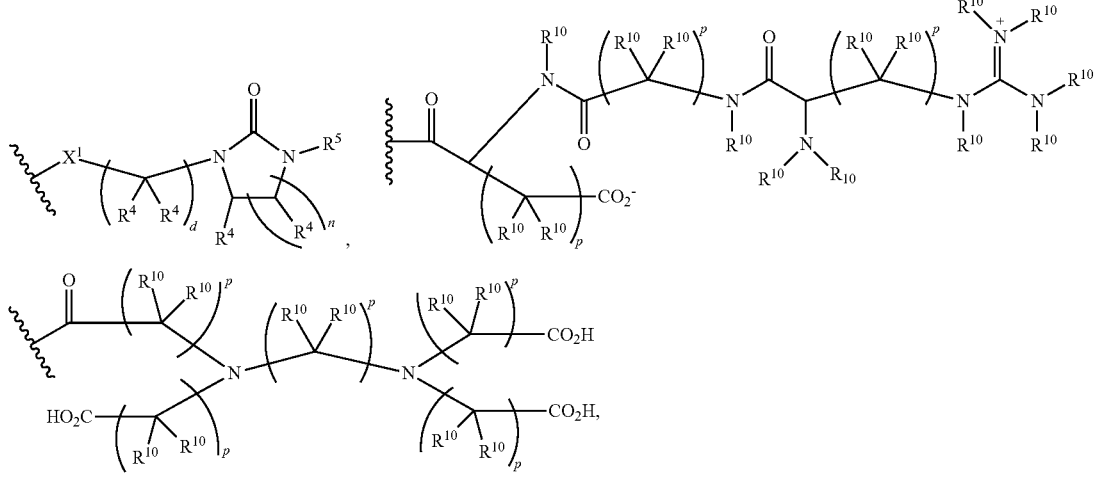

or a carbohydrate radical;

$R^3$ represents independently for each occurrence H or

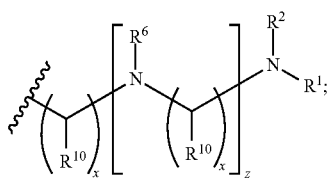

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

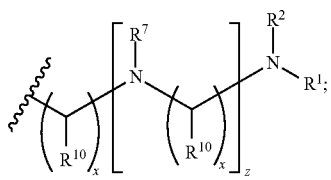

$R^7$ represents independently for each occurrence H or

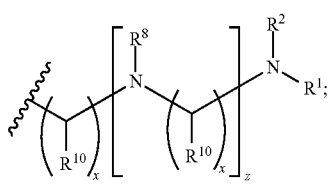

$R^8$ represents independently for each occurrence H or

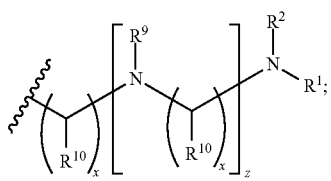

$R^9$ represents independently for each occurrence H or

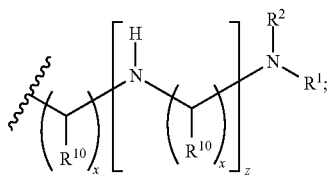

$R^{10}$ represents independently for each occurrence H or $(C_1\text{-}C_3)$alkyl;

$X^1$ represents independently for each occurrence a bond or —C(O)—;

$A^1$ represents independently for each occurrence

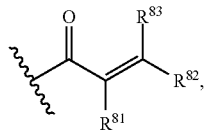

wherein $R^{81}$, $R^{82}$, and $R^{83}$ each represent independently for each occurrence H, alkyl, aryl, or aralkyl;

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; and formula III is represented by:

$$B\text{---}(R^1)_t \qquad \text{III}$$

wherein $R^1$ represents independently for each occurrence —(C$(R^2)_2)_j$C(O)—X—$R^3$, —C(O)(C$(R^2)_2)_k$C(O)—X—$R^3$, or —$R^3$;

$R^2$ represents independently for each occurrence H, alkyl, or halogen;

$R^3$ represents

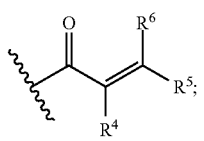

$R^4$, $R^5$, and $R^6$ each represent independently for each occurrence H, alkyl, aryl, or aralkyl;

X represents independently for each occurrence O or —N($R^5$)—;

B is

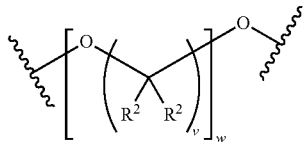

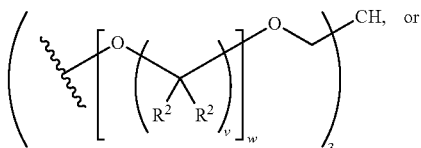

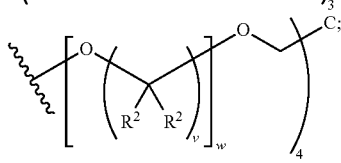

f and k each are independently selected for each occurrence from the group consisting of 1-25 inclusive;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

Another aspect of the present invention relates to a method of adhering tissue of a patient, comprising the steps of:

applying an effective amount of a polymerization agent to a first tissue of a patient, contacting said first tissue of a patient with a second tissue of a patient, and exposing said polymerization agent to visible light or ultraviolet light sufficient to polymerize said polymerization agent; wherein said polymerization agent is a compound of formula I, formula III, or a mixture thereof; or a pharmaceutically acceptable salt of any of them; and formula I is represented by:

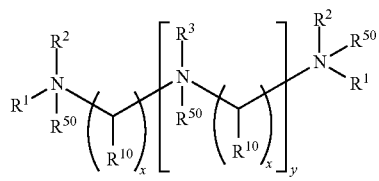

I wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)N($R^5$)$_2$, —$X^1$—[C($R^4$)$_2$]$_d$N($R^5$)C(O)N($R^5$)$_2$, —$X^1$—[C($R^4$)$_2$]$_d$OC(O)CH$_2$C(O)—alkyl,

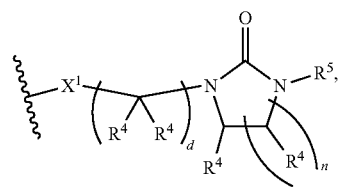

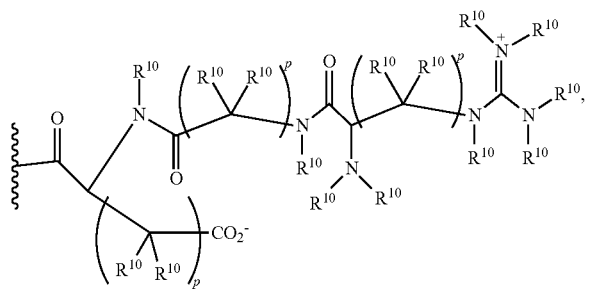

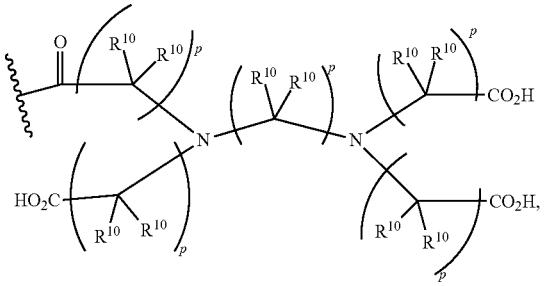

or a carbohydrate radical;

$R^3$ represents independently for each occurrence H or

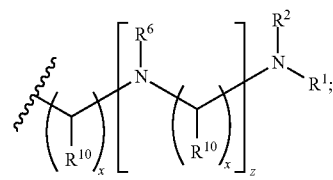

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

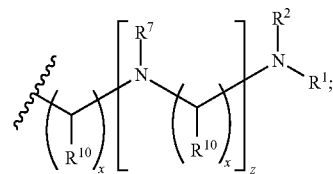

$R^7$ represents independently for each occurrence H or

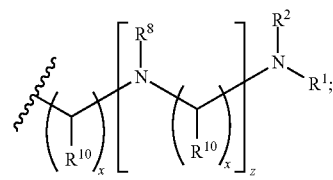

$R^8$ represents independently for each occurrence H or

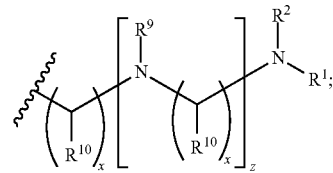

$R^9$ represents independently for each occurrence H or

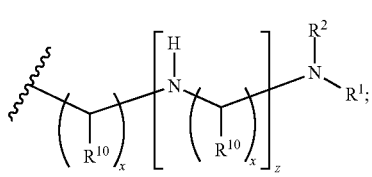

$R^{10}$ represents independently for each occurrence H or $(C_1-C_3)$alkyl;

$X^1$ represents independently for each occurrence a bond or —C(O)—;

$A^1$ represents independently for each occurrence

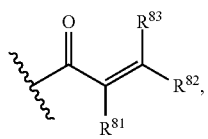

wherein $R^{81}$, $R^{82}$, and $R^{83}$ each represent independently for each occurrence H, alkyl, aryl, or aralkyl;

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; and formula III is represented by:

$$B\text{---}(R^1)_t \quad\quad\quad III$$

wherein $R^1$ represents independently for each occurrence —(C$(R^2)_2)_n$C(O)—X—$R^3$, —C(O)(C$(R^2)_2)_k$C(O)—X—$R^3$, or —$R^3$;

$R^2$ represents independently for each occurrence H, alkyl, or halogen;

$R^3$ represents

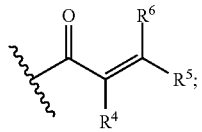

$R^4$, $R^5$, and $R^6$ each represent independently for each occurrence H, alkyl, aryl, or aralkyl;

X represents independently for each occurrence O or —N($R^5$)—;

B is

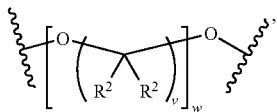

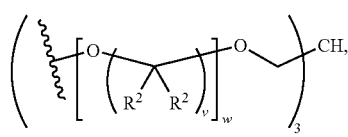

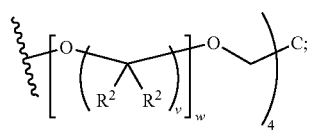

f and k each are independently selected for each occurrence from the group consisting of 1-25 inclusive;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

In certain instances, the present invention relates to the aforementioned method, wherein f and k each represent independently for each occurrence 1, 2, 3, 4, 5, 6, 7, 8, or 9.

In certain embodiments, the present invention relates to the aforementioned method, wherein said polymerization agent is a mixture of a compound of formula I and a compound of formula III.

In certain embodiments, the present invention relates to the aforementioned method, wherein said polymerization agent is exposed to ultraviolet light sufficient to polymerize said polymerization agent.

In certain embodiments, the present invention relates to the aforementioned method, wherein $A^1$ represents independently for each occurrence

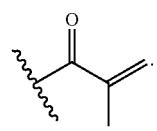 [SMILES: *C(=O)C(=C)C]

In certain embodiments, the present invention relates to the aforementioned method, wherein $R^3$ of Formula III represents

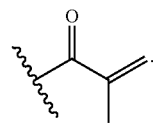 [SMILES: *C(=O)C(=C)C]

Another aspect of the invention relates to a method of sealing a wound of a patient, comprising the steps of:

applying an effective amount of a polymerization agent to a wound of a patient, and exposing said polymerization agent to a compound of formula III sufficient to polymerize said polymerization agent, wherein said polymerization agent is a compound of formula Ia, formula Ib, or formula Ic; or a pharmaceutically acceptable salt of any of them; and formula Ia is represented by:

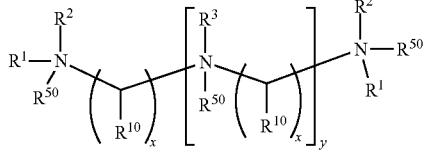

Ia wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —X$^1$—[C(R$^4$)$_2$]$_d$OC(O)CH$_2$C(O)-alkyl,

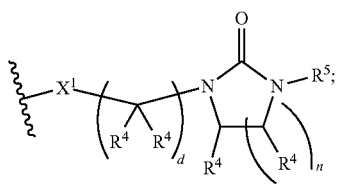

$R^3$ represents independently for each occurrence H or

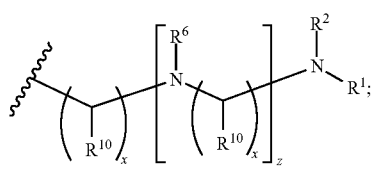

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

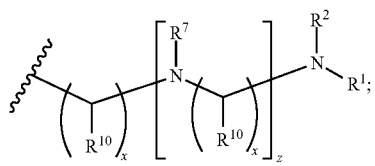

$R^7$ represents independently for each occurrence H or

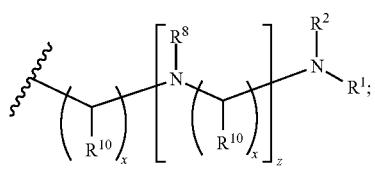

$R^8$ represents independently for each occurrence H or

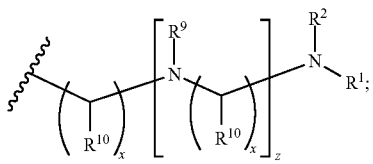

$R^9$ represents independently for each occurrence H or

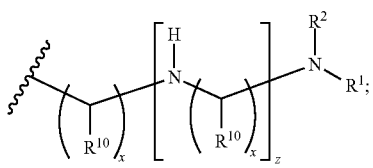

$R^{10}$ represents independently for each occurrence H or (C$_1$-C$_3$)alkyl;

$X^1$ represents independently for each occurrence a bond or —C(O)—;

$A^1$ represents independently for each occurrence

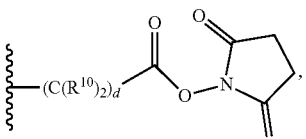

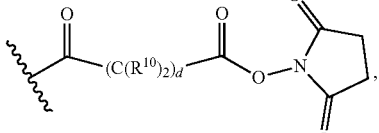

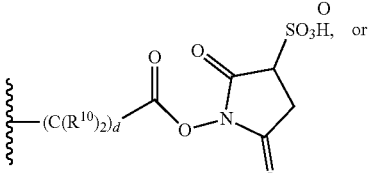

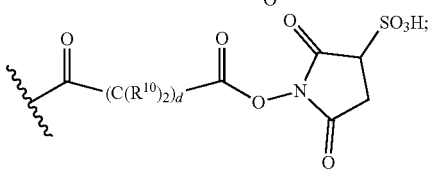

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; formula Ib is represented by:

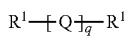

wherein

Q represents independently for each occurrence

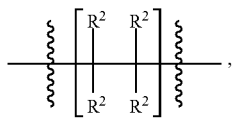

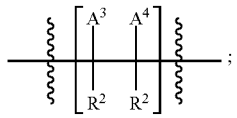

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —$CO_2R^4$;

$A^2$ represents independently for each occurrence H or —$CO_2R^4$;

$A^3$ represents independently for each occurrence —$N(R^1)(R^{50})(R^3)$;

$A^4$ represents independently for each occurrence H, alkyl, aryl, —$CO_2R^4$, or —$OC(O)R^4$;

$R^1$ represents independently for each occurrence H, alkyl,

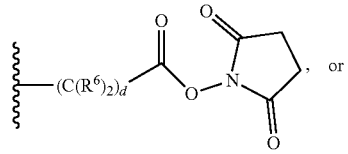

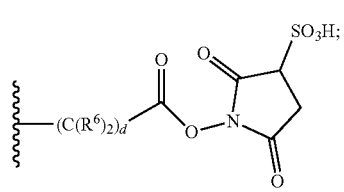

$R^2$ represents independently for each occurrence H, alkyl, aryl or aralkyl;

$R^3$ represents independently for each occurrence H, alkyl, aryl, aralkyl, acyl,

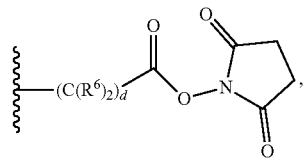

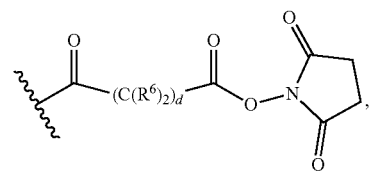

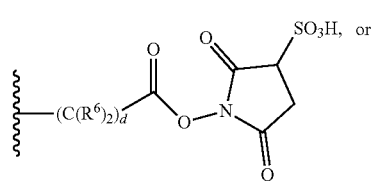

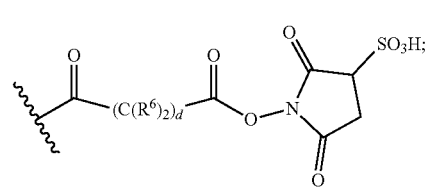

$R^4$ represents independently for each occurrence H, alkyl, aryl, aralkyl,

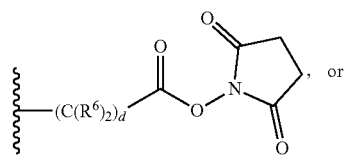

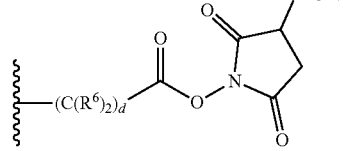

$R^5$ represents independently for each occurrence H or alkyl;

$R^6$ represents independently for each occurrence H or $(C_1-C_3)$alkyl;

$X^1$ represents independently for each occurrence a bond or —C(O)—;

d represents independently for each occurrence 1, 2, 3, 4, 5, 6, 7, or 8;

p represents independently for each occurrence 1, 2, 3, 4, or 5; and q is an integer from about 50 to about 100,000; formula Ic is represented by:

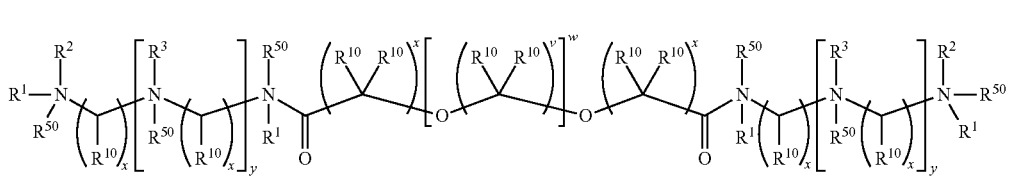

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—$[C(R^4)_2]_dOC(O)CH_2C(O)$-alkyl, or

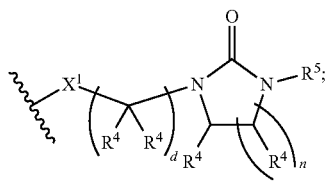

$R^3$ represents independently for each occurrence H or

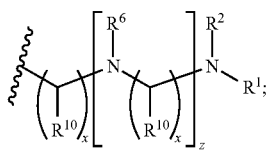

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

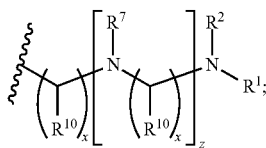

$R^7$ represents independently for each occurrence H or

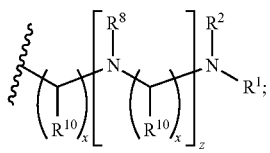

$R^8$ represents independently for each occurrence H or

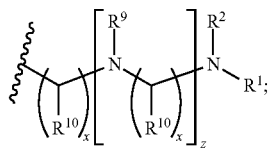

$R^9$ represents independently for each occurrence H or

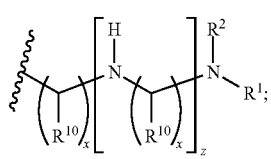

$R^{10}$ represents independently for each occurrence H or $(C_1-C_3)$alkyl;

$X^1$ represents independently for each occurrence a bond or —C(O)—;

$A^1$ represents independently for each occurrence

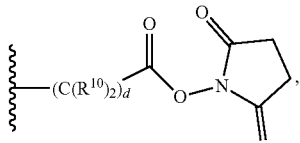

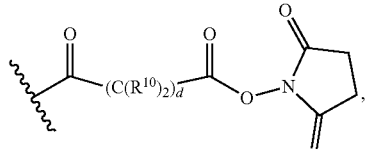

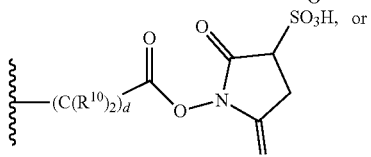

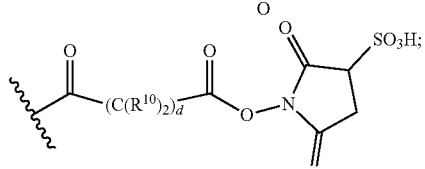

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

v represents independently for each occurrence 2, 3, or 4;

w represents independently for each occurrence an integer in the range of about 5 to 1000, inclusive;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; and formula III is represented by:

III wherein $R^1$ represents independently for each occurrence —$C(R^2)_2)_nC(O)$—X—$R^3$, —$C(O)(C(R^2)_2)_kC(O)$—X—$R^3$, or —$R^3$.

$R^2$ represents independently for each occurrence H, alkyl, or halogen;

$R^3$ represents independently for each occurrence

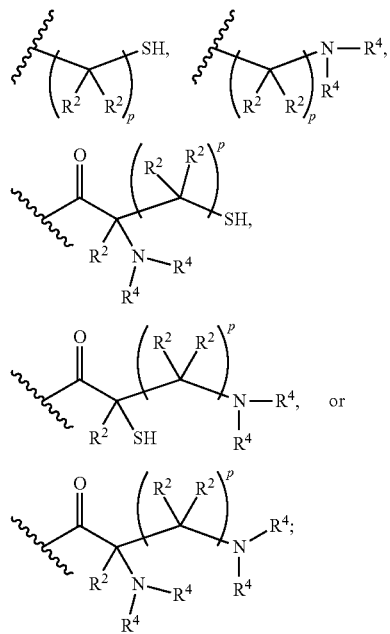

$R^4$ represents independently for each occurrence H, alkyl, aryl, aralkyl,

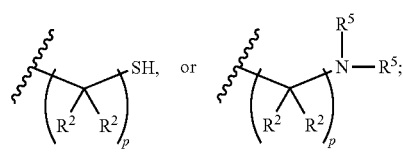

$R^5$ represents independently for each occurrence H or alkyl;

$X^1$ represents independently for each occurrence O or —N($R^5$)—;

B is

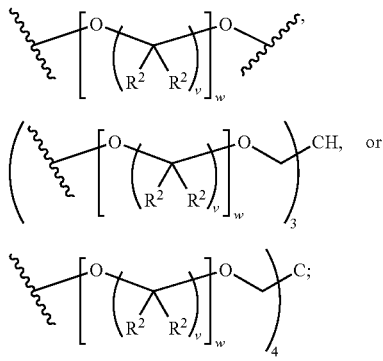

f and k each are independently selected for each occurrence from the group consisting of 1-25 inclusive;

p represents independently for each occurrence 1, 2, 3, 4, or 5;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

Another aspect of the invention relates to a method of augmenting soft tissue or filling a void of a patient, comprising the steps of:

applying an effective amount of a polymerization agent to soft tissue or a void of a patient, and exposing said polymerization agent to a compound of formula III sufficient to polymerize said polymerization agent, wherein said polymerization agent is a compound of formula Ia, formula Ib, or formula Ic; or a pharmaceutically acceptable salt of any of them; and formula Ia is represented by:

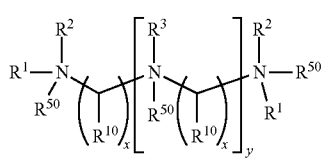

Ia wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—[C($R^4$)$_2$]$_d$OC(O)CH$_2$C(O)-alkyl, or

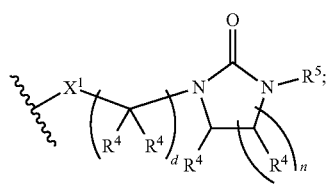

$R^3$ represents independently for each occurrence H or

[structure: wavy-C(R^10)_x-N(R^6)-C(R^10)_x-N(R^2)(R^1), bracketed with subscript z]

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

[structure: wavy-C(R^10)_x-N(R^7)-C(R^10)_x-N(R^2)(R^1), bracketed with subscript z]

$R^7$ represents independently for each occurrence H or

[structure: wavy-C(R^10)_x-N(R^8)-C(R^10)_x-N(R^2)(R^1), bracketed with subscript z]

$R^8$ represents independently for each occurrence H or

[structure: wavy-C(R^10)_x-N(R^9)-C(R^10)_x-N(R^2)(R^1), bracketed with subscript z]

$R^9$ represents independently for each occurrence H or

[structure: wavy-C(R^10)_x-N(H)-C(R^10)_x-N(R^2)(R^1), bracketed with subscript z]

$R^{10}$ represents independently for each occurrence H or $(C_1$-$C_3)$alkyl;

$X^1$ represents independently for each occurrence a bond or —C(O)—;

$A^1$ represents independently for each occurrence

[structure: wavy-(C(R^10)_2)_d-C(O)-O-N-succinimide]

-continued

[structure: wavy-C(O)-(C(R^10)_2)_d-C(O)-O-N-succinimide]

[structure: wavy-(C(R^10)_2)_d-C(O)-O-N-succinimide with SO_3H, or]

[structure: wavy-C(O)-(C(R^10)_2)_d-C(O)-O-N-succinimide with SO_3H;]

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000;

formula Ib is represented by:

$$R^1\text{---}[Q]_q\text{---}R^1 \qquad \text{Ib}$$

wherein

Q represents independently for each occurrence

[structure: bracketed R^2/R^2 over R^2/R^2],

[structure: bracketed A^1/A^2 over R^2/R^2], or

[structure: bracketed A^3/A^4 over R^2/R^2];

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —$CO_2R^4$;

$A^2$ represents independently for each occurrence H or —$CO_2R^4$;

$A^3$ represents independently for each occurrence —$N(R^1)(R^{50})(R^3)$ $A^4$ represents independently for each occurrence H, alkyl, aryl, —$CO_2R^4$, or —$OC(O)R^4$;

$R^1$ represents independently for each occurrence H, alkyl,

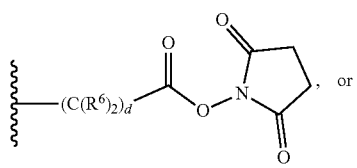, or

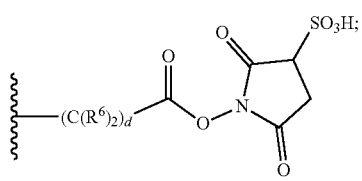

$R^2$ represents independently for each occurrence H, alkyl, aryl, or aralkyl;

$R^3$ represents independently for each occurrence H, alkyl, aryl, aralkyl, acyl,

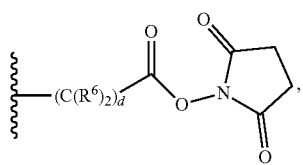,

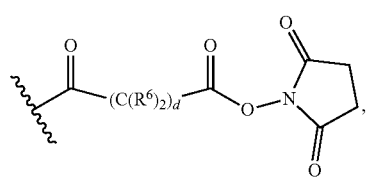,

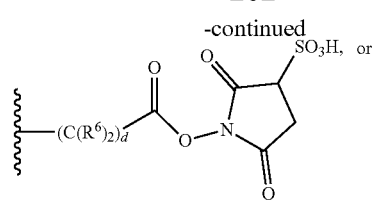

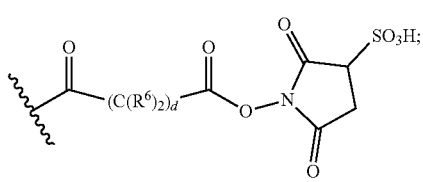

$R^4$ represents independently for each occurrence H, alkyl, aryl, aralkyl,

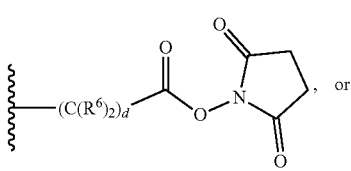, or

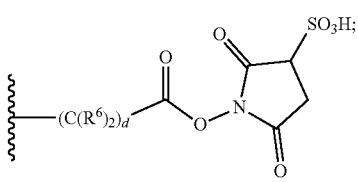

$R^5$ represents independently for each occurrence H or alkyl;

$R^6$ represents independently for each occurrence H or $(C_1\text{-}C_3)$alkyl;

$X^1$ represents independently for each occurrence a bond or —C(O)—;

d represents independently for each occurrence 1, 2, 3, 4, 5, 6, 7, or 8;

p represents independently for each occurrence 1, 2, 3, 4, or 5; and q is an integer from about 50 to about 100,000;

formula Ic is represented by:

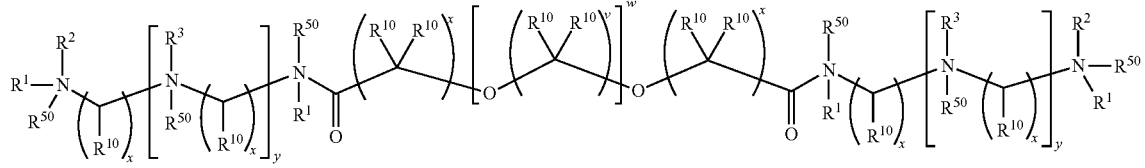

Ic wherein,

R$^{50}$ independently for each occurrence is an electron pair or a substituent selected from the group consisting of H, alkyl, and aralkyl; when an instance of R$^{50}$ represents a substituent a pharmaceutically acceptable counterion is present;

R$^1$ and R$^2$ represent independently for each occurrence A$^1$, alkyl, alkenyl, alkynyl, —C(O)-alkyl, —X$^1$—[C(R$^4$)$_2$]$_d$OC(O)CH$_2$C(O)-alkyl, or

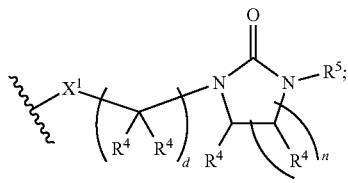

R$^3$ represents independently for each occurrence H or

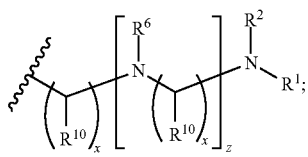

R$^4$ represents independently for each occurrence H, alkyl, alkoxyl, halogen, aryl, or aralkyl;

R$^5$ represents independently for each occurrence H, alkyl, aryl, or aralkyl;

R$^6$ represents independently for each occurrence H or

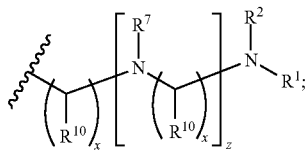

R$^7$ represents independently for each occurrence H or

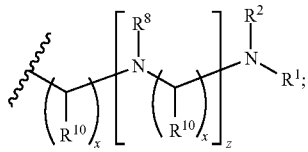

R$^8$ represents independently for each occurrence H or

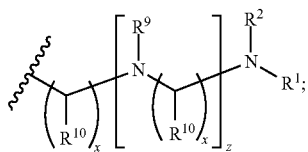

R$^9$ represents independently for each occurrence H or

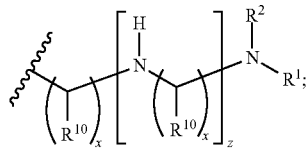

R$^{10}$ represents independently for each occurrence H or (C$_1$-C$_3$)alkyl;

X$^1$ represents independently for each occurrence a bond or —C(O)—;

A$^1$ represents independently for each occurrence

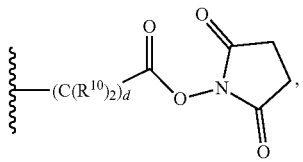

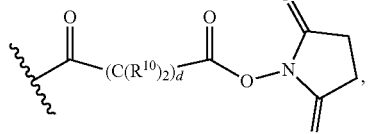

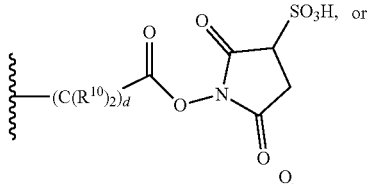

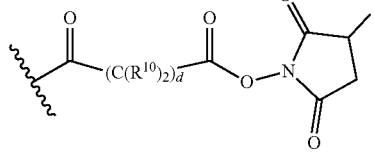

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

v represents independently for each occurrence 2, 3, or 4;

w represents independently for each occurrence an integer in the range of about 5 to 1000, inclusive;

x represents independently for each occurrence 1, 2, 3, 4, or 5;

y is an integer in the range of about 5 to about 40,000;

z represents independently for each occurrence an integer in the range of 0 to about 20,000; and provided at least about 5% of R$^1$ is A$^1$, and the sum of y and z is less than about 50,000; and formula III is represented by:

$$B \text{---} (R^1)_t \qquad \qquad III$$

wherein

R$^1$ represents independently for each occurrence —(C(R$^2$)$_2$)$_v$C(O)—X—R$^3$, —C(O)(C(R$^2$)$_2$)$_k$C(O)—X—R$^3$, or —R$^3$.

R$^2$ represents independently for each occurrence H, alkyl, or halogen;

$R^3$ represents independently for each occurrence

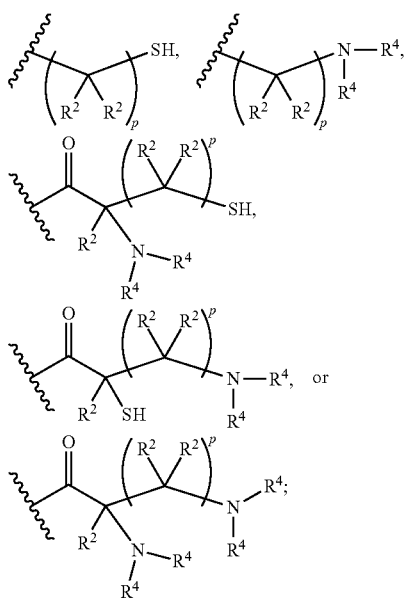

$R^4$ represents independently for each occurrence H, alkyl, aryl, aralkyl,

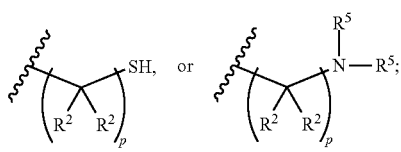

$R^5$ represents independently for each occurrence H or alkyl;
$X^1$ represents independently for each occurrence O or $-N(R^5)-$;
B is

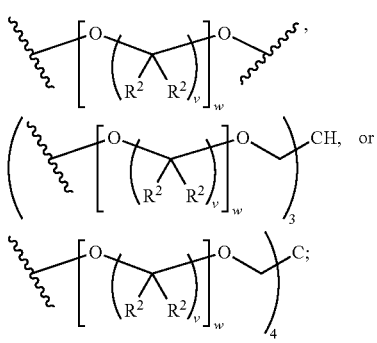

f and k each are independently selected for each occurrence from the group consisting of 1-25 inclusive;
p represents independently for each occurrence 1, 2, 3, 4, or 5;
t represents independently for each occurrence 1, 2, or 3 in accordance with the rules of valence;
v represents independently for each occurrence 2, 3, or 4; and w represents independently for each occurrence an integer in the range of about 5 to 1000, inclusive.

Another aspect of the invention relates to a method of adhering tissue of a patient, comprising the steps of:
applying an effective amount of a polymerization agent to a first tissue of a patient, exposing said polymerization agent to a compound of formula III to form an adhesive composition, and contacting said adhesive composition with a second tissue of a patient, wherein the amount of said compound of formula III is sufficient to polymerize said polymerization agent and said polymerization agent is a compound of formula Ia, formula Ib, or formula Ic; or a pharmaceutically acceptable salt of any of them; and formula Ia is represented by:

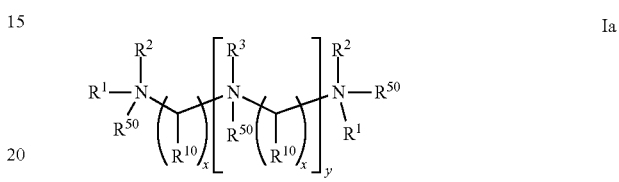

Ia wherein,
$R^{50}$ independently for each occurrence is an electron pair or a substituent selected from the group consisting of H, alkyl, and aralkyl; when an instance of $R^{50}$ represents a substituent a pharmaceutically acceptable counterion is present;
$R^1$ and $R^2$ represent independently for each occurrence $A^1$, alkyl, alkenyl, alkynyl, $-C(O)$-alkyl, $-X^1-[C(R^4)_2]_dOC(O)CH_2C(O)$-alkyl, or

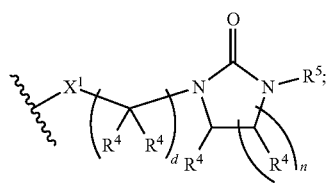

$R^3$ represents independently for each occurrence H or

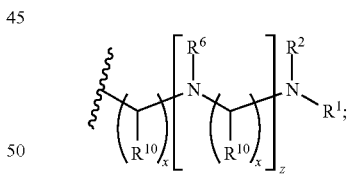

$R^4$ represents independently for each occurrence H, alkyl, alkoxyl, halogen, aryl, or aralkyl;
$R^5$ represents independently for each occurrence H, alkyl, aryl, or aralkyl;
$R^6$ represents independently for each occurrence H or

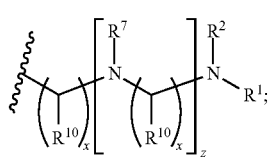

R⁷ represents independently for each occurrence H or

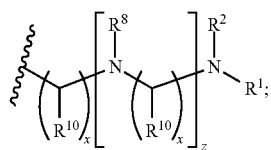

R⁸ represents independently for each occurrence H or

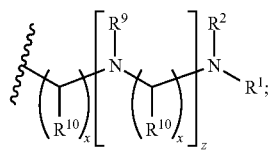

R⁹ represents independently for each occurrence H or

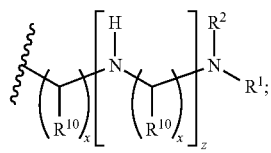

R¹⁰ represents independently for each occurrence H or (C₁-C₃)alkyl;

X¹ represents independently for each occurrence a bond or —C(O)—;

A¹ represents independently for each occurrence

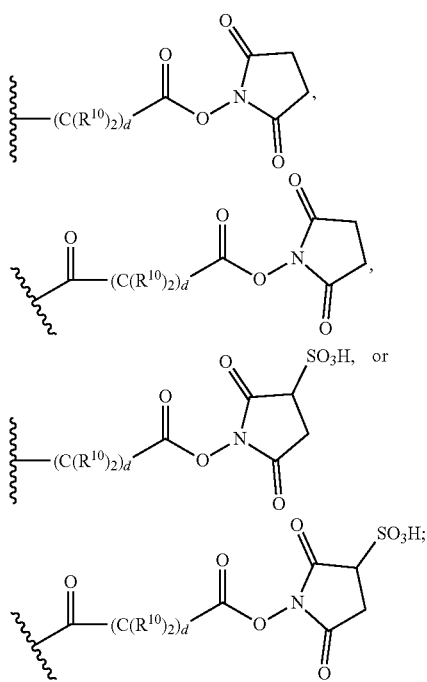

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of R¹ is A¹, and the sum of y and z is less than about 50,000;

formula Ib is represented by:

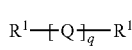

Ib wherein

Q represents independently for each occurrence

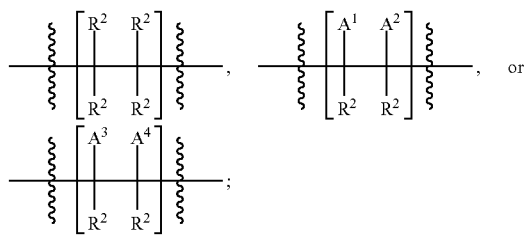

or

R⁵⁰ independently for each occurrence is an electron pair or a substituent selected from the group consisting of H, alkyl, and aralkyl; when an instance of R⁵⁰ represents a substituent a pharmaceutically acceptable counterion is present;

A¹ represents independently for each occurrence —CO₂R⁴;

A² represents independently for each occurrence H or —CO₂R⁴;

A³ represents independently for each occurrence —N(R¹)(R⁵⁰)(R³);

A⁴ represents independently for each occurrence H, alkyl, aryl, —CO₂R⁴, or —OC(O)R⁴;

R¹ represents independently for each occurrence H, alkyl,

[structure]

R² represents independently for each occurrence H, alkyl, aryl, or aralkyl;

R³ represents independently for each occurrence H, alkyl, aryl, aralkyl, acyl,

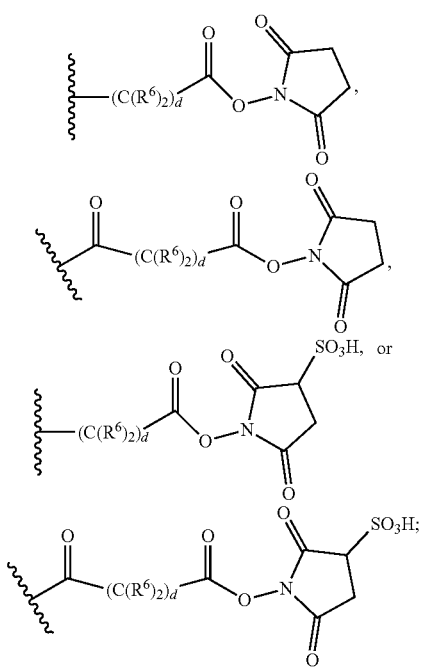

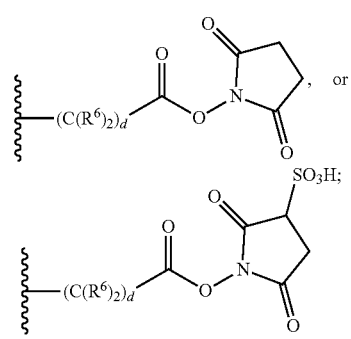

R[4] represents independently for each occurrence H, alkyl, aryl, aralkyl,

R[5] represents independently for each occurrence H or alkyl;
R[6] represents independently for each occurrence H or (C[1]-C[3])alkyl;
X[1] represents independently for each occurrence a bond or —C(O)—;
d represents independently for each occurrence 1, 2, 3, 4, 5, 6, 7, or 8;
p represents independently for each occurrence 1, 2, 3, 4, or 5; and
q is an integer from about 50 to about 100,000;
formula Ic is represented by:

wherein,
R[50] independently for each occurrence is an electron pair or a substituent selected from the group consisting of H, alkyl, and aralkyl; when an instance of R[50] represents a substituent a pharmaceutically acceptable counterion is present;
R[1] and R[2] represent independently for each occurrence A[1], alkyl, alkenyl, alkynyl, —C(O)-alkyl, —X[1]—[C(R[4])[2]][d]OC(O)CH[2]C(O)-alkyl, or

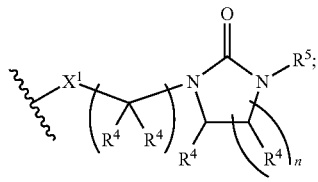

R[3] represents independently for each occurrence H or

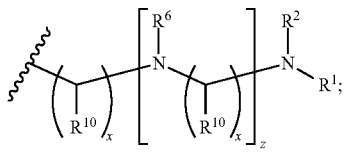

R[4] represents independently for each occurrence H, alkyl, alkoxyl, halogen, aryl, or aralkyl;
R[5] represents independently for each occurrence H, alkyl, aryl, or aralkyl;
R[6] represents independently for each occurrence H or

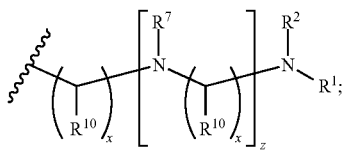

R[7] represents independently for each occurrence H or

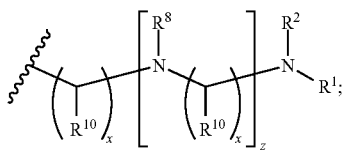

R[8] represents independently for each occurrence H or

Ic

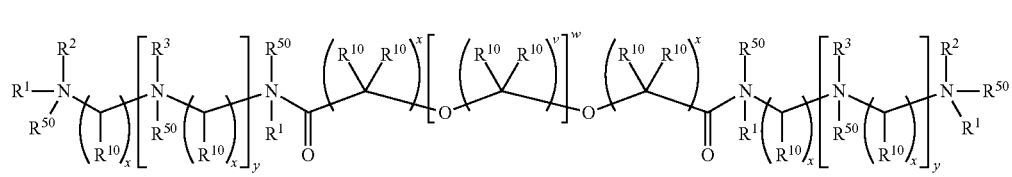

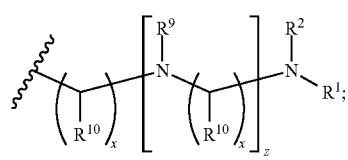

R⁹ represents independently for each occurrence H or

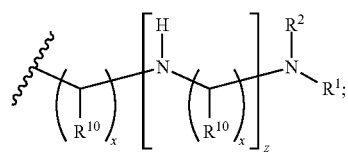

R¹⁰ represents independently for each occurrence H or (C₁-C₃)alkyl;

X¹ represents independently for each occurrence a bond or —C(O)—;

A¹ represents independently for each occurrence

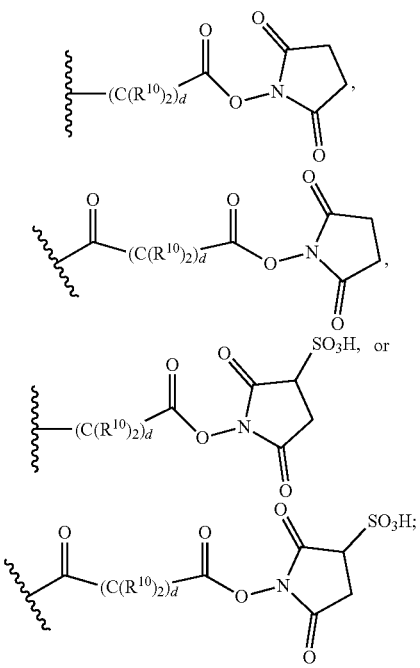

d represents independently for each occurrence 1, 2, 3, 4, 5, 6, 7, or 8;

n represents independently for each occurrence 1, 2, 3, or 4;

p represents independently for each occurrence 1, 2, 3, 4, or 5;

v represents independently for each occurrence 2, 3, or 4;

w represents independently for each occurrence an integer in the range of about 5 to 1000, inclusive;

x represents independently for each occurrence 1, 2, 3, 4, or 5;

y is an integer in the range of about 5 to about 40,000;

z represents independently for each occurrence an integer in the range of 0 to about 20,000; and provided at least about 5% of R¹ is A¹, and the sum of y and z is less than about 50,000; and formula III is represented by:

$$B\!-\!(R^1)_f \qquad \qquad III$$

wherein

R¹ represents independently for each occurrence —(C(R²)₂)ₙC(O)—X—R³, —C(O)(C(R²)₂)ₖC(O)—X—R³, or —R³;

R² represents independently for each occurrence H, alkyl, or halogen;

R³ represents independently for each occurrence

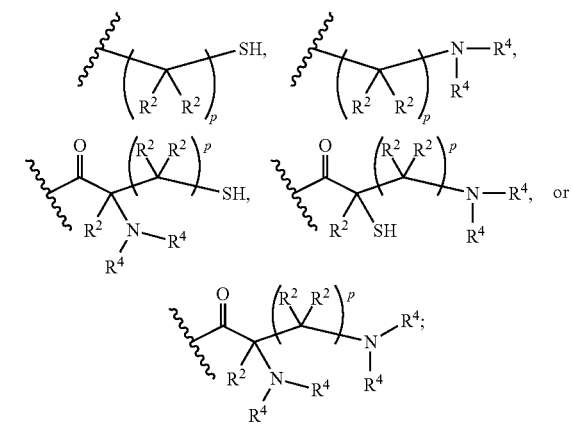

R⁴ represents independently for each occurrence H, alkyl, aryl, aralkyl,

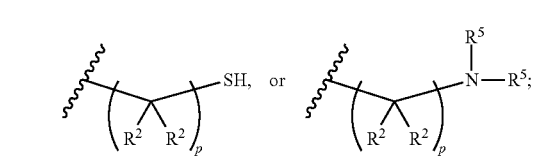

R⁵ represents independently for each occurrence H or alkyl;

X¹ represents independently for each occurrence O or —N(R⁵)—;

B is

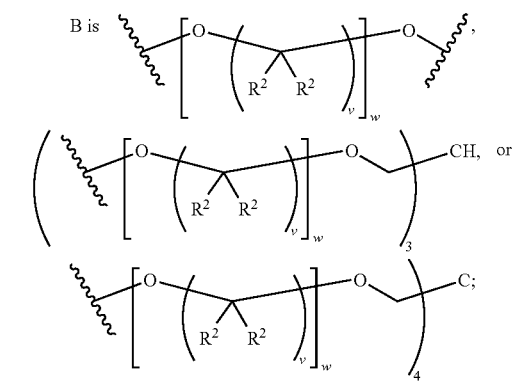

f and k each are independently selected for each occurrence from the group consisting of 1-25 inclusive;

p represents independently for each occurrence 1, 2, 3, 4, or 5;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

Another aspect of the invention relates to a method of sealing a wound of a patient, comprising the steps of:

exposing an effective amount of a polymerization agent to a compound of formula III to form an adhesive composition, and applying said adhesive composition to a wound of a patient, wherein said polymerization agent is a compound of formula Ia, formula Ib, or formula Ic; or a pharmaceutically acceptable salt of any of them; and formula Ia is represented by:

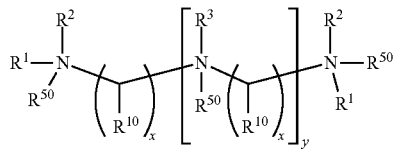

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—$[C(R^4)_2]_d$OC(O)CH$_2$C(O)-alkyl, or

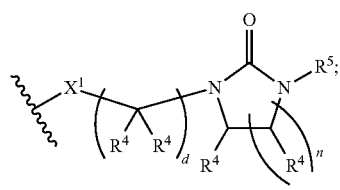

$R^3$ represents independently for each occurrence H or

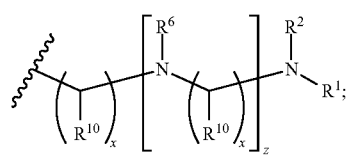

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

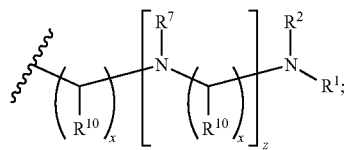

$R^7$ represents independently for each occurrence H or

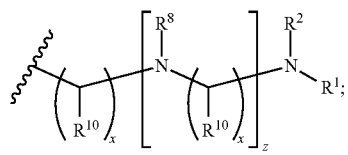

$R^8$ represents independently for each occurrence H or

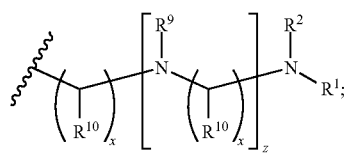

$R^9$ represents independently for each occurrence H or

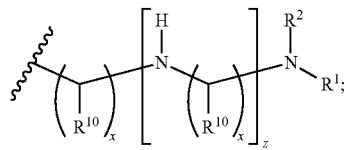

$R^{10}$ represents independently for each occurrence H or $(C_1$-$C_3)$alkyl;

$X^1$ represents independently for each occurrence a bond or —C(O)—;

$A^1$ represents independently for each occurrence H,

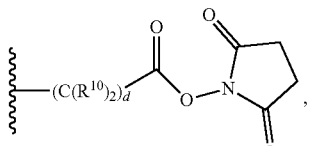

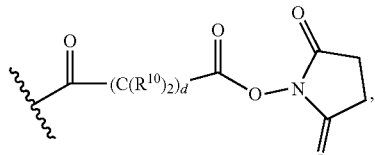

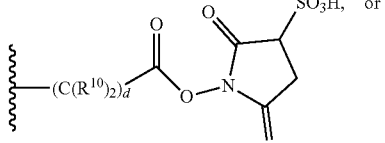

-continued

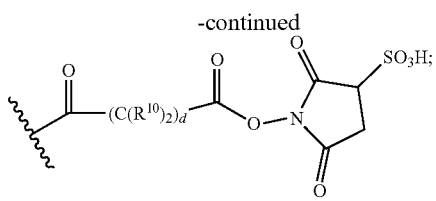

d represents independently for each occurrence 1, 2, 3, 4, 5, 6, 7, 8, 9, or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000;

formula Ib is represented by:

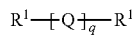

Ib wherein

Q represents independently for each occurrence

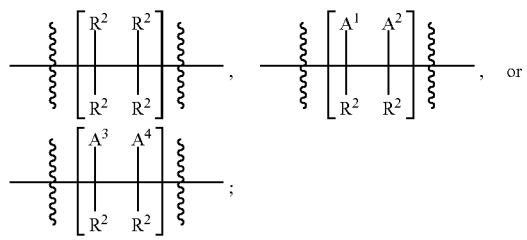

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —$CO_2R^4$;

$A^2$ represents independently for each occurrence H or —$CO_2R^4$;

$A^3$ represents independently for each occurrence —$N(R^1)(R^{50})(R^3)$ $A^4$ represents independently for each occurrence H, alkyl, aryl, —$CO_2R^4$, or —$OC(O)R^4$;

$R^1$ represents independently for each occurrence H, alkyl,

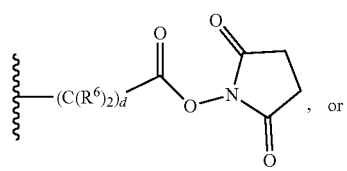, or

-continued

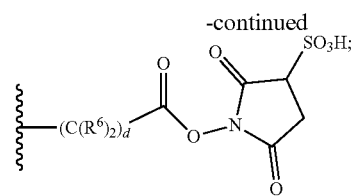

$R^2$ represents independently for each occurrence H, alkyl, aryl, or aralkyl;

$R^3$ represents independently for each occurrence H, alkyl, aryl, aralkyl, acyl,

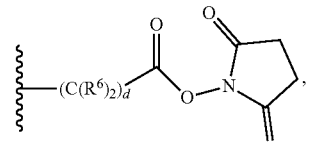

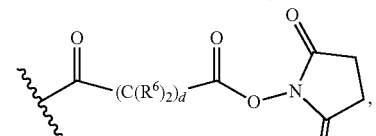

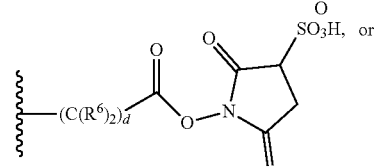

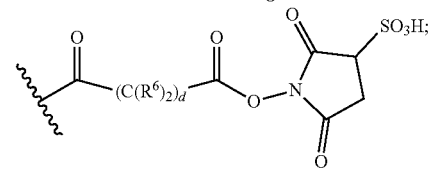

$R^4$ represents independently for each occurrence H, alkyl, aryl, aralkyl,

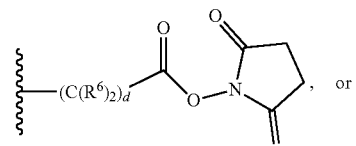, or

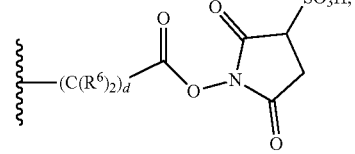

$R^5$ represents independently for each occurrence H or alkyl;

$R^6$ represents independently for each occurrence H or ($C_1$-$C_3$)alkyl;

$X^1$ represents independently for each occurrence a bond or —C(O)—;

d represents independently for each occurrence 1, 2, 3, 4, 5, 6, 7, 8, 9, or 10;

p represents independently for each occurrence 1, 2, 3, 4, or 5; and q is an integer from about 50 to about 100,000;
formula Ic is represented by:

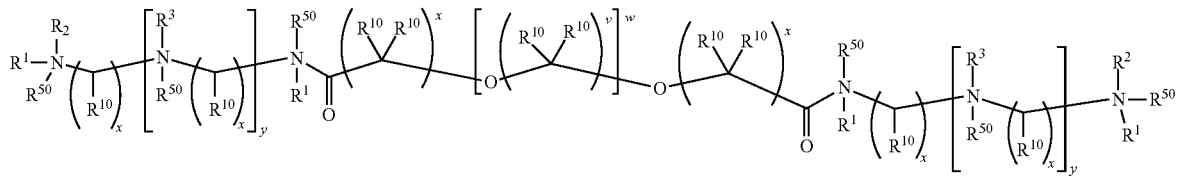

Ic wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—[C($R^4$)$_2$]$_d$OC(O)CH$_2$C(O)-alkyl, or

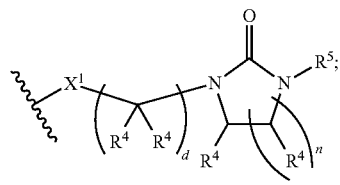

$R^3$ represents independently for each occurrence H or

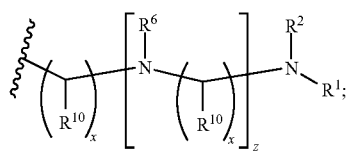

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

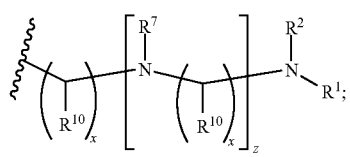

$R^7$ represents independently for each occurrence H or

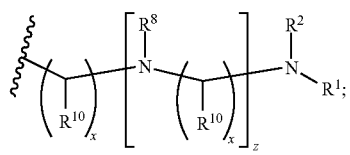

$R^8$ represents independently for each occurrence H or

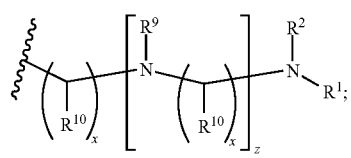

$R^9$ represents independently for each occurrence H or

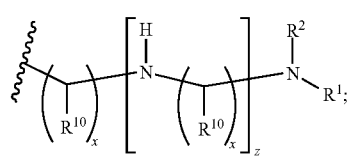

$R^{10}$ represents independently for each occurrence H or ($C_1$-$C_3$)alkyl;

$X^1$ represents independently for each occurrence a bond or —C(O)—;

$A^1$ represents independently for each occurrence H,

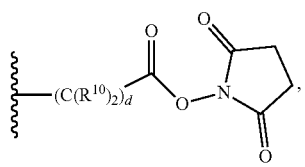

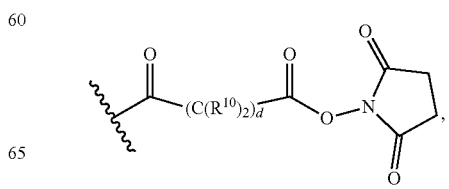

219

-continued

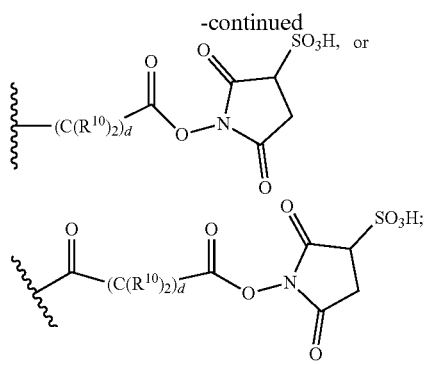

d represents independently for each occurrence 1, 2, 3, 4, 5, 6, 7, 8, 9 or 10;

n represents independently for each occurrence 1, 2, 3, or 4;

p represents independently for each occurrence 1, 2, 3, 4, or 5;

v represents independently for each occurrence 2, 3, or 4;

w represents independently for each occurrence an integer in the range of about 5 to 1000, inclusive;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; and formula III is represented by:

$$B\text{\textendash}(R^1)_t \quad \quad \quad III$$ 

wherein $R^1$ represents independently for each occurrence —C$(R^2)_2)_n$C(O)—X—$R^3$, —C(O)(C$(R^2)_2)_k$C(O)—X—$R^3$, or —$R^3$;

$R^2$ represents independently for each occurrence H alkyl or halogen;

$R^3$ represents independently for each occurrence

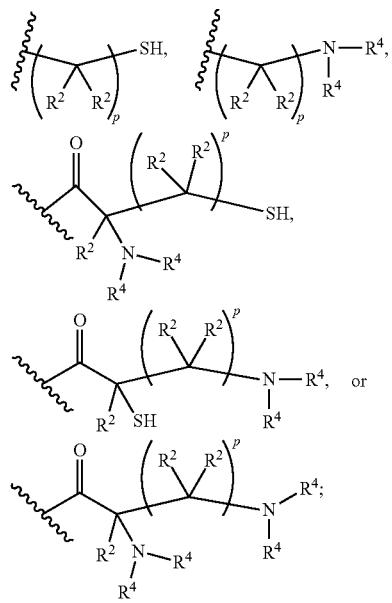

220

$R^4$ represents independently for each occurrence H, alkyl, aryl, aralkyl,

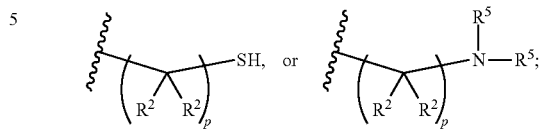

$R^5$ represents independently for each occurrence H or alkyl;

$X^1$ represents independently for each occurrence O or —N($R^5$)—;

B is

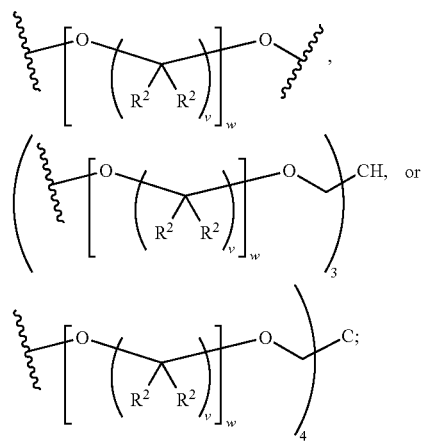

f and k each are independently selected for each occurrence from the group consisting of 1-25 inclusive;

p represents independently for each occurrence 1, 2, 3, 4, or 5;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

Another aspect of the invention relates to a method of augmenting soft tissue or filling a void of a patient, comprising the steps of:

exposing an effective amount of a polymerization agent to a compound of formula III to form an adhesive composition, and applying said adhesive composition to soft tissue or a void of a patient, wherein said polymerization agent is a compound of formula Ia, formula Ib, or formula Ic; or a pharmaceutically acceptable salt of any of them; and formula Ia is represented by:

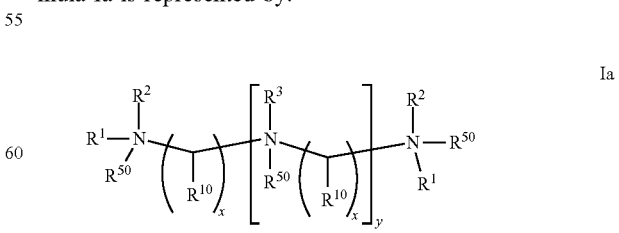

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—[C($R^4$)$_2$]$_d$OC(O)CH$_2$C(O)-alkyl, or

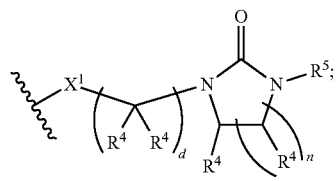

$R^3$ represents independently for each occurrence H or

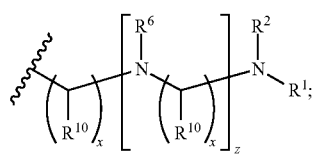

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

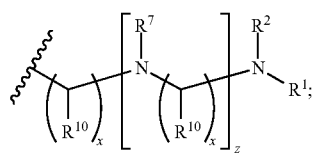

$R^7$ represents independently for each occurrence H or

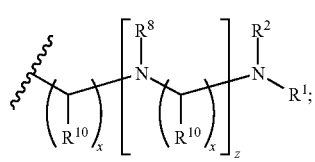

$R^8$ represents independently for each occurrence H or

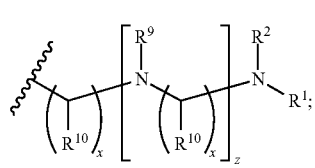

$R^9$ represents independently for each occurrence H or

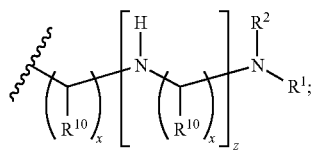

$R^{10}$ represents independently for each occurrence H or ($C_1$-$C_3$)alkyl;

$X^1$ represents independently for each occurrence a bond or —C(O)—;

$A^1$ represents independently for each occurrence H,

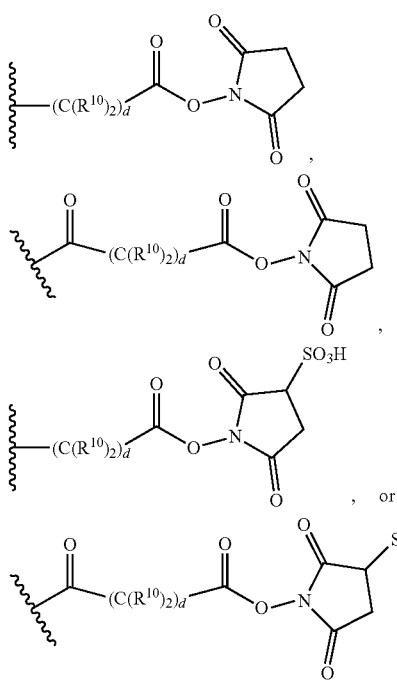

d represents independently for each occurrence 1, 2, 3, 4, 5, 6, 7, 8, 9 or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; formula Ib is represented by:

Ib $R^1$—$\left[Q\right]_q$—$R^1$ wherein

Q represents independently for each occurrence

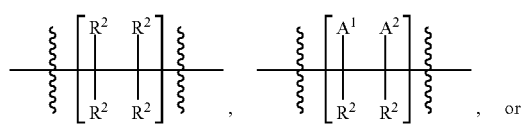, or

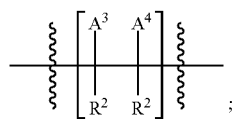;

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —$CO_2R^4$;

$A^2$ represents independently for each occurrence H or —$CO_2R^4$.

$A^3$ represents independently for each occurrence —$N(R^1)(R^{50})(R^3)$ $A^4$ represents independently for each occurrence H, alkyl, aryl, —$CO_2R^4$, or —$OC(O)R^4$;

$R^1$ represents independently for each occurrence H, alkyl,

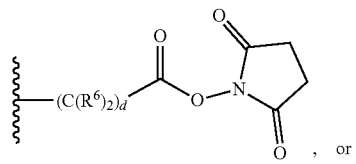, or

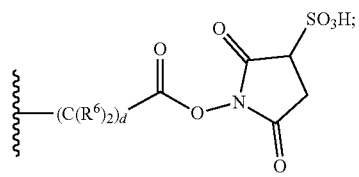;

$R^2$ represents independently for each occurrence H, alkyl, aryl, or aralkyl;

$R^3$ represents independently for each occurrence H, alkyl, aryl, aralkyl, acyl,

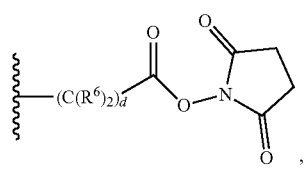,

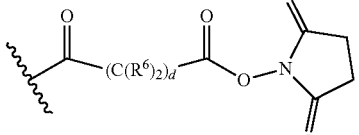,

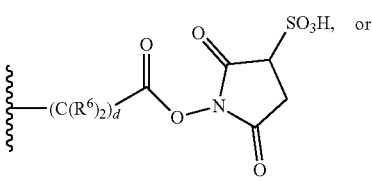, or

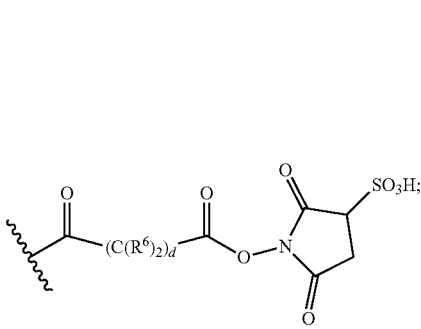

$R^4$ represents independently for each occurrence H, alkyl, aryl, aralkyl,

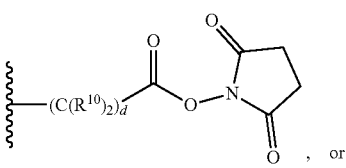, or

;

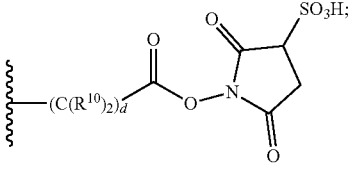

$R^5$ represents independently for each occurrence H or alkyl;

$R^6$ represents independently for each occurrence H or $(C_1$-$C_3)$alkyl;

$X^1$ represents independently for each occurrence a bond or —C(O)—;

d represents independently for each occurrence 1, 2, 3, 4, 5, 6, 7, 8, 9, or 10;

p represents independently for each occurrence 1, 2, 3, 4, or 5; and q is an integer from about 50 to about 100,000;

formula Ic is represented by:

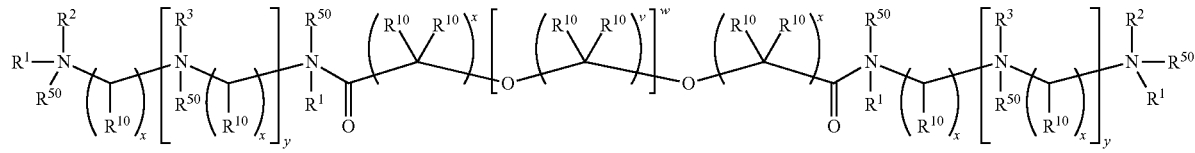

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—[C($R^4$)$_2$]$_d$OC(O)CH$_2$C(O)-alkyl, or

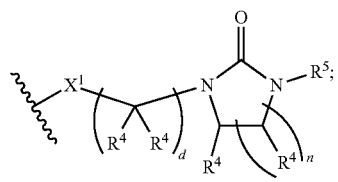

$R^3$ represents independently for each occurrence H or

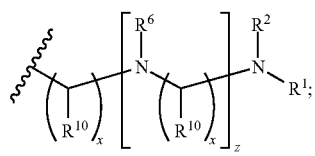

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

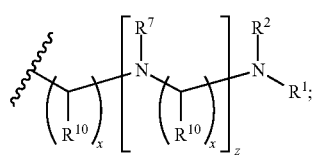

$R^7$ represents independently for each occurrence H or

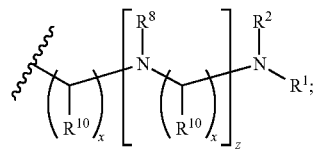

$R^8$ represents independently for each occurrence H or

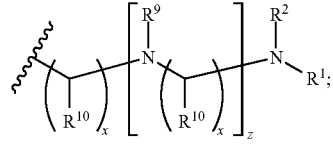

$R^9$ represents independently for each occurrence H or

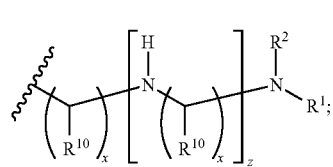

$R^{10}$ represents independently for each occurrence H or ($C_1$-$C_3$)alkyl;

$X^1$ represents independently for each occurrence a bone or —C(O)—;

$A^1$ represents independently for each occurrence H,

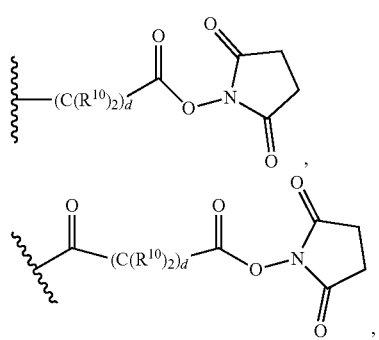

-continued

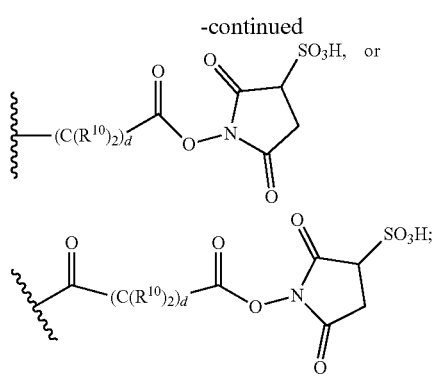

d represents independently for each occurrence 1, 2, 3, 4, 5, 6, 7, 8, 9 or 10;
n represents independently for each occurrence 1, 2, 3, or 4;
p represents independently for each occurrence 1, 2, 3, 4, or 5;
v represents independently for each occurrence 2, 3, or 4;
w represents independently for each occurrence an integer in the range of about 5 to 1000, inclusive;
x represents independently for each occurrence 1, 2, 3, 4, or 5;
y is an integer in the range of about 5 to about 40,000;
z represents independently for each occurrence an integer in the range of 0 to about 20,000; and
provided at least about 5% of $R^1$ is $A^1$, and the sum of y and z is less than about 50,000; and
formula III is represented by:

    III wherein
$R^1$ represents independently for each occurrence —(C$(R^2)_2)_n$C(O)—X—$R^3$, —C(O)(C$(R^2)_2)_k$C(O)—X—$R^3$, or —$R^3$.
$R^2$ represents independently for each occurrence H, alkyl, or halogen;
$R^3$ represents independently for each occurrence

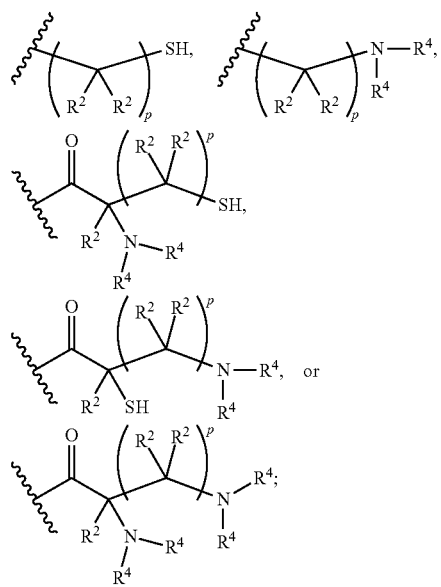

$R^4$ represents independently for each occurrence H, alkyl, aryl, aralkyl,

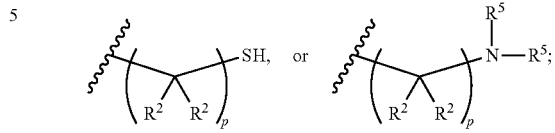

$R^5$ represents independently for each occurrence H or alkyl;
$X^1$ represents independently for each occurrence O or —N($R^5$)—;

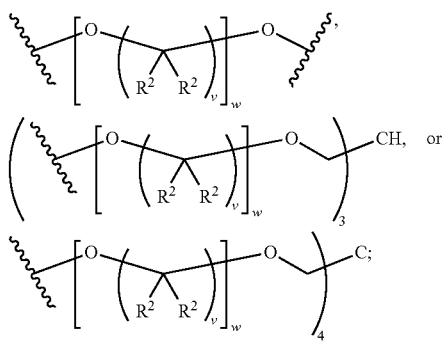

f and k each are independently selected for each occurrence from the group consisting of 1-25 inclusive;
p represents independently for each occurrence 1, 2, 3, 4, or 5;
t represents independently for each occurrence 1, 2, or 3 in accordance with the rules of valence;
v represents independently for each occurrence 2, 3, or 4; and w represents independently for each occurrence an integer in the range of about 5 to 1000, inclusive.

Another aspect of the invention relates to a method of adhering tissue of a patient, comprising the steps of:
exposing an effective amount of a polymerization agent to a compound of formula III to form an adhesive composition, applying said adhesive composition to a first tissue of a patient to form an adhesive tissue, and contacting said adhesive tissue with a second tissue of a patient, wherein said polymerization agent is a compound of formula Ia, formula Ib, or formula Ic; or a pharmaceutically acceptable salt of any of them; and formula Ia is represented by:

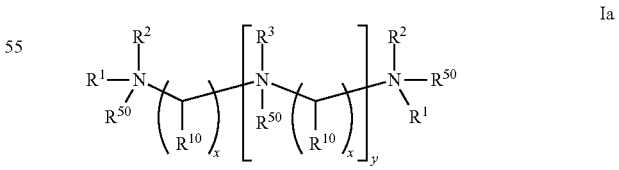

wherein,
$R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—[C($R^4$)$_2$]$_d$OC(O)CH$_2$C(O)-alkyl, or

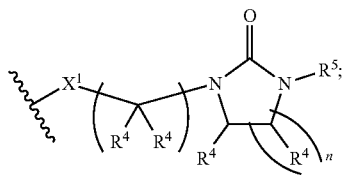

$R^3$ represents independently for each occurrence H or

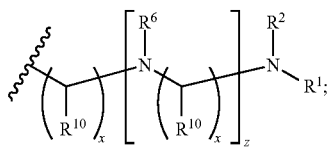

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

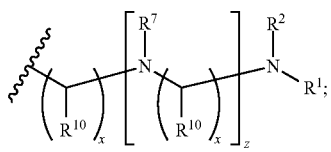

$R^7$ represents independently for each occurrence H or

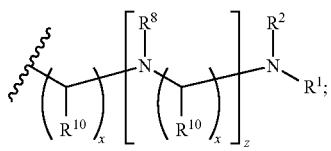

$R^8$ represents independently for each occurrence H or

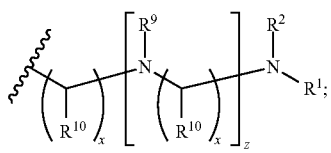

$R^9$ represents independently for each occurrence H or

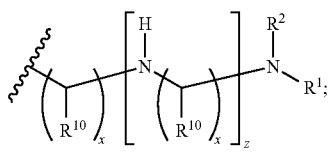

$R^{10}$ represents independently for each occurrence H or ($C_1$-$C_3$)alkyl;

$X^1$ represents independently for each occurrence a bond or —C(O)—;

$A^1$ represents independently for each occurrence H,

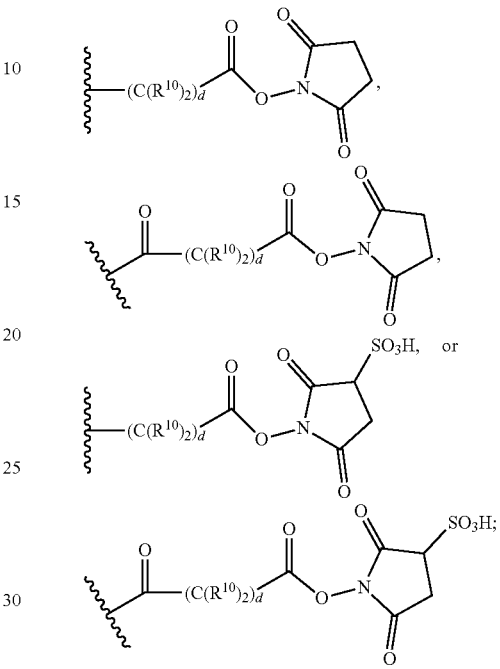

d represents independently for each occurrence 1, 2, 3, 4, 5, 6, 7, 8, 9 or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; formula Ib is represented by:

$$R^1 \!-\!\!\left[Q\right]_{\!q}\!\!-\!R^1 \qquad \text{Ib}$$

wherein

Q represents independently for each occurrence

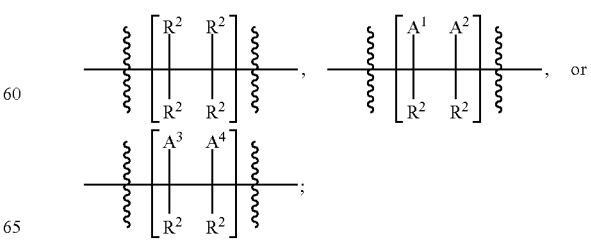

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence $-CO_2R^4$;

$A^2$ represents independently for each occurrence H or $-CO_2R^4$;

$A^3$ represents independently for each occurrence $-N(R^1)(R^{50})(R^3)$;

$A^4$ represents independently for each occurrence H, alkyl, aryl, $-CO_2R^4$, or $-OC(O)R^4$;

$R^1$ represents independently for each occurrence H, alkyl,

[structure: $-(C(R^6)_2)_d-C(O)-O-N$(succinimide)], or

[structure: $-(C(R^6)_2)_d-C(O)-O-N$(sulfo-succinimide, $SO_3H$)];

$R^2$ represents independently for each occurrence H, alkyl, aryl, or aralkyl;

$R^3$ represents independently for each occurrence H, alkyl, aryl, aralkyl, acyl,

[structure: $-(C(R^6)_2)_d-C(O)-O-N$(succinimide)],

[structure: $-C(O)-(C(R^6)_2)_d-C(O)-O-N$(succinimide)],

[structure: $-(C(R^6)_2)_d-C(O)-O-N$(sulfo-succinimide, $SO_3H$)], or

[structure: $-C(O)-(C(R^6)_2)_d-C(O)-O-N$(sulfo-succinimide, $SO_3H$)];

$R^4$ represents independently for each occurrence H, alkyl, aryl, aralkyl,

[structure: $-(C(R^6)_2)_d-C(O)-O-N$(succinimide)], or

[structure: $-(C(R^6)_2)_d-C(O)-O-N$(sulfo-succinimide, $SO_3H$)];

$R^5$ represents independently for each occurrence H or alkyl;

$R^6$ represents independently for each occurrence H or $(C_1-C_3)$alkyl;

$X^1$ represents independently for each occurrence a bond or $-C(O)-$;

d represents independently for each occurrence 1, 2, 3, 4, 5, 6, 7, 8, 9, or 10;

p represents independently for each occurrence 1, 2, 3, 4, or 5; and q is an integer from about 50 to about 100,000;

formula Ic is represented by:

$$R^1-N(R^{50})-[C(R^{10})_x-N(R^{50})-(C(R^{10})_x)_y]-[C(R^{10})_x-N(R^{50})-(C(R^{10})_x)_y]-N(R^1)-C(O)-(C(R^{10}R^{10}))_x-[O-(C(R^{10}R^{10}))_y]_w-O-(C(R^{10}R^{10}))_x-C(O)-N(R^1)-[(C(R^{10})_x)_y-N(R^{50})-(C(R^{10})_x)]-[(C(R^{10})_x)_y-N(R^{50})-R^{50}]-N(R^2)-R^{50}$$

Ic wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —$X^1$—[C($R^4$)$_2$]$_d$OC(O)CH$_2$C(O)-alkyl, or

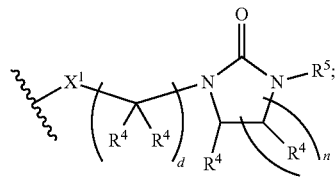

$R^3$ represents independently for each occurrence H or

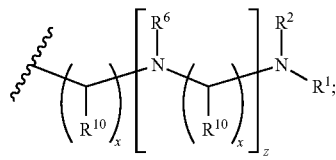

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

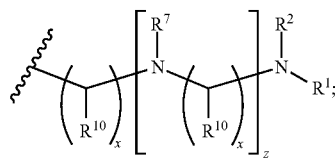

$R^7$ represents independently for each occurrence H or

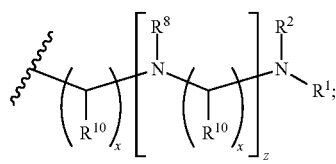

$R^8$ represents independently for each occurrence H or

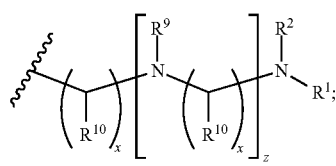

$R^9$ represents independently for each occurrence H or

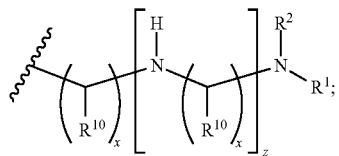

$R^{10}$ represents independently for each occurrence H or (C$_1$-C$_3$)alkyl;

$X^1$ represents independently for each occurrence a bond or —C(O)—;

$A^1$ represents independently for each occurrence H,

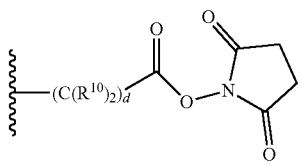

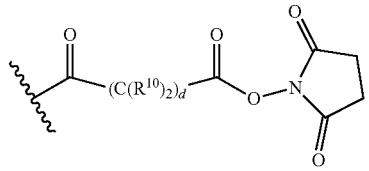

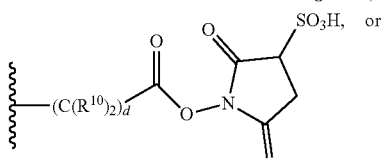

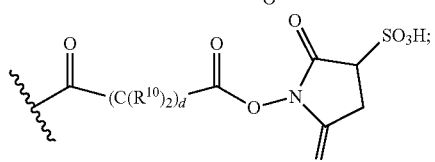

d represents independently for each occurrence 1, 2, 3, 4, 5, 6, 7; 8, 9, or 10;

n represents independently for each occurrence 1, 2, 3, or 4;

p represents independently for each occurrence 1, 2, 3, 4, or 5;

v represents independently for each occurrence 2, 3, or 4;

w represents independently for each occurrence an integer in the range of about 5 to 1000, inclusive;

x represents independently for each occurrence 1, 2, 3, 4, or 5;

y is an integer in the range of about 5 to about 40,000;

z represents independently for each occurrence an integer in the range of 0 to about 20,000; and provided at least about 5% of $R^1$ is $A^1$, and the sum of y and z is less than about 50,000; or formula III is represented by:

$$B\text{---}(R^1)_t \qquad \qquad III$$

wherein $R^1$ represents independently for each occurrence —(C($R^2$)$_2$)$_v$C(O)—X—$R^3$, —C(O)(C($R^2$)$_2$)$_k$C(O)—X—$R^3$, or —$R^3$;

$R^2$ represents independently for each occurrence H, alkyl, or halogen;

$R^3$ represents independently for each occurrence

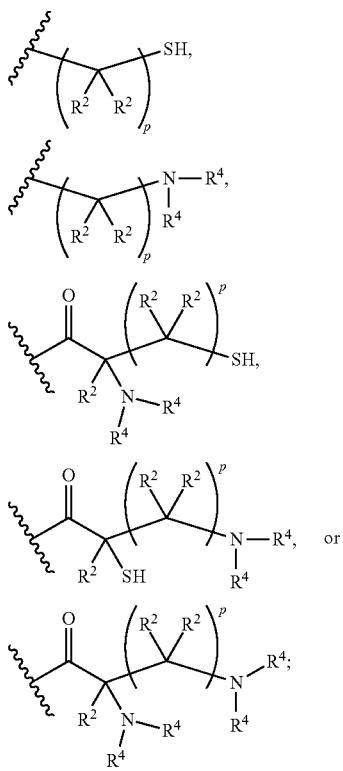

$R^4$ represents independently for each occurrence H, alkyl, aryl, aralkyl,

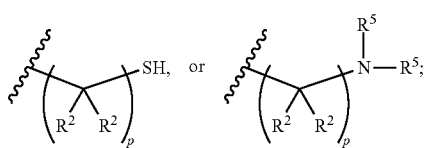

$R^5$ represents independently for each occurrence H or alkyl;

$X^1$ represents independently for each occurrence O or $-N(R^5)-$;

B is

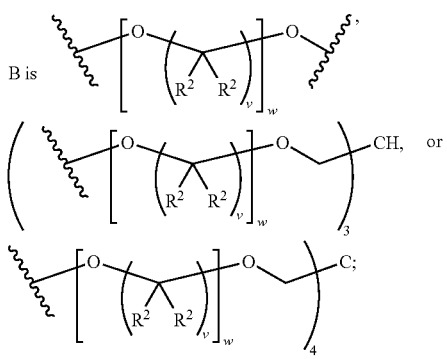

f and k each are independently selected for each occurrence from the group consisting of 1-25 inclusive;

p represents independently for each occurrence 1, 2, 3, 4, or 5;

t represents independently for each occurrence 1, 2, or 3 in accordance with the rules of valence;

v represents independently for each occurrence 2, 3, or 4; and w represents independently for each occurrence an integer in the range of about 5 to 1000, inclusive.

In certain instances, the present invention relates to the aforementioned method, wherein f and k each represent independently for each occurrence 1, 2, 3, 4, 5, 6, 7, 8, or 9.

In certain embodiments, the present invention relates to any of the aforementioned methods, wherein said polymerization agent is a compound of formula Ia, wherein $A^1$ represents independently for each occurrence

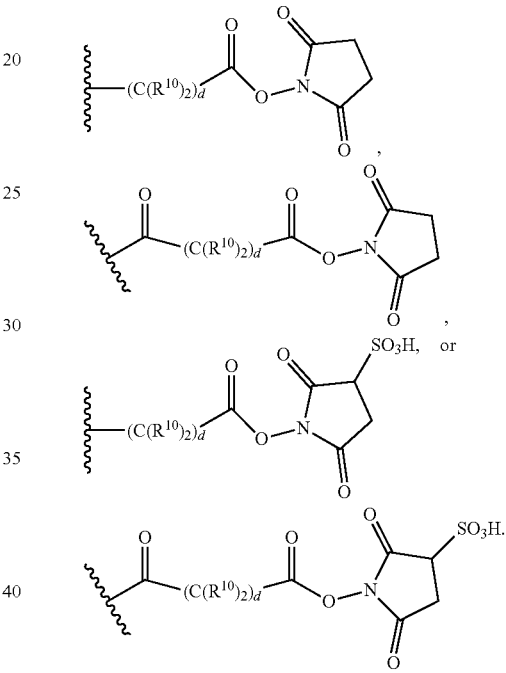

In certain embodiments, the present invention relates to any of the aforementioned methods, wherein said polymerization agent is a compound of formula Ia, wherein d represents independently for each occurrence 1, 2, 3, 4, 5, 6, 7, or 8.

In certain embodiments, the present invention relates to any of the aforementioned methods, wherein said polymerization agent is a compound of formula Ib, wherein d represents independently for each occurrence 1, 2, 3, 4, 5, 6, 7, or 8.

In certain embodiments, the present invention relates to any of the aforementioned methods, wherein said polymerization agent is a compound of formula Ic, wherein $A^1$ represents independently for each occurrence

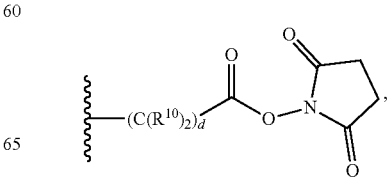

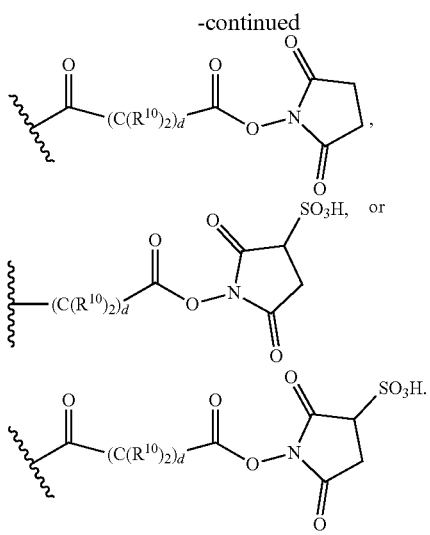

In certain embodiments, the present invention relates to any of the aforementioned methods, wherein said polymerization agent is a compound of formula Ia, wherein d represents independently for each occurrence 1, 2, 3, 4, 5, 6, 7, or 8. In certain embodiments, the present invention relates to any of the aforementioned methods, wherein said polymerization agent is a compound of formula Ia.

In certain embodiments, the present invention relates to any of the aforementioned methods, wherein said polymerization agent is a compound of formula Ia, $R^{10}$ is H, and $R^1$ is H or $A^1$.

In certain embodiments, the present invention relates to any of the aforementioned methods, wherein said polymerization agent is a compound of formula Ib.

In certain embodiments, the present invention relates to any of the aforementioned methods, wherein said polymerization agent is a compound of formula Ic.

In certain embodiments, the present invention relates to any of the aforementioned methods, wherein said polymerization agent is a compound of formula Ic, $R^{10}$ is H, and $R^1$ is H or $A^1$.

In certain embodiments, the present invention relates to any of the aforementioned methods, wherein x is 2.

In certain embodiments, the present invention relates to any of the aforementioned methods, wherein x is 3 or 4.

In certain embodiments, the present invention relates to any of the aforementioned methods, wherein y is an integer in the range of about 2 to about 100.

In certain embodiments, the present invention relates to any of the aforementioned methods, wherein at least about 10% of $R^1$ is $A^1$.

In certain embodiments, the present invention relates to any of the aforementioned methods, wherein at least about 25% of $R^1$ is $A^1$.

In certain embodiments, the present invention relates to any of the aforementioned methods, wherein at least about 50% of $R^1$ is $A^1$.

In certain embodiments, the present invention relates to any of the aforementioned methods, further comprising the step of applying a biodegradable polymer to the wound, void, or tissue of a patient; wherein said biodegradable polymer is poly(lactic acid), poly(glycolic acid), or a copolymer thereof.

In certain embodiments, the present invention relates to any of the aforementioned methods, further comprising the step of applying a polymer to the wound, void, or tissue of a patient; wherein said polymer is collagen, hyaluronic acid, albumin, cellulose, elastin, fibrin, fibronectin, gelatine, heparin, heparin sulfate, polylysine, poly(vinyl acetate), polyvinylpyrrolidone, poly(acrylic acid), poly(ethylene glycol), poly(propylene glycol)-poly(ethylene glycol) copolymer, trimethylene carbonate, or a polypeptide comprising the tripeptide Arg-Gly-Asp.

In certain embodiments, the present invention relates to any of the aforementioned methods, further comprising the step of applying a pre-formed hydrogel to the wound, void, or tissue of a patient; wherein said pre-formed hydrogel is a polyalkyleneimine hydrogel as described herein.

In certain embodiments, the present invention relates to any of the aforementioned methods, further comprising the step of applying a dissolvable polymer or inorganic salt to the wound, void, or tissue of a patient.

In certain embodiments, the present invention relates to the aforementioned method, wherein said dissolvable polymer is formulated as a microsphere or nanosphere.

In certain embodiments, the present invention relates to any of the aforementioned methods, further comprising the step of applying a mesh to the wound, void, or tissue of a patient.

In certain embodiments, the present invention relates to any of the aforementioned methods, wherein the hydrogel formed has pores in the range of about 1 micron to about 100 microns in diameter.

In certain embodiments, the present invention relates to any of the aforementioned methods, wherein the hydrogel formed has pores in the range of about 10 microns to about 100 microns in diameter.

In certain embodiments, the present invention relates to any of the aforementioned methods, wherein the hydrogel formed has pores in the range of about 40 microns to about 80 microns in diameter.

In certain embodiments, the present invention relates to any of the aforementioned methods, wherein said wound is an ophthalmic wound.

In certain embodiments, the present invention relates to any of the aforementioned methods, wherein said wound is a wound to the cornea of an eye.

In certain embodiments, the present invention relates to any of the aforementioned methods, wherein said wound is an epithelial defect, cornea incision, corneal laceration, corneal perforation, corneal ulceration, retinal hole, filtering bleb, corneal transplant, trabeculectomy incision, sclerotomy incision, blepharoplasty, or skin incision.

In certain embodiments, the present invention relates to any of the aforementioned methods, wherein said wound is an epithelial defect, corneal incision, corneal laceration, corneal perforation, or corneal ulceration.

In certain embodiments, the present invention relates to any of the aforementioned methods, wherein said wound is a corneal incision or corneal laceration.

In certain embodiments, the present invention relates to any of the aforementioned methods, wherein said wound is in the liver.

In certain embodiments, the present invention relates to any of the aforementioned methods, wherein said wound is in the lung.

In certain embodiments, the present invention relates to any of the aforementioned methods, wherein said wound is in the heart.

In certain embodiments, the present invention relates to any of the aforementioned methods, wherein said wound is the pancreas.

In certain embodiments, the present invention relates to any of the aforementioned methods, wherein said wound is in the dura matter.

In certain embodiments, the present invention relates to any of the aforementioned methods, wherein said wound is in an artery or vein.

In certain embodiments, the present invention relates to any of the aforementioned methods, wherein said wound is in cartilage.

In certain embodiments, the present invention relates to any of the aforementioned methods, wherein said wound is in a vertebral disk.

In certain embodiments, the present invention relates to any of the aforementioned methods, wherein said wound is of the type classified as a tissue plane.

In certain embodiments, the present invention relates to any of the aforementioned methods, wherein said wound is associated with a mastectomy.

In certain embodiments, the present invention relates to any of the aforementioned methods, wherein said wound is associated with a lumpectomy.

In certain embodiments, the present invention relates to any of the aforementioned methods, wherein said wound is associated with abdominoplasty.

In certain embodiments, the present invention relates to any of the aforementioned methods, wherein said wound is associated with rhytidectomy or rhinoplasty.

In certain embodiments, the present invention relates to any of the aforementioned methods, wherein said wound is associated with mammaplasty.

In certain embodiments, the present invention relates to any of the aforementioned methods, wherein said wound is associated with a forehead or buttocks lift.

In certain embodiments, the present invention relates to any of the aforementioned methods, wherein said wound is associated with a skin graft.

In certain embodiments, the present invention relates to any of the aforementioned methods, wherein said wound is associated with a biopsy closure.

In certain embodiments, the present invention relates to any of the aforementioned methods, wherein said wound is associated with a cleft-palate reconstruction.

In certain embodiments, the present invention relates to any of the aforementioned methods, wherein said wound is associated with hernia or groin repair.

In certain embodiments, the present invention relates to any of the aforementioned methods, wherein said wound is associated with a Caesarean section.

In certain embodiments, the present invention relates to any of the aforementioned methods, wherein said wound is associated with a laparoscopic trocar repair.

In certain embodiments, the present invention relates to any of the aforementioned methods, wherein said wound is associated with a vaginal tear repair.

In certain embodiments, the present invention relates to any of the aforementioned methods, wherein said wound is associated with hand surgery.

In certain embodiments, the present invention relates to any of the aforementioned methods, wherein said wound is associated with gastrointestinal anastomosis.

In certain embodiments, the present invention relates to any of the aforementioned methods, wherein said wound is associated with prostatectomy urethral-bladder anastomosis.

In certain embodiments, the present invention relates to any of the aforementioned methods, wherein said wound is associated with a myocardial infarction.

In certain embodiments, the present invention relates to any of the aforementioned methods, wherein said wound is associated with a perforated eardrum.

In certain embodiments, the present invention relates to any of the aforementioned methods, wherein said wound is associated with a partially penetrating keratoplasty procedure.

In certain embodiments, the present invention relates to any of the aforementioned methods, wherein said wound is associated with a LASIK procedure.

In certain embodiments, the present invention relates to any of the aforementioned methods, wherein said wound is a corneal flap associated with a LASIK procedure.

In certain embodiments, the present invention relates to any of the aforementioned methods, wherein said wound is associated with tooth extraction, oral surgery or periodontal disease.

In certain embodiments, the present invention relates to any of the aforementioned methods, wherein said wound is associated with a cornea-replacement procedure.

In certain embodiments, the present invention relates to any of the aforementioned methods, wherein said wound is in the dura mater of the nervous system.

In certain embodiments, the present invention relates to any of the aforementioned methods, wherein said wound is in a cardiac artery or cardiac vein.

In certain embodiments, the present invention relates to any of the aforementioned methods, wherein said wound is in a parenchymal organ.

In certain embodiments, the present invention relates to any of the aforementioned methods, wherein said wound is in the spleen.

In certain embodiments, the present invention relates to any of the aforementioned methods, wherein said wound is in bone.

In certain embodiments, the present invention relates to any of the aforementioned methods, wherein said wound is in the skeletal system.

In certain embodiments, the present invention relates to any of the aforementioned methods, wherein said wound is in the gastrointestinal system.

In certain embodiments, the present invention relates to any of the aforementioned methods, wherein said wound is in the genitourinary system.

In certain embodiments, the present invention relates to any of the aforementioned methods, wherein said wound is associated with mentoplasty.

In certain embodiments, the present invention relates to any of the aforementioned methods, wherein said wound is associated with brachioplasty.

In certain embodiments, the present invention relates to any of the aforementioned methods, wherein said wound is associated with gynecomastia reduction.

In certain embodiments, the present invention relates to any of the aforementioned methods, further comprising applying a medicament, colorant, flavoring, scent, fibrous additive, thickener or plasticizer.

In certain embodiments, the present invention relates to any of the aforementioned methods, wherein said patient is a primate, bovine, equine, feline, or canine.

In certain embodiments, the present invention relates to any of the aforementioned methods, wherein said patient is a human.

In certain embodiments, the present invention relates to any of the aforementioned methods, wherein the adhesive composition forms upon exposing an effective amount of a polymerization agent to a compound of formula III in less than 60 seconds.

In certain embodiments, the present invention relates to any of the aforementioned methods, wherein the adhesive composition forms upon exposing an effective amount of a polymerization agent to a compound of formula III in less than 30 seconds.

In certain embodiments, the present invention relates to any of the aforementioned methods, wherein the adhesive composition forms upon exposing an effective amount of a polymerization agent to a compound of formula III in less than 5 seconds.

Compositions of the Invention

One aspect of the present invention relates to a polymeric composition in contact with mammalian tissue, wherein said polymeric composition is formed by exposing a polymerization agent to a compound of formula III sufficient to polymerize said polymerization agent, said polymerization agent is a compound of formula Ia, or formula Ib; and formula Ia is represented by:

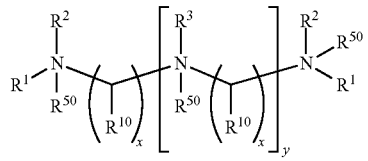

wherein, $R^{50}$ independently for each occurrence is an electron pair or a substituent selected from the group consisting of H, alkyl, and aralkyl; when an instance of $R^{50}$ represents a substituent a pharmaceutically acceptable counterion is present;

$R^1$ and $R^2$ represent independently for each occurrence $A^1$, alkyl, alkenyl, alkynyl, —C(O)-alkyl, —C(O)O[C($R^4$)$_2$]$_d$N($R^5$)$_2$, —C(O)N($R^5$)[C($R^4$)$_2$]$_d$N($R^5$)$_2$, —C(O)N($R^5$)$_2$, —X$^1$—[C($R^4$)$_2$]$_d$N($R^5$)C(O)N($R^5$)$_2$, —X$^1$—[C($R^4$)$_2$]$_d$N($R^5$)C(O)N($R^5$)$_2$, —X$^1$—[C($R^4$)$_2$]$_d$OC(O)CH$_2$C(O)-alkyl,

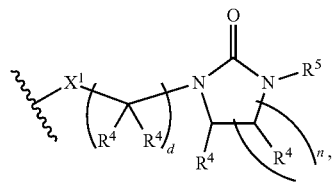

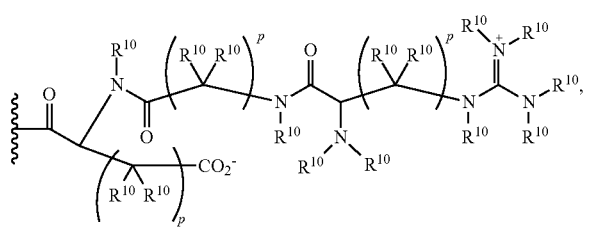

or a carbohydrate radical;

$R^3$ represents independently for each occurrence H or

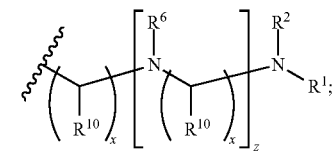

$R^4$ represents independently for each occurrence H, alkyl, alkoxyl, halogen, aryl, or aralkyl;

$R^5$ represents independently for each occurrence H, alkyl, aryl, or aralkyl;

$R^6$ represents independently for each occurrence H or

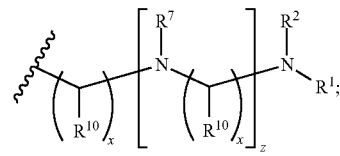

$R^7$ represents independently for each occurrence H or

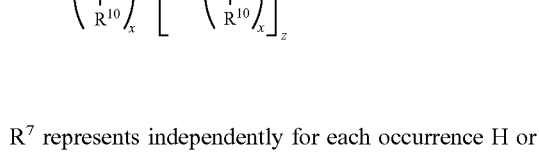

$R^8$ represents independently for each occurrence H or

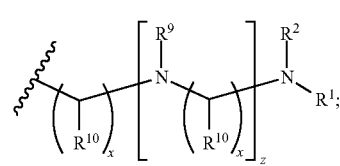

$R^9$ represents independently for each occurrence H or

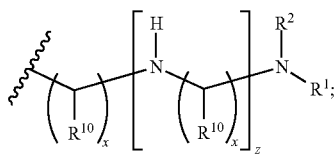

$R^{10}$ represents independently for each occurrence H or $(C_1-C_3)$alkyl;

$X^1$ represents independently for each occurrence a bond or —C(O)—;

$A^1$ represents independently for each occurrence H, —C(O)NH$_2$, —X$^1$—[C(R$^4$)$_2$]$_d$N(R$^5$)C(O)NH$_2$,

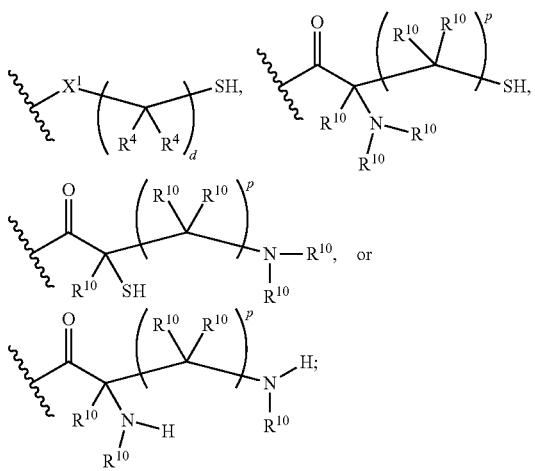

d represents independently for each occurrence 1, 2, 3, 4, 5, 6, 7, 8, 9, or 10;

n represents independently for each occurrence 1, 2, 3, or 4;

p represents independently for each occurrence 1, 2, 3, 4, or 5;

x represents independently for each occurrence 1, 2, 3, 4, or 5;

y is an integer in the range of 1 to about 40,000;

z represents independently for each occurrence an integer in the range of 0 to about 20,000; and provided at least about 5% of $R^1$ is $A^1$, and the sum of y and z is less than about 50,000; formula Ib is represented by:

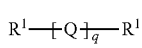

Ib wherein

Q represents independently for each occurrence

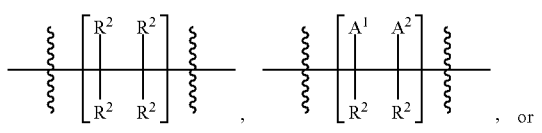

-continued

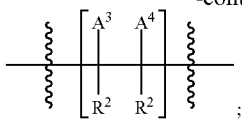

$R^{50}$ independently for each occurrence is an electron pair or a substituent selected from the group consisting of H, alkyl, and aralkyl; when an instance of $R^{50}$ represents a substituent a pharmaceutically acceptable counterion is present;

$A^1$ represents independently for each occurrence —CO$_2$R$^4$;

$A^2$ represents independently for each occurrence H or —CO$_2$R$^4$;

$A^3$ represents independently for each occurrence —N(R$^1$)(R$^{50}$)(R$^3$)

$A^4$ represents independently for each occurrence H, alkyl, aryl, —CO$_2$R$^4$, or —OC(O)R$^4$;

$R^1$ represents independently for each occurrence H, alkyl or polymerization initiator;

$R^2$ represents independently for each occurrence H, alkyl, aryl, or aralkyl;

$R^3$ represents independently for each occurrence H, alkyl, aryl, aralkyl, acyl, —C(O)NH$_2$, —X$^1$—[C(R$^5$)$_2$]$_d$N(R$^5$)C(O)NH$_2$,

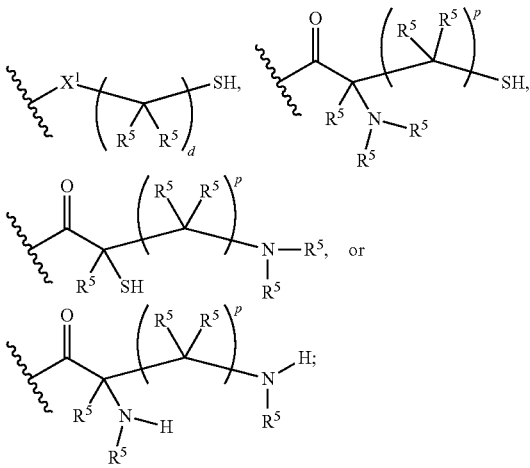

$R^4$ represents independently for each occurrence H, alkyl, aryl, aralkyl,

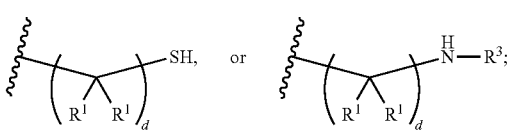

$R^5$ represents independently for each occurrence H or alkyl;

$X^1$ represents independently for each occurrence a bond or —C(O)—;

d represents independently for each occurrence 1, 2, 3, 4, 5, 6, 7, 8, 9, or 10;

p represents independently for each occurrence 1, 2, 3, 4, or 5; and q is an integer from about 50 to about 100,000; and formula III is represented by:

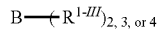

III wherein $R^{1-III}$ represents independently for each occurrence —(C($R^{2-III}$)$_2$)$_j$C(O)$R^{3-III}$, —C(O)(C($R^{2-III}$)$_2$)$_k$C(O)$R^{3-III}$, —(C($R^{2-III}$)$_2$)$_j$$R^{4-III}$, —C(O)(C($R^{2-III}$)$_2$)$_k$$R^{4-III}$, —(C($R^{2-III}$)$_2$)$_j$C(O)N($R^{5-III}$)-[$A^{4-III}$]$_t$—C(O)—$R^{3-III}$, —(C($R^{2-III}$)$_2$)$_j$CO$_2$-[$A^{4-III}$]$_t$-C(O)—$R^{3-III}$,

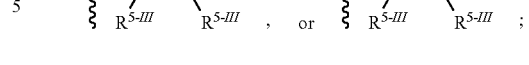

$R^{5-III}$ represents independently for each occurrence H, alkyl, or aralkyl;

$R^{6-III}$ represents independently for each occurrence H or ($C_1$-$C_6$)alkyl;

$R^{7-III}$ represents independently for each occurrence —CO$_2$H, —(C($R^{6-III}$)$_2$)$_p$N=C=O,

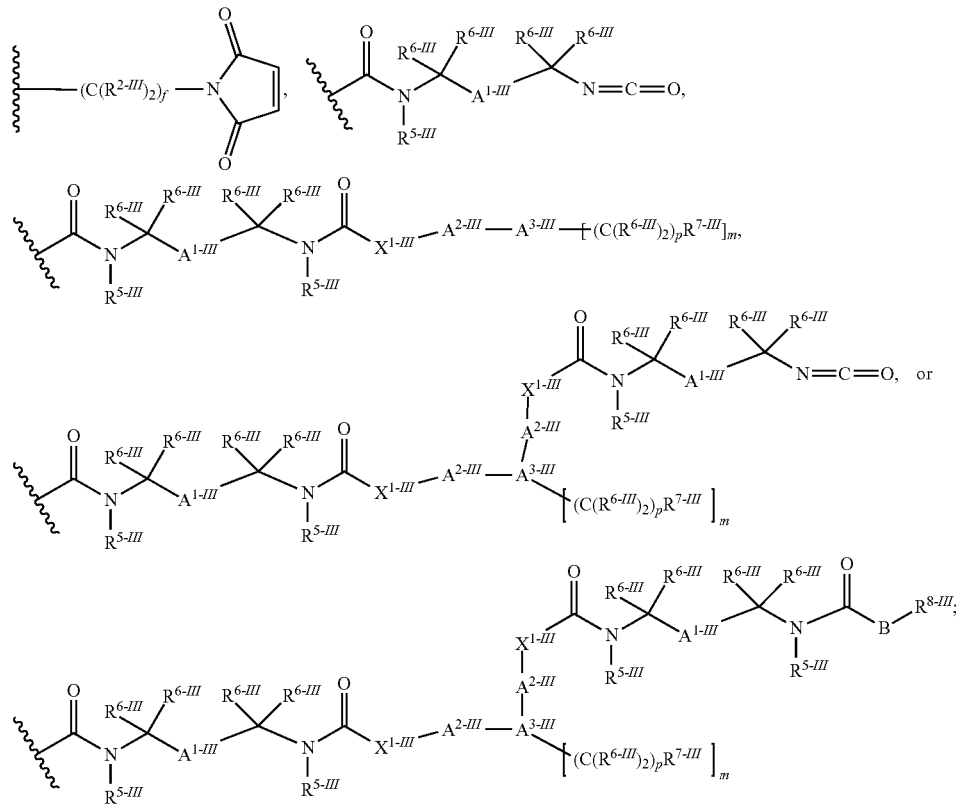

$R^{2-III}$ represents independently for each occurrence H, alkyl, or halogen;

$R^{3-III}$ represents independently for each occurrence H, alkyl, fluoroalkyl, chloroalkyl, —CH$_2$NO$_2$,

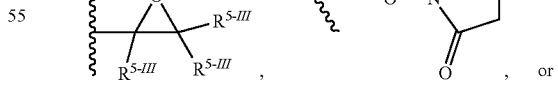

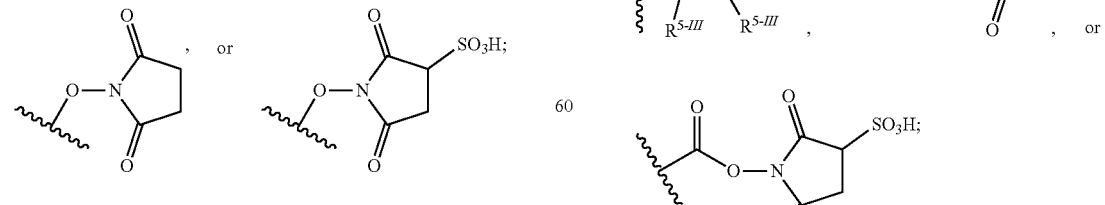

$R^{4-III}$ represents independently for each occurrence —N=C=O, —N=C=S,

R$^{8\text{-}III}$ represents independently for each occurrence

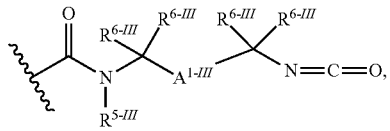

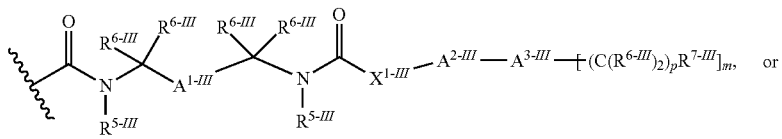

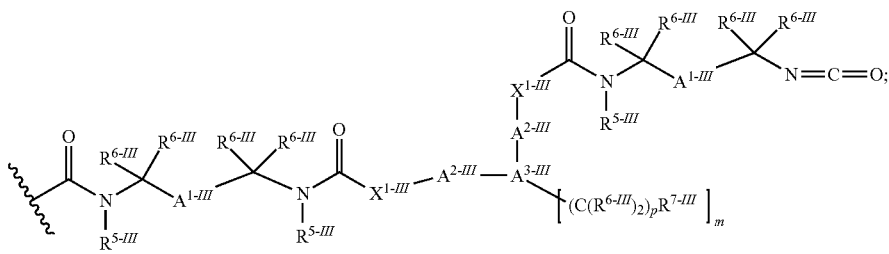

A$^{1\text{-}III}$ and A$^{3\text{-}III}$ represent independently for each occurrence alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

A$^{2\text{-}III}$ represents independently for each occurrence a bond, alkyl diradical, heteroalkyl diradical, cycloalkyl diradical, heterocycloalkyl diradical, alkenyl diradical, alkynyl diradical, aryl diradical, heteroaryl diradical, aralkyl diradical, or heteroaralkyl diradical;

A$^{4\text{-}III}$ represents independently for each occurrence an alkyl diradical, cycloalkyl diradical, aryl diradical, or aralkyl diradical;

B represents independently for each occurrence alkyl diradical, heteroalkyl diradical, or

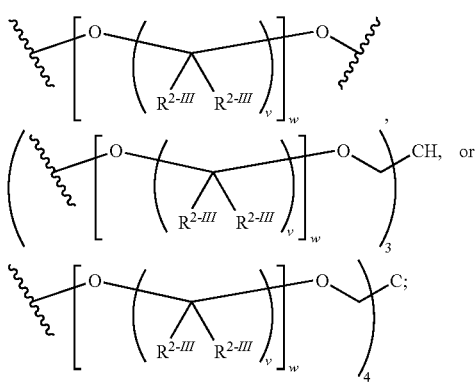

X$^{1\text{-}III}$ represents independently for each occurrence O or —N(R$^{5\text{-}III}$)—;

m represents independently for each occurrence 1, 2, 3, 4, or 5 in accordance with the rules of valence;

p represents independently for each occurrence 0, 1, 2, 3, 4, or 5;

t represents independently for each occurrence 1, 2, 3 or 4;

v represents independently for each occurrence 2, 3, or 4;

w is independently for each occurrence an integer in the range of about 5 to 1000, inclusive; and f and k each are independently selected for each occurrence from the group consisting of 1-25 inclusive.

In certain instances, the present invention relates to the aforementioned method, wherein f and k each represent independently for each occurrence 1, 2, 3, 4, 5, 6, 7, 8, or 9.

In certain instances, the present invention relates to the aforementioned composition, wherein said polymerization agent is a compound of formula Ia.

In certain instances, the present invention relates to the aforementioned composition, wherein said polymerization agent is a compound of formula Ia, d represents independently for each occurrence 1, 2, 3, 4, 5, 6, 7, or 8.

In certain instances, the present invention relates to the aforementioned composition, wherein said polymerization agent is a compound of formula Ia, R$^1$ and R$^2$ represent independently for each occurrence A$^1$, alkyl, alkenyl, alkynyl, —C(O)-alkyl, —C(O)N(R$^5$)$_2$, —X$^1$—[C(R$^4$)$_2$]$_d$N(R$^5$)C(O)N(R$^5$)$_2$, —X$^1$—[C(R$^4$)$_2$]$_d$OC(O)CH$_2$C(O)-alkyl,

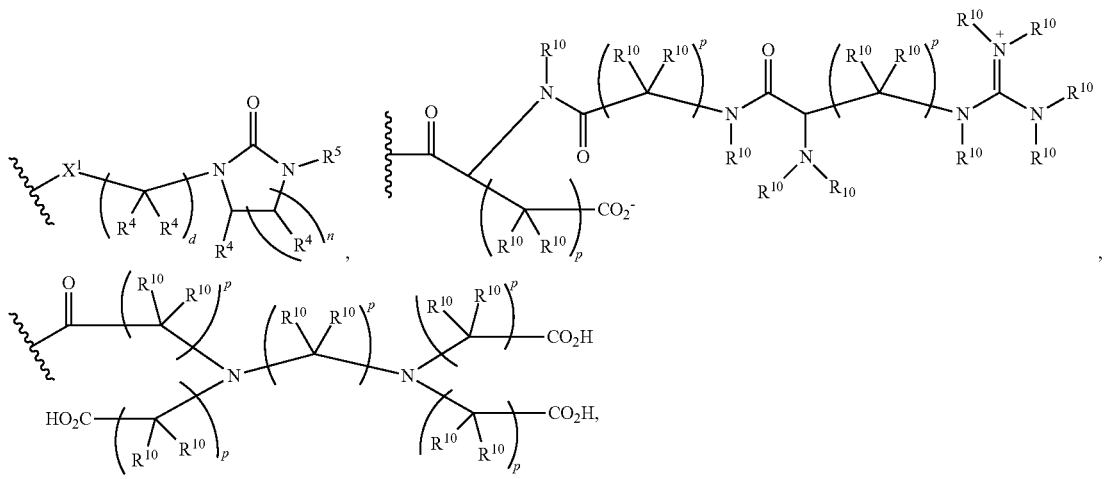

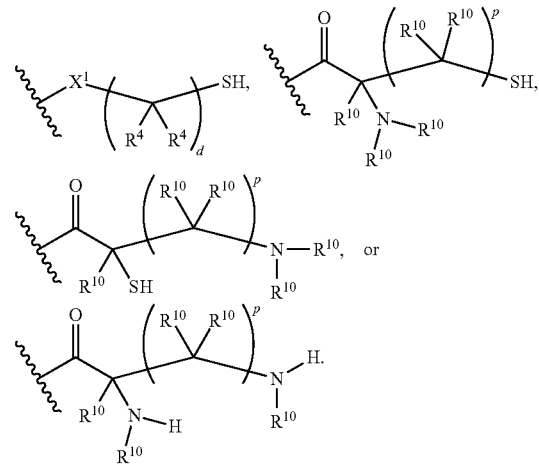

or a carbohydrate radical.

In certain instances, the present invention relates to the aforementioned composition, wherein said polymerization agent is a compound of formula Ia, $R^{10}$ is H, and x is 2 or 3.

In certain instances, the present invention relates to the aforementioned composition, wherein said polymerization agent is a compound of formula Ia, $R^{10}$ is H, x is 2 or 3, at least about ½ of $R^1$ are H, and at least about ½ of $R^2$ are H.

In certain instances, the present invention relates to the aforementioned composition, wherein said polymerization agent is a compound of formula Ia, $R^{10}$ is H, x is 2 or 3, at least about ½ of $R^1$ are H, at least about ½ of $R^2$ are H, and the sum of y and z is an integer in the range of about 20 to about 500.

In certain instances, the present invention relates to the aforementioned composition, wherein said polymerization agent is a compound of formula Ia, $R^{10}$ is H, x is 2 or 3, at least about 90% of $R^1$ are $A^1$, and $A^1$ represents independently for each occurrence H,

In certain instances, the present invention relates to the aforementioned composition, wherein said polymerization agent is a compound of formula Ia, $R^{10}$ is H, x is 2 or 3, at least about 90% of $R^1$ and $R^2$ are $A^1$, and $A^1$ represents independently for each occurrence H, In certain instances, the present invention relates to the aforementioned composition, wherein said polymerization agent is a compound of formula Ia, $R^{10}$ is H, x is 2 or 3, at least about 95% of $R^1$ and $R^2$ are H, and the sum of y and z is an integer in the range of about 20 to about 500.

In certain instances, the present invention relates to the aforementioned composition, wherein said polymerization agent is a compound of formula Ia, $R^{10}$ is H, and x is 3 or 4.

In certain instances, the present invention relates to the aforementioned composition, wherein said polymerization agent is a compound of formula Ia, $R^{10}$ is H, x is 3 or 4, and at least about 95% of $R^1$ and $R^2$ are H.

In certain instances, the present invention relates to the aforementioned composition, wherein said polymerization agent is $NH_2(CH_2)_2N(H)(CH_2)_4N(H)(CH_2)_2NH_2$.

In certain instances, the present invention relates to the aforementioned composition, wherein said polymerization agent is $NH_2(CH_2)_3N(H)(CH_2)_4N(H)(CH_2)_3NH_2$.

In certain instances, the present invention relates to the aforementioned composition, wherein said polymerization agent is a compound of formula Ib.

In certain instances, the present invention relates to the aforementioned composition, wherein said polymerization agent is a compound of formula Ib, and $A^3$ is —N(H)$R^3$.

In certain instances, the present invention relates to the aforementioned composition, wherein said polymerization agent is a compound of formula Ib, $A^3$ is —N(H)$R^3$, and $R^1$ and $R^3$ are H.

In certain instances, the present invention relates to the aforementioned composition, wherein said polymerization agent is a compound of formula Ib, $A^3$ is —N(H)$R^3$, $R^1$ and $R^3$ are H, and x is 0.

In certain instances, the present invention relates to the aforementioned composition, wherein said polymerization agent is a compound of formula Ib, and $A^1$ is $-CO_2R^4$.

In certain instances, the present invention relates to the aforementioned composition, wherein said polymerization agent is a compound of formula Ib, $A^1$ is $-CO_2R^4$, $R^4$ is

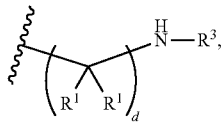

$R^1$ and $R^3$ are H.

In certain instances, the present invention relates to the aforementioned composition, wherein said polymerization agent is a compound of formula Ib, $A^1$ is $-CO_2R^4$, $R^4$ is

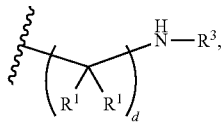

$R^1$ and $R^3$ are H, and x is 0.

In certain instances, the present invention relates to the aforementioned composition, wherein w is independently for each occurrence an integer in the range of about 50 to about 250.

In certain instances, the present invention relates to the aforementioned composition, wherein w is independently for each occurrence an integer in the range of about 60 to about 90.

In certain instances, the present invention relates to the aforementioned composition, wherein $R^{1-III}$ is $-(C(R^{2-III})_2)_jC(O)R^3$ or $-C(O)(C(R^{2-III})_2)_kC(O)R^{3-III}$, $R^{2-III}$ is H, and $R^{3-III}$ is

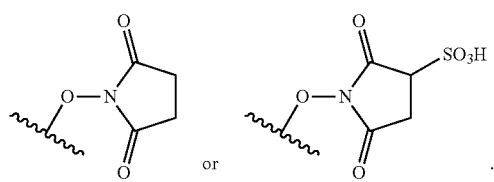 [SMILES: *ON1C(=O)CCC1=O ; *ON1C(=O)CC(S(=O)(=O)O)C1=O]

In certain instances, the present invention relates to the aforementioned composition, wherein $R^{1-III}$ is $-(C(R^{2-III})_2)_jC(O)R^{3-III}$ or $-C(O)(C(R^{2-III})_2)_kC(O)R^{3-III}$, $R^{2-III}$ is H, $R^{3-III}$ is

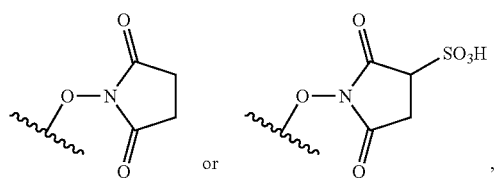

B is

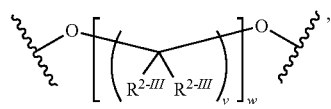

and v is 2.

In certain instances, the present invention relates to the aforementioned composition, $R^{1-III}$ is $-(C(R^{2-III})_2)_jC(O)R^{3-III}$ or $-C(O)(C(R^{2-III})_2)_kC(O)R^{3-III}$, $R^{2-III}$ is H, $R^{3-III}$ is

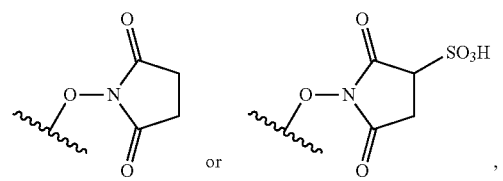 [SMILES: *ON1C(=O)CCC1=O ; *ON1C(=O)CC(S(=O)(=O)O)C1=O]

B is

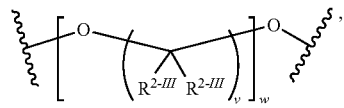

v is 2, and w is independently for each occurrence an integer in the range of about 15-90.

In certain instances, the present invention relates to the aforementioned composition, wherein $R^{1-III}$ is $-(C(R^{2-III})_2)_jC(O)R^{3-III}$ or $-C(O)(C(R^{2-III})_2)_kC(O)R^{3-III}$, $R^{2-III}$ is H, $R^{3-III}$ is

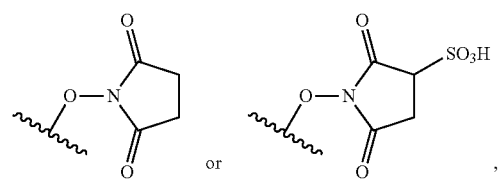 [SMILES: *ON1C(=O)CCC1=O ; *ON1C(=O)CC(S(=O)(=O)O)C1=O]

B is

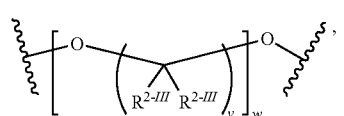

and v is 2.

In certain instances, the present invention relates to the aforementioned composition, wherein $R^{1\text{-}III}$ is —(C($R^{2\text{-}III}$)$_2$)$_k$C(O)$R^{3\text{-}III}$ or —C(O)(C($R^{2\text{-}III}$)$_2$)$_k$C(O)$R^{3\text{-}III}$, $R^{2\text{-}III}$ is H, $R^{3\text{-}III}$ is

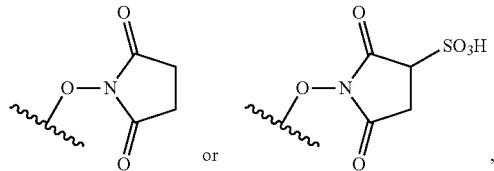 [SMILES: *ON1C(=O)CCC1=O ; *ON1C(=O)CC(S(=O)(=O)O)C1=O]

or

B is

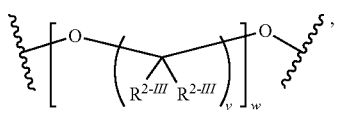

v is 2, and w is independently for each occurrence an integer in the range of about 15-90, B is

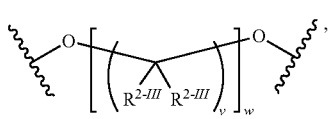

v is 2, said polymerization agent is a compound of formula Ia, $R^{10}$ is H, x is 2, at least about ½ of R are H, and at least about ½ of $R^2$ are H.

In certain instances, the present invention relates to the aforementioned composition, wherein $R^{1\text{-}III}$ is —(CH$_2$)$_3$C(O)$R^{3\text{-}III}$, $R^{3\text{-}III}$ is

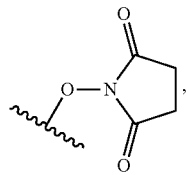

B is

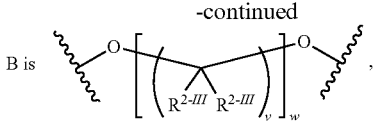

and v is 2.

In certain instances, the present invention relates to the aforementioned composition, wherein $R^{1\text{-}III}$ is —C(O)(CH$_2$)$_2$C(O)$R^{3\text{-}III}$ or —C(O)(CH$_2$)$_3$C(O)$R^{3\text{-}III}$, $R^{3\text{-}III}$ is

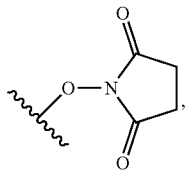 [SMILES: *ON1C(=O)CCC1=O]

B is

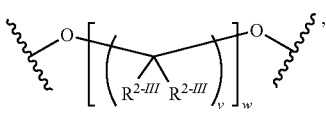

and v is 2.

In certain instances, the present invention relates to the aforementioned composition, wherein formula III is

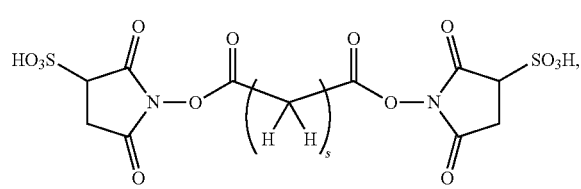

and s is an integer in the range of about 1-20 inclusive.

In certain instances, the present invention relates to the aforementioned composition, wherein $R^{1\text{-}III}$ represents independently for each occurrence

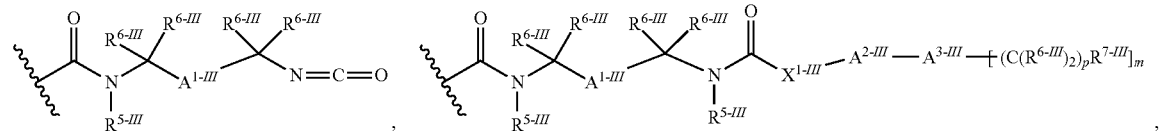

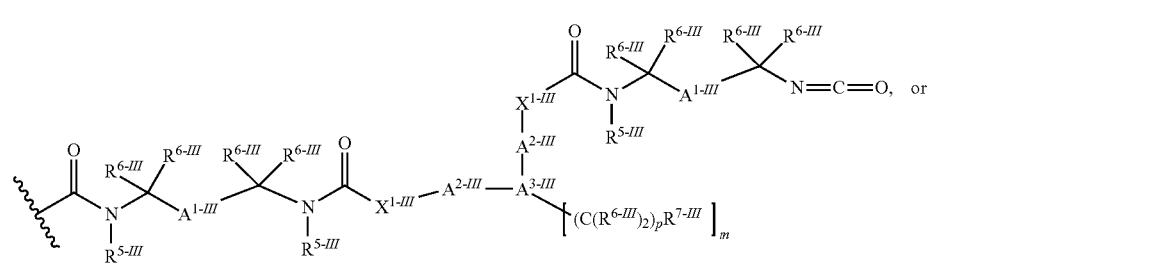

-continued

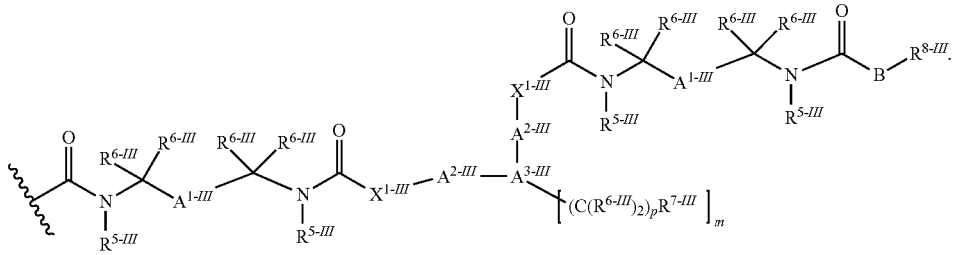

In certain instances, the present invention relates to the aforementioned composition, wherein, B is

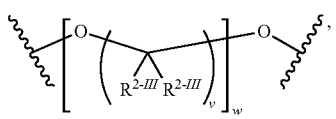

$R^{2-III}$ is H, and $A^{1-III}$ is aryl diradical.

In certain instances, the present invention relates to the aforementioned composition, wherein, B is

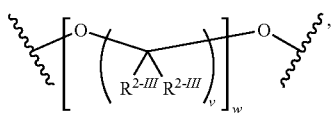

$R^{2-III}$ is H, and $A^{1-III}$ is optionally substituted phenyl diradical.

In certain instances, the present invention relates to the aforementioned composition, wherein, B is

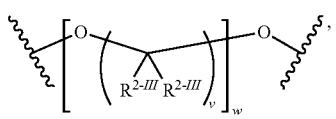

$R^{2-III}$ is H, $A^{2-III}$ is a bond, and $A^{3-III}$ is alkyl diradical.

In certain instances, the present invention relates to the aforementioned composition, wherein, B is

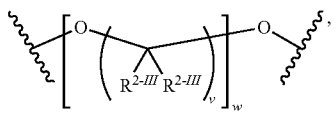

$R^{2-III}$ is H, $A^{2-III}$ is a bond, $A^{3-III}$ is alkyl diradical, and $R^{7-III}$ is

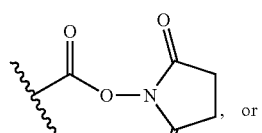, or

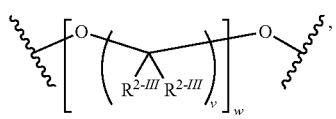

In certain instances, the present invention relates to the aforementioned composition, wherein, B is

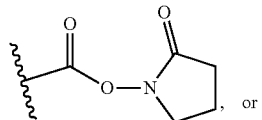

$R^{2-III}$ is H, $A^{2-III}$ is aryl diradical, $A^{3-III}$ is aralkyl diradical, and $R^{7-III}$ is

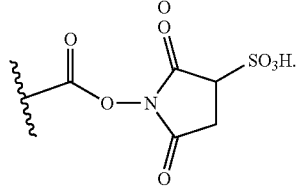, or

In certain instances, the present invention relates to the aforementioned composition, wherein, B is

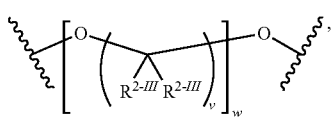

$A^{2\text{-}III}$ is H, $A^{2\text{-}III}$ is optionally substituted phenyl diradical, $A^{3\text{-}III}$ is optionally substituted benzyl diradical, and $R^{7\text{-}III}$

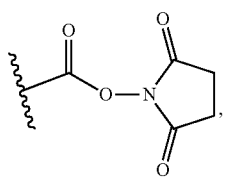 [SMILES: *C(=O)ON1C(=O)CCC1=O]

or

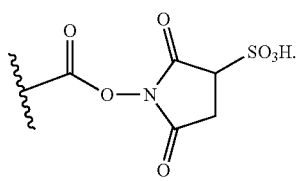 [SMILES: *C(=O)ON1C(=O)CC(S(=O)(=O)O)C1=O]

In certain instances, the present invention relates to the aforementioned composition, wherein, B is

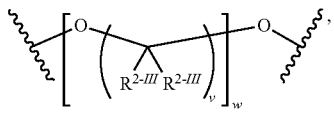

$R^{2\text{-}III}$ is H, v is 2, and $R^{1\text{-}III}$ is

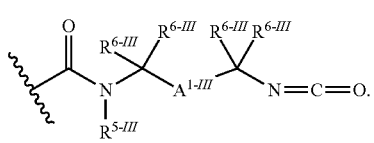

In certain instances, the present invention relates to the aforementioned composition, wherein, B is

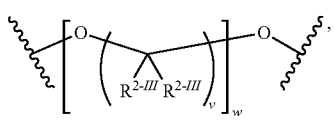

$R^{2\text{-}III}$ is H, v is 2, $R^{1\text{-}III}$ is

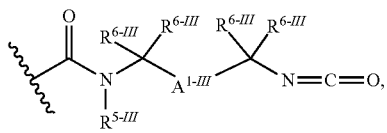

$R^{6\text{-}III}$ is $(C_1\text{-}C_4)$alkyl, and $A^{1\text{-}III}$ is aryl diradical.

In certain instances, the present invention relates to the aforementioned composition, wherein, B is

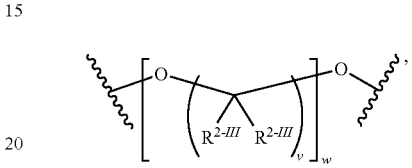

$R^{2\text{-}III}$ is H, v is 2, $R^{1\text{-}III}$ is

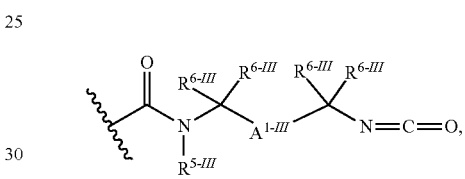

$R^{6\text{-}III}$ is $(C_1\text{-}C_4)$alkyl, and $A^{1\text{-}III}$ is optionally substituted phenyl diradical.

In certain instances, the present invention relates to the aforementioned composition, wherein, B is

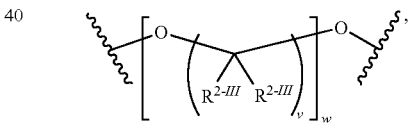

$R^{2\text{-}III}$ is H, v is 2, $R^{1\text{-}III}$ is

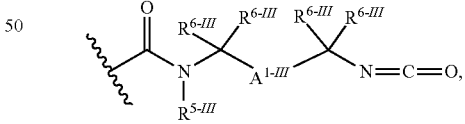

$R^{6\text{-}III}$ is methyl, and $A^{1\text{-}III}$ is phenyl diradical.

In certain instances, the present invention relates to the aforementioned composition, wherein, B is

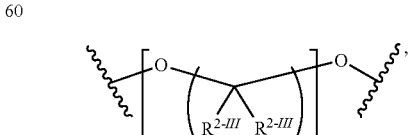

$R^{2-III}$ is H, v is 2, $R^{1-III}$ is

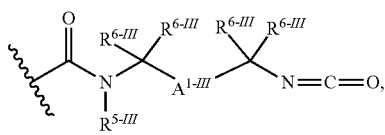

$R^{6-III}$ is methyl, $A^{1-III}$ is phenyl diradical, said polymerization agent is a compound of formula Ia, $R^{10}$ is H, x is 2, at least about ½ of $R^1$ are H, and at least about ½ of $R^2$ are H.

In certain embodiments, the present invention relates to the aforementioned composition, wherein said polymerization agent is a compound of formula Ia, said compound of formula Ia has a weight average molecular weight of about 600 to about 10,000 Daltons, said compound of formula III has a weight average molecular weight of about 500 to about 20,000 Daltons, and the molar ratio of said compound of formula Ia to said compound of formula III is about 0.025:1 to about 0.4:1.

In certain embodiments, the present invention relates to the aforementioned composition, wherein $R^{1-III}$ is $-(C(R^{2-III})_2)_fC(O)N(R^{5-III})-[A^{4-III}]_t-C(O)-R^{3-III}$, $A^{4-III}$ is an alkyl diradical, t and f are 1, $R^{2-III}$ and $R^{5-III}$ are hydrogen, and $R^{3-III}$ is

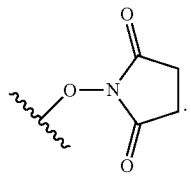 [SMILES: *ON1C(=O)CCC1=O]

In certain embodiments, the present invention relates to any of the aforementioned compositions, wherein $R^{1-III}$ represents independently for each occurrence $-(C(R^{2-III})_2)_fC(O)N(R^{5-III})-[A^{4-III}]_t-C(O)-R^{3-III}$ or $-(C(R^{2-III})_2)_fCO_2[A^{4-III}]_t-C(O)-R^{3-III}$.

In certain embodiments, the present invention relates to any of the aforementioned compositions, wherein $R^{1-III}$ is $-(C(R^{2-III})_2)_fC(O)N(R^{5-III})-[A^{4-III}]_t-C(O)-R^{3-III}$, $A^{4-III}$ is an alkyl diradical, t is 1, $R^{2-III}$ is H, and $R^{3-III}$ represents independently for each occurrence

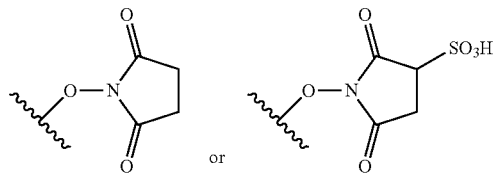

In certain embodiments, the present invention relates to any of the aforementioned compositions, wherein $R^{1-III}$ is $-(C(R^{2-III})_2)_fC(O)N(R^{5-III})-[A^{4-III}]_t-C(O)-R^{3-III}$, $A^{4-III}$ is an alkyl diradical, t is 1, $R^{2-III}$ is H, $R^{3-III}$ represents independently for each occurrence

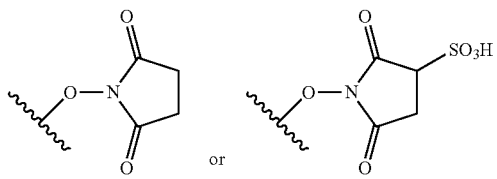

B is

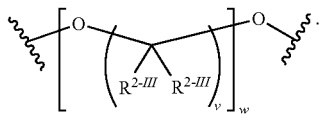

In certain embodiments, the present invention relates to any of the aforementioned compositions, wherein said compound of formula III is one of the following:

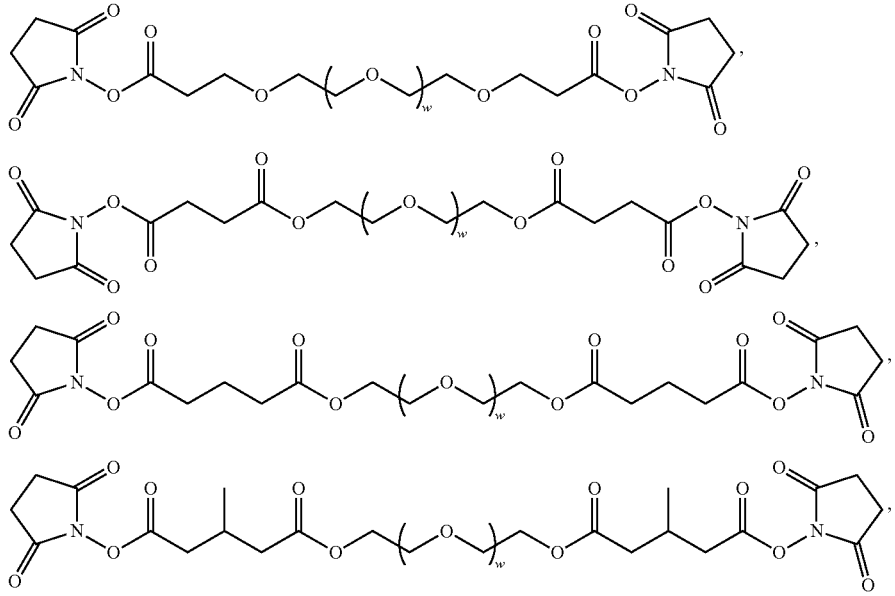

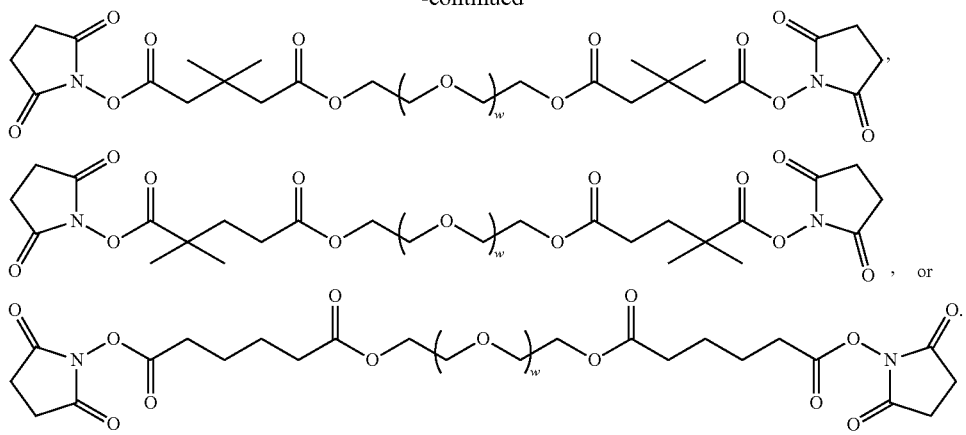

Another aspect of the invention relates to the polymeric composition formed by exposing a polymerization agent to a compound of formula III sufficient to polymerize said polymerization agent, wherein said polymerization agent is a compound of formula Ia or formula Ib, wherein formulae Ia, Ib, and III are as defined above.

Another aspect of the invention relates to the polymeric composition formed by exposing a polymerization agent to a compound of formula III sufficient to polymerize said polymerization agent, wherein said polymerization agent is a compound of formula Ic, wherein formulae Ic and III are as defined above.

In certain embodiments, the present invention relates to any of the aforementioned compositions, wherein the hydrogel formed has pores in the range of about 1 micron to about 100 microns in diameter.

In certain embodiments, the present invention relates to any of the aforementioned compositions, wherein the hydrogel formed has pores in the range of about 10 microns to about 100 microns in diameter.

In certain embodiments, the present invention relates to any of the aforementioned compositions, wherein the hydrogel formed has pores in the range of about 40 microns to about 80 microns in diameter.

Another aspect of the invention relates to the polymeric composition produced using any one of the methods described above.

Another aspect of the present invention relates to a composition formed by reacting a first crosslinkable component containing three or more reactive amines and internal cationic charge at physiological pH with a second crosslinkable component comprising a polyalkylene glycol and at least two electrophilic groups. The reaction generates covalent bonds. In certain instances, one or both of the first and second crosslinkable components are dissolved in an aqueous solution. In certain instances, crosslinking results in a biocompatible crosslinked hydrogel in less than 10 minutes.

Another aspect of the present invention relates to a composition formed by reacting a first crosslinkable component containing three or more reactive amines and also containing secondary and tertiary amines which are cationic at physiological pH with a second crosslinkable component comprising a polyalkylene glycol and at least two electrophilic groups. The reaction generates covalent bonds. In certain instances, one or both of the first and second crosslinkable components are dissolved in an aqueous solution. In certain instances, crosslinking results in a biocompatible crosslinked hydrogel in less than 10 minutes.

Another aspect of the present invention relates to a composition formed by reacting a first synthetic crosslinkable component containing three or more reactive amines with a second crosslinkable component comprising a polyalkylene glycol and at least two electrophilic groups. The reaction generates covalent bonds. In certain instances, one or both of the first and second crosslinkable components are dissolved in an aqueous solution. In certain instances, crosslinking results in a biocompatible crosslinked hydrogel in less than 10 minutes. In certain instances, the reaction is carried out in a solution having a pH in the range of about 6.5 to about 8.75. In certain instances, the pH is in the range of about 6.5 to about 8.0. In certain instances, the pH is in the range of about 6.5 to about 7.5. In certain instances, the resulting composition is characterized in that placing the composition in a non-buffered 0.9% NaCl solution provides a solution having a pH in the range of about 6.5 to about 8.75. In certain instances, the resulting composition is characterized in that placing the composition in a non-buffered 0.9% NaCl solution provides a solution having a pH in the range of about 6.5 to about 8.0. In certain instances, the resulting composition is characterized in that placing the composition in a non-buffered 0.9% NaCl solution provides a solution having a pH in the range of about 6.5 to about 7.5. In certain instances, the solution contains between about 5 wt % and 75 wt % of said composition. In certain instances, the solution contains between about 10 wt % and 25 wt % of said composition.

Another aspect of the present invention relates to a composition formed by reacting a first crosslinkable component with a second crosslinkable component; wherein said first crosslinkable component comprises three or more reactive amines and has a weight average molecular weight of less than or equal to 2,000 g/mol; said second crosslinkable component comprises a polyethylene glycol comprising N-hydroxysuccinimide. The reaction generates covalent bonds. In certain instances, one or both of the first and second crosslinkable components are dissolved in an aqueous solution. In certain instances, crosslinking results in a biocompatible crosslinked hydrogel in less than 10 minutes. In certain instances, the reaction is carried out in a solution having a pH in the range of about 6.5 to about 8.75. In certain instances, the pH is in the range of about 6.5 to about 8.0. In certain instances, the pH is in the range of about 6.5 to about 7.5. In certain instances, the resulting composition is characterized in that placing the composition in a non-buffered 0.9% NaCl solution provides a solution having a pH in the range of about 6.5 to about 8.75. In certain instances, the resulting composition is characterized in that placing the composition in a non-buffered 0.9% NaCl solution provides a solution having a pH in the range of about 6.5 to about 8.0. In certain instances, the resulting composition is characterized in that placing the composition in a non-buffered 0.9% NaCl solution provides a solution having a pH in the range of about 6.5 to about 7.5. In certain instances, the solution contains between about 5 wt % and 75 wt % of said composition. In certain instances, the solution contains between about 10 wt % and 25 wt % of said composition.

Another aspect of the present invention relates to a composition formed by reacting a first synthetic crosslinkable component containing three or more reactive amines with a second crosslinkable component comprising a polyalkylene glycol and at least two electrophilic groups. The reaction generates covalent bonds. In certain instances, one or both of the first and second crosslinkable components are dissolved in an aqueous solution. In certain instances, crosslinking results in a biocompatible crosslinked hydrogel in less than 10 minutes. In certain instances, the reaction is carried out such that the first and/or second component provide an inherent buffering capacity.

Another aspect of the present invention relates to a composition formed by reacting a first synthetic crosslinkable component containing three or more reactive amines with a second crosslinkable component comprising a polyalkylene glycol and at least two electrophilic groups. The reaction generates covalent bonds. In certain instances, one or both of the first and second crosslinkable components are dissolved in an aqueous solution. In certain instances, crosslinking results in a biocompatible crosslinked hydrogel in less than 10 minutes. In certain instances, the reaction is carried out such that the first and/or second component provide an inherent antimicrobial activity.

Another aspect of the present invention relates to a composition formed by reacting a first synthetic crosslinkable component containing three or more reactive amines with a second crosslinkable component comprising a polyalkylene glycol and at least two electrophilic groups. The reaction generates covalent bonds. In certain instances, one or both of the first and second crosslinkable components are dissolved in an aqueous solution. In certain instances, crosslinking results in a biocompatible crosslinked hydrogel in less than 10 minutes. In certain instances, the reaction is carried out such that the first and/or second component provide an inherent positive charge.

Another aspect of the present invention relates to a composition formed by reacting a first synthetic crosslinkable component with m functional groups with a second crosslinkable component containing n functional groups (n+m is greater than or equal to 5) wherein at least one of the crosslinkable components imparts inherent antimicrobial properties. The reaction generates covalent bonds. In certain instances, one or both of the first and second crosslinkable components are dissolved in an aqueous solution. In certain instances, crosslinking results in a biocompatible crosslinked hydrogel in less than 10 minutes.

Another aspect of the present invention relates to a composition formed by reacting a first synthetic crosslinkable component with m functional groups with a second crosslinkable component containing n functional groups (n+m is greater than or equal to 5) wherein at least one of the crosslinkable components imparts buffering capacity (buffering capacity resulting from functionalities other than the crosslinking functionalities themselves). The reaction generates covalent bonds. In certain instances, one or both of the first and second crosslinkable components are dissolved in an aqueous solution. In certain instances, crosslinking results in a biocompatible crosslinked hydrogel in less than 10 minutes.

Another aspect of the present invention relates to a composition formed by reacting a first synthetic crosslinkable component with m functional groups with a second crosslinkable component containing n functional groups (n+m is greater than or equal to 5) wherein at least one of the crosslinkable components imparts a cationic charge to the composition. The reaction generates covalent bonds. In certain instances, one or both of the first and second crosslinkable components are dissolved in an aqueous solution. In certain instances, crosslinking results in a biocompatible crosslinked hydrogel in less than 10 minutes.

In certain embodiments, the present invention relates to any of the aforementioned methods, wherein the hydrogel formed has extracts after 24 hours in a non-buffered 0.9% NaCl solution that provide a solution having a pH in the range of about 6.0 to about 9.0

Kits of the Invention

One aspect of the present invention relates to a kit for the preparation of a sealant comprising:

a polymerization agent selected from the group consisting of a compound of formula Ia or formula Ib, wherein formulae Ia or Ib are as defined above; and instructions for preparing said sealant.

Another aspect of the present invention relates to a kit for the preparation of a sealant comprising:

a polymerization agent selected from the group consisting of a compound of formula Ia, formula Ib, and formula Ic, wherein formulae Ia, Ib, and Ic are as defined above; and instructions for preparing said sealant.

Another aspect of the present invention relates to a kit for the preparation of a sealant comprising:

a compound of formula I and formula III, wherein formulae I and III are as defined above; and instructions for preparing said sealant.

Another aspect of the present invention relates to a kit for the preparation of a sealant comprising:

a compound of formula Ic, wherein formula Ic is as defined above; and instructions for preparing said sealant.

In certain embodiments, the present invention relates to the aforementioned kit, further comprising a compound of formula III, wherein formula III is as defined above.

In certain embodiments, the present invention relates to the aforementioned kit, further comprising a desiccant.

In certain embodiments, the present invention relates to the aforementioned kit, further comprising an antioxidant.

In certain embodiments, the present invention relates to the aforementioned kit, wherein said antioxidant is selected from the group consisting of sodium metabisulfite, citric acid, and ascorbic acid.

In certain embodiments, the present invention relates to the aforementioned kit, further comprising an inert atmosphere.

In certain embodiments, the present invention relates to the aforementioned kit, wherein said kit has a sterility assurance level of at least about $10^3$.

In certain embodiments, the present invention relates to the aforementioned kit, wherein said kit has a sterility assurance level of at least about 10-6.

In certain embodiments, the present invention relates to the aforementioned kit, wherein said kit was sterilized using E-beam or gamma radiation.

In certain embodiments, the present invention relates to the aforementioned kit, wherein said kit was sterilized using E-beam radiation.

In certain embodiments, the present invention relates to the aforementioned kit, wherein said e-beam radiation is between 2 and 100 kGy.

In certain embodiments, the present invention relates to the aforementioned kit, wherein said e-beam radiation is between 10 and 80 kGy.

In certain embodiments, the present invention relates to the aforementioned kit, wherein said e-beam radiation is between 15 and 40 kGy.

In certain embodiments, the present invention relates to the aforementioned kit, wherein said e-beam radiation is between 2 and 40 kGy.

In certain embodiments, the present invention relates to the aforementioned kit, wherein said e-beam radiation is between 3 and 20 kGy.

In certain embodiments, the present invention relates to the aforementioned kit, wherein said e-beam radiation is between 5 and 12 kGy.

In certain embodiments, the present invention relates to the aforementioned kit, wherein said kit was sterilized by multiple exposures to E-beam or gamma radiation.

In certain embodiments, the present invention relates to the aforementioned kit, wherein said kit comprises more than one compound of formula III.

In certain embodiments, the present invention relates to the aforementioned kit, wherein said kit comprises more than one compound of formula Ia or Ib.

In certain embodiments, the present invention relates to the aforementioned kit, wherein said kit further comprises a medicament, colorant, flavoring, scent, fibrous additive, thickener or plasticizer.

In certain embodiments, the present invention relates to the aforementioned kit, further comprising a moisture-barrier element. The moisture-barrier element may be conditioned for use in the preparation of a solution to be used in a method according to the present invention. Alternatively, a second component of the kit may be contained within the moisture-barrier element. For example, a water-sensitive reagent, such as a PEG-bis(NHS ester), may be contained in a moisture-barrier element, thereby limiting or preventing hydrolysis of the water-sensitive reagent between the manufacture date and the use date of the kit. Further, a kit may contain a plurality of moisture-barrier elements, each of which may be conditioned for use in the same or distinct ways. For example, for a kit containing a plurality of water-sensitive reagents each of them may be contained in an individual moisture-barrier element. Alternatively, a moisture-barrier element may contain a plurality of water-sensitive reagents.

A moisture-barrier element may be characterized in a number of ways or a combination of them. For example, a moisture-barrier element may be characterized by its shape (e.g., pouch, vial, sachet, ampule); composition (e.g., glass, foil, Teflon®, stainless steel); and/or it may be characterized by a functional quality (e.g., moisture-vapor transmission rate (MVTR)). MVTR is an important means of characterizing a moisture-barrier element because: those of ordinary skill in the art understand how to measure the MVTR of a material; MVTR values for various materials are known; and the MVTR of a moisture-barrier element quantifies its ability to exclude water from it contents.

In certain embodiments, the present invention relates to the aforementioned kit, further comprising a moisture-barrier element with a moisture vapor transmission rate (MVTR) less than or equal to about 0.15 gram per 100 square inches per day.

In certain embodiments, the present invention relates to the aforementioned kit, further comprising a moisture-barrier element with a moisture vapor transmission rate (MVTR) less than or equal to about 0.02 gram per 100 square inches per day.

In certain embodiments, the present invention relates to the aforementioned kit, further comprising a moisture-barrier element with a moisture vapor transmission rate (MVTR) less than or equal to about 0.15 gram per 100 square inches per day; wherein said moisture-barrier element comprises said polymerization agent selected from the group consisting of a compound of formula Ia and formula Ib.

In certain embodiments, the present invention relates to the aforementioned kit, further comprising a moisture-barrier element with a moisture vapor transmission rate (MVTR) less than or equal to about 0.02 gram per 100 square inches per day; wherein said moisture-barrier element comprises said polymerization agent selected from the group consisting of a compound of formula Ia and formula Ib.

In certain embodiments, the present invention relates to the aforementioned kit, further comprising a catheter.

In certain embodiments, the present invention relates to the aforementioned kit, further comprising a syringe.

In certain embodiments, the present invention relates to the aforementioned kit, further comprising a brush.

In certain embodiments, the present invention relates to the aforementioned kit, further comprising a spray container and/or an aerosol container.

In certain embodiments, the present invention relates to the aforementioned kit, further comprising a device for endoscopic delivery. Endoscopy is a surgical technique that involves the use of an endoscope, a special viewing instrument that allows a surgeon to see images of the body's internal structures through very small incisions. Endoscopic surgery has been used for decades in a number of different procedures, including gallbladder removal, tubal ligation, and knee surgery. An endoscope typically consists of two basic parts: A tubular probe fitted with a tiny camera and bright light, which is inserted through a small incision; and a viewing screen, which magnifies the transmitted images of the body's internal structures. During surgery, the surgeon watches the screen while moving the tube of the endoscope through the surgical area.

In certain embodiments, the present invention relates to the aforementioned kit, further comprising a device for laparoscopic delivery. Laparoscopic surgery is a "minimally invasive" surgical technique. Laparoscopy has been used successfully to treat gynecological problems, gallbladder disease, and perform colorectal surgery for many years. The word "laparoscopy" means to look inside the abdominal cavity with a special camera or "scope." Laparoscopy, also known as "keyhole" surgery, has also been used for many years to diagnose medical conditions inside the abdominal cavity.

In certain embodiments of the kits, a liquid reagent is contained in a vial, and a powdered reagent is contained in a single-barreled syringe. At time of use, the vial and syringe are placed into liquid communication, and the liquid is withdrawn from the vial into the powder-filled syringe, thereby mixing the two reagents.

In another embodiment, the liquid portion is housed within an outer housing into which at least one hollow, inner piston is placed. The at least one hollowed, inner piston is then filled with the powdered portion of the hydrogel formulation. The at least one hollow, inner piston is designed to exclude the liquid portion until it is manually depressed. When depressed, the bottom of the piston passed through a sealing ring in the outer housing and liquid is allowed to pass into the hollowed center of the at least one piston, thereby contacting and dissolving the powder. The powder is thereby dissolved and optionally mixed using an applicator component, such as a brush, swab or syringe canula. The mixture is then applied to the surface of the tissue to be augmented, sealed or bonded.

In another embodiment, the liquid and powder reagents that produce the hydrogel formulation are sealed within two separate, but adjacent, formed wells of a form/fill/seal pouch or sachet. The seal between the two wells is designed to be frangible. At time of use, the user manually pressurizes the liquid-containing well, thus rupturing the frangible seal and allowing the liquid to flow into the powder-containing well. The mixture can then be mixed with a kneading action and liberated from the form/fill/seal pouch either through another frangible seal, a valve, or by tearing or cutting the pouch or sachet.

In another embodiment, the liquid and solid reagents that produce the hydrogel formulation are separate, where the solid reagent is absorbed to a bush and separated from the liquid. At time of use, the user manually pushes the liquid into the brush where the solid and liquid mix to afford the adhesive, which is then subsequently applied.

Definitions

For convenience, certain terms employed in the specification, examples, and appended claims are collected here.

The term "tissue plane" refers to a tissue having an exposed surface area.

The term "polymerize" as used herein refers to the process of converting a monomer to a chain of momomers, wherein the chain of momomers comprises at least about 5 monomers. In certain instances, the chain of monomers comprises at least about 10 or 15 momomers. In certain instances, the chain of monomers comprises at least about 25 or 40 momomers. In certain instances, the chain of monomers comprises at least about 50 or 75 momomers. In certain instances, the chain of monomers comprises at least about 100 or 150 momomers. In instances wherein the monomeric unit has more than one functional group capable of forming a bond in the polymerization reaction, the term "polymerize" indicates that at least one of functional groups capable of forming a bond in the polymerization reaction forms a bond with another compound, generally speaking, the other compound is another monomer. In certain instances, at least about 10% of the functional groups capable of forming a bond in a polymerization reaction form a bond to another monomer. In certain instances, at least about 25% of the functional groups capable of forming a bond in a polymerization reaction form a bond to another monomer. In certain instances, at least about 50% of the functional groups capable of forming a bond in a polymerization reaction form a bond to another monomer. In certain instances, at least about 75% of the functional groups capable of forming a bond in a polymerization reaction form a bond to another monomer. In certain instances, about 20% to about 50% of the functional groups capable of forming a bond in a polymerization reaction form a bond to another monomer.

The term "seal" as used herein indicates that a protective barrier is formed over the wound. In certain instances, the protective barrier is a continuous layer. In certain instances, the protective barrier is a discontinous layer, i.e., a layer that has holes or pores in the layer. In certain instances, the discontinous layer comprises less than about 25% holes. In certain instances, the discontinous layer comprises about less than 15% holes. In certain instances, the discontinous layer comprises about less than 5% holes. In the instance where the protective barrier is a continuous layer, certain fluids or gases can penetrate through the layer. In certain instances, the fluid is a liquid located in the eye. In certain instances, the fluid is water. In instances when the wound is an ophthalmic wound, the seal prevents fluid from exiting the wound when the pressure in the eye is less than about 40 mm Hg. In certain instances, the seal prevents fluid from exiting the wound when the pressure in the eye is less than about 60 mm Hg. In certain instances, the seal prevents fluid from exiting the wound when the pressure in the eye is less than about 80 mm Hg. In certain instances, the seal prevents fluid from exiting the wound when the pressure in the eye is less than about 100 mm Hg. In certain instances, the seal prevents fluid from exiting the wound when the pressure in the eye is less than about 120 or about 150 mm Hg. In certain instances, the seal prevents fluid from exiting the wound when the pressure in the eye is less than about 180 or about 200 mm Hg.

The term "PEG(NHS)$_2$" refers to a polyethylene glycol having the following functional group attached at both ends of the polymer chain:

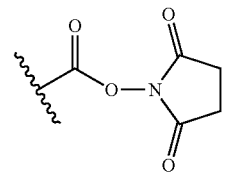 [SMILES: *C(=O)ON1C(=O)CCC1=O]

PEG(NHS)$_2$ can be prepared using either of the following methods. In method 1, a polyethylene glycol is subjected to oxidative conditions in order to oxidize the two termini to the corresponding carboxylic acids [HO$_2$CCH$_2$O—PEG-OCH$_2$CO$_2$H], followed by transformation to the bis(NHS ester). In method 2, PEG(NHS)$_2$ is prepared by alkylation of the two termini of a polyethylene glycol with acrylonitrile to give NCCH$_2$CH$_2$O—PEG-OCH$_2$CH$_2$CN, followed by hydrolysis to the bis(acid) [HO$_2$CCH$_2$CH$_2$O—PEG-OCH$_2$CH$_2$CO$_2$H], and then transformation to the bis(NHS ester).

The term "SS" refers to the following chemical group:

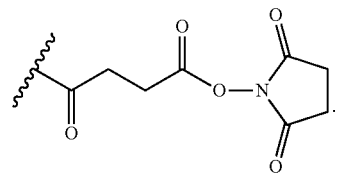 [SMILES: *C(=O)CCC(=O)ON1C(=O)CCC1=O]

The term "SG" refers to the following chemical group:

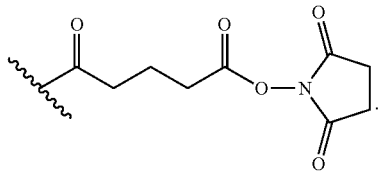 [SMILES: *C(=O)CCCC(=O)ON1C(=O)CCC1=O]

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

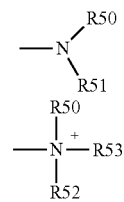

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

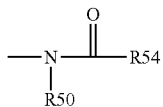

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

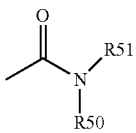

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S—alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

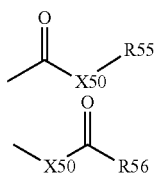

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

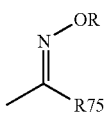

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$R61, where m and R61 are described above.

The term "sulfonate" is art recognized and refers to a moiety that may be represented by the general formula:

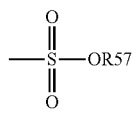

in which R57 is an electron pair, hydrogen, alkyl, cycloalkyl, or aryl.

The term "sulfate" is art recognized and includes a moiety that may be represented by the general formula:

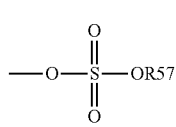

in which R57 is as defined above.

The term "sulfonamido" is art recognized and includes a moiety that may be represented by the general formula:

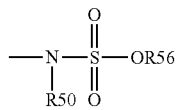

in which R50 and R56 are as defined above.

The term "sulfamoyl" is art-recognized and refers to a moiety that may be represented by the general formula:

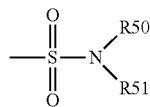

in which R50 and R51 are as defined above.

The term "sulfonyl" is art-recognized and refers to a moiety that may be represented by the general formula:

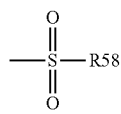

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

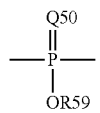

wherein Q50 represents S or O, and R59 represents hydrogen, a lower alkyl or an aryl. When used to substitute, e.g., an alkyl, the phosphoryl group of the phosphorylalkyl may be represented by the general formulas:

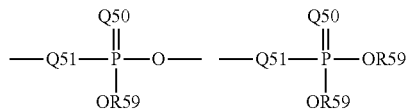

wherein Q50 and R59, each independently, are defined above, and Q51 represents 0, S or N. When Q50 is S, the phosphoryl moiety is a "phosphorothioate".

The term "phosphoramidite" is art-recognized and may be represented in the general formulas:

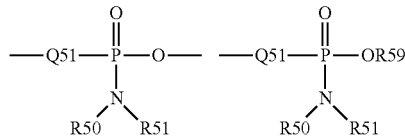

wherein Q51, R50, R51 and R59 are as defined above.

The term "phosphonamidite" is art-recognized and may be represented in the general formulas:

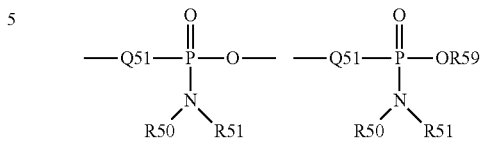

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T.W.; Wuts, P.G.M. *Protective Groups in Organic Synthesis*, 2$^{nd}$ ed.; Wiley: New York, 1991). Protected forms of the inventive compounds are included within the scope of this invention.

The term "alkali metal" refer to those elements listed in Group 1 of the periodic table. The following elements are alkali metals: Li, Na, K, Rb, Cs, and Fr.

For purposes of this invention, the chemical elements are identified in accordance with the Periodic Table of the Elements, CAS version, *Handbook of Chemistry and Physics,* 67th Ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Activated PEGs (PEG-NHS) were either synthesized according to the procedures detailed or they were commercially available and purchased from various vendors. The polyalkyleneimines and various components used in the formulations were purchased from various vendors.

Example 1

Synthesis of Difunctional N-Hydoxysuccinimide Activated PEGs from Difunctional PEG-OH with Internal Ester Linkages.

A general synthetic process is as follows, the detailed list of various PEGs, linkages, and amounts of various reagents are listed in the table. In general, difunctional PEG-OH was added to a 3-neck, dry round bottom flask affixed with a nitrogen/vacuum line, heating apparatus and stirring mechanism. While being stirred, the flask was heated to 120° C. until all PEG had melted. The flask was then allowed to stir for 30 minutes under high vacuum, with the temperature being lowered to ~80° C. for the duration of the reaction. Prior to any subsequent reagent addition, the flask was purged three times with nitrogen. To the flask, a catalytic amount of a diacid acid was added and allowed to dissolve. Next, an excess of the diacid anhydride was added to the flask and the system was put under nitrogen. The reaction was allowed to stir under nitrogen at 80° C. for a minimum of 18 hours. The flask was then cooled and the content dissolved in a minimum amount of dichloromethane (DCM). This solution was slowly added to approximately five times that volume of diethyl ether while stirring at room temperature. Using vacuum filtration, the precipitate was isolated and rinsed with a minimum of diethyl ether. The precipitate was then transferred to a round bottom flask and allowed to dry under high vacuum. The derivatized PEG was transferred to a 3-neck, dry round bottom flask and affixed with a nitrogen line, chilling apparatus, liquid addition apparatus and stirring mechanism. While stirring under nitrogen, an amount of dichloromethane equal to twice the amount of derivatized PEG was added. The appropriate excess of N-Hydroxysuccinimide was then added and allowed to stir at room temperature for a minimum of 30 minutes. The flask was cooled to −2.5-2.5° C. An approximate 1M solution of N,N'-dicylcohexylcarbodiimide (DCC) was then added via syringe pump over 6 hours to the cooled flask. The reaction was allowed to stir for an additional 18 hours while still under nitrogen at approximately 0° C. The insoluble N,N'-dicylcohexylurea (DCU) was filtered and rinsed with a minimum of DCM using vacuum filtration. The resulting solution was then concentrated before a volume of diethyl ether approximately six times the volume of the concentrate was slowly added while stirring at room temperature. The precipitate was filtered and rinsed with a minimum of diethyl ether using vacuum filtration. While still wet with ether, the precipitate was then added to a soxhlet extractor thimble and extracted with diethyl ether for 24-48 hours. The extracted powder was then transferred to a round bottom flask and dried under high vacuum for at least 8 hours.

For more sterically hindered derivatives such as the 3-methylglutarate and the 3,3-dimethylglutarate, a modified synthetic difunctional PEG-OH was added to a dry round bottom affixed with a stirring mechanism and dissolved in a volume of DCM equal to 2 times the weight of the PEG. While being stirred, a volume of TEA equal to one fifth the weight of the PEG was added followed by the addition of the appropriate amount of the diacid anhydride. The flask was then allowed to stir overnight at room temperature. The DCM solution was washed with 0.1 N HCl until the aqueous phase remained pH 1. The DCM layer was isolated, dried with magnesium sulfate, and filtered. The remaining DCM solution was slowly added to approximately five times that volume of diethyl ether while stirring at room temperature. Using vacuum filtration, the precipitate was isolated and rinsed with a minimum of diethyl ether. The precipitate was then transferred to a round bottom flask and allowed to dry under high vacuum. The carboxylate end groups were converted to N-hydroxysuccinimide esters in the same manner previously reported.

TABLE 2

| PEG $M_w$ | Mass of PEG (g) | Desired Difunctional Derivative | Mass of Diacid (g) | Mass of Diacid Anhydride (g) | Mass of N-Hydroxysuccinimide (g) | Mass of DCC (g) |
|---|---|---|---|---|---|---|
| PEG-(OH)$_2$ 3350 | 200 | succinimidyl glutarate (SG) | 0.63 | 27.25 | 27.48 | 49.27 |
| PEG-(OH)$_2$ 3350 | 200 | succinimidyl succinate (SS) | 0.63 | 27.25 | 27.48 | 49.27 |
| PEG-(OH)$_2$ 3350 | 200 | succinimidyl adipate (SA) | 0.63 | 27.25 | 27.48 | 49.27 |
| PEG-(OH)$_2$ 4600 | 48.18 | succinimidyl glutarate (SG) | 0.1642 | 4.82 | 6.60 | 11.83 |
| PEG-(OH)$_2$ 6000 | 65.69 | succinimidyl glutarate (SG) | 0.1298 | 4.93 | 9.21 | 16.51 |
| PEG-(OH)$_2$ 8000 | 68.40 | succinimidyl glutarate (SG) | 0.0932 | 3.18 | 9.40 | 16.50 |
| PEG-(OH)$_2$ 10000 | 200.76 | succinimidyl glutarate (SG) | 0.2243 | 9.18 | 6.02 | 11.5 |
| Pluronic F-127 | 50 | succinimidyl glutarate (SG) | .042 | 2.82 | 1.26 | 3.21 |
| Ethox CO-200 | 67 | succinimidyl glutarate (SG) | 0.041 | 3.14 | 2.53 | 5.49 |
| PEG-(OH)$_2$ 3350 | 20.03 | succinimidyl 3-methyl-glutarate (S3MG) | — | 2.007 | 1.80 | 4.59 |
| PEG-(OH)$_2$ 3350 | 52.58 | succinimidyl 3,3-dimethyl-glutarate (S3DMG) | — | 6.69 | 4.68 | 11.21 |

Example 2

Synthesis of difunctional N-hydoxysuccinimide activated PEGs (succinimidyl propionic acid) from difunctional PEG-OH.

A general synthetic process is as follows, the detailed list of various PEG molecular weights and amounts of various reagents are listed in the table. In general, difunctional PEG-OH was added to a 3-neck, dry round bottom flask affixed with a cooling apparatus and stirring mechanism. While stirring, a volume of deionized water equal to the mass of PEG-OH was added until dissolved. The flask was then cooled to approximately 0° C. and potassium hydroxide (KOH) pellets were added. The reaction was left to stir until the pellets were dissolved. The appropriate excess of acrylonitrile was then added via syringe pump over 1.5 hours, and then left stirring for an additional 1.0 hour after addition. The solution was transferred to a liquid-liquid extractor and extracted with DCM for 6-12 hours. The collected DCM used in the extractor was concentrated before a volume of diethyl ether approximately ten times the volume of the concentrate was slowly added while stirring at room temperature. The precipitate was filtered and rinsed with a minimum of diethyl ether using vacuum filtration. While still wet with ether, the precipitate was then added to a soxhlet extractor thimble and extracted with diethyl ether for 24-48 hours. The extracted powder was then transferred to a round bottom flask and dried under high vacuum for at least 8 hours. The derivatized PEG-Nitrile was transferred to a dry, 3-neck round bottom flask equipped with a stirring mechanism and heating apparatus. A volume of concentrated HCl equal the mass of the PEG-Nitrile was added, and the temperature was brought to 50° C. while stirring. The reaction was allowed to run for 3 hours before being transferred to a separatory funnel. A volume of diH$_2$O equal to 2 times the volume of HCl and a volume of saturated NaCl equal to the volume of HCl were added to the acidic solution. The solution was then extracted three times with a volume of DCM equal to the volume of the total aqueous solution. The collected DCM fractions were combined, concentrated, and slowly added to a volume of diethyl ether approximately ten times the volume of the concentrate while stirring at room temperature. The precipitate was filtered and rinsed with a minimum of diethyl ether using vacuum filtration. The powder was then transferred to a round bottom flask and dried under high vacuum for at least 8 hours. The derivatized PEG was transferred to a dry, 3-neck round bottom flask equipped with a stirring mechanism and heating apparatus. While stirring, a volume of 2.25 N KOH equal six times the mass of the derivatized PEG was then added to dissolve the polymer. The flask was then brought to 40° C. and allowed to stir for 10-12 hours. The flask was then cooled to <10° C. and neutralized with HCl to approximately pH 3.2. A mass of NaCl equal to approximately one half the mass of PEG was then added and allowed to dissolve. The solution was then transferred to a separatory funnel and extracted twice with a volume of DCM equal to approximately two thirds the volume of total aqueous solution, and the combined DCM was subsequently dried with magnesium sulfate. The DCM was concentrated and slowly added to a volume of diethyl ether approximately ten times the volume of the concentrate while stirring at room temperature. The precipitate was filtered and rinsed with a minimum of diethyl ether using vacuum filtration. The powder was then transferred to a round bottom flask and dried under high vacuum for at least 8 hours. The derivatized PEG was transferred to a 3-neck, dry round bottom flask and affixed with a nitrogen line, chilling apparatus, liquid addition apparatus and stirring mechanism. While stirring under nitrogen, an amount of dichloromethane equal to twice the amount of derivatized PEG was added. The appropriate excess of N-hydroxysuccinimide was then added and allowed to stir at room temperature for a minimum of 30 minutes. The flask was cooled to −2.5-2.5° C. An approximate 1M solution of N,N'-dicylcohexylcarbodiimide (DCC) was then added via syringe pump over 6 hours to the cooled flask. The reaction was allowed to stir for an additional 18 hours while still under nitrogen at approximately 0° C. The insoluble N,N'-dicylcohexylurea (DCU) was filtered and rinsed with a minimum of DCM using vacuum filtration. The resulting solution was then concentrated and slowly added to a volume of diethyl ether approximately six times the volume of the concentrate while stirring at room temperature. The precipitate was filtered and rinsed with a minimum of diethyl ether using vacuum filtration. While still wet with ether, the precipitate was then added to a soxhlet extractor thimble and extracted with diethyl ether for 24-48 hours. The precipitate was then transferred to a round bottom flask and allowed to dry under high vacuum.

TABLE 3

| PEG $M_w$ | Mass of PEG (g) | Mass of KOH in Nitrile Synthesis (g) | Volume of Acrylonitrile (mL) | Mass of N-Hydroxy-succinimide (g) | Mass of DCC (g) |
|---|---|---|---|---|---|
| PEG-(OH)$_2$ 3350 | 200 | 11.8 | 89 | 27.48 | 49.27 |
| PEG-(OH)$_2$ 10000 | 700 | 41.12 | 120 | 32.08 | 57.75 |
| PEG-(OH)$_3$ 20000 | 200 | 17.64 | 23.85 | 15.02 | 20.13 |

Example 3

Synthesis of (Succinic Acid Cesium Salt)$_2$-PEG.

PEG succinimidyl succinate (1 g, 0.3 mmol) was dissolved in water and the pH was adjusted to 7.5 with CsCO$_3$. The solvent was removed to obtain the pure compound (99%).

Example 4

Synthesis of (Dimethyl Acetal Succinic Ester)$_2$-PEG.

(Dimethyl acetal succinic ester)$_2$-PEG was prepared by reaction of (succinic acid cesium salt)$_2$-PEG (1 g, 0.3 mmol) with bromoacetaldehyde dimethyl acetal (133 µl, 1.2 mmol) in DMF (5 mL) at 60° C. for 3 days. The solvent was removed by vacuum, and the mixture was precipitated in ethyl ether.

Example 5

Synthesis of (Dialdehyde Succinic Ester)$_2$-PEG.

(Dialdehyde succinic ester)$_2$-PEG was obtain by treatment of (dimethyl acetal succinic ester)$_2$-PEG with TFA (5% H$_2$O) in CH$_2$Cl$_2$ (1:3) at room temperature for 20 minutes. The solvent was removed by vacuum, and the product was precipitated in ethyl ether.

Example 6

Application of Two Component PEG$_{3400}$-NHS:PEI$_{2000}$ 15:1 PEG:PEI Weight Ratio 15 Wt % Hydrogel Sealant Formulation to Various Tissues In Vitro.

A PEI$_{2000}$/PEG$_{3400}$-NHS formulation was applied to the following tissue types: Porcine Cornea, Porcine Aorta, Porcine Liver, Porcine Lung, Porcine Skin Full Thickness Wound, and Porcine Skin Flap. All tissues were harvested the morning of the experiment from a local slaughterhouse. Tissues were placed on ice for transportation prior to sealant application.

Tissue samples were prepared by dissecting approximately 2"×2" or 2" long samples. Porcine eyes were left whole. Porcine eyes were soaked in BSS at room temperature for 1 hour. Corneal epithelium tissue was either left intact or was scraped off with a 2.75 mm ophthalmic slit knife.

Tissue incisions were made as follows: Cornea—2.75 mm limbal stab incision; Aorta—3 mm long full thickness incision transverse to the direction of blood flow; Liver—3 mm long stab incision at a depth of 3.5 mm; Lung—3 mm long stab incision at a depth of 3.5 mm; Skin Full Thickness—approximately 1 cm×1 cm incision; and Skin Flap—approximately 1.5 cm×1.5 cm flap incision.

Tissue samples were allowed to equilibrate to room temperature prior to sealant application. All tissue samples were blotted dry. BSS was applied via a spray bottle positioned 20 cm above the tissue sample. Sealant was placed on tissue samples within 30 seconds of BSS wetting. Sealant was allowed to cure for 5 minutes. After 5 minutes, the tissue/sealant samples were immersed in BSS. Tissue samples were stored in BSS-filled closed containers at room temperature and were followed for 7 days—qualitative observations were recorded approximately every 24 hours.

Sealant remained on the Aorta, Lung, and Liver for seven days while soaking in BSS. The sealant was present on skin for a maximum of 1-2 days. Durability may be influenced by the oily nature of porcine skin tissue. The level of moisture present on the tissue surface prior to polymer application had little to no effect on the durability and curing of the hydrogel sealant formulation. On eyes with intact epithelium, the polymer was not present after 24 hours, but the hydrogel formulation remains adhered to the corneal surface throughout the experiment when the epithelium is removed.

Example 7

Comparison of Mechanical Properties of PEG$_{3400}$-NHS/PEI$_{2000}$ 15:1 PEG:PEI Weight Ratio, 15 wt % Gels to Various Commercially Available Adhesives.

For reference see Campbell, Bennett, and Sawhney; "Evaluation of Absorbable Surgical Sealants: In vitro Testing" which is hereby incorporated by reference.

Figure 21:
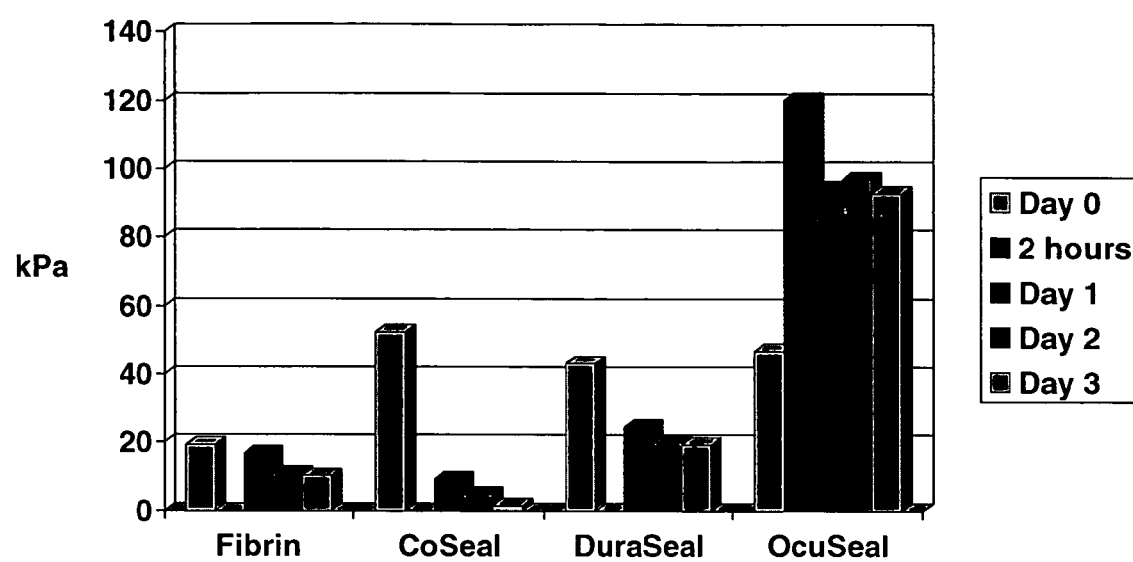
FIG. 21 depicts the elastic moduli of various commercial sealants as a function of time.

Samples were prepared by injecting solutions into 6.00 mm ID glass tubing. The samples were carefully removed from the tubing and cut into 6.00 mm lengths to produce cylindrical sealant plugs. These cylindrical samples were compression tested at time zero and after soaking in BSS at 37° C. for 2 hours, and 1, 2 and 3 days. Compressive elastic modulus (E, kPa) tests were conducted at ambient room temperature and humidity using a screw-driven load frame, at 1 mm per minute crosshead speed. All load displacement data was digitally collected and analyzed. See FIG. 21.

Figure 22:
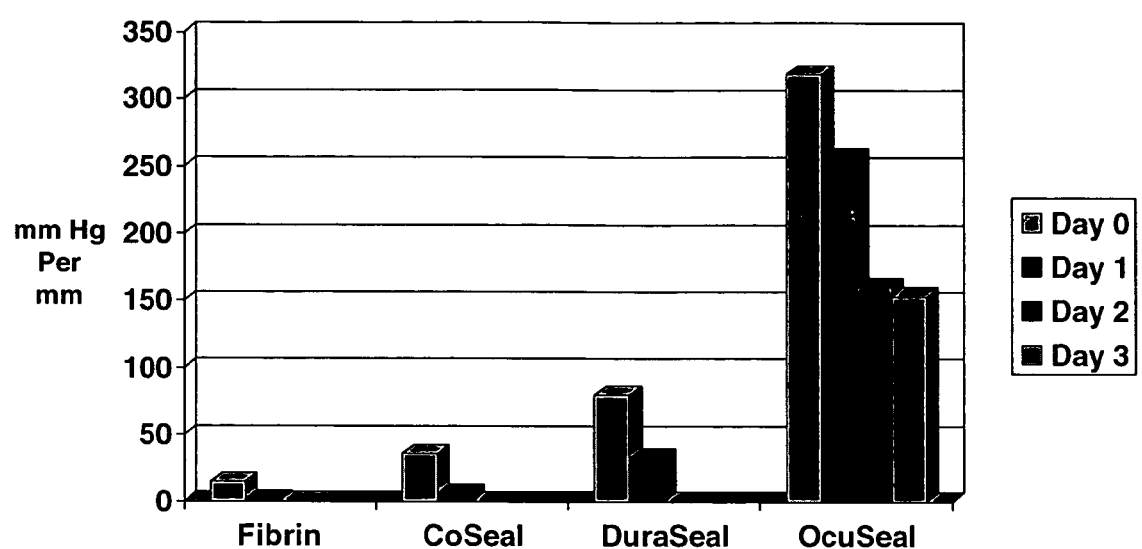
FIG. 22 depicts the average burst pressure of various commercial sealants as a function of time.
Figure 23:
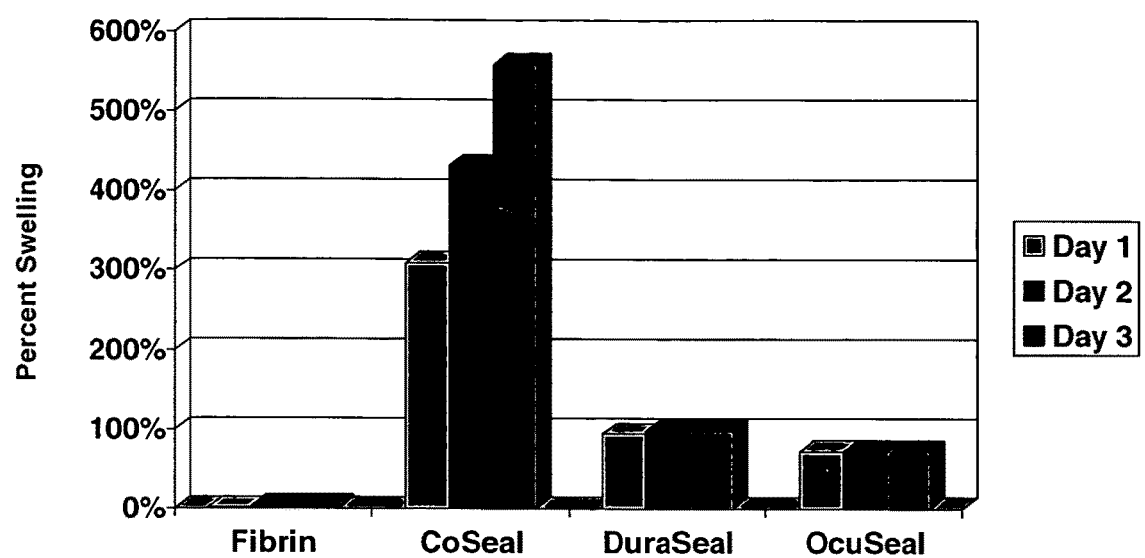
FIG. 23 depicts the weight change of plugs of various commercial sealants as a function of time.

Burst-pressure testing was performed to determine the strength of the interface bonding between collagenous materials and the sealant (ASTM 2392-04). Natural sausage casing with a uniform 3.0 mm skin biopsy punch defect was used as the tissue substrate onto which each hydrogel was applied. Sealant thickness was measured with calipers and the sample was either tested immediately, or after 1, 2 or 3 days of soaking in BSS at 37°. The pressure at which sealant failure occurred (adhesive or cohesive failure) was recorded as the burst pressure. See FIG. 22. Sealant plugs were weighed immediately after creation, and after soaking for 1, 2, and 3 days in 37° C. PBS. See FIG. 23.

Example 8

Degradation Study of PEG$_{3400}$-NHS/PE$_{2000}$ Gels Through Gravimetric Analysis.

Figure 24:
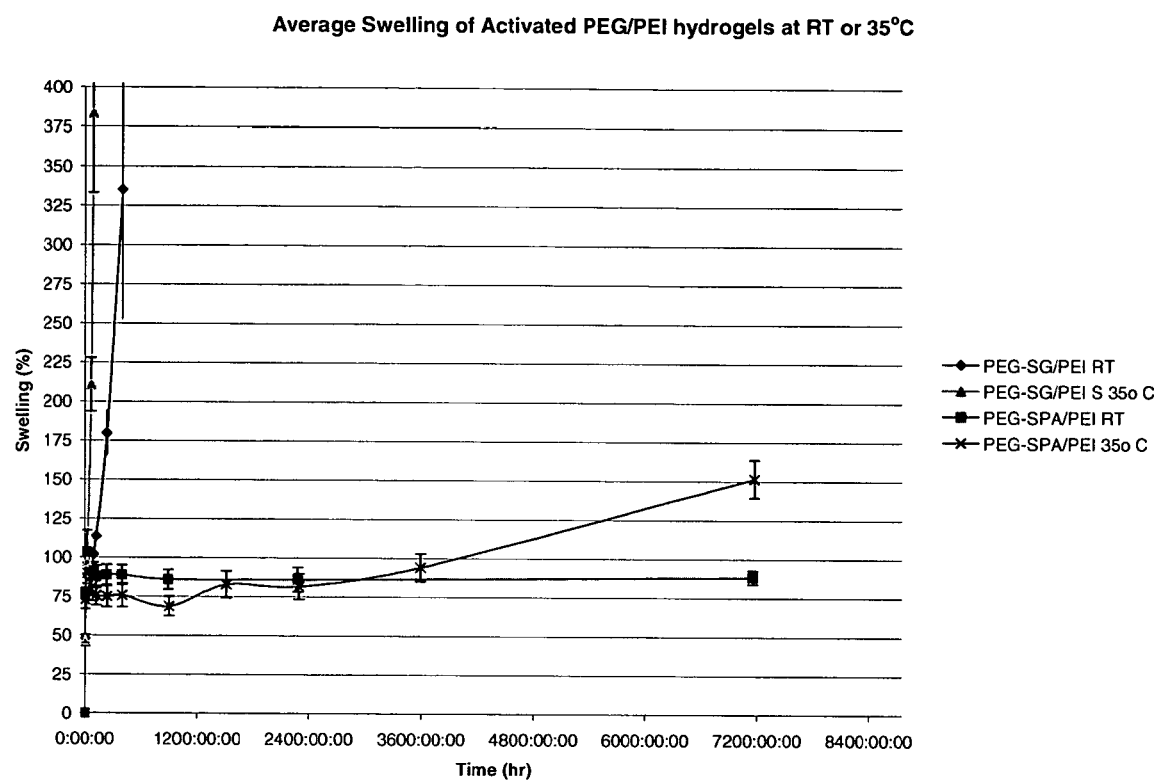
FIG. 24 depicts the average swelling of activated PEG/PEO hydrogels at RT or 35° C. as a function of time.
Figure 25:
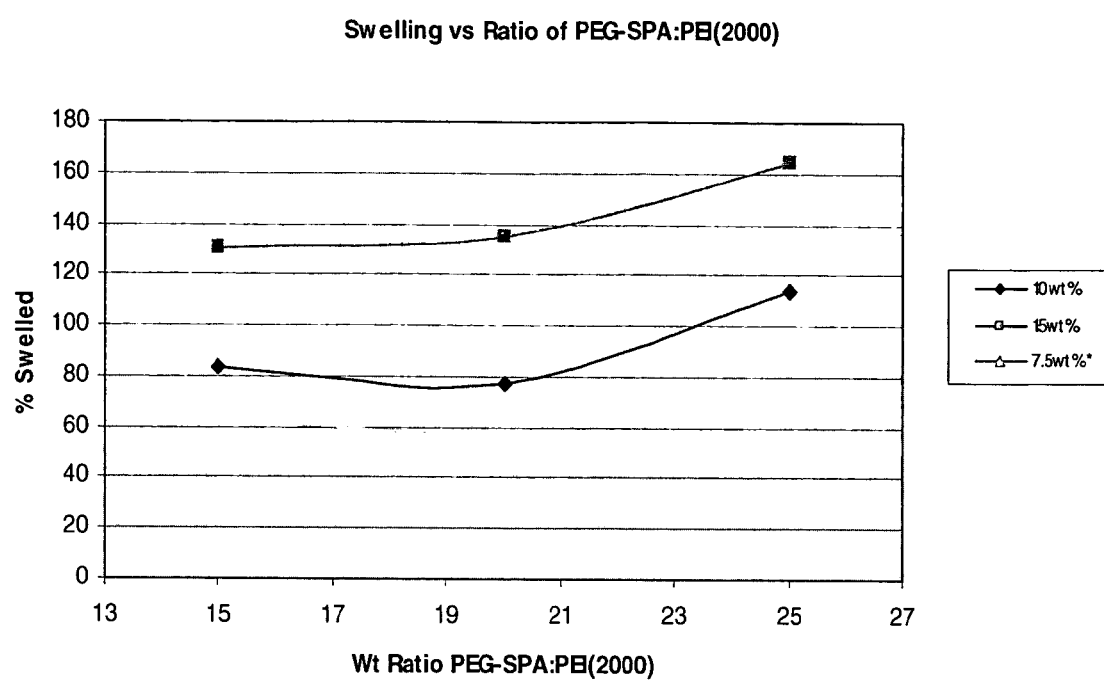
FIG. 25 depicts the swelling behavior of gels of the present invention as a function of the ratio of PEG-SPA to PEI.
Figure 26:
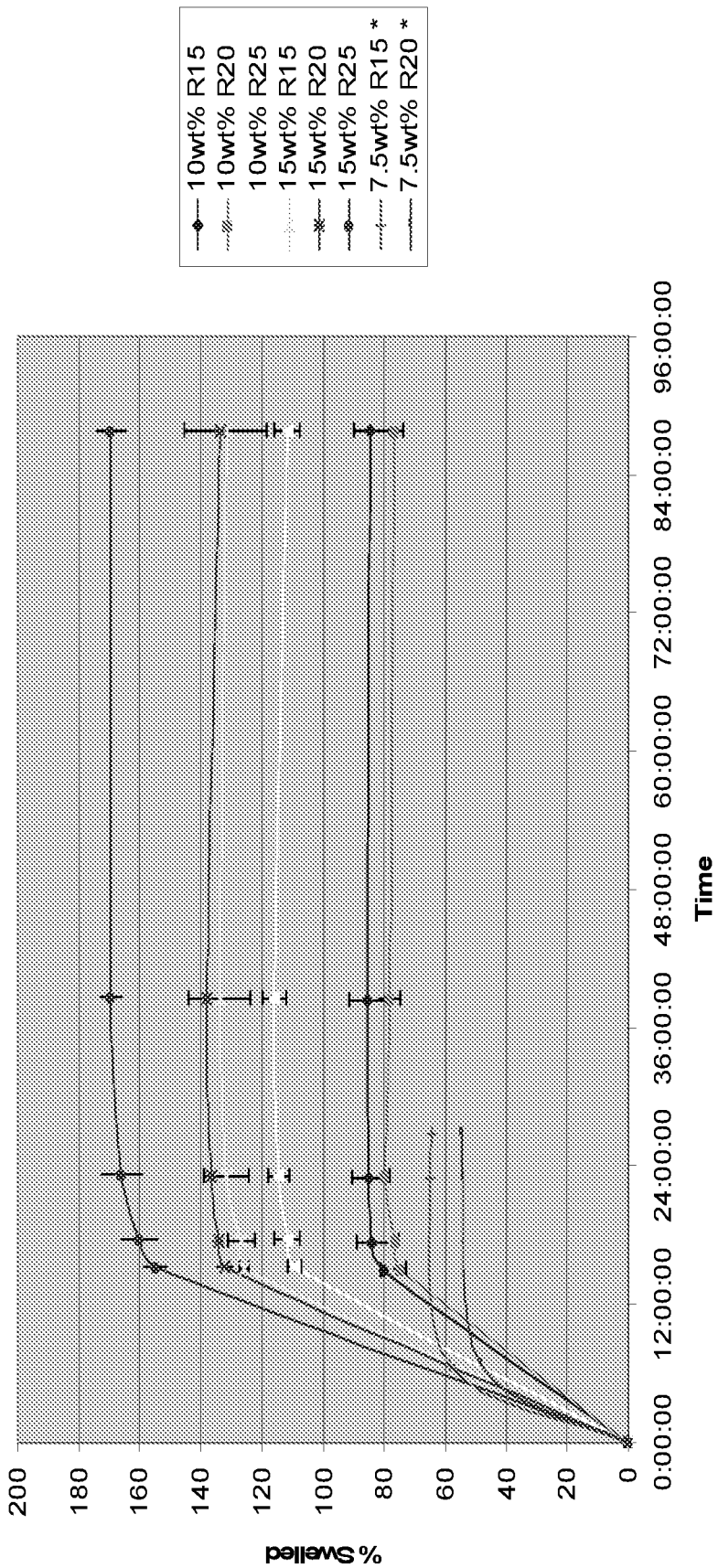
FIG. 26 depicts the swelling behavior of gels of the present invention as a function of time.

PEG$_{3400}$-NHS/PEI$_{2000}$ gels were prepared for degradation studies by loading either difunctional PEG$_{3400}$-SPA (36 mg) or PEG$_{34}$W-SG (36 mg) into a 1 mL BD syringe. The activated PEGs were dissolved in 220 µL of a PEI solution adjusted to pH 8.84 to produce a 15 wt % gel with a 15:1 PEG:PEI ratio. The samples were soaked in BSS (pH 7.4, 290 mOsm/Kg) and placed in oven at 37° C. The mass of recoverable gel was monitored over the course of up to 300 days to determine gravimetric swelling (See FIG. 24).

Example 9

Hydrogels with Ester Linkages.

Hydrogels with internal ester linkages were prepared in a similar manner to the gels previously discussed. Difunctional $PEG_{3400}$-SS (36 mg) was loaded into a 1 mL BD syringe and was dissolved 220 μL of a PEI solution 15:1 PEG:PEI (w/w) adjusted to pH 8.84 (also containing NaCl, KCl, phosphate, and carbonate). A 15 wt % gel formed within 40 seconds of reconstitution of the PEG-SS with the PEI solution and expression of the resulting solution into molds. The resulting hydrogel samples were soaked in BSS (pH 7.4, 290 mOsm/Kg) and appeared to degrade within 1 day.

Difunctional $PEG_{3400}$-SG (36 mg) was loaded into a 1 mL BD syringe and was dissolved 220 μL of a PEI solution 15:1 PEG:PEI (w/w) adjusted to pH 8.84 (also containing NaCl, KCl, phosphate, and carbonate). A 15 wt % gel formed within 20 seconds of reconstitution of the PEG-SG with the PEI solution and expression of the resulting solution into molds.

Tetrafunctional $PEG_{100000}$-SG (36 mg) was loaded into a 1 mL BD syringe and was dissolved in 215 μL of a PEI solution 24.2:1 PEG:PEI (w/w) adjusted to pH 8.20 (also containing NaCl, KC, phosphate, and carbonate). A 15 wt % gel formed within 15 seconds of reconstitution of the PEG-SG with the PEI solution and expression of the resulting solution into molds. The resulting hydrogel samples were soaked in BSS (pH 7.4, 290 mOsm/Kg) and swelled to 180-190% within 2 days and completely dissolved within 6 days.

Difunctional PEG-butyraldehyde ($PEG_{3400}$-BA) (36 mg) was loaded into a 1 mL BD syringe and was dissolved in 220 μL of a PEI solution adjusted to pH 8.35 (also containing NaCl, KCl, phosphate, and carbonate). A 15 wt % gel formed within 20 seconds of reconstitution of the PEG-BA with the PEI solution and expression of the resulting solution into molds.

Example 10

Burst Pressure of Gels.

Figure 31:
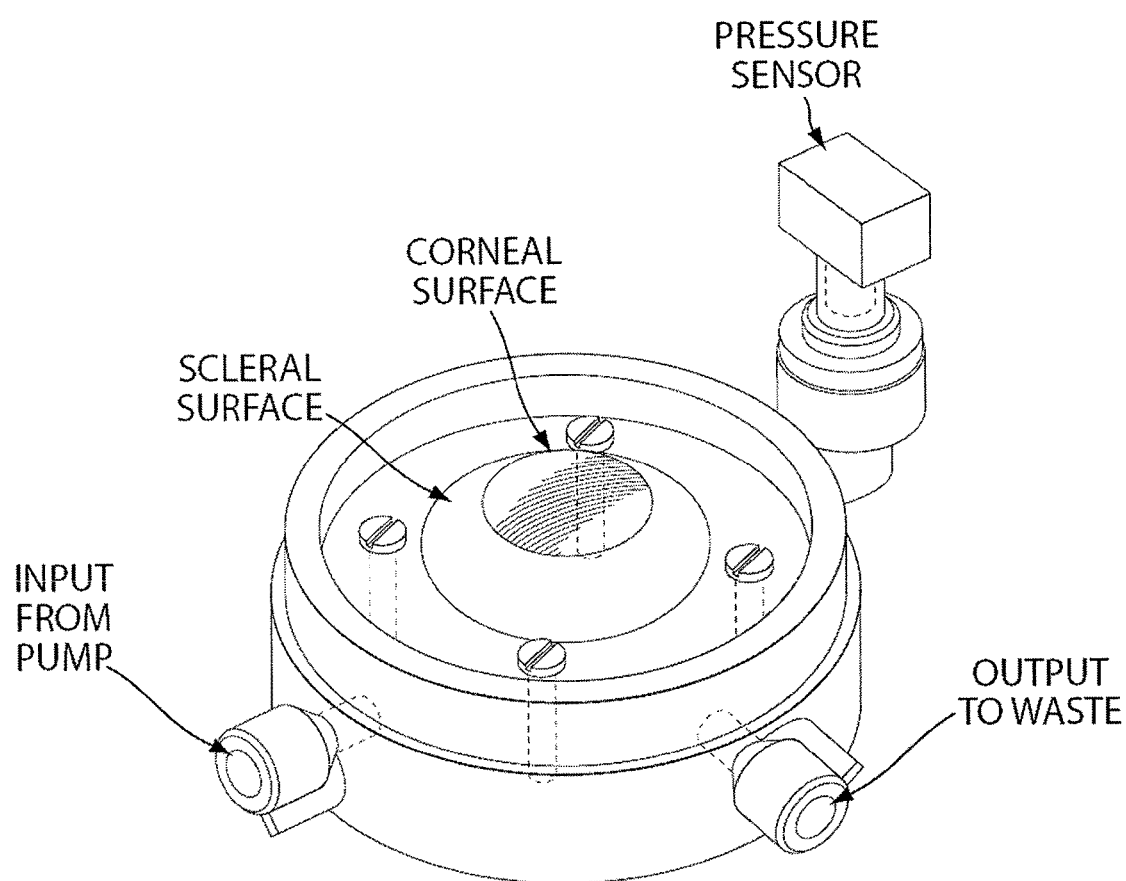
FIG. 31 depicts an apparatus for measuring burst pressure.

The burst pressure of a range of gels was examined in an attempt to evaluate the abilities of various polymers to seal a wound. Results are shown in Table 4. The burst pressure studies were performed using a custom designed model in which the anterior half of the eye is placed in a plastic mould with the surface of the cornea exposed to the atmosphere, and the posterior portion can be back filled using a peristaltic pump (Carter 8/4 Manostat). See FIG. 31. The back fill pressure can then be measured using an analog sensor which is connected to an A/D converter and subsequently to a computer.

Before placing the eye in the mold, the anterior section of enucleated porcine eyes were surgically removed from the posterior section of the eye with an incision around the globe approximately 5 mm posteriorly from the limbus. Once the posterior section was removed, the lens, cilliary body and iris were all removed through the posterior opening. A laboratory wipe was used to remove the remnants of the iris and cilliary body. This anterior section was then placed onto the pressure cell and screwed down tightly to make an effective seal in the pressure cell. Once the anterior section is seated properly and is back filled to normal pressure, the pump was turned off and a 2.5 mm stab incision was made in the cornea using a keratome blade. The various formulations to be tested were then applied.

Gels were produced in duplicate at a ratio of 15:1 and 20:1 PEG:PEI (w/w), over the weight percents of 7.5 wt %%, 10 wt %, and 15 wt %, with set times ranging between 30 and 60 seconds. After PEG-NHS was mixed with the appropriate PEI solution, the sample was subsequently used to close a 3 mm wound on an eye mounted on the burst pressure apparatus. The samples were allowed to cure for 15 minutes before the pressure was measured as the eye was back filled. The test was stopped if the pressure reached 243 mmHg (the limit of the sensor).

At least one gel from each formulation, except the first formulation, was found to withstand pressures up to the limit of the sensor (243 mmHg). Notably, when PEG-NHS compositions was used alone (i.e., without a PEI solution) the incisions were not sealed.

TABLE 4

Burst Pressure Results.

| Specimen ID | Set Time (sec) | % Solids | PEG:PEI Ratio (wt) | Burst Pressure (inches water) | Burst Pressure (mm Hg) |
| --- | --- | --- | --- | --- | --- |
| Formulation G1 | NA | 10 | 15:1 | 10.2 | 19.0 |
| Formulation G2 | 27 | 15 | 15:1 | 130.0 | 242.8 |
| Formulation G2 | 27 | 15 | 15:1 | 50.0 | 93.3 |
| Formulation G3 | 25 | 10 | 20:1 | 130.0 | 242.8 |
| Formulation G3 | 25 | 10 | 20:1 | 130.0 | 242.8 |
| Formulation G4 | 39 | 15 | 20:1 | 72.7 | 135.8 |
| Formulation G4 | 39 | 15 | 20:1 | 127.2 | 237.5 |
| Formulation G5 | 10 | 7.5 | 15:1 | N/A | NA |
| Formulation G6 | 63 | 7.5 | 20:1 | 130.0 | 242.8 |
| Formulation G6 | 63 | 7.5 | 20:1 | 130.0 | 242.8 |
| Formulation G5 | 60 | 7.5 | 15:1 | 23.6 | 44.2 |
| Formulation G5 | 60 | 7.5 | 15:1 | 130.0 | 242.8 |

Example 11

Quantitative Evaluation of PEG-NHS:PEI Gel Systems.

Several PEG N-hydroxysuccinimide esters (PEG-NHS) were used in the following experiments. The PEG-NHS reagents used include but are not limited to PEG succinimidyl propionic acid (PEG-SPA), PEG succinimidyl succinate (PEG-SS), and PEG succinimidyl glutarate (PEG-SG). The reagents were purchased or synthesized from various molecular weight PEGs. Further, PEG butyraldehdye (PEG-BA) reagent, which was purchased, was also used to make a gel. The PEG-NHS:PEI gel system was optimized by varying several factors, including: (1) concentration of reactants; (2) the ratio of PEG-NHS to PEI; and (3) the pH of the reagent mixture. The concentration of the reactants influences the set time; the more concentrated the solution, the faster the gel will form. Concentrations are reported as weight percent of solids (wt %). The ratio (R) of the two reactants relates the mass of crosslinker to the mass of polymer used. The ratio influences the swelling characteristics of the resulting gel matrix.

Third, the pH of the reagent mixture influences the set time of a particular gel. The pH of the PEI solution should be sufficiently basic to provide unprotonated amine nucleophiles capable of reacting with the activated esters of PEG-NHS. However, PEG-NHS is quickly hydrolyzed in basic (>pH 8.0) aqueous solutions. Therefore, the pH must be sufficiently high to allow the reaction between the reagents to compete effectively with the background rate of hydrolysis of PEG-NHS.

A set of gels was prepared from reagent mixtures with PEG-NHS:PEI ratios from R15-R35 (i.e., 15:1 to 35:1 PEG-NHS:PEI (w/w)). As outlined in tables 5 and 6 below, also explored was a range of pHs for the PEI solutions. The resulting gels were evaluated based on their respective degrees of swelling. Swelling was quantified by first measuring the initial mass of a gel approximately 15-30 minutes after gelation. The gels were then placed in a buffered saline solution (BSS) designed to be similar in pH and salt concentration to the environment on the eye. The mass of a gel was then repeatedly measured over the course of several days to evaluate the equilibrium swelling point. Gels were assessed by removing them from solution, rolling them on a moistened laboratory wipe to remove excess BSS, and then weighing them.

Unless otherwise indicated, mixing was performed by dissolving the PEG-NHS powder in deionized water in a centrifuge tube, and placing the tube in a conical centrifuge for at least 30 seconds. The PEI solution was then pipetted into the barrel of a 1 mL BD tuberculin syringe fitted with a 20G needle, and the plunger replaced. The PEI was then injected into the centrifuge tube, and the solution taken back into the syringe, followed by subsequently exchanging three times. Lastly, the mixture was expressed into the desired container or mold.

To determine the set time, the mixed solution was injected into a vial (either an autosampler vial or modified conical vial) in which a mini stir-bar was spinning at 1080 rpm. The set time is the elapsed time from injection to the vial to when the gelling process caused the stir bar to stop spinning properly.

TABLE 5

Gel Formulations.

| Sample ID | PEG-NHS (mg) | H$_2$O added (uL) | PEI in Soln (mg) | PEI Soln Used (µL) | PEI Soln wt %/100 | PEG-NHS Soln wt %/100 | Wt Ratio PEG:PEI | Total wt % |
|---|---|---|---|---|---|---|---|---|
| E01 | 36 | 193 | 1.4 | 19 | 0.074 | 0.157 | 25 | 15.0 |
| E02 | 36 | 193 | 1.4 | 19 | 0.074 | 0.157 | 25 | 15.0 |
| E03 | 36 | 193 | 1.4 | 20 | 0.073 | 0.157 | 25 | 15.0 |
| E04 | 36 | 185 | 2.4 | 33 | 0.073 | 0.163 | 15 | 15.0 |
| E05 | 36 | 185 | 2.4 | 32 | 0.074 | 0.163 | 15 | 15.0 |
| E06 | 36 | 196 | 1.0 | 13 | 0.077 | 0.155 | 35 | 15.0 |
| E07 | 36 | 193 | 1.4 | 19 | 0.077 | 0.157 | 25 | 15.0 |
| E08 | 36 | 186 | 2.4 | 31 | 0.077 | 0.162 | 15 | 15.0 |
| E09 | 36 | 193 | 1.4 | 19 | 0.074 | 0.157 | 25 | 15.0 |
| E10 | 36 | 196 | 1.0 | 14 | 0.074 | 0.155 | 35 | 15.0 |
| E11 | 36 | 196 | 1.0 | 14 | 0.073 | 0.155 | 35 | 15.0 |
| E12 | 36 | 193 | 1.4 | 19 | 0.074 | 0.157 | 25 | 15.0 |
| E13 | 36 | 193 | 1.4 | 19 | 0.074 | 0.157 | 25 | 15.0 |
| E14 | 36 | 193 | 1.4 | 20 | 0.073 | 0.157 | 25 | 15.0 |
| E15 | 36 | 185 | 2.4 | 33 | 0.073 | 0.163 | 15 | 15.0 |
| E16 | 36 | 186 | 2.4 | 32 | 0.074 | 0.162 | 15 | 15.0 |
| E17 | 36 | 196 | 1.0 | 13 | 0.077 | 0.155 | 35 | 15.0 |
| E18 | 36 | 193 | 1.4 | 19 | 0.077 | 0.157 | 25 | 15.0 |
| E19 | 36 | 186 | 2.4 | 31 | 0.077 | 0.162 | 15 | 15.0 |
| E20 | 36 | 193 | 1.4 | 19 | 0.074 | 0.157 | 25 | 15.0 |
| E21 | 36 | 196 | 1.0 | 14 | 0.074 | 0.155 | 35 | 15.0 |
| E22 | 36 | 196 | 1.0 | 14 | 0.073 | 0.155 | 35 | 15.0 |

TABLE 6

Results.

| Sample ID | Block | pH | Ratio PEG:PEI | Set Time (sec) | % Swelling |
|---|---|---|---|---|---|
| E01 | 1 | 9.39 | 25 | 41 | 164 |
| E02 | 1 | 9.39 | 25 | 19 | 138 |
| E03 | 1 | 9.25 | 25 | 54 | 127 |
| E04 | 1 | 9.25 | 15 | 10 | 128 |
| E05 | 1 | 9.39 | 15 | 1 | 124 |
| E06 | 1 | 9.6 | 35 | 165 | DNG |
| E07 | 1 | 9.6 | 25 | 35 | 131 |
| E08 | 1 | 9.6 | 15 | 1 | 113 |
| E09 | 1 | 9.39 | 25 | 40 | 148 |
| E10 | 1 | 9.39 | 35 | 45 | 165 |
| E11 | 1 | 9.25 | 35 | 270 | 214 |
| E12 | 2 | 9.39 | 25 | 19 | 146 |
| E13 | 2 | 9.39 | 25 | 22 | 141 |
| E14 | 2 | 9.25 | 25 | 66 | 140 |
| E15 | 2 | 9.25 | 15 | 8 | 130 |
| E16 | 2 | 9.39 | 15 | 1 | 152 |
| E17 | 2 | 9.6 | 35 | 285 | DNG |
| E18 | 2 | 9.6 | 25 | 1 | 198 |
| E19 | 2 | 9.6 | 15 | 1 | 69 |
| E20 | 2 | 9.39 | 25 | 42 | DNG |
| E21 | 2 | 9.39 | 35 | 240 | 240 |
| E22 | 2 | 9.25 | 35 | 415 | 154 |

The "set time" results, shown in the table above, indicate that the weight ratio correlates with swelling and set time: lower weight ratios correlate with less swelling, presumably due to a more efficient network. Set time was observed to increase as the ratio of PEG:PEI decreased, which may be a result of the higher mix pH and the larger number of nucleophilic amino groups, resulting from the increased relative concentration of PEI. The least amount of swelling was observed at a 15:1 ratio, implying the presence of a more efficient network. The initial pH of the PEI solution is directly related to the set time; a higher pH results in a faster setting gel. All gels at 35R either did not gel or formed a poor gel indicating the amount of PEI was too low for efficient reaction, perhaps because the PEG-NHS degraded before the gel formed. Variability in the observed set times were attributed to systematic error associated with working with the small volumes of ~7% PEI solutions. Subsequent experiments utilized larger volumes of a more dilute solution of PEI (~1.7%) in order to reduce the effect of the systemic error.

Drawing on the aforementioned experiments, a second set of gels was produced with varying wt ratios of R15, R20, R25, and weight percentages of 10 wt % and 15 wt %. Solutions of PEI were prepared with varying pH, such that the gels were formed with similar set times, thereby reducing the degradation of the PEG-NHS prior to gelation. Decreased swelling is observed as the wt % solids decreased. Also observed was a swelling minimum for the 10 wt % gels at 20R.

TABLE 7

PEI Solutions Used.

| | PEI Solution ID | | | | | |
|---|---|---|---|---|---|---|
| | S01 | S02 | S03 | S04 | S05 | S06 |
| pH | 8.46 | 9.00 | 8.77 | 9.24 | 9.57 | 9.75 |
| PEI wt % | 1.69 | 1.71 | 1.70 | 1.73 | 1.77 | 1.75 |

TABLE 8

Sample Formulations and Set Times.

| Sample | PEG-NHS (mg) | H₂O added (µL) | PEI (mg) | PEI soln used (µL) | PEI soln wt % | PEG soln wt % | Wt ratio PEG-NHS: PEI | Total wt % solids | PEI soln used | Avg. (n = 3) set time (sec) |
|---|---|---|---|---|---|---|---|---|---|---|
| R15-10 wt % | 36 | 206 | 2.4 | 140 | 0.0171 | 0.149 | 15 | 10.0 | S02 | 49 |
| R15-15 wt % | 36 | 77 | 2.4 | 141 | 0.017 | 0.32 | 15 | 15.0 | S03 | 27 |
| R20-10 wt % | 36 | 237 | 1.8 | 102 | 0.0177 | 0.132 | 20 | 10.0 | S05 | 25 |
| R20-15 wt % | 36 | 109 | 1.8 | 105 | 0.0171 | 0.248 | 20 | 15.0 | S02 | 39 |
| R25-10 wt % | 36 | 254 | 1.4 | 82 | 0.0175 | 0.124 | 25 | 10.0 | S06 | 56 |
| R25-15 wt % | 36 | 128 | 1.4 | 83 | 0.0173 | 0.219 | 25 | 15.0 | S04 | 62 |

TABLE 9

E30 Set Time and Swelling Results.

| Formulation | Average Set Time [SD] (sec) | Average % Swelling | pH PEI Solution |
|---|---|---|---|
| R15 - 10 wt % | 49 [2.08] | 84 | 9.00 |
| R20 - 10 wt % | 25 [7.55] | 77 | 9.57 |
| R25 - 10 wt % | 56 [0.58] | 113 | 9.75 |
| R15 - 15 wt % | 27 [1.53] | 130 | 8.77 |
| R20 - 15 wt % | 39 [1.56] | 135 | 9.00 |
| R25 - 15 wt % | 62 [3.60] | 163 | 9.24 |

Swelling data also shows for sets at 10 wt % and 15 wt % a much smaller difference in swelling between R15 and R20 systems than between the R20 and R25 systems. Therefore, there appears to be a range of ratios where the swelling properties of gels at the same wt % are similar. This fact means the gels and methods of the invention are robust because minor variations around the optimal system will not result in appreciable erosion of desirable macroscopic characteristics.

Despite the relatively high initial pH (as measured by litmus paper) of the PEI solution, the pH immediately after mixing for all the gel systems was found to be in the range of 8.2-8.5, dropping to about 6.5 near the time of gelation.

Gels were produced in duplicate at ratios of R15 and R20, over 7.5 wt %, 10 wt %, and 15 wt %, with set times ranging between 30 and 60 seconds. After PEG-NHS was reconstituted in deionized (DI) water, and mixed with a PEI solution, three drops of the polymer were placed on a de-epithelialized eye. The sample was subsequently used to close at least one 3 mm wound on an eye mounted on the burst-pressure apparatus. The durability, and burst-pressure tests were performed as outlined in the preceding Example (Burst Pressure).

Examples 12-26

Preparation of Tetramethylenexylene Diisocyanate/Polyethylene Glycol Prepolymers.

In a representative experiment, polyethylene glycol (PEG), dimethylolpropionic acid (DMPA), and a stir bar are charged to a flask. The flask is placed under inert gas, and then the reaction flask is heated to 80-95° C. in an oil bath. After the PEG melts and the DMPA disperses in the melt, tetramethylenexylene diisocyanate (TMXDI) is added to the reaction via syringe. The reaction is then heated to 120-130° C. for 2 hours, at which point the reaction is highly viscous and the stir bar has stopped spinning. The material was used as is for subsequent gel formation. The table below (Table 10) shows the prepolymers prepared by this method. The "*" indicates block-PEG-block-PPG-block-PEG. In general the polymers are referred to as TMXDI(PEG Mw) (i.e. TMXDI (1000) indicating PEG with Mw=1000 was derivatized/chain extended with TMXDI.

TABLE 10

| Example | TMXDI (g) | PEG (mw) | PEG (g) | DMPA (g) |
|---|---|---|---|---|
| 12 | 26.35 | 400 | 30.63 | 2.74 |
| 13 | 8.60 | 400 | 10 | 0.89 |
| 14 | 6.90 | 1500 | 30 | 0.72 |
| 15 | 8.65 | 1000 | 25.14 | 0.90 |
| 16 | 20 | 600 | 34.88 | 2.08 |
| 17 | 18.60 | 600 | 28.18 | 2.90 |
| 18 | 3.50 | 2000 | 20.34 | 0.36 |
| 19 | 2.85 | 2900* | 24 | 0.30 |
| 20 | 18.30 | 1000 | 20 | 1.90 |
|  |  | 600 | 20 |  |
| 21 | 14.35 | 1000 | 25 | 1.49 |
|  |  | 1500 | 25 |  |
| 22 | 39.89 | 1000 | 80 | 9 |
| 23 | 25.60 | 1000 | 40 | 7.3 |
| 24 | 15.72 | 3400 | 40 | 6.2 |
| 25 | 2.00 | 3400 | 19.76 | 0.21 |
| 26 | 14.9 | 4600 | 40 | 6.2 |

Examples 27-32

Hydrogels from TMXDI-PEG-DMPA Prepolymers.

Representative examples of the formation of hydrogels from TMXDI-PEG-DMPA prepolymers are described below.

Example 27

A 20 mL vial was charged with 1 gram of the material from Example 13, 9 grams of DI water, and 0.47 mL of triethyl amine (TEA). The material was mixed until the entire prepolymer emulsified into solution. The resulting solution was milky white in color and was water like in viscosity. 1.0 mL of a 10 wt % polyethylenimine in water was then added to the prepolymer solution with rapid stirring. The solution instantaneously setup into a white gel. The gel sliced into 3 portions, weighed, and then were placed in into a 20 mL vials. 5 mL of BSS solution was then added to each vial. After reaching equilibrium, the gels on average lost 24 wt % by weight of water. The gels maintained there integrity even after soaking in BSS solution for 3 months.

Example 28

0.1 grams of material from Example 15 was dissolved in ~5 mL of water. 0.1 mL of PEI 1,300 (10 to 1 dilution in water) was added to the solution. After mixing for 1 minute, the material gelled into a firm hydrogel. This material was loaded into a syringe and extruded through a 25 gauge syringe needle. After extrusion, the material maintained its resulting shape.

Example 29

0.199 grams of material from Example 15 was dissolved in 0.70 mL of water, and then 4.0 mg of TEA was added to the solution. 0.04 mL of PEI (m.w.1,300; 10 to 1 dilution in water; pH adjusted to 8.5) was added to the solution with rapid stirring. The material set up in ~15 seconds. The gel was transferred to a vial containing 5 mL of BSS solution. After swelling for 40 hours, the gel had increased in weighed 89 wt %.

Example 30

0.191 grams of material from Example 15 was dissolved in 1.088 mL of water, and then 4.9 mg of TEA was added to the solution. 0.077 mL of PEI (m.w.1,300; 10 to 1 dilution in water; pH adjusted to 8.5) was added to the solution with rapid stirring. The material set up in ~30 seconds. The gel was transferred to a vial containing 5 mL of BSS solution. After swelling for 40 hours, the gel had increased in weighed 93 wt %.

Example 31

A 14.9 wt % solution was prepared of material from Example 15 in DI water. A stoichiometric amount of TEA was added (relative to the DMPA in the prepolymer) to the solution. 1.4 mL of this solution was charged to a vial with a stir bar. With stirring was added 0.6 mL of 5 wt % PEI (mw 800, pH 8.0). The resulting material setup into a sticky white gel.

Example 32

A 14.9 wt % solution was prepared of material from Example 15 in DI water. A stoichiometric amount of TEA was added (relative to the DMPA in the prepolymer) to the solution. 2.0 mL of this solution was charged to a vial with a stir bar. With stirring was added 0.6 mL of 5 wt % PEI (mw 2,000, pH 8.0). The resulting material setup into a opaque gel.

Example 33

Mixed PEG-SPA and TMXDI-PEG-DMPA Hydrogels.

39.1 mg of material from Example 13 was charged to a 20 mL vial. 0.634 mL of water was added to the vial, followed by 1 drop (28 gauge syringe needle) of TEA. The solution was vortex mixed until the material dissolved. This solution was then transferred to a vial with 34.6 mg of PEG(3400)-SPA. The mixture was mixed until the PEG-SPA dissolved to form a homogeneous optically clear solution. A PEI solution was prepared by dissolving 1.0 gram of 50 wt % PEI (1,300 mw) in 9.0 grams of water. 0.067 grams of concentrated HCl was then added to 3.05 grams of the PEI solution. With rapid stirring was added 0.1 mL of PEI solution was added to the PEG-SPA/TMXDI-PEG-DMPA solution. The resulting solution rapidly polymerized into a firm hydrogen. The resulting hydrogel was allowed to stand for 15 minutes. The gel was then placed in 5 mL of BSS solution. After reaching equilibrium, the hydrogel had gained 20 wt % by weight in water.

Examples 34-38

Synthesis of MacroPrepolymers.

10.13 grams of PEI (mw 2,000; 50 wt % solids in water) was dissolved in 91 grams of DI water. 4.85 grams of concentrated HCl was then added to the solution with stirring to form a stock solution of pH adjusted PEI. 2.0 grams of material from Example 15 and 50 mg of TEA were dissolved in 18.0 grams of water to yield a stock solution of material from Example 15. The following mixtures were prepared by the slow addition of the stock solution of material from Example 15 to the stock solution of PEI.

TABLE 11

Results of Examples 34-38.

| Example | Example 4 Stock Solution (mL) | PEI (mL) | Results |
|---|---|---|---|
| 34 | 1.5 | 1.5 | Liquid |
| 35 | 1.5 | 0.75 | Liquid |
| 36 | 1.5 | 0.375 | Liquid |
| 37 | 1.5 | 0.1 | Very viscous liquid |
| 38 | 3.0 | 0.1 | Gelled polymer |

Example 39

5 mg of PEG-3400-SPA was dissolved in 0.015 mL of DI water. This solution was then added to the stirring solution 2.3 mL of material from Example 36. The material set up into a firm polymer gel in 10-15 minutes.

Example 40

20 mg of PEG-3400-SPA was dissolved in 0.030 mL of DI water. This solution was then added to the stirring solution 0.300 mL of material from Example 36. The material set up into a tacky polymer gel in ~4 minutes. This gel was allowed to swell in BSS solution and resulted in a 300% weight gain after 24 hours of swelling.

Example 41

1.22 grams of material from Example 15 and 23 mg of TEA were dissolved into 9.0 grams of water. 1.5 mL of this solution was slowly added to a vial containing 0.4 mL of a 5 wt % PEI solution (m.w. 1,300, pH 8), which resulted in an optically clear macro-prepolymer liquid. 0.38 ml of the resulting macro-prepolymer solution was charged to a vial. 36 mg of PEG-3400-SPA was dissolved in PEG buffer solution and was subsequently added to the macro-prepolymer solution. The resulting solution set up into a gel in 90 seconds. A portion of the gel was swelled in BSS solution. After 4 hours, the gel had increased in weight by 156%.

Example 42

1.85 grams of material from Example 15 and 34.6 mg of TEA were dissolved in 13.57 grams of water. A 20 mL vial was charged with 1.07 mL of a PEI solution, which was previously prepared by diluting 50% PEI (m.w. 2,000) to 5 wt % with water and then adjusting the pH to 8 with concentrated HCl. With a syringe pump, 4 mL of the Example 145 solution was added to the PEI solution with rapid stirring over 12 minutes, which resulted in a slightly viscous optical clear macro-prepolymer liquid. This material was allowed to stand for about 2½ months in a capped vial, which resulted in no visible change in the material's appearance. 0.300 mL of the aged material was charged to a GC vial. 36 mg of PEG-3400-SPA was dissolved in DI water and then the resulting solution was added with rapid stirring to 0.300 mL of the aged macro-prepolymer. The resulting solution set up into a firm translucent hydrogel polymer in 90 seconds.

Example 43

2 grams of material from Example 15 and 50 mg of TEA were dissolved in 18 grams of water to yield a stock solution of Example 15. A 20 mL vial was charged with 0.2 mL of a PEI solution, which was previously prepared by diluting 50% PEI (m.w. 800) to 5 wt % with water. With a syringe, 1.5 mL of the stock solution was added to the PEI solution with rapid stirring, which resulted in a slightly viscous optical clear macro-prepolymer liquid. This material was allowed to stand for about 2½ months in a capped vial, which resulted in no visible change in the material's appearance. 0.300 mL of the aged material was charged to a GC vial. 36 mg of PEG-3400-SPA was dissolved in DI water and then the resulting solution was added with rapid stirring to 0.300 mL of the aged macro-prepolymer. The resulting solution set up into a firm translucent hydrogel polymer in 23 seconds.

Example 44

Adhesion Studies with TMXDI Prepolymers.

39 mg of the product of material from Example 13 was dissolved into 0.26 mL of water. A PEI solution was prepared by dissolving 1.0 gram of 50 wt % PEI (1,300 mw) in 9.0 grams of water, and then the pH was adjusted to 8.5. 0.05 mL of the PEI was added to the other solution. The solution was mixed via syringe. The small amounts of the material were then applied to an enucleated pig eye. The material was allowed to setup for 15 minutes. The eye was placed in BSS solution at 35° C. The material was checked periodically for adhesion. The material adhered to the eye for 50 hours.

Example 45

In Vitro Application of PEI:PEG-NHS Gel Systems to Enucleated Eyes.

The PEI:PEG-NHS hydrogel system was applied to enucleated porcine eyes to test both durability and burst pressure. A single barreled syringe was filled with 36 mg of 3400 molecular weight PEG-NHS powder. A separate vial was filled with 220 µl of an aqueous buffer solution (25 mM sodium bicarbonate, 25 mM sodium tetraborate decahydrate, 5 mM sodium meta-bisulfite, and 125 mM sodium phosphate monobasic) containing 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe were expressed back into the vial. The process was repeated two additional times in order to thoroughly mix the powder and liquid components. The final solution was then applied to the surface of an enucleated porcine eye.

Example 46

In Vitro Application of PEI:PEG-NHS Gel Systems to Enucleated Eyes.

The PEI:PEG-NHS hydrogel system was brushed on enucleated porcine eyes to test both durability and burst pressure. A single barreled syringe was filled with 36 mg of 3400 molecular weight PEG-NHS powder. A separate vial was filled with 220 µl of an aqueous buffer (25 mM sodium bicarbonate, 25 mM sodium tetraborate decahydrate, 5 mM sodium meta-bisulfite, and 125 mM sodium phosphate monobasic) containing 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe were expressed back into the vial. The process was repeated two additional times in order to thoroughly mix the powder and liquid components. Using a brush applicator, the final solution was then applied the surface of an enucleated porcine eye. The thickness of the application of sealant was 0.30 mm.

Example 47

Controlling the Set Time of PEI:PEG-NHS Gel Systems with Base at Time of Delivery.

A single barreled syringe was filled with 36 mg of 3400 molecular weight PEG-NHS powder. A separate vial was filled with 300 µl of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI pH 7.6 (11.4% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe were expressed back into the vial. The process was repeated two additional times in order to thoroughly mix the powder and liquid components. The final solution gelled in 3.5 minutes.

Next, a single-barreled syringe was filled with 36 mg of 3400 molecular weight PEG-NHS powder. A separate vial was filled with 300 µl of an aqueous buffer solution and 2000 molecular weight PEI pH 7.6 (11.4% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe were expressed back into the vial. The process was repeated two additional times in order to thoroughly mix the powder and liquid components. The original cannula was removed, and a second cannula with a 4 mm Millex-HV (PVDF) membrane was attached to the luer lock syringe. The membrane had been previously doped with 1.1 mg of sodium phosphate dibasic. The final solution gelled in 3.5 minutes if left within the syringe, but gelled in 1.87 minutes when expressed through the membrane.

Finally, a single barreled syringe was filled with 36 mg of 3400 molecular weight PEG-NHS powder. A separate vial was filled with 300 µl of an aqueous buffer solution and 2000 molecular weight PEI pH 7.6 (11.4% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe were expressed back into the vial. The process was repeated two additional times in order to thoroughly mix the powder and liquid components. A hydrophilic sponge was used to absorb the thoroughly mixed solution. The hydrophilic sponge had been previously doped with 4.4 mg of sodium phosphate dibasic. The final solution gelled in 3.5 minutes if no contact was made with the sponge, but gelled in 0.57 minutes when absorbed and applied by the hydrophilic sponge.

These data show that the rate of crosslinking of a two component system dissolved in an aqueous solution can be controlled by modifying the pH of the solution during application using a base-loaded matrix. This approach allows the components in aqueous solution to mix thoroughly in a single container before application without excessive crosslinking, and then speed up the crosslinking at the time of application. Conceivably, the pH and buffering components of the initial solution may be modified to extend the time of crosslinking once mixed (e.g., to 10-30 minutes; or an hour) before applying the mixed components depending on the user's requirements. The amount of base on the matrix might allow the materials to gel quickly once expressed through or loaded onto an applicator.

Example 48

In Vivo Application of PEI:PEG-NHS Gel Systems.

A single barreled syringe was filled with 36 mg of 3400 molecular weight PEG-NHS powder. A separate vial was filled with 220 µl of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe was expressed back into the vial. The process was repeated two additional times in order to thoroughly mix the powder and liquid components. The final solution was then applied through the cannula onto the cornea of a rabbit in which a 3.0 mm linear incision had been made. The resulting application of sealant was found to be approximately 1.5 mm thick and resulted in effectively sealing the incision.

Example 49

In Vivo Application of PEI:PEG-NHS Gel Systems.

A single barreled syringe was filled with 36 mg of 3400 molecular weight PEG-NHS powder. A separate vial was filled with 220 µl of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe was expressed back into the vial. The process was repeated two additional times in order to thoroughly mix the powder and liquid components. The final solution was then applied onto the cornea of a rabbit in which a 3.0 mm linear incision using a small, nylon bristled paint brush. The resulting application of sealant was found to be approximately 0.3 mm thick and resulted in effectively sealing the incision.

Example 50

In Vitro Application of PEI:PEG-NHS Gel Systems.

A single barreled syringe was filled with 36 mg of 3400 molecular weight PEG-NHS powder. A separate vial was filled with 220 µl of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe was expressed back into the vial. The process was repeated two additional times in order to thoroughly mix the powder and liquid components. The final solution was then applied onto an edible collagen based sausage casing in which a 3 mm diameter hole was placed prior to the application of the sealant. The thickness of the application of sealant was 0.30 mm. The sausage casing test specimen was them placed into a fixture and slowly pressurized from below the application of sealant using balance saline solution similar to the procedure specified in ASTM F2392-04. The failure pressure for the sealant was found to be 103.4 mm Hg.

Example 51

In Vitro Application of PEI:PEG-NHS Gel Systems.

A single barreled syringe was filled with 36 mg of 3400 molecular weight PEG-NHS powder. A separate vial was filled with 220 µl of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe were expressed back into the vial. The process was repeated two additional times in order to thoroughly mix the powder and liquid components. The final solution was then applied onto an edible collagen based sausage casing in which a 3 mm diameter hole was placed prior to the application of the sealant. The specimen was placed into a vial filled with balanced saline solution and set into a 35° C. water bath. After 3 days the specimen was removed and pressure tested in a procedure similar to ASTM F2392-04. The thickness of the application of sealant was 0.50 mm and the failure pressure was found to be 76.7 mm Hg.

Example 52

Testing Various Delivery Devices for Two-Component Gel Systems.

200 µl of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI was filled into the bottom portion of a commercially available single unit dose applicator (Dip-N-Do, Sonic Packaging). The hollow plunger was then seated and filled with 32.7 mg of 3400 molecular weight PEG-NHS (15% total solids 15:1 PEG:PEI Ratio (w/w)).

The device was activated, allowing the liquid and powder portions to come into contact with each other. Using the brush applicator, the material mixture was mixed within the container. The resulting mixture was then applied to the surface of an enucleated porcine eye. The resulting application of sealant was approximately 0.3 mm thick and gelled in approximately 20 seconds.

Example 53

Testing Various Delivery Devices for Two-Component Gel Systems.

Two boluses of 125 µl each of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI was filled into the bottom portion of a commercially available single unit dose applicator (Dip-N-Mix, Sonic Packaging). The hollow plunger was then seated and filled with 22.4 mg of 3400 molecular weight PEG-NHS (15% total solids 15:1 PEG:PEI Ratio (w/w)).

The device was activated, allowing the liquid and powder portions to come into contact with each other. Using the brush applicator, the material mixture was mixed within the container. The resulting mixture was then applied to the surface of an enucleated porcine eye. The resulting application of sealant was approximately 0.3 mm thick and gelled in approximately 20 seconds.

Example 54

Testing Various Delivery Devices for Two-Component Gel Systems.

Two boluses of 125 µl each of an aqueous buffer solution (approximately 25 mM sodium bicarbonate, 25 mM sodium tetraborate decahydrate, 5 mM sodium meta-bisulfite, and 125 mM sodium phosphate monobasic) containing 2000 molecular weight PEI was filled into the bottom portion of a commercially available single unit dose applicator (Dip-N-Mix, Sonic Packaging). The hollow plunger was then seated and filled with 22.4 mg of 3400 molecular weight PEG-NHS (15% total solids 15:1 PEG:PEI Ratio (w/w)). The device was activated, allowing the liquid and powder portions to come into contact with each other. Using a sponge applicator, the material mixture was mixed within the container. The resulting mixture was then applied to the surface of an enucleated porcine eye. The resulting application of sealant was approximately 0.3 mm thick and gelled in approximately 20 seconds.

Example 55

Sterilization of PEI:PEG-NHS Gel Systems.

A single barreled syringe was filled with 36 mg of 3400 molecular weight PEG-SPA powder and was sealed within a foil pouch under inert atmosphere. A separate vial was filled with 220 µl of an aqueous buffer solution containing 2000 molecular weight PEI and sealed within a foil pouch (15% total solids 15:1 PEG:PEI Ratio (w/w)). The two components were combined and exposed to varying doses (10-50 kGy) of E-beam irradiation.

Initially, samples showed a change in set time with increased irradiation. The samples were designed to gel in approximately 20 seconds, indicating that at least one of the components had changed. The 10 kGy irradiated PEG-SPA and 222 µL of the nonirradiated PEI stock solution used to prepared the PEI solution samples for irradiation set in 25 seconds and swelled 78 percent in approximately 21 hours. 36 mg of nonirradiated PEG-SPA and 222 µL of the nonirradiated PEI stock solution also set in 24 seconds and swelled 78 percent in 21 hours.

Based on these observations, the PEI solution was identified as problematic. As proof, various dosages of PEG-SPA were tested with 222 µL of the nonirradiated PEI stock solution (Table 12) with little change in set time or swelling.

TABLE 12

Set time and swelling of irradiated PEG-SPA with non-irradiated PEI solution.

| E-beam dose received by PEG-SPA (KES-170) | Set time when combined with stock PEI solution (sec.) | Swelling after 20.667 hours |
|---|---|---|
| 0 kGy | 24 | 78% |
| 10 kGy | 25 | 74% |
| 20 kGy | 30 | 99% |
| 30 kGy | 20 | 87% |
| 40 kGy | 22 | 84% |
| 50 kGy | 31 | 98% |

E-beamed PEG-SPA and the PEI solution were tested and results are summarized in Table 13. This experiment indicated a dose responsive change in the PEI solution with increased irradiation.

TABLE 13

Set time of irradiated PEG-SPA combined with irradiated PEI solution.

| E-beam dose received by PEG-SPA (KES-170) and PEI solution | Set time when combined (sec.) |
|---|---|
| 0 kGy | 24 |
| 10 kGy | 76 |
| 20 kGy | 204 |
| 30 kGy | 341 |
| 40 kGy | 451 |
| 50 kGy | 5265 |

In an attempt to reduce the degradation in set time and swelling performance of the polyalkyleneimine formulations post e-beam sterilization, a series of solutions were prepared with anti-oxidants, radical scavengers, and/or the removal of various buffers. All solutions were designed using $PEI_{2000}$ to produce 15 wt % gels with set times typically between 15-45 seconds.

Inhibitors included Methyl Hydroquinone (MeHQ), Hydroquinone (HQ), Ascorbic Acid, and elevated levels of sodium meta bisulfite (SMBS), as SMBS was already present in the formulation at a concentration of 0.1 w/v %. Of the inhibitors used, ascorbic acid was most effective in reducing the swelling related performance loss, followed by MeHQ. However, the set times of gels with ascorbic acid were significantly increased post e-beam, whereas those using MeHQ had only a minor increase in set time. Hydroquinone also helped reduce the degradation of performance; however resulting gels had a bright orange coloration after exposure to oxygen.

Solutions were also prepared such that the polyalkyleneimine was dissolved in approximately one half of the water and contained SMBS along with various levels of the inhibitors MeHQ, HQ, Ascorbic Acid, and elevated levels of SMBS. The remaining buffers and salts were dissolved in a separate solution. The two solutions were combined post e-beam and gels were prepared to examine the performance characteristics. These tests afforded a polyalkyleneimine solution of higher pH during the e-beam process, which resulted in improve performance of the formulations in retention of both set time and swelling characteristics.

The beneficial effects of the inhibitors and the separation of the salts from the polyalkyleneimine were combined to produce an overall improvement. For example, the relative change in swelling of the MeHQ system went from an increase of 28% for the mixed system, to an increase of 20% when the polyalkyleneimine was separated from the salts. The relative change in set time also improved, changing from a 22% increase, for the mixed system, to only about an increase of 6% in the separated solution system. A similar trend was observed for all inhibitors used. However, the removal of all salts and the addition of antioxidants and radical scavengers did not completely prevent a deterioration in the set time and swelling performance of the formulations post e-beam sterilization. See FIG. 32.

In the course of these studies, a polyalkyleneimine was also sterilized neat to observe any impacts of irradiation on subsequent set time and swelling. Samples of neat PEI 8515 were irradiated simultaneously with the other formulations previously discussed. The same concentration of this irradiated PEI or non-irradiated PEI were prepared and combined with the same volume of buffered salt stock solution. The samples, whether irradiated or not, had nearly the same set time and swelling. These observations experiments demonstrated that the PEI component should either be sterilized neat or as PEI in solution with antioxidants and/or radical scavengers with no other salts or buffers.

Example 56

Osmolality of PEI Solution Used in the PEI:PEG-NHS Gel Systems.

A solution with an osmolality of 290-310 and a pH of 7.4 is most desirable to maintain normal structure and function of the various tissue layers found in the cornea (more specifically the epithelium and the endothelium layers). However, the literature also suggests a hyperosmolar solution is preferable to a hypoosmolar solution. A solution mimicking balanced saline solution (BSS) was used as the aqueous solution to dissolve the PEI and PEG components. Tabulated below are the typical solution components.

TABLE 14

Examples of Typical Solution Components.

| Component | Mw (g/mol) | mM |
|---|---|---|
| $PEI_{2000}$ | 2000 | 5.44 |
| $NaHCO_3$ | 84.01 | 25.0 |
| $Na_2HPO_4$ | 141.96 | 3.45 |
| NaCl | 58.44 | 117.8 |
| KCl | 74.56 | 5.1 |

With between 50-150 mM of phosphoric acid or $Na_2HPO_4$ to adjust the pH of the solution to obtain set times between 10 seconds and 1 minute. The osmolality was measured on an Osmette A5002 calibrated at 100 and 500 mOs. The solution with or without PEI typically had an osmolality of 275-289 mOs/kg. The osmolality of the salt solution with the expected amount of N-hydroxysuccinimide in solution (87.5 mM), or the osmolality of the solution immediately after polymerization, was also measured and found to be 351 mOs/kg.

Example 57

Extractables from PEI:PEG-NHS Gel Systems.

Figure 33:
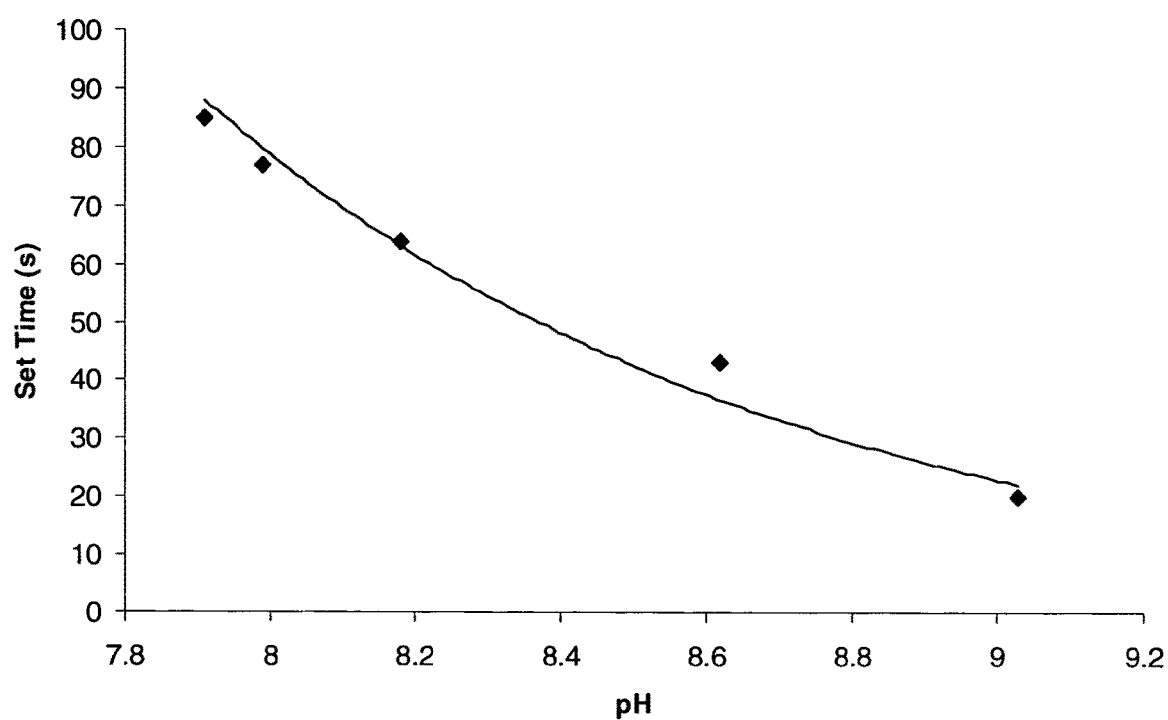
FIG. 33 depicts a graph of set time versus pH for $PEG_{3400}$-SPA:$PEI_{2000}$.

A single barreled syringe was filled with 36 mg of 3400 molecular weight PEG-NHS powder. A separate vial was filled with 220 μl of an aqueous buffer solution (initially pH 8.0-9.0) and 2000 molecular weight PEI (15% total solids 15:1 PEG:PEI Ratio (w/w)). A 20 gauge cannula was attached to the luer lock syringe and the tip of the cannula was placed into the buffer filled vial. The plunger of the syringe was pulled backward to draw the buffer solution into the powder filled syringe. The plunger was then pushed forward and the contents of the syringe was expressed back into the vial. The process was repeated two additional times in order to thoroughly mix the powder and liquid components. The final solution was then applied through the cannula into a mold and allowed to cure for 15 minutes. FIG. 33 shows a graphical depiction of cure time as a function of pH.

Each sample was subsequently placed in $diH_2O$ for 12-18 hours. 2.4 mL of each extract were combined with 100 μL of 150 mM $CuNO_3$ and the UV absorbance at 622 nm was monitored and compared to a PEI calibration curve generated from 5 points ranging in concentration from 0.642 μg/ml to 71 μg/ml (y=9.358E−04x−9.041E-05 $R^2$=9.999E−01). The data, which is tabulated below (Table 15), indicates very low if any amount of PEI extracts from the gels after crosslinking.

TABLE 15

Set time and PEI extract from $PEG_{3400}$-SPA:$PEI_{2000}$ gels.

| pH of solution | ABS (622 nm) | Corrected ABS | [PEI] (μg/mL) | PEI in extract (mg) | % of initial PEI |
|---|---|---|---|---|---|
| Blank | 0.005 | NA | NA | NA | NA |
| 8.0 | 0.007 | 0.002 | 2.327 | 0.0116344 | 0.5 |
| 8.2 | 0.006 | 0.001 | 1.214 | 0.0060688 | 0.3 |

TABLE 15-continued

Set time and PEI extract from $PEG_{3400}$-SPA:$PEI_{2000}$ gels.

| pH of solution | ABS (622 nm) | Corrected ABS | [PEI] (μg/mL) | PEI in extract (mg) | % of initial PEI |
|---|---|---|---|---|---|
| 8.6 | 0.004 | −0.001 | <DL | <DL | <DL |
| 9.0 | 0.005 | 0 | <DL | <DL | <DL |

Example 58

Sealing a Tissue Plane In Vivo.

Female Sprague-Dawley rats weighing approximately 300 grams were anesthetized intraperitoneally with a mixture of ketamine/xylazine. Animals were shaved and prepped with providone iodine. The animals were placed in a lateral decubitus position and a 3 cm longitudinal mid-axillary incision was made. The cutaneous trunci muscle was stripped/peeled from the underling dermis using electrocautery and sharp dissection when needed. The latissimus dorsi muscle was elevated from its insertion along the lower thoracic and upper lumbar vertebrae to its insertion at the humerus. Blunt planar dissection was performed to separate the muscle from the underlying tissue. Electrocautery was used to ligate the vascular pedicle and the latissimus dorsi and cutaneous trunci muscles were excised and measured. Axillary lymph nodes and surrounding fatty tissue pads were removed and cauterized. The exposed dermis and underlying tissue bed were traumatized by scrapping.

A 3400 molecular weight PEG-NHS powder dissolve in a phosphate monobasic buffer (120 mM) was mixed at time of use with a buffer solution (approximately 25 mM sodium bicarbonate, 25 mM sodium tetraborate decahydrate, and 5 mM sodium meta-bisulfite) containing 2000 molecular weight PEI to produce a hydrogel with 15% total solids 16.4:1 PEG:PEI Ratio (w/w)). Alternatively, a 10000 molecular weight PEG-NHS powder dissolve in a phosphate monobasic buffer (60 mM) was mixed at time of use with a buffer solution (approximately 25 mM sodium bicarbonate, 25 mM sodium tetraborate decahydrate, and 5 mM sodium meta-bisulfite) containing 2000 molecular weight PEI to produce a hydrogel with 15% total solids 46.1:1 PEG:PEI Ratio (w/w)). Either formulation was sprayed or applied via a syringe and cannula to the underlying tissue bed. The skin flap was repositioned and light pressure was held for 4 minutes to assure adhesive cure. The wound was closed with intradermal nylon (4-0) and sealed with Dermabond. Control animals received the same treatment with the exception that no adhesive was applied. The animals were monitored daily for seroma production. The adhesive held the tissue together.

Example 59

Sealing a Tissue Plane In Vivo.

Female Sprague-Dawley rats weighing approximately 300 grams were anesthetized intraperitoneally with a mixture of ketamine/xylazine. Animals were shaved and prepped with providone iodine. The animals were placed in a lateral decubitus position and a 3 cm incision line was marked along the frontal plane starting at the axillary extending caudally. Hemispherically arcs were marked from the ends on the frontal plane marker 2 cm towards the dorsal and ventral. The 3 cm frontal incision was made. The cutaneous trunci muscle was stripped/peeled from the underling dermis using electrocautery and sharp dissection when needed. The latissimus dorsi muscle was elevated from its insertion along the lower thoracic and upper lumbar vertebrae to its insertion at the humerus. Blunt planar dissection was performed to separate the muscle from the underlying tissue. Electrocautery was used to ligate the vascular pedicle and the latissimus dorsi and cutaneous trunci muscles were excised and measured. Axillary lymph nodes and surrounding fatty tissue pads were removed and cauterized. The exposed dermis and underlying tissue bed were traumatized by scrapping. The marked hemispherical skin areas were excised in an attempt to compensate for the loose-skin nature of the rat.

A 3400 molecular weight PEG-NHS powder dissolve in a phosphate monobasic buffer (120 mM) was mixed at time of use with a buffer solution (approximately 25 mM sodium bicarbonate, 25 mM sodium tetraborate decahydrate, and 5 mM sodium meta-bisulfite) containing 2000 molecular weight PEI to produce a hydrogel with 15% total solids 16.4:1 PEG:PEI Ratio (w/w)). Alternatively, a 10000 molecular weight PEG-NHS powder dissolve in a phosphate monobasic buffer (60 mM) was mixed at time of use with a buffer solution (approximately 25 mM sodium bicarbonate, 25 mM sodium tetraborate decahydrate, and 5 mM sodium meta-bisulfite) containing 2000 molecular weight PEI to produce a hydrogel with 15% total solids 46.1:1 PEG:PEI Ratio (w/w)). Either formulation was applied to the axillary region, dorsal flap, and ventral flap. In each region the skin flap was repositioned and light pressure was held for 2 minutes to assure adhesive cure. The wound was closed with intradermal nylon (4-0) and sealed with Dermabond. Control animals received the same treatment with the exception that no adhesive was applied. The animals were monitored daily for seroma production. Again the adhesive sealed the tissue.

Example 60

Corneal Endothelium Exposure to Adhesive.

One aspect of this example is to examine the potential damaging effect on the corneal endothelium of extracts from the adhesive formed between PEI and PEG-$(SPA)_2$ or PEG-$(SG)_2$. The utility and sensitivity of the experiment has been well-documented (Hartmann, C.; Rieck, P. A New Test for Endothelial Viability: The Janus Green Photometry Technique. *Arch. Ophthalmol.* 1989,107, 1511-1515; and Pels, E.; Nuyts, R. M. M. A.; Breebaart, A. C.; Hartmann, C. Rapid Quantitative Assays for Corneal Endothelial Cell Viability In Vitro. *Cornea.* 1993, 12, 289-294; both of which are incorporated by reference.)

Hydrogel films were prepared for extraction in a similar manner to ANSI/AAMI/ISO 10993-12:2002, *Biological Evaluation of Medical Devices-Part 12:Sample Preparation and Reference Materials* except BSS (Alcon, Fort Worth, Tex.) was used instead of 0.9% sodium chloride solution. In general, OcuSeal Liquid Ocular Bandage was mixed and expelled onto a casting block to produce a 0.8 mm sheet with an approximate 15 $cm^2$ area. The specimens were allowed to cure for 15 minutes. After curing, the film was placed in a pre-extracted vial and 5 mL of BSS was added to the vial. The films in BSS were placed in an oven set to 35° C. for approximately 68 hours. The hydrogels were subsequently removed and the BSS solution with extracts was used in the endothelial toxicity study.

Fresh eyes of 6-month-old pigs were obtained from a local abattoir. Enucleation was performed soon after death. Corneas were carefully excised with a 1.0-2.0 mm scleral rim and bathed in BSS until exposed to either BSS or BSS with extracts. To determine the potential for endothelial damage with increasing storage time, porcine corneas were stored for 3, 6, and 9.75 hours (n=2 corneas at each time point) under 300 µL of BSS or BSS with extracts at 35° C.

At the appropriate time points, after a brief rinse of the corneas with BSS, the corneoscleral segment was placed on a wax cup with the endothelial side up. The whole endothelium was stained for 90 seconds with 200 µL a 1% Janus green solution (Sigma, St. Louis, Mo.). After thorough rinsing in BSS for 2 minutes, the central corneal area was punched out with a 6.0-mm diameter hand trephine. The stain from each trephined button was eluted in a scintillation vial that was filled with 1 mL of isopropanol. Complete extraction of the stain was achieved after 90 seconds.

Figure 27:
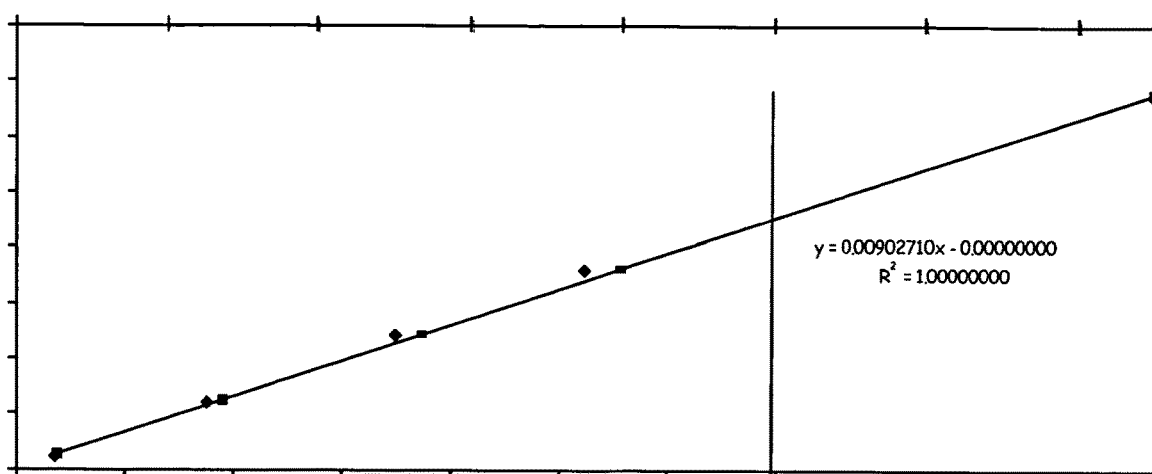
FIG. 27 depicts a Janus Green Standard Curve prepared in isopropanol.

Photometric measurement of the eluate was performed with a spectrophotometer (Shimadzu UV-1700, Kyoto, Japan) at 650 nm, taking isopropanol as the blank value. The extinction values corresponding to "normal" endothelial damage in fresh corneas and complete (100%) damage were determined by taking (1) freshly excised corneas for the 0% lesion and (2) for the 100% lesion, freshly excised corneas treated with isopropanol to alter endothelial viability of the whole endothelial layer. This data is presented in FIG. 27.

Figure 28:
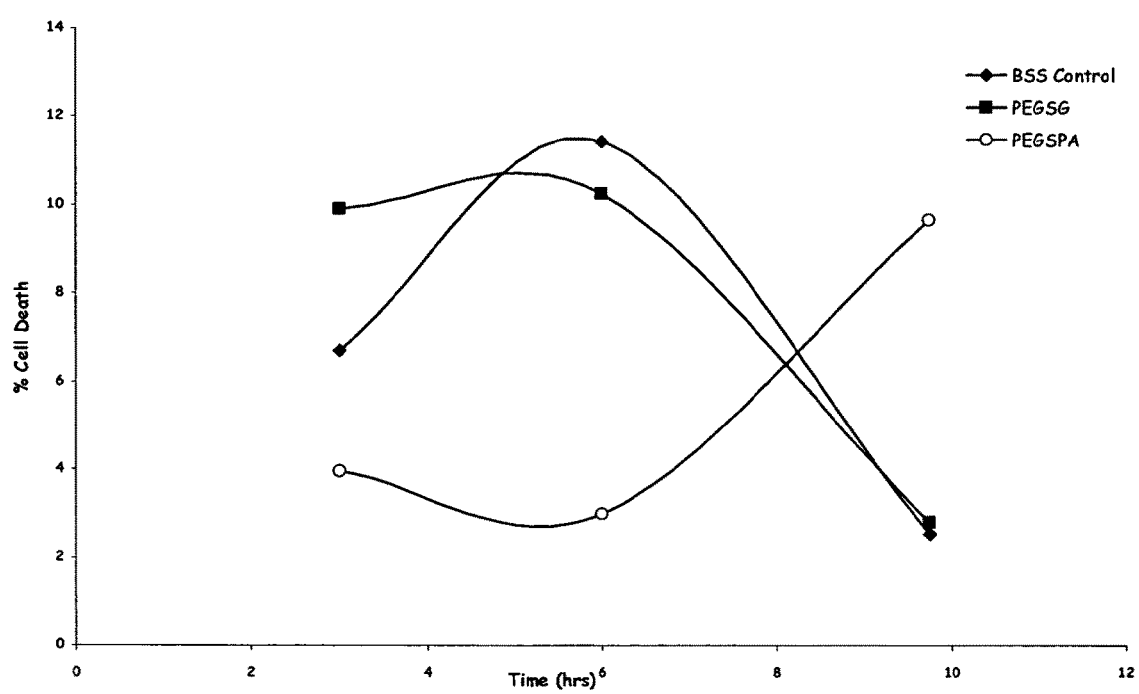
FIG. 28 depicts a comparison of endothelial damage of 12 pig corneas stored for various time intervals under either BSS or BSS used to extract liquid polyalyleneimine hydrogel formulations.

A linear relation was established so that with a given extinction value, the damaged area in the percentage of the whole trephined endothelial surface could be determined. The experimental data for each time point is presented in FIG. 28.

Figure 34:
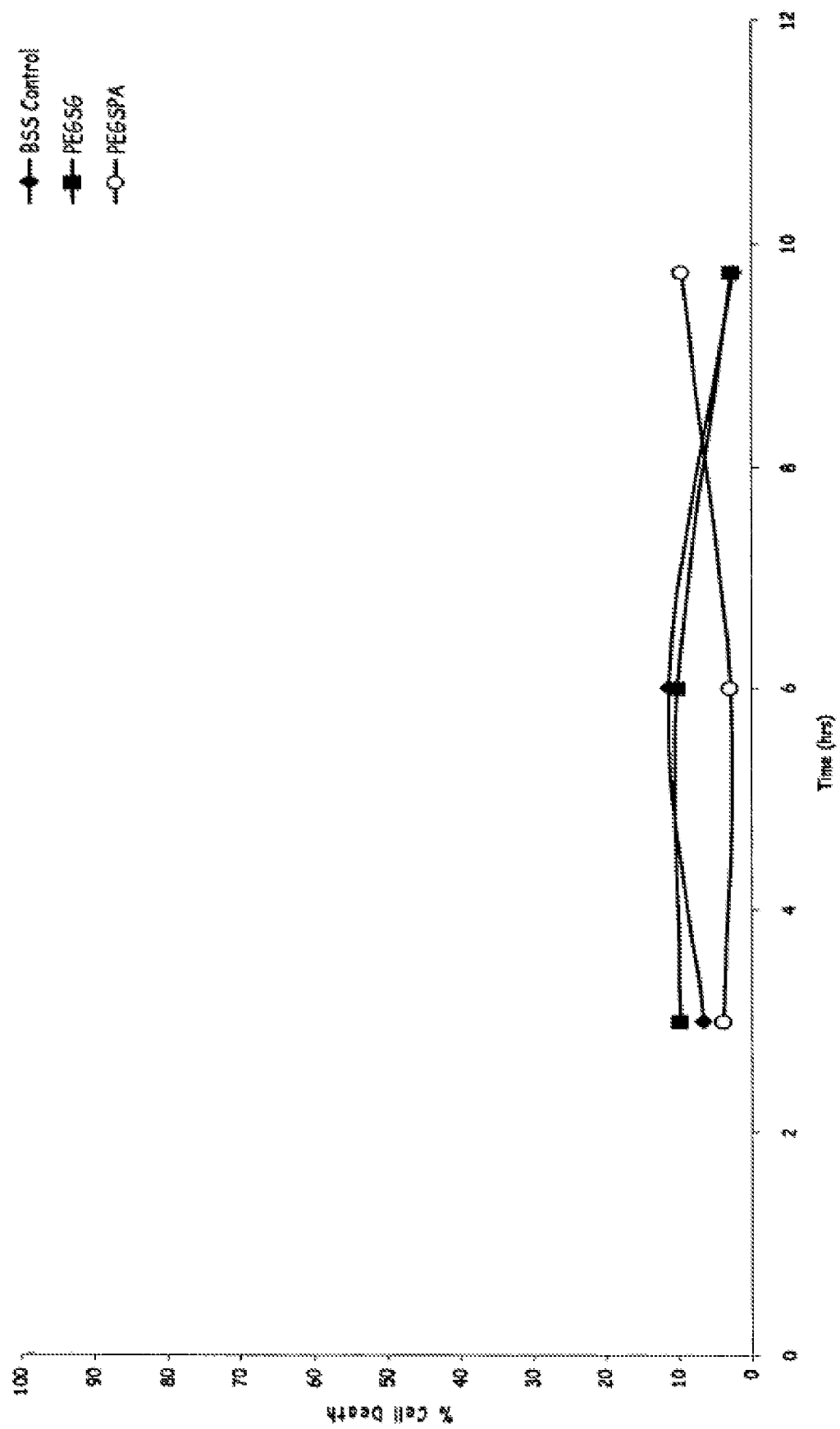
FIG. 34 depicts endothelial viability results in a graph of percent cell death versus time.

Based on literature precedent, as noted in the references above, small areas of endothelium may be altered by enucleation and the corneal excision procedure, even when it is done under the most careful conditions. Therefore, within error of the experiment, BSS containing the extracts of the adhesive formed between PEI and PEG-(SPA)$_2$ and PEG-(SG)$_2$ did not cause any more corneal damage than the BSS control group. Any observable damage did not follow any trend and is most likely due to the corneal excision procedure. See FIG. 34.

Example 61

Shear and Peel Strength.

Figure 29:
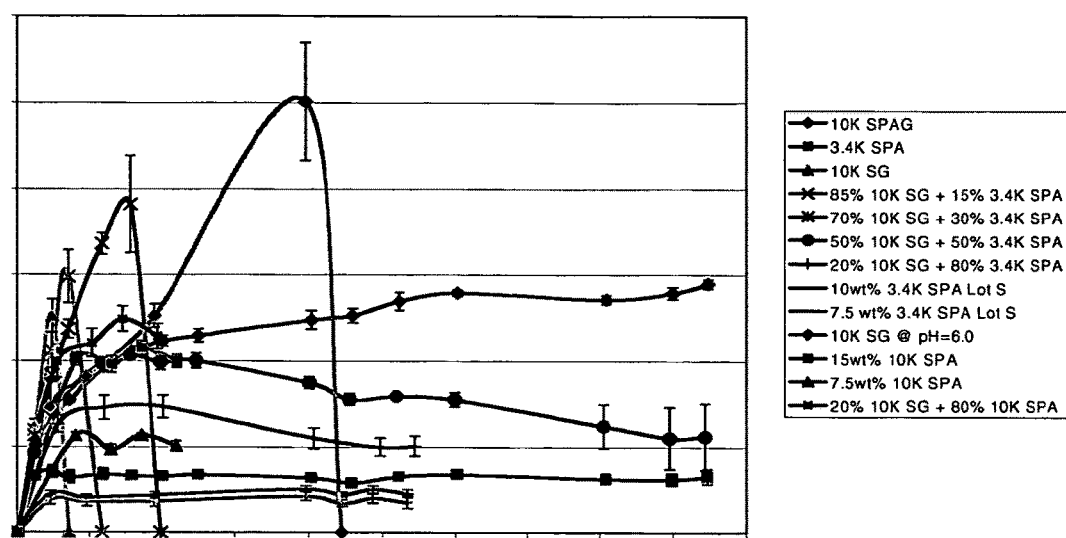
FIG. 29 depicts a chart showing sheer strength of various hydrogels.
Figure 30:
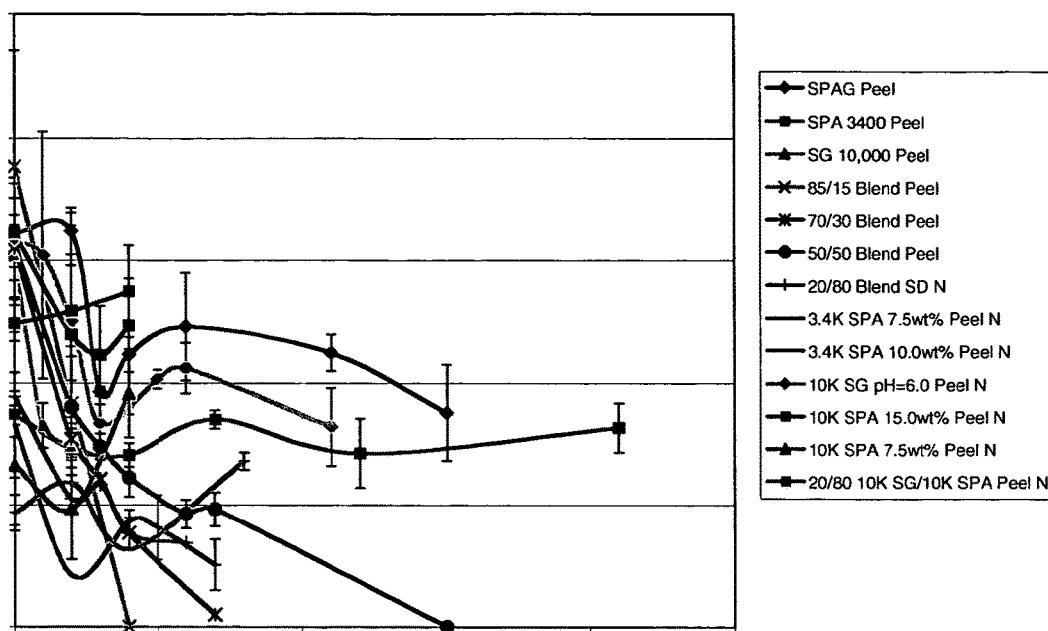
FIG. 30 depicts a chart showing peel strength of various hydrogels.

Following standard ASTM protocols (shear F2255 peal F2256) using Nippon #320 sausage casing, we performed the experiments with varying adhesive formulations. As shown in the FIGS. 29 and 30, all the adhesive formulations possess some peel and shear strength. As shown in FIGS. 29 and 30, adhesives can be prepared that maintained the property over more than 20 days while others lasted only a few days.

Example 62

PEG$_{3400}$-NHS and PEI$_{2000}$ in buffered solution (approximately 25 mM sodium bicarbonate, 25 mM sodium tetraborate decahydrate, 5 mM sodium meta-bisulfite, and 125 mM sodium phosphate monobasic) both E-beamed @ 12 kGy were mixed by withdrawing the PEI solution into a syringe containing PEG (1:1 molar ratio of primary amines to active esters) and expressing back and forth between PEI vial and syringe four times. The mixed solution was expressed into a mold and 0.9% saline was poured over the hydrogel at a ratio of 4 g of test article per 16 mL of saline. The contents were incubated for over 25 hours at 37° C. The pH of the extract solution was found to be pH 6.68±0.02.

Example 63

Tissue Ingrowth Studies.

This study evaluated the biodegradation of hydrogel formulations in a Sprague-Dawley rat model at timepoints up to 10 weeks post application. Thirty two male Sprague-Dawley rats were anesthetized with isoflurane. The test sites were shaved and cleaned with alcohol and Betadine scrub. Betadine solution was applied and each rat was opened using scissors. Four hydrogel formulations were applied by subcutaneous spray application in two areas in each rat on Day 1. Each rat was closed using 4.0 suture material and treated with Buprenorphine for pain.

The four formulations tested containing either 1) PEG$_{3400}$-SPA 15 wt % 2) PEG$_{3400}$-SPA 7.5 wt % 3) PEG$_{10000}$-SG/PEG$_{3400}$-SPA 20-80 blend (w/w) or 4) PEG$_{10000}$-SPA 15 wt %. Each activated PEG-NHS powder was dissolved in a phosphate monobasic buffer (60 to 120 mM) and was mixed at time of use with a buffer solution (approximately 25 mM sodium bicarbonate, 25 mM sodium tetraborate decahydrate, and 5 mM sodium meta-bisulfite) containing 2000 molecular weight PEI to produce a hydrogel with 15% total solids and a PEG:PEI Ratio (w/w) so that the theoretical number of primary amines was equal to the number of activated esters.

Two animals per formulation group were sacrificed by carbon dioxide asphyxiation at 1, 2, 8, and 10 weeks post-op. Necropsy of area of application was performed. All excised tissues were histologically processed, sectioned, stained with hematoxylin and eosin, and examined microscopically.

Figure 35:
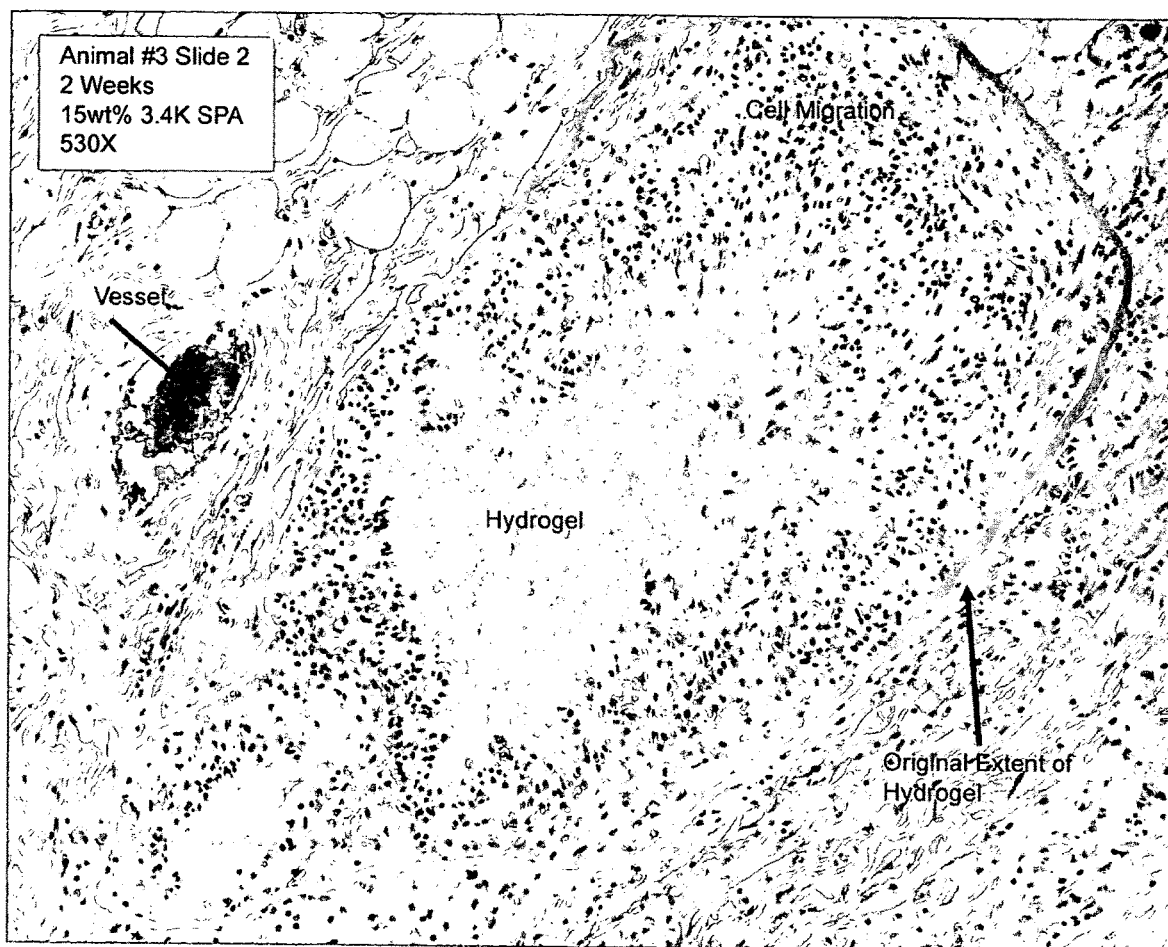
FIG. 35 depicts cell migration and biodegradation of the formulation containing $PEG_{3400}$-SPA at 15 wt % at 2 weeks.
Figure 36:
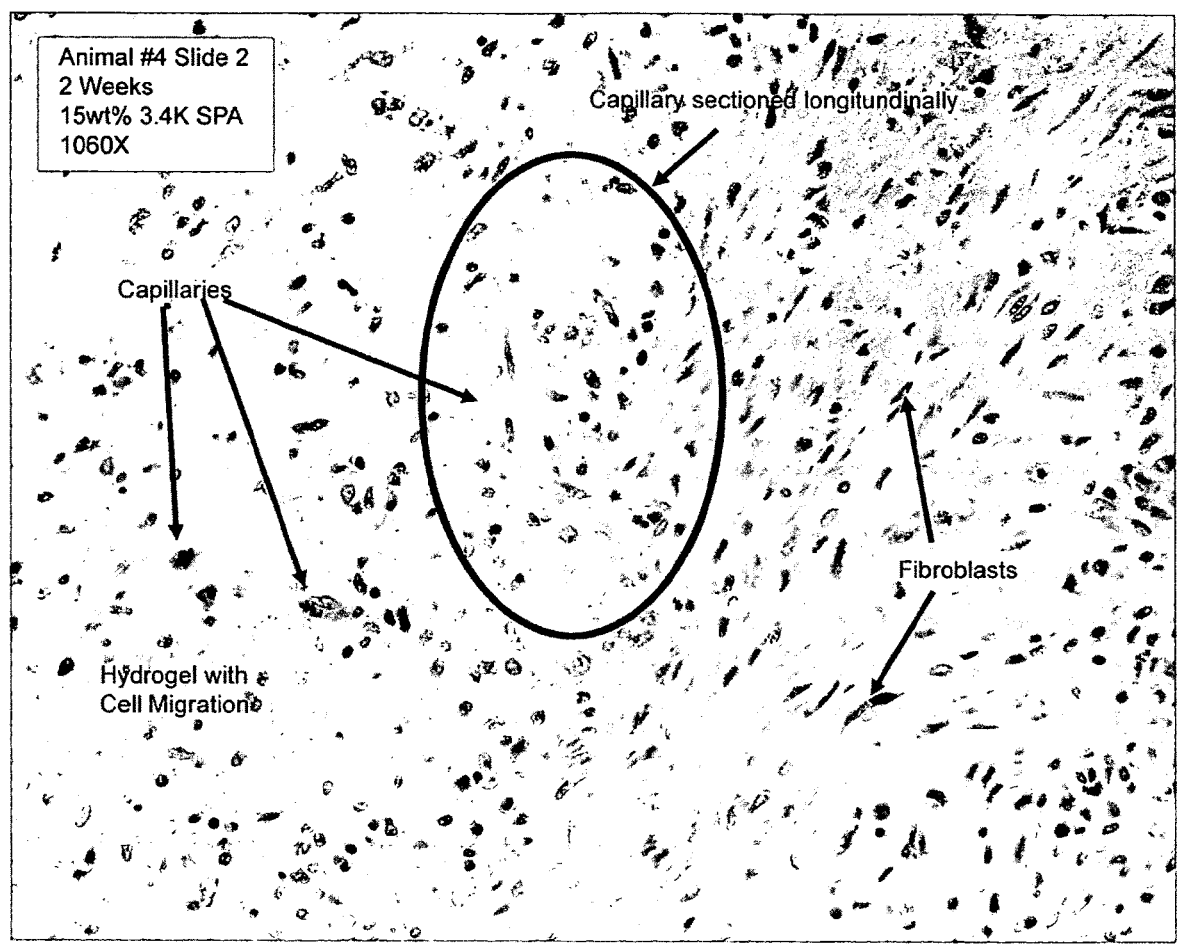
FIG. 36 depicts vascularization of the formulation containing $PEG_{3400}$-SPA at 15 wt % at 2 weeks.

Upon examination, it was noted that all 4 formulations appeared similar histologically at all time points. All formulations showed minimal inflammatory response with no fibrous encapsulation and no foreign body reaction (FIGS. 35 and 36). All formulations also showed cell migration, tissue ingrowth, and vascularization (FIGS. 35 and 36). Degradation, evidenced by foamy macrophages, was evident within each formulation, but at least a portion of the hydrogel material was observed throughout the ten week study.

Example 64

Summary of Various Polyalkyleneimine (PAI)/Polyalkyleneglycol (PAG) Hydrogel Formulations.

The table in FIG. 38 lists various PAI and activated PAG combinations (or derivatized PAG combinations) that can be used to make various hydrogels. The table lists the composition and molecular weight of the PAI and activated PAG, the weight percent of PAI and activated PAG used in the formulation, the weight ratio of PAG:PAI, the swelling at 24 hours in PBS pH 7.4 at 37° C. when available, the set time of the formulation, and the amounts of various components used to achieve the reported set time. Typically, various combinations of sodium phosphate monobasic, sodium tetraborate decahydrate, and sodium bicarbonate were dissolved in an appropriate amount of deionized water also containing PAI before mixing with the activated PAG. In specified cases, only phosphoric acid was used to adjust the pH to achieve the appropriate set time, and in two noted cases, phosphoric acid was used instead of sodium phosphate monobasic because of the large amount of PAI in the system.

Example 65

Derivatization of PEI with Approximately Two Equivalents of Hexadecylisocyanate.

Under inert gas, 1.0 grams of neat PEI (Lupasol PR8515) and about 15 mL of dichloromethane (DCM) were charged to a flask. After the PEI dissolved, 0.31 grams of hexadecyl isocyanate was added via syringe. The solution was allowed to stir for ~48 h, which resulted in a slightly cloudy solution. The DCM was removed under dynamic vacuum to yield an off-white powder. The derivatized PEI was combined with $PEG_{3400}$-NHS in a 15:1 ratio, 15 wt % in a manner similar to the preparation described in example 64 to produce a hydrogel.

Example 66

Derivatization of PEI with Approximately Four Equivalents of Hexadecylisocyanate.

Under inert gas, 1.0 grams of neat PEI (Lupasol PR8515) and about 15 mL of dichloromethane (DCM) were charged to a flask. After the PEI dissolved, 0.62 grams of hexadecyl isocyanate was added via syringe. The solution was allowed to stir for ~48 h, which resulted in a slightly cloudy solution. The DCM was removed under dynamic vacuum to yield an off-white powder. The derivatized PEI was combined with $PEG_{3400}$-NHS in a 15:1 ratio, 15 wt % in a manner similar to the preparation described in example 64 to produce a hydrogel.

Example 67

Derivatization of PEI with Myristoyl Chloride.

Under inert gas, 8.3 grams of neat PEI (Lupasol PR8515) and about 100 mL of dichloromethane (DCM) were charged to a flask.

After the PEI dissolved, 1.0 grams of myristoyl chloride was added dropwise via syringe. The solution was allowed to stir overnight, which resulted in a slightly cloudy solution. The DCM was removed under dynamic vacuum to yield a yellowish viscous oil. 220 mg of the resulting material was dissolved in to 10 mL of DI water. 131 µL of this solution was mixed with an aqueous solution of PEG-3400-NHS (37 mg in 95 µL of DI water). The material gelled in about 30 seconds to produce a firm gel.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating a patient, comprising the steps of:
    exposing an effective amount of polyethyleneimine (PEI) to an activated polyethylene glycol represented by the following formula III to form an adhesive composition; and
    applying said adhesive composition to a tissue of the patient,
    wherein formula III is represented by:

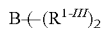

wherein B is

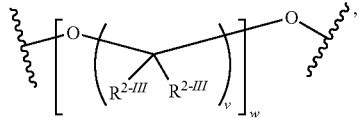

wherein R2-III is H, v is 2, and w is 15 to 90,
    wherein $R^{1\text{-}III}$ is

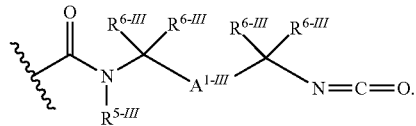

wherein R5-III is H, R6-III is C1 to C4 alkyl, and A1-III is optionally substituted phenyl radical.

* * * * *